United States Patent
Hendrickson et al.

(10) Patent No.: US 9,174,984 B2
(45) Date of Patent: Nov. 3, 2015

(54) CHEMICAL COMPOUNDS

(71) Applicant: GlaxoSmithKline Intellectual Property (No. 2) Limited, Brentford, Middlesex (GB)

(72) Inventors: Thomas Francis Hendrickson, Encinitas, CA (US); Koc-Kan Ho, Holladay, UT (US); Michael David Saunders, Sandy, UT (US); Brian John Stevens, Salt Lake City, UT (US); Krzysztof Swierczek, West Jordan, UT (US); Kevin Bret Wright, Cottonwood Heights, UT (US)

(73) Assignee: GLAXOSMITHKLINE INTELLECTUAL PROPERTY (NO.2) LIMITED, Brentford, Middlesex (GB)

( * ) Notice: Subject to any disclaimer, the term of this patent is extended or adjusted under 35 U.S.C. 154(b) by 0 days.

(21) Appl. No.: 14/353,858

(22) PCT Filed: Oct. 23, 2012

(86) PCT No.: PCT/US2012/061441
§ 371 (c)(1),
(2) Date: Apr. 24, 2014

(87) PCT Pub. No.: WO2013/062945
PCT Pub. Date: May 2, 2013

(65) Prior Publication Data
US 2014/0296204 A1    Oct. 2, 2014

Related U.S. Application Data

(60) Provisional application No. 61/550,681, filed on Oct. 24, 2011.

(51) Int. Cl.
| | |
|---|---|
| *C07D 401/14* | (2006.01) |
| *C07D 401/02* | (2006.01) |
| *C07D 401/10* | (2006.01) |
| *C07D 471/04* | (2006.01) |
| *C07D 487/04* | (2006.01) |

(52) U.S. Cl.
CPC ............ *C07D 471/04* (2013.01); *C07D 487/04* (2013.01)

(58) Field of Classification Search
CPC ... C07D 401/14; C07D 401/02; C07D 401/10
USPC .................. 546/113, 117, 118, 119
See application file for complete search history.

(56) References Cited

U.S. PATENT DOCUMENTS

| | | |
|---|---|---|
| 6,169,088 B1 | 1/2001 | Matsuno et al. |
| 6,207,667 B1 | 3/2001 | Matsuno et al. |
| 6,472,391 B2 | 10/2002 | Matsuno et al. |
| 6,750,218 B2 | 6/2004 | Matsuno et al. |
| 7,560,467 B2 | 7/2009 | Drewry et al. |
| 2002/0068734 A1 | 6/2002 | Matsuno et al. |
| 2008/0132525 A1 | 6/2008 | Wahhab et al. |
| 2009/0082370 A1 | 3/2009 | Thompson et al. |

FOREIGN PATENT DOCUMENTS

| | | |
|---|---|---|
| CA | 2030875 | 7/2002 |
| WO | WO 2006/078752 | 7/2006 |
| WO | 2007002433 | * 1/2007 |
| WO | WO 2007/002433 | 1/2007 |
| WO | WO 2010/036632 | 4/2010 |

OTHER PUBLICATIONS

Amara, et al., *Cancer Sci.*, 101:1722-1730 (2010).
Berge, et al., *J. Pharm. Sci.*, 66:1-19 (1977).
Cahn, *Angew. Chem. Int. Ed. Engl.*, 5:385-415 (1966).
Chiou, et al., *J. Pharm. Sci.*, 60:1281-1300 (1971).
Cohen, et al., *Org. Biomol. Chem.*, 3:152-161 (2005).
Dhonde, et al., *J. Chem. Pharm. Res.*, 2(4):518-525 (2010).
Isakovic L., et al., *Bioorg. Med. Chem. Lett.*, 19:2742-2746 (2009).
*J. Org. Chem.*, 35(9):2849-2867 (1970).
Jones, et al., *National Rev. Genet.*, 3:415-428 (2002).
Leady, *Synthetic Communications*, 7(8):509-514 (1977).
Leister, et al., *J. Comb. Chem.*, 5(3):322-9 (2003).
Linhart, et al., *Genes Dev.*, 21:3110-3122 (2007).
Robertson, et al., *Oncogene*, 20:3139-3155 (2001).
Rosentreter, et al., *J. Comb. Chem.*, 6(2):159-64 (2004).
Rybar, et al., *Collect Czech Chem. Commun.*, 38:1571-1578 (1973).
Saavedra O. M., *Bioorg. Med. Chem. Lett.*, 19:2747-2751 (2009).
Siedlecki, et al., *Biochem. And Biophys. Res. Communications*, 306:558-563 (2003).
Sinha, et al., *Mol. Cancer Ther.*, 5:1909 (2006).
Strickly, et al., *Pharmaceutical Research*, 21(2):201-230 (2004).
Williams, et al., *J. Control. Release*, 91(102):167-172 (2003).
Yang, et al., *Nature Structural Biology*, 10(10:849-855 (2003).
Yoo, et al., *J. Comput. Aided Mol. Des.*, 25:555-567 (2011).
Zhao, et al., *J. of Biomedicine and Biotechnology*, vol. 2010, Article ID 737535, 10 pages.
Supplementary EP Search Report, PCT/US2012061441, Mar. 16, 2015.

* cited by examiner

*Primary Examiner* — Niloofar Rahmani
(74) *Attorney, Agent, or Firm* — Wayne J. Dustman; Edward R. Gimmi

(57) ABSTRACT

The invention is directed to substituted heteroaryl derivatives. Specifically, the invention is directed to compounds according to Formula Q:

(Q)

wherein D, L, M, W, X, Y, and Z are defined herein.
The compounds of the invention are inhibitors of DNA methyltransferase (DNMT) activity—including DNMT1, DNMT3a, or DNMT3b—and are useful in the treatment of cancer and hyperproliferative diseases. Accordingly, the invention is further directed to pharmaceutical compositions comprising a compound of the invention. The invention is still further directed to methods of inhibiting DNMT activity and treatment of disorders associated therewith using a compound of the invention or a pharmaceutical composition comprising a compound of the invention.

19 Claims, No Drawings

CHEMICAL COMPOUNDS

This application is a 371 of International Application No. PCT/US2012/061441, filed 23 Oct. 2012, which claims the benefit of U.S. Provisional Application No. 61/550,681.

FIELD OF THE INVENTION

The invention relates generally to heteroaryl compounds, containing an indole moiety, that inhibit DNA methyltransferase (DNMT) activity, and to compositions and methods related thereto. In particular, the invention relates to heteroaryl compounds, containing an indole moiety, that inhibit DNA methyltransferase (DNMT) activity—including DNMT1, DNMT3a, or DNMT3b—useful in the treatment of cancer and hyperproliferative diseases.

BACKGROUND OF THE INVENTION

Cancer (and other hyperproliferative diseases) is characterized by uncontrolled cell proliferation. This loss of the normal control of cell proliferation often appears as the result of genetic damage to cell pathways that control progress through the cell cycle. Such damage includes abnormal DNA methylation in malignant cells, in particular methylation of tumor suppressor genes. (Robertson, K. D., et al., Oncogene, 2001, 20, 3139-3155; Jones P. A., et al., Nat. Rev. Genet., 2002, 3, 415-428).

DNA methylation is mediated through DNA methyltransferases (DNMTs). DNMT1, 3a and 3b activity in tumors is essential for perpetuating gene silencing in growth-regulating genes. Elevated levels of DNA methyltransferases, in tumors contribute to tumorigenesis by improper de novo methylation and silencing of tumor suppressor genes (Linhart H. G., et al., Genes Dev., 2007, 21, 3110-3122). For example, DNMT3b protein overexpression was reported as an independent prognostic factor for predicting cancer survival in diffused large B-cell lymphoma patients (Amara, K., et al., Cancer Sci., 2010, 101, 1722-1730). In another example, depletion of DNMT3a was shown to suppress cell proliferation and to restore PTEN in hepatocellular carcinoma cells (Zhao Z., et al., J. of Biomed. & Biotech., Volume 2010, Article ID 737535, 10 pages).

It has been proven that DNA hypomethylating agents, such as decitabine, are useful for the treatment of cancers. Inhibition of DNMT function would lead to a DNA hypomethylating stage. Thus, small molecule inhibitors of DNMTs should be useful in the treatment of diseases involving uncontrolled cell proliferation, and in particular of cancers (Sippl, W., et al., Methods and Principles in Medicinal Chemistry Volume 42, Epigenetic Targets in Drug Discovery, Chapter 8, 2009, 163-183).

One approach to design DNMT inhibitors is to mimic the co-factor (L)-S-adenosyl-L-methionine (SAM) or its metabolite (L)-S-adenosyl-L-homocysteine (SAH). Such an approach has been described in various publications (Wehhab A., et al., US2008/0132525; Isakovic L., et al., Bioorg. Med. Chem. Lett., 2009, 19, 2742-2746; Saavedra O. M., Bioorg. Med. Chem. Lett., 2009, 19, 2747-2751). The present invention is focusing on SAM or SAH mimics. These mimics contain a functional group that is suitable to interact with the DNA binding region, in particular the cytosine binding pocket. Similarly, novel functional groups that can serve as adenosine mimics are described. Such small molecules can bind to DNMTs in a covalent or non-covalent manner, and in turn inhibits the enzymes. Such small molecules should be useful for treating diseases involving uncontrolled cell proliferation, in particular for cancer.

US 2008/0132525 and WO 2006/078752 describe inhibitors of DNA methyltransferase. CA 2030875 describes methods and probes for detecting nucleoside transporter and method for producing the probes. U.S. Pat. No. 7,560,467 describes indazolo-tetrahydropyrimidine-carboxamide derivative kinase inhibitors. US 2002/0068734, U.S. Pat. No. 6,472,391 and U.S. Pat. No. 6,750,218 describe nitrogen-containing heterocyclic compounds. U.S. Pat. No. 6,169,088 and U.S. Pat. No. 6,207,667 describe 1,3 diazines with platelet-derived growth factor receptor inhibitory activity.

SUMMARY OF THE INVENTION

The present invention provides compounds according to formula (I). The present invention provides compounds which are useful in therapy, in particular in the treatment of cancer and hyperproliferative diseases. The compounds of formula may be inhibitors of DNA methyltransferase (DNMT) activity and especially DNMT1, DNMT3a, or DNMT3b and may be useful in the treatment of conditions mediated by DNMT.

According to a first aspect of the invention, there is provided a compound of formula (Q):

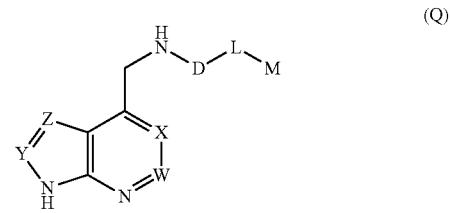

wherein:
W, X and Y independently represent CH or N;
Z represents $CR_1$ or N;
$R_1$ represents hydrogen, halogen, alkyl, cycloalkyl, heterocyclyl, aryl, heteroaryl, alkylaryl, alkylheterocyclyl, alkylheteroaryl, wherein cycloalkyl, heterocyclyl, aryl, heteroaryl, at each occurrence, may be optionally substituted by one or more $R_c$ groups;
D represents C=O, C=S, C=N—C=N, C=N—$NO_2$, C=N—$SO_2Me$ or —$SO_2$—; L represents

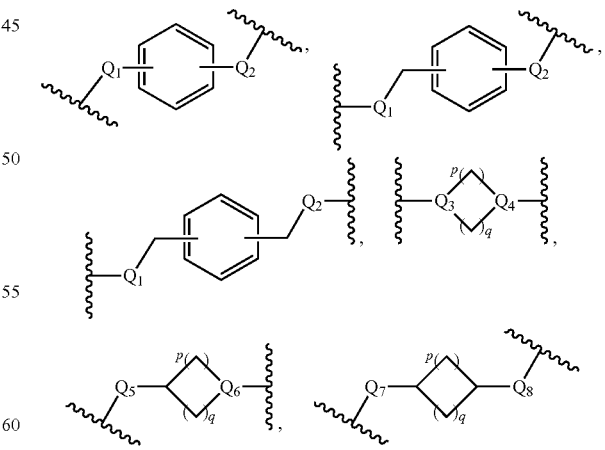

or -$Q_9$-$(CR_aR_b)_n$-$Q_{10}$-, wherein said ring systems of L may be optionally substituted by one or more $R_c$ groups;
$Q_1$ represents $CR_2R_3$, $NR_4$, $NR_4CR_2R_3$ or O;
$R_2$, $R_3$ and $R_4$ independently represent hydrogen, alkyl, cycloalkyl, heterocyclyl, aryl, heteroaryl, wherein alkyl, cycloalkyl, heterocyclyl, aryl, heteroaryl, at each occurrence, may be optionally substituted by one or more $R_c$ groups; $R_2$ and $R_3$ together with the carbon atom to which they are attached may form a carbocyclic or heterocyclic ring which may be optionally substituted by one or more $R_c$ groups;

$Q_2$ is absent or represents $CR_2R_3$, $NR_4$, $NR_4CR_2R_3$ or O;

$R_2$, $R_3$ and $R_4$ independently represent hydrogen, alkyl, cycloalkyl, heterocyclyl, aryl, heteroaryl, wherein alkyl, cycloalkyl, heterocyclyl, aryl, heteroaryl, at each occurrence, may be optionally substituted by one or more $R_c$ groups; $R_2$ and $R_3$ together with the carbon atom to which they are attached may form a carbocyclic or heterocyclic ring which may be optionally substituted by one or more $R_c$ groups;

$Q_3$ and $Q_4$ independently represent $CR_5$ or N;

$R_5$ represents hydrogen, alkyl, cycloalkyl, heterocyclyl, aryl, heteroaryl, wherein cycloalkyl, heterocyclyl, aryl, heteroaryl, at each occurrence may be optionally substituted by one or more $R_c$ groups;

p and q independently represent an integer selected from 0 to 4, such that the sum of integers for p and q do not exceed 5;

$Q_5$ represents $CR_6R_7$, $NR_8$, $NR_8CR_6R_7$ or O;

$R_6$, $R_7$ and $R_8$ independently represent hydrogen, alkyl, cycloalkyl, heterocyclyl, aryl, heteroaryl, wherein cycloalkyl, heterocyclyl, aryl, heteroaryl, at each occurrence, may be optionally substituted by one or more $R_c$ groups; $R_6$ and $R_7$ together with the carbon atom to which they are attached may form a carbocyclic or heterocyclic ring which may be optionally substituted by one or more $R_c$ groups;

$Q_6$ represents $CR_9$ or N;

$R_9$ represents hydrogen, alkyl, cycloalkyl, heterocyclyl, aryl, heteroaryl, wherein cycloalkyl, heterocyclyl, aryl, heteroaryl, at each occurrence, may be optionally substituted by one or more $R_c$ groups;

$Q_7$ and $Q_8$ are independently $CR_{10}R_{11}$, $NR_{12}$ or O;

$R_{10}$, $R_{11}$ and $R_{12}$ independently represent hydrogen, alkyl, cycloalkyl, heterocyclyl, aryl, heteroaryl, wherein cycloalkyl, heterocyclyl, aryl, heteroaryl, at each occurrence, may be optionally substituted by one or more $R_c$ groups; $R_{10}$ and $R_{11}$ together with the carbon atom to which they are attached may form a carbocyclic or heterocyclic ring which may be optionally substituted by one or more $R_c$ groups;

$Q_9$ and $Q_{10}$ independently represent $CR_{14}R_{15}$, $NR_{16}$, $CR_{14}R_{15}NR_{16}$ or O;

$R_a$ and $R_b$ independently represent hydrogen, alkyl or alkenyl;

$R_{14}$, $R_{15}$ and $R_{16}$ independently represent hydrogen, alkyl, amino, alkenyl, cycloalkyl, heterocyclyl, aryl, heteroaryl, wherein cycloalkyl, heterocyclyl, aryl, heteroaryl, at each occurrence, may be optionally substituted by one or more $R_c$ groups; $R_{14}$ and $R_{15}$ together with the carbon atom to which they are attached may form a carbocyclic or heterocyclic ring which may be optionally substituted by one or more $R_c$ groups;

n represents an integer selected from 0 to 5;

M is absent or represents

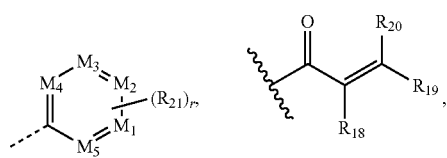

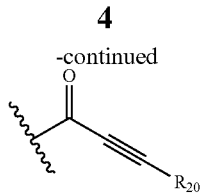

or $-CO-R_{22}$;

$M_1$, $M_2$, $M_3$, $M_4$ and $M_5$ independently represent CH or N;

$R_{18}$, $R_{19}$ and $R_{20}$ independently represent hydrogen, alkyl, alkoxy, cycloalkyl, heterocyclyl, aryl, heteroaryl, wherein cycloalkyl, heterocyclyl, aryl, heteroaryl, at each occurrence, may be optionally substituted by one or more $R_c$ groups;

$R_{21}$ represents hydrogen, F, Cl, $CF_3$, $NH_2$, $NO_2$, thiazolyl or pyridyl;

r represents an integer selected from 0 to 3;

$R_{22}$ represents alkyl, hydroxyl, alkanol, alkoxy, haloalkyl or aminoalkyl;

$R_c$ represents halogen, $C_{1-6}$ alkyl, $C_{2-6}$ alkenyl, $C_{2-6}$ alkynyl, $-(CH_2)_{0-4}-C_{3-8}$ cycloalkyl, $-(CH_2)_{0-4}-C_{3-8}$ cycloalkenyl, $-(CH_2)_{0-4}$-phenyl, $-(CH_2)_{0-4}$-(heterocyclyl), $-(CH_2)_{0-4}$-(heteroaryl), $-(CR^xR^y)_{0-4}-O-R^z$, $-O-(CR^xR^y)_{1-4}-OR^z$, halo$C_{1-6}$ alkyl, halo$C_{1-6}$ alkoxy, $C_{1-6}$ alkanol, $=O$, $=S$, nitro, $Si(R^x)_4$, $-(CH_2)_{0-4}-CN$, $-S(O)_{0-2}-R^x$, $-C(=O)R^x$, $-(CR^xR^y)_{0-4}-CO(=O)R^z$, $-(CR^xR^y)_{0-4}-O-C(=O)-R^z$, $-(CR^xR^y)_{0-4}-C(=O)NR^xR^y$, $-(CH_2)_{0-4}-NR^xC(=O)R^y$, $-(CH_2)_{0-4}-OC(=O)NR^xR^y$, $-(CH_2)_{0-4}-NR^xC(=O)OR^y$, $-(CH_2)_{0-4}-NR^xR^y$, $-NR^x-(CH_2)_{0-4}-R^z$, $-(CH_2)_{0-4}-O-C(=O)-C_{1-4}$alkyl-$NR^xR^y$, $-(CH_2)_{0-4}-NR^x-(CH_2)_{1-4}-O-C(=O)-R^z$, $-(CH_2)_{0-4}-NR^x-(CH_2)_{0-4}-SO_2-R^y$, $-(CH_2)_{0-4}-NH-SO_2-NR^xR^y$, $-(CH_2)_{0-4}-SO_2NR^xR^y$ and $-P(=O)(R^x)_2$ groups;

$R^x$, $R^y$ and $R^z$ independently represent hydrogen, $C_{1-6}$ alkyl, $C_{2-6}$ alkenyl, $C_{2-6}$ alkynyl, $-(CH_2)_{0-4}-C_{3-8}$ cycloalkyl, $-(CH_2)_{0-4}-C_{3-8}$ cycloalkenyl, $-(CH_2)_{0-4}$-(heterocyclyl), $-(CH_2)_{0-4}$-(heteroaryl), $C_{1-6}$ alkanol optionally substituted with one or more halo, $-CO(=O)C_{1-6}$ alkyl, hydroxy, $C_{1-6}$ alkoxy, halo$C_{1-6}$ alkyl, $-(CH_2)_{1-4}-O-C_{1-6}$alkyl, $-C(=O)-(CH_2)_{1-4}-C_{1-6}$ alkoxy, $-C(=O)-C_{1-6}$alkyl, $-(CH_2)_{0-4}-CN$, $C_{1-6}$ alkyl-$N(H)_{2-s}(C_{1-6}$alkyl$)_s$, $-N(H)_{2-s}(C_{1-6}$alkyl$)_s$, $-C(=O)-N(H)_{2-s}(C_{1-6}$alkyl$)_s$, $-(CH_2)_{0-4}-NH-SO_2-N(H)_{2-s}(C_{1-6}$alkyl$)_s$, $-(CH_2)_{0-4}-N(C_{1-4}$alkyl)-$SO_2-N(H)_{2-s}(C_{1-6}$ alkyl$)_s$ and $-(CH_2)_{0-4}-O-C(=O)-C_{1-4}$alkyl-$N(H)_{2-s}(C_{1-6}$alkyl$)_s$, and when attached to nitrogen or carbon or phosphorus or silicon atom $R^x$ and $R^y$ may join to form a 3-7 membered ring optionally containing a one or two heteroatoms selected from O, N, S and oxidised forms of N or S; and s represents an integer selected from 0 to 2;

provided that when $Q_2$ is absent, M is absent;

or a pharmaceutically acceptable salt thereof.

In a further aspect of the invention there is provided a compound of formula (I) for use in the propylaxis or treatment of a disease or condition as described herein, pharmaceutical compositions comprising a compound of formula (I) and processes for the synthesis of compound of formula (I).

DEFINITIONS

Unless the context indicates otherwise, references to formula (I) in all sections of this document (including the uses, methods and other aspects of the invention) include references to all other sub-formula, sub-groups, preferences, embodiments and examples as defined herein.

Unless otherwise stated the following terms used in the specification and claims have the meanings discussed below:

"Alkyl" refers to a saturated straight or branched hydrocarbon radical. Examples include methyl, ethyl, propyl, 2-propyl, n-butyl, iso-butyl, tert-butyl, pentyl, hexyl, and the like, preferably methyl, ethyl, propyl or 2-propyl. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Cyclic alkyls are referred to herein as a "cycloalkyl." "$C_{0-4}$alkyl" refers to an alkyl with 0, 1, 2, 3, or 4 carbon atoms. $C_{0-4}$alkyl with 0 carbon atoms is a hydrogen atom when terminal and is a direct bond when linking.

"Cycloalkyl" refers to a saturated cyclic hydrocarbon radical. Examples include cyclopropyl, cyclobutyl, cyclopentyl and cyclohexyl.

"Halogen" means fluoro, chloro, bromo or iodo, preferably fluoro and chloro.

"Aryl" refers to an all-carbon monocyclic or fused-ring polycyclic (i.e. rings which share adjacent pairs of carbon atoms) groups of 6 to 12 carbon atoms having a completely conjugated pi-electron system. Examples, without limitation, of aryl groups are phenyl, naphthyl and anthracenyl.

"Heteroaryl" refers to a monocyclic or fused ring (i.e. rings which share an adjacent pair of atoms) of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be substituted or unsubstituted.

"Heterocyclyl" refers to a saturated, unsaturated or aromatic cyclic ring system having 3 to 14 ring atoms in which one, two or three ring atoms are heteroatoms selected from N, O, or $S(O)_m$ (where m is an integer from 0 to 2), the remaining ring atoms being C, where one or two C atoms may be optionally replaced by a carbonyl group. The term "heterocyclyl" includes heteroaryl unless otherwise specified (for example, "saturated heterocyclyl").

A combination of substituents is permissible only if such as combination results in a stable or chemically feasible compound (i.e. one that is not substantially altered when kept at 40° C. or less for at least a week).

The various functional groups and substituents making up the compounds of the invention are typically chosen such that the molecular weight of the compound of the invention does not exceed 1000. More usually, the molecular weight of the compound will be less than 750, for example less than 700, or less than 650, or less than 600, or less than 550. More preferably, the molecular weight is less than 525 and, for example, is 500 or less.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with the alkyl group.

A "pharmaceutical composition" refers to a mixture of one or more of the compounds described herein, or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Therapeutically effective amount" refers to that amount of the compound being administered which will relieve to some extent one or more of the symptoms of the disorder being treated. In reference to the treatment of cancer, a therapeutically effective amount refers to that amount which has the effect of: (1) reducing the size of the tumor; (2) inhibiting tumor metastasis; (3) inhibiting tumor growth; and/or (4) relieving one or more symptoms associated with the cancer.

The term "DNMT mediated condition" or "disease", as used herein, means any disease or other deleterious condition in which DNMT is known to play a role. The term "DNMT mediated condition" or "disease" also means those diseases or conditions that are alleviated by treatment with a DNMT inhibitor. Such conditions include, without limitation, cancer and other hyperproliferative disorders. In certain embodiments, the cancer is a cancer of colon, breast, stomach, prostate, pancreas, or ovarian tissue.

The term "DNMT activity-mediated condition" or "disease", as used herein, means any disease or other deleterious condition in which DNMT activity is known to play a role. The term "DNMT activity-mediated condition" also means those diseases or conditions that are alleviated by treatment with a DNMT inhibitor.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur.

As used herein, "administer" or "administration" refers to the delivery of an inventive compound or of a pharmaceutically acceptable salt thereof or of a pharmaceutical composition containing an inventive compound or a pharmaceutically acceptable salt thereof of this invention to an organism for the purpose of prevention or treatment of a DNMT-related disorder.

DETAILED DESCRIPTION OF THE INVENTION

In one embodiment of the invention, there is provided a coNmpound of formula (I):

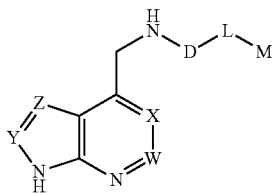

(I)

wherein:
W, X and Y independently represent CH or N;
Z represents $CR_1$ or N;
$R_1$ represents hydrogen, halogen, alkyl, cycloalkyl, heterocyclyl, aryl, heteroaryl, alkylaryl, alkylheterocyclyl, alkylheteroaryl, wherein cycloalkyl, heterocyclyl, aryl, heteroaryl, at each occurrence, may be optionally substituted by one or more $R_c$ groups;
D represents C=O, C=S, C=N—C≡N, C=N—$NO_2$, C=N—$SO_2$Me or —$SO_2$—;
L represents

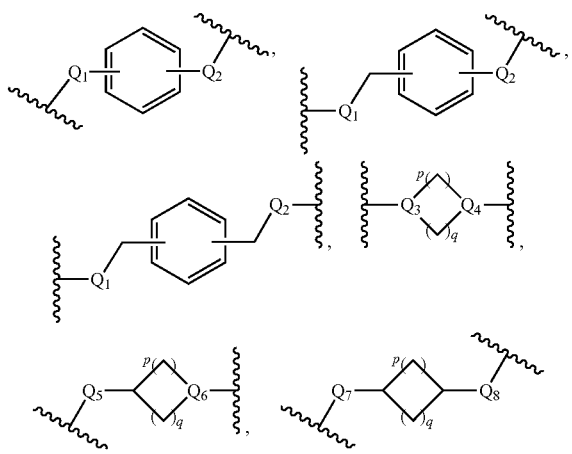

or -$Q_9$-$(CR_aR_b)_n$-$Q_{10}$-, wherein said ring systems of L may be optionally substituted by one or more $R_c$ groups;
$Q_1$ and $Q_2$ independently represent $CR_2R_3$, $NR_4$, $NR_4CR_2R_3$ or O;
$R_2$, $R_3$ and $R_4$ independently represent hydrogen, alkyl, cycloalkyl, heterocyclyl, aryl, heteroaryl, wherein cycloalkyl, heterocyclyl, aryl, heteroaryl, at each occurrence, may be optionally substituted by one or more $R_c$ groups; $R_2$ and $R_3$ together with the carbon atom to which they are attached may form a carbocyclic or heterocyclic ring which may be optionally substituted by one or more $R_c$ groups;
$Q_3$ and $Q_4$ independently represent $CR_5$ or N;
$R_5$ represents hydrogen, alkyl, cycloalkyl, heterocyclyl, aryl, heteroaryl, wherein cycloalkyl, heterocyclyl, aryl, heteroaryl, at each occurrence may be optionally substituted by one or more $R_c$ groups;
p and q independently represent an integer selected from 0 to 4, such that the sum of integers for p and q do not exceed 5;
$Q_5$ represents $CR_6R_7$, $NR_8$, $NR_8CR_6R_7$ or O;
$R_6$, $R_7$ and $R_8$ independently represent hydrogen, alkyl, cycloalkyl, heterocyclyl, aryl, heteroaryl, wherein cycloalkyl, heterocyclyl, aryl, heteroaryl, at each occurrence, may be optionally substituted by one or more $R_c$ groups; $R_6$ and $R_7$ together with the carbon atom to which they are attached may form a carbocyclic or heterocyclic ring which may be optionally substituted by one or more $R_c$ groups;
$Q_6$ represents $CR_9$ or N;
$R_9$ represents hydrogen, alkyl, cycloalkyl, heterocyclyl, aryl, heteroaryl, wherein cycloalkyl, heterocyclyl, aryl, heteroaryl, at each occurrence, may be optionally substituted by one or more $R_c$ groups;
$Q_7$ and $Q_8$ are independently $CR_{10}R_{11}$, $NR_{12}$ or O;
$R_{10}$, $R_{11}$ and $R_{12}$ independently represent hydrogen, alkyl, cycloalkyl, heterocyclyl, aryl, heteroaryl, wherein cycloalkyl, heterocyclyl, aryl, heteroaryl, at each occurrence, may be optionally substituted by one or more $R_c$ groups; $R_{10}$ and $R_{11}$ together with the carbon atom to which they are attached may form a carbocyclic or heterocyclic ring which may be optionally substituted by one or more $R_c$ groups;
$Q_9$ and $Q_{10}$ independently represent $CR_{14}R_{15}$, $NR_{16}$, $CR_{14}R_{15}NR_{16}$ or O;
$R_a$ and $R_b$ independently represent hydrogen, alkyl or alkenyl;
$R_{14}$, $R_{15}$ and $R_{16}$ independently represent hydrogen, alkyl, amino, alkenyl, cycloalkyl, heterocyclyl, aryl, heteroaryl, wherein cycloalkyl, heterocyclyl, aryl, heteroaryl, at each occurrence, may be optionally substituted by one or more $R_c$ groups; $R_{14}$ and $R_{15}$ together with the carbon atom to which they are attached may form a carbocyclic or heterocyclic ring which may be optionally substituted by one or more $R_c$ groups;
n represents an integer selected from 0 to 5;
M represents

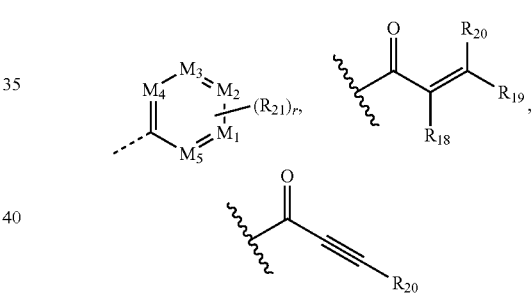

or —CO—$R_{22}$;
$M_1$, $M_2$, $M_3$, $M_4$ and $M_5$ independently represent CH or N;
$R_{18}$, $R_{19}$ and $R_{20}$ independently represent hydrogen, alkyl, alkoxy, cycloalkyl, heterocyclyl, aryl, heteroaryl, wherein cycloalkyl, heterocyclyl, aryl, heteroaryl, at each occurrence, may be optionally substituted by one or more $R_c$ groups;
$R_{21}$ represents hydrogen, F, Cl, $CF_3$, $NH_2$, $NO_2$, thiazolyl or pyridyl;
r represents an integer selected from 0 to 3;
$R_{22}$ represents alkyl, hydroxyl, alkanol, alkoxy, haloalkyl or aminoalkyl;
$R_c$ represents halogen, $C_{1-6}$ alkyl, $C_{2-6}$ alkenyl, $C_{2-6}$ alkynyl, —$(CH_2)_{0-4}$—$C_{3-8}$ cycloalkyl, —$(CH_2)_{0-4}$—$C_{3-8}$ cycloalkenyl, —$(CH_2)_{0-4}$-phenyl, —$(CH_2)_{0-4}$-(heterocyclyl), —$(CH_2)_{0-4}$-(heteroaryl), —$(CR^xR^y)_{0-4}$—O—$R^z$, —O—$(CR^xR^y)_{1-4}$—$OR^z$, halo$C_{1-6}$ alkyl, halo$C_{1-6}$ alkoxy, $C_{1-6}$ alkanol, =O, =S, nitro, $Si(R^x)_4$, —$(CH_2)_{0-4}$—CN, —$S(O)_{0-2}$—$R^x$, —C(=O)$R^x$, —$(CR^xR^y)_{0-4}$—CO(=O)$R^z$, —$(CR^xR^y)_{0-4}$—O—C(=O)—$R^z$, —$(CR^xR^y)_{0-4}$—C(=O)$NR^xR^y$, —$(CH_2)_{0-4}$—$NR^xC(=O)R^y$, —$(CH_2)_{0-4}$—OC(=O)$NR^xR^y$, —$(CH_2)_{0-4}$—$NR^xC(=O)OR^y$, —$(CH_2)_{0-4}$—$NR^xR^y$, —$NR^x$—$(CH_2)_{0-4}$—$R^z$, —$(CH_2)_{0-4}$—O—C(=O)—$C_{1-4}$alkyl-$NR^xR^y$, —$(CH_2)_{0-4}$—$NR^x$—$(CH_2)_{1-4}$—O—C (=O)—R$^z$, —(CH$_2$)$_{0-4}$—NR$^x$—(CH$_2$)$_{0-4}$—SO$_2$—R$^y$, —(CH$_2$)$_{0-4}$—NH—SO$_2$—NR$^x$R$^y$, —(CH$_2$)$_{0-4}$—SO$_2$NR$^x$R$^y$ and —P(=O)(R$^x$)$_2$ groups;

R$^x$, R$^y$ and R$^z$ independently represent hydrogen, C$_{1-6}$ alkyl, C$_{2-6}$ alkenyl, C$_{2-6}$ alkynyl, —(CH$_2$)$_{0-4}$—C$_{3-8}$ cycloalkyl, —(CH$_2$)$_{0-4}$—C$_{3-8}$ cycloalkenyl, —(CH$_2$)$_{0-4}$-(heterocyclyl), —(CH$_2$)$_{0-4}$-(heteroaryl), C$_{1-6}$ alkanol optionally substituted with one or more halo, —CO(=O)C$_{1-6}$ alkyl, hydroxy, C$_{1-6}$ alkoxy, haloC$_{1-6}$ alkyl, —(CH$_2$)$_{1-4}$—O—C$_{1-6}$alkyl, —C(=O)—(CH$_2$)$_{1-4}$—C$_{1-6}$ alkoxy, —C(=O)—C$_{1-6}$alkyl, —(CH$_2$)$_{0-4}$—CN, C$_{1-6}$ alkyl-N(H)$_{2-s}$(C$_{1-6}$alkyl)$_s$, —N(H)$_{2-s}$(C$_{1-6}$alkyl)$_s$, —C(=O)—N(H)$_{2-s}$(C$_{1-6}$alkyl)$_s$, —(CH$_2$)$_{0-4}$—NH—SO$_2$—N(H)$_{2-s}$(C$_{1-6}$alkyl)$_s$, —(CH$_2$)$_{0-4}$—N(C$_{1-4}$alkyl)-SO$_2$—N(H)$_{2-s}$(C$_{1-6}$ alkyl)$_s$ and —(CH$_2$)$_{0-4}$—O—C(=O)—C$_{1-4}$alkyl-N(H)$_{2-s}$(C$_{1-6}$alkyl)$_s$, and when attached to nitrogen or carbon or phosphorus or silicon atom R$^x$ and R$^y$ may join to form a 3-7 membered ring optionally containing a one or two heteroatoms selected from O, N, S and oxidised forms of N or S; and s represents an integer selected from 0 to 2;

or a pharmaceutically acceptable salt thereof.

In one embodiment, W represents CH.

In one embodiment, X represents CH or N. In a further embodiment, X represents CH.

In one embodiment, Y represents CH.

In one embodiment, Z represents CR$_1$.

In one embodiment, R$_1$ represents hydrogen, halogen (such as chlorine, bromine or fluorine) or alkylheterocyclyl (such as —CH$_2$-pyrrolidinyl). In a further embodiment, R$_1$ represents hydrogen or halogen (such as chlorine, bromine or fluorine). In a yet further embodiment, R$_1$ represents hydrogen.

In one embodiment, D represents C=O, C=S, C=N—C≡N, C=N—NO$_2$ or C=N—SO$_2$Me. In a further embodiment, D represents C=O or C=S.

In one embodiment, L represents

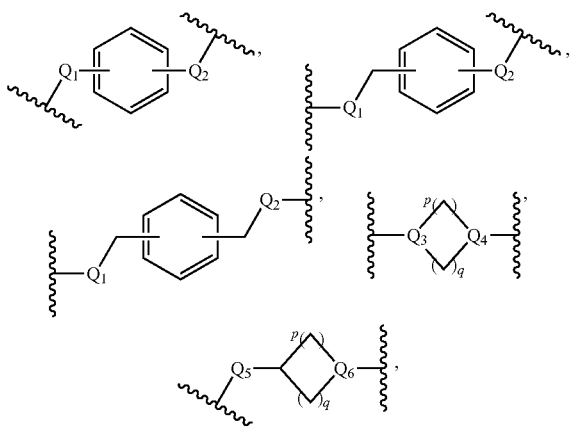

or -Q$_9$-(CH$_2$)$_n$-Q$_{10}$-, wherein said ring systems of L may be optionally substituted by one or more R$_c$ groups.

When L represents

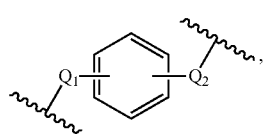

in one embodiment Q$_1$ and Q$_2$ both represent NR$_4$ (such as NH), wherein said phenyl ring of L may be optionally substituted by one or two R$_c$ groups selected from hydroxy, NO$_2$, CF$_3$, alkoxy (e.g. methoxy) or halogen (e.g. fluorine or chlorine).

When L represents

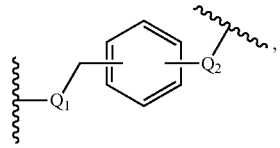

in one embodiment Q$_1$ and Q$_2$ both represent NR$_4$ (such as NH) or Q$_1$ represents NR$_4$CR$_2$R$_3$ (such as NHCH$_2$) and Q$_2$ represents NR$_4$ (such as NH) or Q$_1$ represents CR$_2$R$_3$ (such as CH$_2$) and Q$_2$ represents NR$_4$ (such as NH) wherein said phenyl ring of L may be optionally substituted by one or two R$_c$ groups selected from hydroxy, NO$_2$, CF$_3$, alkoxy (e.g. methoxy) or halogen (e.g. fluorine or chlorine).

When L represents

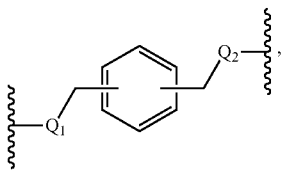

in one embodiment Q$_1$ and Q$_2$ both represent NR$_4$ (such as NH) wherein said phenyl ring of L may be optionally substituted by one or two R$_c$ groups selected from hydroxy, NO$_2$, CF$_3$, alkoxy (e.g. methoxy) or halogen (e.g. fluorine or chlorine).

When L represents -Q$_9$-(CR$_a$R$_b$)$_n$-Q$_{10}$-, in one embodiment:

Q$_9$ and Q$_{10}$ both represent NR$_{16}$ (such as NH or NMe) and n represents 2 (i.e. —NH—(CH$_2$)$_2$—NH—, —NH—(CH$_2$)$_2$—NMe- or —NH—CH$_2$—CH(CH$_2$CH=CH$_2$)—NH—); or Q$_9$ and Q$_{10}$ both represent NR$_{16}$ (such as NH or NMe) and n represents 3 (i.e. —NH—(CH$_2$)$_3$—NH—, —NH—CH$_2$—C(H)(Me)—CH$_2$—NH— or —NH—CH$_2$—C(Me)$_2$-CH$_2$—NH—); or Q$_9$ represents NR$_{16}$ (such as NH), n represents 0 and Q$_{10}$ represents C$_{14}$R$_{15}$ (such as CH$_2$) (i.e. —NH—CH$_2$—); or Q$_9$ represents C$_{14}$R$_{15}$ (such as CH$_2$), n represents 2 and Q$_{10}$ represents NR$_{16}$ (such as NH) (i.e. —(CH$_2$)$_3$—NH—); or Q$_9$ represents NR$_{16}$ (such as NH), n represents 4 and Q$_{10}$ represents C$_{14}$R$_{15}$ (such as CH(NH$_2$)) (i.e. —NH—(CH$_2$)$_4$—CH(NH$_2$)—); or Q$_9$ represents NR$_{16}$ (such as NH), n represents 1 and Q$_{10}$ represents C$_{14}$R$_{15}$NR$_{16}$ (such as —CH(CH$_2$CH=CH$_2$)—NH—) (i.e. —NH—CH$_2$—CH(CH$_2$CH=CH$_2$)—NH—).

When L represents

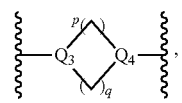

in one embodiment, p and q both represent 2 and Q$_3$ and Q$_4$ both represent N (i.e. the ring system is a piperazinyl ring).

When L represents

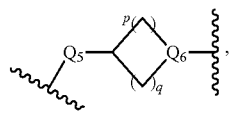

in one embodiment:
$Q_5$ represents $NR_8$ (such as NH) or $CR_6R_7$ (such as $CH_2$), p and q both represent 1 and $Q_6$ represents N (i.e. the ring system is an azetidinyl ring); or
$Q_5$ represents $NR_8$ (such as NH), p and q both represent 2 and $Q_6$ represents N (i.e. the ring system is a piperidinyl ring); or
$Q_5$ represents $NR_8$ (such as NH), p represents 1, q represents 2 and $Q_6$ represents N (i.e. the ring system is a pyrrolidinyl ring); or
$Q_5$ represents $NR_8$ (such as NH), p represents 1, q represents 3 and $Q_6$ represents N (i.e. the ring system is a piperidinyl ring); or
$Q_5$ represents $NR_8CR_6R_7$ (such as —NH—$CH_2$), p represents 0 and q represents 4 and $Q_6$ represents N (i.e. the ring system is a piperidinyl ring); or
$Q_5$ represents $NR_8CR_6R_7$ (such as —NH—$CH_2$), p and q both represent 2 and $Q_6$ represents N (i.e. the ring system is a piperidinyl ring); or
$Q_5$ represents $NR_8CR_6R_7$ (such as —NH—$CH_2$), p represents 1 and q represents 3 and $Q_6$ represents N (i.e. the ring system is a piperidinyl ring); or
$Q_5$ represents $NR_8CR_6R_7$ (such as —NH—$CH_2$), p represents 1, q represents 2 and $Q_6$ represents N (i.e. the ring system is a pyrrolidinyl ring).

When M represents

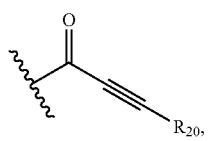

in one embodiment $R_{20}$ represents hydrogen, alkyl (such as methyl), cycloalkyl (such as cyclopropyl), alkoxy (such as —$CH_2$OMe), aryl (such as phenyl) or heterocyclyl (such as 1,3-benzodioxolyl), wherein said phenyl ring may be optionally substituted by one or two $R_c$ groups selected from halogen (such as fluorine or chlorine), alkyl (such as methyl), alkoxy (such as methoxy) or $NO_2$ groups.

When M represents

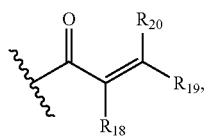

in one embodiment, $R_{18}$, $R_{19}$ and $R_{20}$ each represent hydrogen.

When M represents —CO—$R_{22}$, in one embodiment, $R_{22}$ represents alkyl (such as methyl), hydroxyl, alkanol (such as —$CH_2$—OH), alkoxy (such as methoxy or —$CH_2$OMe), haloalkyl (such as —$CH_2$—$CH_2$—Br) or aminoalkyl (such as —$CH_2NH_2$).

When M represents

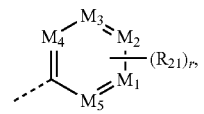

in one embodiment, $M_1$, $M_2$, $M_3$, $M_4$ and $M_5$ each represent CH (i.e. the ring system is a phenyl ring), r represents 1 or 2 and $R_{21}$ represents hydrogen, F, Cl, $CF_3$, $NH_2$, $NO_2$, thiazolyl or pyridyl.

When M represents

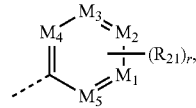

in one embodiment, $M_1$, $M_2$, $M_3$ each represent CH and $M_4$ and $M_5$ both represent N (i.e. the ring system is a pyrimidinyl ring), r represents 1 and $R_{21}$ represents Cl.

In one embodiment M is absent.

According to a further aspect of the invention, there is provided a compound of formula (IA) or a pharmaceutically acceptable salt thereof:

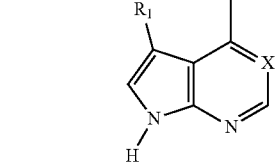

(IA)

wherein $R_1$, X, D, L and M are as defined herein for compounds of formula (I).

According to a further aspect of the invention, there is provided a compound of formula (IAA) or a pharmaceutically acceptable salt thereof:

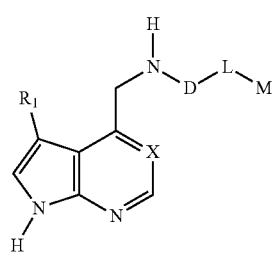

(IAA)

wherein $R_1$, X, D, L and M are as defined herein for compounds of formula (Q).

According to a further aspect of the invention, there is provided a compound of formula (IB) or a pharmaceutically acceptable salt thereof:

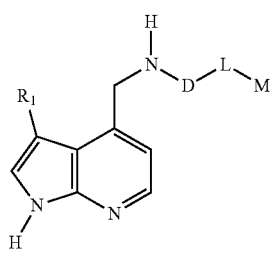

(IB)

wherein $R_1$, D, L and M are as defined herein for compounds of formula (I).

According to a further aspect of the invention, there is provided a compound of formula (IBB) or a pharmaceutically acceptable salt thereof:

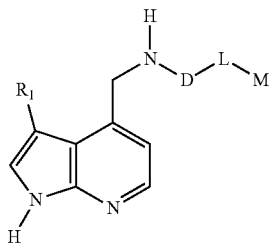
(IBB)

wherein $R_1$, D, L and M are as defined herein for compounds of formula (Q).

In one embodiment of the compound of formula (IB), $R_1$ represents hydrogen, halogen (such as chlorine, bromine or fluorine) or alkylheterocyclyl (such as —$CH_2$-pyrrolidinyl). In a further embodiment of the compound of formula (IA), $R_1$ represents hydrogen or halogen (such as chlorine, bromine or fluorine). In a yet further embodiment of the compound of formula (IA), $R_1$ represents hydrogen.

In one embodiment of the compound of formula (IB), D represents C=O, C=S, C=N—$NO_2$, C=N—$SO_2$Me or —$SO_2$—.

In one embodiment of the compound of formula (IB), L represents

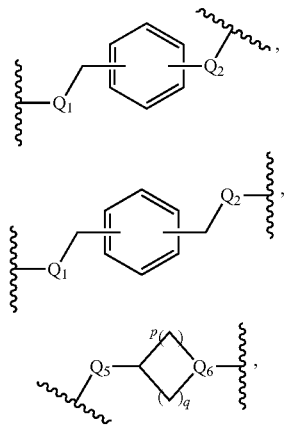

or -$Q_9$-$(CH_2)_n$-$Q_{10}$-, wherein said ring systems of L may be optionally substituted by one or more $R_c$ groups.

When L represents

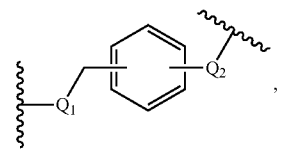

in one embodiment of the compound of formula (IB), $Q_1$ and $Q_2$ both represent $NR_4$ (such as NH) or $Q_1$ represents $CR_2R_3$ (such as $CH_2$) and $Q_2$ represents $NR_4$ (such as NH).

When L represents

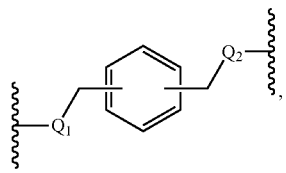

in one embodiment of the compound of formula (IB), $Q_1$ and $Q_2$ both represent $NR_4$ (such as NH).

When L represents

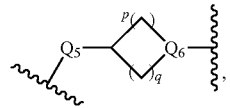

in one embodiment of the compound of formula (IB):
$Q_5$ represents $NR_8$ (such as NH) or $CR_6R_7$ (such as $CH_2$), p and q both represent 1 and $Q_6$ represents N (i.e. the ring system is an azetidinyl ring); or
$Q_5$ represents $NR_8$ (such as NH), p represents 1, q represents 3 and $Q_6$ represents N (i.e. the ring system is a piperidinyl ring); or
$Q_5$ represents $NR_8$ (such as NH), p represents 1, q represents 2 and $Q_6$ represents N (i.e. the ring system is a pyrrolidinyl ring); or
$Q_5$ represents $NR_8CR_6R_7$ (such as —NH—$CH_2$), p represents 1, q represents 3 and $Q_6$ represents N (i.e. the ring system is a piperidinyl ring).

When L represents -$Q_9$-$(CR_aR_b)_n$-$Q_{10}$-, in one embodiment of the compound of formula (IB):
$Q_9$ and $Q_{10}$ both represent $NR_{16}$ (such as NH or NMe) and n represents 2 (i.e. —NH—$(CH_2)_2$—NH— or —NH—$(CH_2)_2$—NMe-); or
$Q_9$ and $Q_{10}$ both represent $NR_{16}$ (such as NH or NMe) and n represents 3 (i.e. —NH—$(CH_2)_3$—NH— or —NH—$CH_2$—C(Me)$_2$-$CH_2$—NH—); or
$Q_9$ represents $NR_{16}$ (such as NH), n represents 0 and $Q_{10}$ represents $C_{14}R_{15}$ (such as $CH_2$) (i.e. —NH—$CH_2$—).

In one embodiment of the compound of formula (IB), M represents

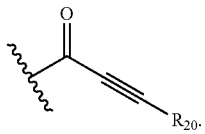

In one embodiment of the compound of formula (IB), $R_{20}$ represents hydrogen, alkyl (such as methyl), cycloalkyl (such as cyclopropyl), alkoxy (such as —$CH_2$OMe), aryl (such as phenyl) or heterocyclyl (such as 1,3-benzodioxolyl), wherein said phenyl ring may be optionally substituted by one or two $R_c$ groups selected from halogen (such as fluorine or chlorine), alkyl (such as methyl), alkoxy (such as methoxy) or $NO_2$ groups.

In a further embodiment of the compound of formula (IB), $R_{20}$ represents alkyl (such as methyl), cycloalkyl (such as cyclopropyl) or aryl (such as phenyl), wherein said phenyl ring may be optionally substituted by one or two $R_c$ groups (such as one) selected from alkoxy (such as methoxy).

In one embodiment, the invention provides a compound of formula (I) which is selected from Examples 1 to 114 or tautomeric or stereochemically isomeric forms, N-oxides, pharmaceutically acceptable salts or the solvates thereof.

In one embodiment, the invention provides a compound of formula (Q) which is selected from Examples 1 to 114 or pharmaceutically acceptable salts thereof.

In one embodiment, the invention provides a compound of formula (Q) which is selected from Examples 1 to 114 or tautomeric or stereochemically isomeric forms, N-oxides, pharmaceutically acceptable salts or the solvates thereof.

For the avoidance of doubt, it is to be understood that each general and specific preference, embodiment and example for one substituent may be combined with each general and specific preference, embodiment and example for one or more, preferably, all other substituents as defined herein and that all such embodiments are embraced by this application.

SALTS, SOLVATES, TAUTOMERS, ISOMERS, N-OXIDES, ESTERS, PRODRUGS AND ISOTOPES

A reference to a compound of the formula (I) and sub-groups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof.
Salts Many compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-aminosalicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

If the compound is anionic, or has a functional group which may be anionic (e.g., —COOH may be —COO⁻), then a salt may be formed with an organic or inorganic bases, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (I) and sub-groups and examples thereof as described herein in the form of a salt in a concentration of greater than 10 mg/ml, typically greater than 15 mg/ml and preferably greater than 20 mg/ml.
N-Oxides Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Geometric Isomers and Tautomers

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, certain heteroaryl rings can exist in the two tautomeric forms such as A and B shown below. For simplicity, a formula may illustrate one form but the formula is to be taken as embracing both tautomeric forms.

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

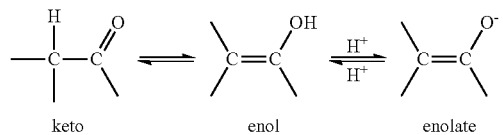

Stereoisomers

Unless otherwise mentioned or indicated, the chemical designation of compounds denotes the mixture of all possible stereochemically isomeric forms.

Stereocentres are illustrated in the usual fashion, using 'hashed' or 'wedged' lines. e.g.

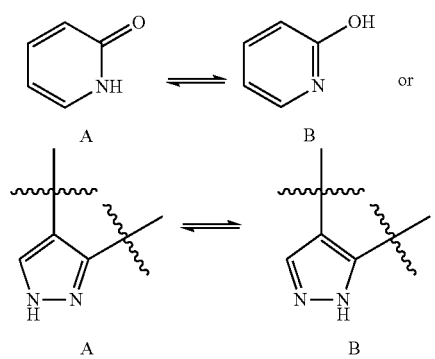

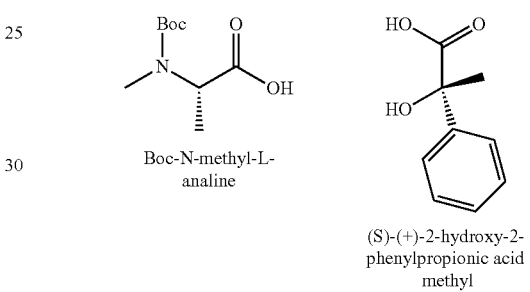

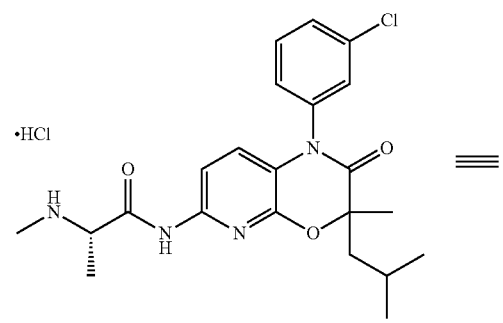

Where a compound is described as a mixture of two diastereoisomers/epimers, the configuration of the stereocentre is not specified and is represented by straight lines.

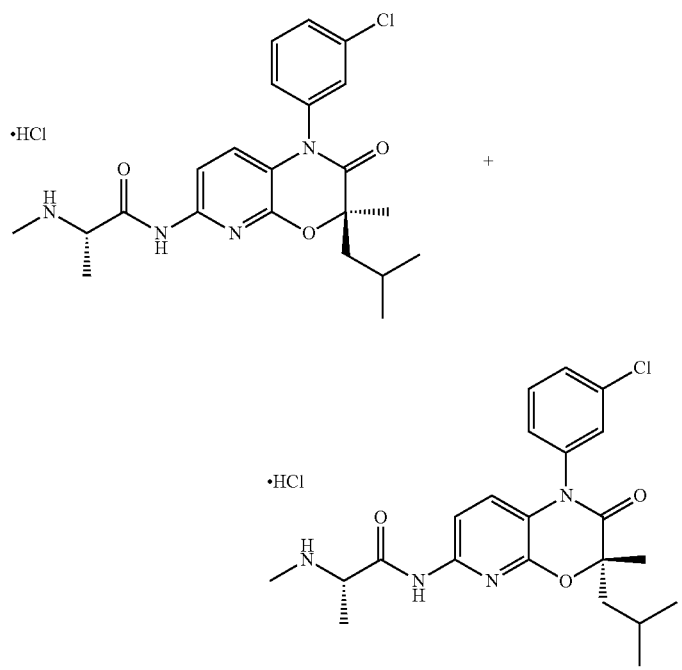

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic, separating the diastereoisomers by preferential crystallisation, and then dissociating the salts to give the individual enantiomer of the free base.

Additionally enantiomeric separation can be achieved by covalently linking an enantiomerically pure chiral auxiliary onto the compound and then performing diastereoisomer separation using conventional methods such as chromatography. This is then followed by cleavage of the aforementioned covalent linkage to generate the appropriate enantiomerically pure product.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^{2}$H (D) and $^{3}$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}$H (T), and carbon-14, i.e. $^{14}$C, are particularly useful for this purpose in view of their ease of incorporation and ready means of detection.

Substitution with heavier isotopes such as deuterium, i.e. $^{2}$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Esters

Esters such as carboxylic acid esters, acyloxy esters and phosphate esters of the compounds of formula (I) bearing a carboxylic acid group or a hydroxyl group are also embraced by Formula (I). Examples of esters are compounds containing the group —C(═O)OR, wherein R is an ester substituent, for example, a $C_{1-7}$ alkyl group, a $C_{3-12}$ heterocyclyl group, or a $C_{5-12}$ aryl group, preferably a $C_{1-6}$ alkyl group. Particular examples of ester groups include, but are not limited to, —CO(═O)CH$_3$, —C(═O)OCH$_2$CH$_3$, —C(═O)OC(CH$_3$)$_3$, and —C(═O)OPh. Examples of acyloxy (reverse ester) groups are represented by —OC(═O)R, wherein R is an acyloxy substituent, for example, a $C_{1-6}$ alkyl group, a $C_{3-12}$ heterocyclyl group, or a $C_{5-12}$ aryl group, preferably a $C_{1-6}$ alkyl group. Particular examples of acyloxy groups include, but are not limited to, —OC(═O)CH$_3$ (acetoxy), —OC(═O)CH$_2$CH$_3$, —OC(═O)C(CH$_3$)$_3$, —OC(═O)Ph, and —OC(═O)CH$_2$Ph.

Examples of phosphate esters are those derived from phosphoric acid.

In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group.

Solvates and Crystalline Forms

Also encompassed by formula (I) are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, $R_c$ HPLC and MS.

Alternatively the skilled person can deliberately form a solvate using crystallisation conditions that include an amount of the solvent required for the particular solvate. Thereafter the standard methods described above, can be used to establish whether solvates had formed.

Furthermore, the compounds of the present invention may have one or more polymorph or amorphous crystalline forms and as such are intended to be included in the scope of the invention.

Complexes

Formula (I) also includes within its scope complexes (e.g. inclusion complexes or clathrates with compounds such as cyclodextrins, or complexes with metals) of the compounds. Inclusion complexes, clathrates and metal complexes can be formed by means of methods well known the skilled person.

Prodrugs

Also encompassed by formula (I) are any pro-drugs of the compounds of the formula (I). By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl (e.g., -Me, -Et, -nPr, -iPr, -nBu, -sBu, -iBu, -tBu); $C_{1-7}$aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formula (I) does not include pro-drugs of the compounds of the formula (I) within its scope.

METHODS FOR THE PREPARATION OF COMPOUNDS OF FORMULA (I)

In this section, as in all other sections of this application unless the context indicates otherwise, references to formula (I) also include all other sub-groups and examples thereof as defined herein.

Compounds of the formula (Q) can be prepared in accordance with synthetic methods well known to the skilled person.

According to a further aspect of the invention there is provided a process for preparing a compound of formula (Q) as hereinbefore defined which comprises:
(a) preparing a compound of formula (Q) wherein $Q_2$ represents $NR_4$ or $Q_4$ represents N or $Q_6$ represents N or $Q_8$ represents $NR_{12}$ or $Q_{10}$ represents $NR_{16}$ and M represents

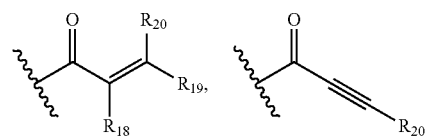

or —CO—$R_{22}$ by reacting a compound of formula (II):

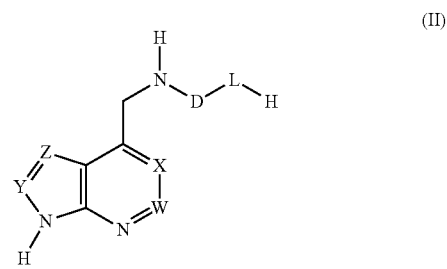

wherein W, X, Y, Z, D and L are as defined hereinbefore for compounds of formula (I), with a compound of formula HO-M wherein M is as defined hereinbefore for compounds of formula (I);

(b) preparing a compound of formula (Q) wherein D represents C=S, L represents -$Q_9$-$(CR_aR_b)_n$-$Q_{10}$, $Q_9$ represents NH and M represents

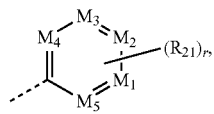

which comprises reacting a compound of formula (III)

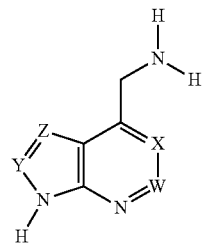
(III)

wherein W, X, Y and Z are as defined hereinbefore for compounds of formula (I), with a compound of formula S=C=N—$(CR_aR_b)_n$-$Q_{10}$-M, wherein $R_a$, $R_b$, n, $Q_{10}$ and M are as defined hereinbefore for compounds of formula (I);

(c) reacting a compound of formula (III)

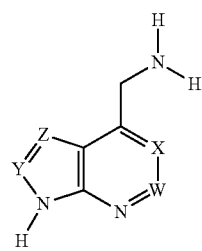
(III)

wherein W, X, Y and Z are as defined hereinbefore for compounds of formula (I), with a compound of formula $L_1$-D-$L_2$ and a compound of formula H-L-M wherein D, L and M are as defined hereinbefore for compounds of formula (I) and $L_1$ and $L_2$ represent a suitable leaving group, such as chlorine;

(d) preparing a compound of formula (I) wherein $Q_2$ represents $NR_4$ or $Q_4$ represents N or $Q_6$ represents N or $Q_8$ represents $NR_{12}$ or $Q_{10}$ represents $NR_{16}$ and M represents

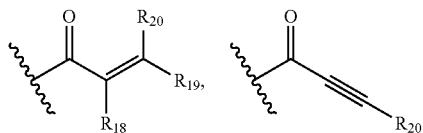

or —CO—$R_{22}$ by reacting a compound of formula (II):

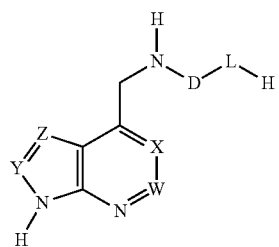
(II)

wherein W, X, Y, Z, D and L are as defined hereinbefore for compounds of formula (I), with a compound of formula $L_3$-M, wherein M is as defined hereinbefore for compounds of formula (I) and $L_3$ represents a suitable leaving group, such as chlorine;

(e) preparing a compound of formula (Q) wherein D represents C=S, $Q_2$ represents $NR_4$ or $Q_4$ represents N or $Q_6$ represents N or $Q_8$ represents $NR_{12}$ or $Q_{10}$ represents $NR_{16}$, which comprises reacting a compound of formula (IV)

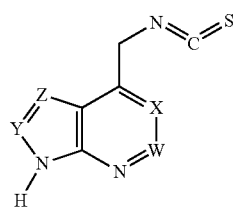
(IV)

wherein W, X, Y and Z are as defined hereinbefore for compounds of formula (I), with a compound of formula H-L-M, wherein L and M are as defined hereinbefore for compounds of formula (I);

(f) preparing a compound of formula (Q) wherein $Q_2$ represents $NR_4$ or $Q_4$ represents N or $Q_6$ represents N or $Q_8$ represents $NR_{12}$ or $Q_{10}$ represents $NR_{16}$ and M represents

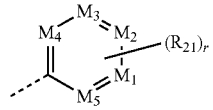

by reacting a compound of formula (II):

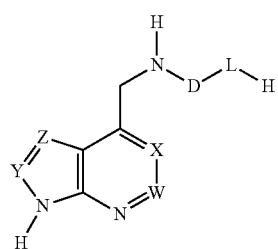
(II)

wherein W, X, Y, Z, D and L are as defined hereinbefore for compounds of formula (Q), with a compound of formula (V)

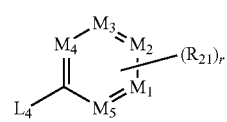
(V)

wherein $M_1$, $M_2$, $M_3$, $M_4$, $M_5$, $R_{21}$ and r are as defined hereinbefore for compounds of formula (Q) and $L_4$ represents a suitable leaving group, such as chlorine;

(g) preparing a compound of formula (Q) wherein D represents C=O, which comprises reacting a compound of formula (III)

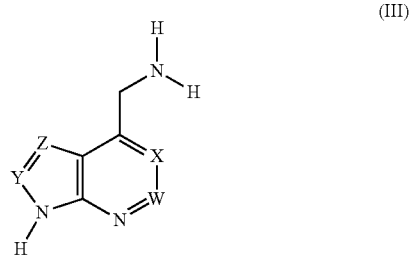

(III)

wherein W, X, Y and Z are as defined hereinbefore for compounds of formula (I), with a compound of formula (VI)

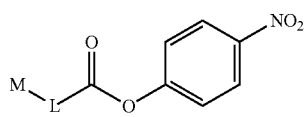

(VI)

wherein M and L are as defined hereinbefore for compounds of formula (I);
(h) deprotection of a protected derivative of a compound of formula (I);
(i) interconversion of a compound of formula (Q) or protected derivative thereof to a further compound of formula (Q) or protected derivative thereof; and
(j) optional formation of a pharmaceutically acceptable salt of a compound of formula (I).

Process (a) typically comprises a procedure as described in Example 1 inter alia.

Process (b) typically comprises a procedure as described in Example 5 inter alia.

Process (c) typically comprises a procedure as described in Example 26 inter alia.

Process (d) typically comprises a procedure as described in Example 27 inter alia.

Process (e) typically comprises a procedure as described in Example 30 inter alia.

Process (f) typically comprises a procedure as described in Example 31 inter alia.

Process (g) typically comprises a procedure as described in Example 52 inter alia.

Compounds of formula (II), (III), (IV), (V), (VI), HO-M, H-L-M, $L_1$-D-$L_2$, $L_3$-M and S=C=N—$(CR_aR_b)_n$-$Q_{10}$-M are either known or may be prepared in accordance with known procedures.

A wide range of well known functional group interconversions are know by a person skilled in the art for converting a precursor compound to a compound of formula I and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0]. One example of an interconversion includes conversion of a compound wherein M represents phenyl substituted by an amino group to a compound wherein M represents an $COR_{22}$ group as described in Example 28.

Protecting Groups

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a t-butyl carbamate (—NHCO—OC(CH$_3$)$_3$, —NH-Boc); a 2-biphenyl-2-propyl carbamate (—NHCO—OC(CH$_3$)$_2$C$_6$H$_4$C$_6$H$_5$, —NH-Bpoc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulphonyl)ethyl carbamate (—NH-Psec).

Other protecting groups for amines, such as cyclic amines and heterocyclic N—H groups, include toluenesulphonyl (tosyl) and methanesulphonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art and examples of such methods include chromatographic techniques such as column chromatography (e.g. flash chromatography) and HPLC. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;*

2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

Methods of recrystallisation of compounds of formula (I) and salt thereof can be carried out by methods well known to the skilled person—see for example (P. Heinrich Stahl (Editor), Camille G. Wermuth (Editor), ISBN: 3-90639-026-8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for purification include sublimation, which includes a heating step under vacuum for example using a cold finger, and crystallization from melt (Crystallization Technology Handbook 2nd Edition, edited by A. Mersmann, 2001).

PHARMACEUTICAL FORMULATIONS

While it is possible for the active compound to be administered alone, it is preferable to present it as a pharmaceutical composition (e.g. formulation).

Thus, the present invention further provides pharmaceutical compositions, as defined above, and methods of making a pharmaceutical composition comprising (e.g admixing) at least one compound of formula (I) (and sub-groups thereof as defined herein), together with at least one pharmaceutically acceptable excipient and optionally other therapeutic or prophylactic agents as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and pre-filled syringes, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here. Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively releasing the compound in the stomach or in the ileum, duodenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The compound of formula (I) may be formulated with a carrier and administered in the form of nanoparticles. Nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. Aug. 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) polymers (depending on dose). The film coats of the tablet or capsule typically contain 0-10% (w/w) release-controlling (e.g. delaying) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. In certain embodiments, the preferred routes of administration are oral and intravenous. Alternatively, one may administer the compound in a local rather than systemic manner, for example, via injection of the compound directly into a solid tumor, often in a depot or sustained release formulation. Furthermore, one may administer the drug in a targeted drug delivery system, for example, in a liposome coated with tumor-specific antibody. In this way, the liposomes may be targeted to and taken up selectively by the tumor.

Pharmaceutical compositions of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in any conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also. Pharmaceutical compositions which may also be used include hard gelatin capsules. The capsules or pills may be packaged into brown glass or plastic bottles to protect the active compound from light. The containers containing the active compound capsule formulation are preferably stored at controlled room temperature (15-30° C.).

For administration by inhalation, the compounds for use according to the present invention may be conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound.

Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD cosolvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD:D5W) consists of VPD diluted 1:1 with a 5% dextrose in water solution. This cosolvent system dissolves hydrophobic compounds well, and itself produces low toxicity upon systemic administration. Naturally, the proportions of such a cosolvent system may be varied considerably without destroying its solubility and toxicity characteristics. Furthermore, the identity of the cosolvent components may be varied: for example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

METHODS OF TREATMENT

These compounds have utility over a broad range of therapeutic applications, and may be used to treat diseases, such as cancer, that are mediated and/or associated (at least in part) with DNMT activity.

In another aspect, the invention provides methods for treating or preventing a DNMT activity-mediated disease, such as cancer, which method comprises administering to a patient in need of such a treatment a therapeutically effective amount of a compound described herein or a pharmaceutically acceptable composition comprising said compound.

Another aspect relates to inhibiting DNMT activity in a biological sample, which method comprises contacting the biological sample with a compound described herein, or a pharmaceutically acceptable composition comprising said compound.

Another aspect relates to a method of inhibiting DNMT activity in a patient, which method comprises administering to the patient a compound described herein or a pharmaceutically acceptable composition comprising said compound.

Pharmaceutical compositions suitable for use in the present invention include compositions wherein the active ingredients are contained in an amount sufficient to achieve the intended purpose, e.g., the modulation of DNMT activity and/or the treatment or prevention of a DNMT-related disorder. More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein. For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the DNMT activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, $9^{th}$ ed., Ed. by Hardman, J. et al., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC varies for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations. Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of the present invention may range from approximately 2.5 mg/m$^2$ to 1500 mg/m$^2$ per day. Additional illustrative amounts range from 0.2-1000 mg/qid, 2-500 mg/qid, and 20-250 mg/qid.

In cases of local administration or selective uptake, the effective local concentration of the drug may not be related to plasma concentration, and other procedures known in the art may be employed to determine the correct dosage amount and interval. The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

As mentioned above, the compounds and compositions of the invention will find utility in a broad range of diseases and conditions mediated by DNMTs, including diseases and conditions mediated by DNMT activity. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

The compounds of the invention can be used in combination with one or more other chemotherapeutic agents. The dosage of the inventive compounds may be adjusted for any drug-drug reaction. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN (exemestane).

Examples of alkylating agents that the above method can be carried out in combination with include, without limitation, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethylene-imines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that the above method can be carried out in combination with include, without limitation, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of useful COX-II inhibitors include VIOXX, CELEBREX (celecoxib), valdecoxib, paracoxib, rofecoxib, and Cox 189.

Examples of useful matrix metalloproteinase inhibitors are described in International Patent Publications WO 96/33172, WO 96/27583, WO 98/07697, WO 98/03516, WO 98/34918, WO 98/34915, WO 98/33768, WO 98/30566, WO 90/05719, WO 99/52910, WO 99/52889, and WO 99/29667, European Patent Application Nos. 97304971.1, 99302232.1, and 99308617.2, European Patent Publications 606,046, 780,386, and 931,788, PCT International Application No. PCT/IB98/01113, Great Britain patent application number 9912961.1, and U.S. Pat. Nos. 5,863,949, and 5,861,510, all of which are incorporated herein in their entireties by reference. Preferred MMP-2 and MMP-9 inhibitors are those that have little or no activity inhibiting MMP-1. More preferred are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and compounds selected from: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of these compounds.

Other anti-angiogenesis agents, other COX-II inhibitors and other MMP inhibitors, can also be used in the present invention.

The compounds of the invention can also be used with other signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, such as HERCEPTIN (Genentech, Inc., South San Francisco, Calif.). EGFR inhibitors are described in, for example in WO 95/19970, WO 98/14451, WO 98/02434, and U.S. Pat. No. 5,747,498, and such substances can be used in the present invention as described herein. EGFR-inhibiting agents include, but are not limited to, the monoclonal antibodies C225 and anti-EGFR 22Mab (ImClone Systems, Inc., New York, N.Y.), the compounds erlotinib (OSI Pharmaceuticals, Inc., Melville, N.Y.), ZD-1839 (AstraZeneca), BIBX-1382 (Boehringer Ingelheim), MDX-447 (Medarex Inc., Annandale, N.J.), and OLX-103 (Merck & Co., Whitehouse Station, N.J.), and EGF fusion toxin (Seragen Inc., Hopkinton, Mass.). These and other EGFR-inhibiting agents can be used in the present invention.

VEGF inhibitors, for example SU-5416 and SU-6668 (Sugen Inc., South San Francisco, Calif.), can also be combined with an inventive compound. VEGF inhibitors are described in, for example, International Publications WO 01/60814, WO 99/24440, WO 95/21613, WO 99/61422, WO 99/10349, WO 97/32856, WO 97/22596, WO 98/54093, WO 98/02438, WO 99/16755, WO 01/60814, WO 98/50356, and WO 98/02437, PCT International Application PCT/IB99/00797, and U.S. Pat. Nos. 5,834,504, 5,883,113, 5,886,020, and 5,792,783, all of which are incorporated herein in their entireties by reference. Other examples of some specific VEGF inhibitors useful in the present invention are IM862 (Cytran Inc., Kirkland, Wash.); anti-VEGF monoclonal antibody of Genentech, Inc.; and angiozyme, a synthetic ribozyme from Ribozyme (Boulder, Colo.) and Chiron (Emeryville, Calif.). These and other VEGF inhibitors can be used in the present invention as described herein. Further, pErbB2 receptor inhibitors, such as GW-282974 (Glaxo Wellcome plc), and the monoclonal antibodies AR-209 (Aronex Pharmaceuticals Inc., The Woodlands, Tex.) and 2B-1 (Chiron), can furthermore be combined with an inventive compound, for example, those indicated in International Patent Publications WO 98/02434, WO 99/35146, WO 99/35132, WO 98/02437, WO 97/13760, and WO 95/19970, and U.S. Pat. Nos. 5,587,458, and 5,877,305, which are all hereby incorporated herein in their entireties by reference. ErbB2 receptor inhibitors useful in the present invention are also described in U.S. Pat. No. 6,284,764, incorporated in its entirety herein by reference. The erbB2 receptor inhibitor compounds and substance described in the aforementioned PCT applications, U.S. patents, and U.S. provisional applications, as well as other compounds and substances that inhibit the erbB2 receptor, can be used with an inventive compound, in accordance with the present invention.

The compounds of the invention can also be used with other agents useful in treating cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824.

The above method can also be carried out in combination with radiation therapy, wherein the amount of an inventive compound in combination with the radiation therapy is effective in treating the above diseases. Techniques for administering radiation therapy are known in the art, and these techniques can be used in the combination therapy described herein. The administration of the compound of the invention in this combination therapy can be determined as described herein.

EXAMPLES

The invention will be further understood upon consideration of the following non-limiting Examples. Abbreviations used below are ACN=acetonitrile; DCM=dichloromethane or methylenechloride; MeOH=methanol; EtOH=ethanol; DMSO=dimethylsulfoxide; DIPEA=N,N-diisopropylethylamine; DMAP=4-(dimethylamino)pyridine; HATU=2-(1H-7-azabenzotriazole-1-yl)-1,1,3,3-tetramethyluronium hexafluorophosphate; Boc=tertiary-butyloxycarbamate; HBTU=2-(1H-benzotriazole-1-yl)-1,1,3,3-tetramethyluronium hexafluorophosphate; TEA=triethylamine; THF=tetrahydrofuran; mcpba=meta-chloroperoxybenzoic acid; min, h, d=minutes, hours, days; rt or RT=room temperature; SM=starting material; NMR=nuclear magnetic resonance; TLC=thin layer chromatography.

Chemistry

Compounds of the invention may be made by one of ordinary skill in the chemical arts using conventional synthetic procedures, as well as by the general reaction schemes and examples described below. Without specific statement, all solvents and reagents were available from SIGMA-Aldrich or VWR Chemicals and used as supplied or purified by standard laboratory methods as required. NMR spectra were recorded on a Varian Unity plus 300 at 300 MHz ($^1$H) at 25° C. Chemical shifts are reported in ppm and referenced internally to residual CHCl$_3$ for (d 7.26) or CH$_3$OH for (d 3.33). Low resolution mass spectrometry was performed by The Mass Spectrometry and Proteomics Core facility at the University of Utah. Flash chromatography was performed on Combifalsh (Yamazen) with normal phase silica gel column (RediSep) and CH$_2$Cl$_2$/CH$_3$OH solvent system. TLC used precoated silica gel aluminum sheets.

Example 1

N-(3-((3-((1H-Pyrrolo[2,3-b]pyridin-4-yl)methyl)ureido)methyl)phenyl)-3-phenylpropiolamide (E1)

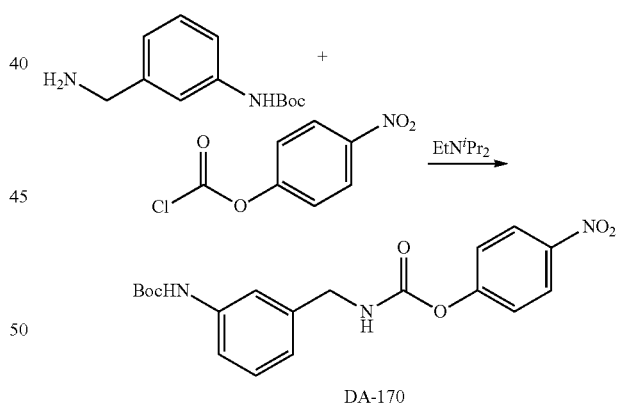

DA-170

To a mixture of tert-butyl(3-(aminomethyl)phenyl)carbamate (857 mg, 3.86 mmol) and 4-nitrophenyl chloroformate (777 mg, 3.86 mmol) in THF (25 mL) DIPEA (498 mg, 3.86 mmol) in THF (5 mL) was added dropwise. Mixture was stirred overnight, diluted with AcOEt, washed with brine, 0.1 M citric acid, brine, sat. aq. NaHCO$_3$, brine and dried with sodium sulfate. Solvent was removed in vacuo to give white, partially yellowish solid. It was suspended in a small volume of MeOH; white solids were filtered off, washed with MeOH and dried in vacuo to give first crop of product as white powder. Filtrate was purified by MPLC (silica, 0-5% MeOH in DCM) to give second crop of product as white solid.

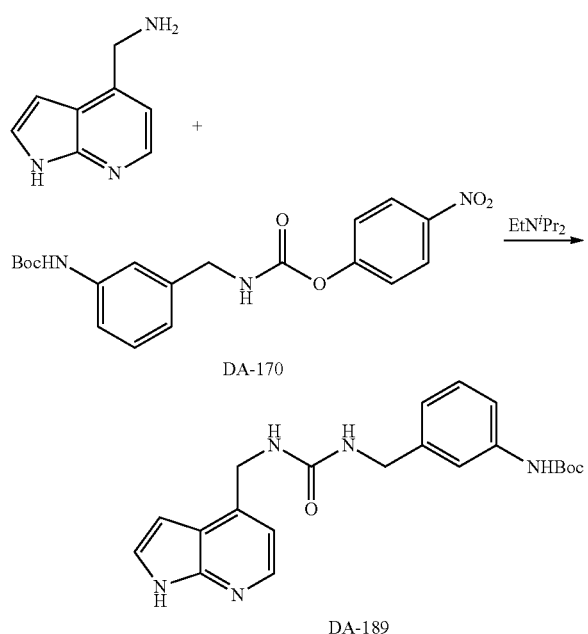

DA-170

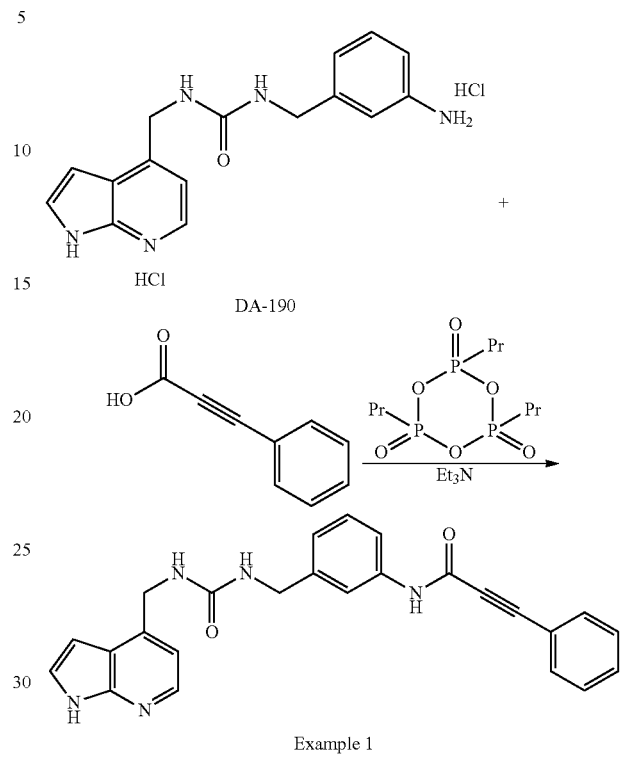

DA-189

To a solution of 1H-pyrrolo[2,3-b]pyridine-4-methanamine (290 mg, 1.972 mmol) and DA-170 (764 mg, 1.972 mmol) in THF (50 mL) DIPEA (255 mg, 1.972 mmol) was added. Mixture was stirred for 2 days. Solvent was removed in vacuo and residual solids were suspended in AcOEt and washed 3× with saturated aqueous solution of NaHCO$_3$. Solids were filtered off from both layers, washed with water, several times with diethyl ether and dried in vacuo to give first crop of product as slightly yellowish powder. Organic layer was dried with sodium sulfate and the solvent was removed in vacuo to give yellow semi-solid. It was purified by MPLC (silica, 0-10% MeOH in DCM) to give second crop of product as slightly yellowish solid.

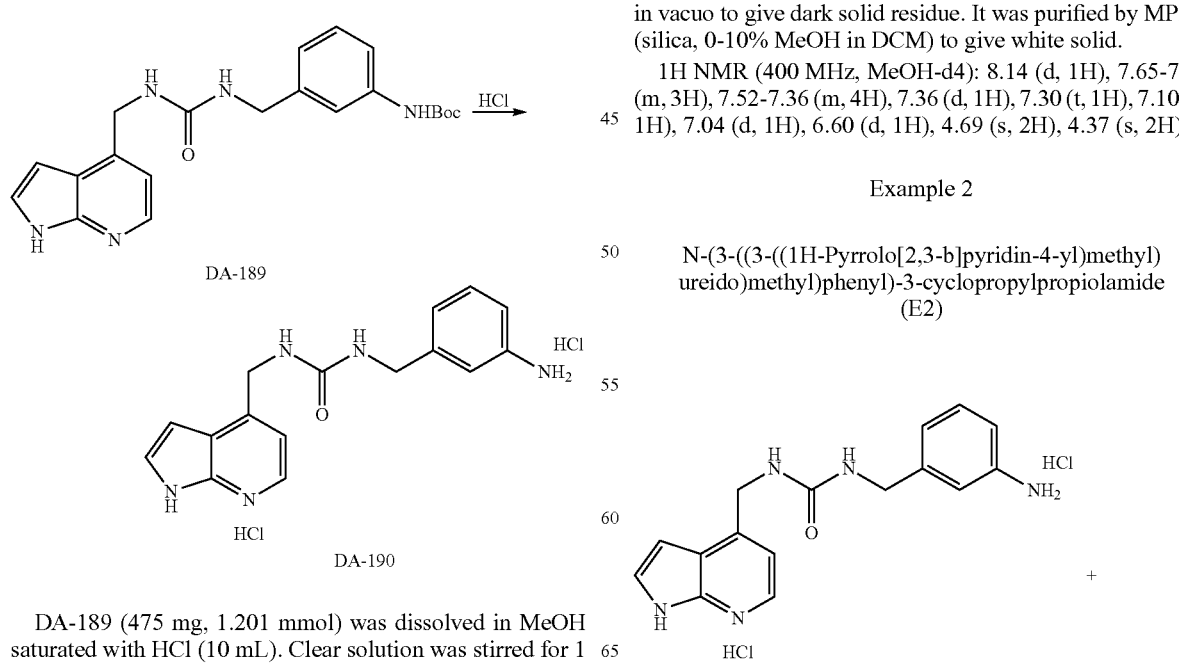

DA-189 (475 mg, 1.201 mmol) was dissolved in MeOH saturated with HCl (10 mL). Clear solution was stirred for 1 h and the solvent was removed in vacuo. Residual oil was dissolved in small volume of MeOH (almost instantly everything solidified in a mass of white crystals) and diluted with diethyl ether. Solids were filtered off, washed with ether and dried in vacuo to give white powder.

Example 1

To a solution of DA-190 (50 mg, 0.136 mmol) and 3-phenylpropiolic acid (40 mg, 0.272 mmol) in DMF (3 mL) TEA (137 mg, 1.358 mmol) followed by PPA (50% solution in AcOEt, 216 mg, 0.339 mmol) was added. Deep red solution was stirred overnight, diluted with AcOEt, washed 3× with brine, dried with sodium sulfate and the solvent was removed in vacuo to give dark solid residue. It was purified by MPLC (silica, 0-10% MeOH in DCM) to give white solid.

1H NMR (400 MHz, MeOH-d4): 8.14 (d, 1H), 7.65-7.63 (m, 3H), 7.52-7.36 (m, 4H), 7.36 (d, 1H), 7.30 (t, 1H), 7.10 (d, 1H), 7.04 (d, 1H), 6.60 (d, 1H), 4.69 (s, 2H), 4.37 (s, 2H).

Example 2

N-(3-((3-((1H-Pyrrolo[2,3-b]pyridin-4-yl)methyl)ureido)methyl)phenyl)-3-cyclopropylpropiolamide (E2)

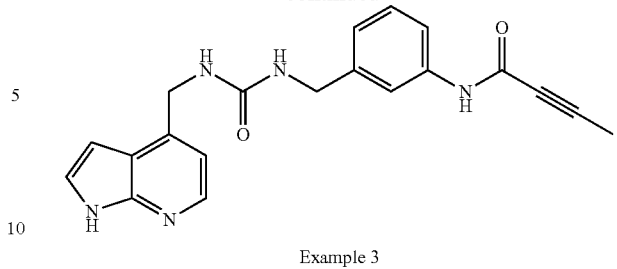

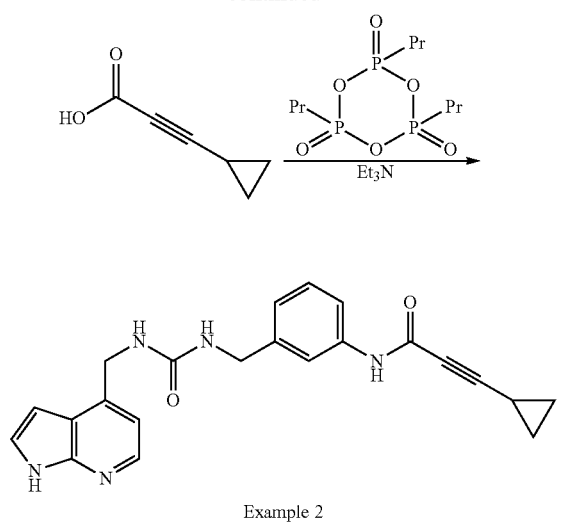

Example 2

To a solution of DA-190 (50 mg, 0.136 mmol) and 3-cyclopropylpropiolic acid (30 mg, 0.272 mmol) in DMF (3 mL) TEA (137 mg, 1.358 mmol) followed by PPA (50% solution in AcOEt, 216 mg, 0.339 mmol) was added. Deep red solution was stirred for 3 h, diluted with AcOEt, washed 3× with brine, dried with sodium sulfate and the solvent was removed in vacuo to give dark solid residue. It was purified by MPLC (silica, 0-10% MeOH in DCM) to give white solid.

1H NMR (400 MHz, MeOH-d4): 8.12 (d, 1H), 7.54 (m, 1H), 7.43-7.40 (m, 1H), 7.36 (d, 1H), 7.25 (t, 1H), 7.05 (d, 1H), 7.03 (d, 1H), 6.59 (d, 1H), 4.67 (s, 2H), 4.33 (s, 2H), 1.52-1.45 (m-1H), 1.01-0.85 (m, 4H).

Example 3

N-(3-((3-((1H-Pyrrolo[2,3-b]pyridin-4-yl)methyl)ureido)methyl)phenyl)but-2-ynamide (E3)

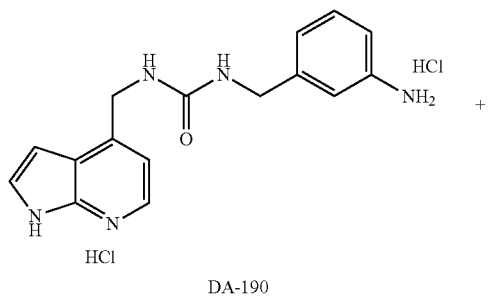

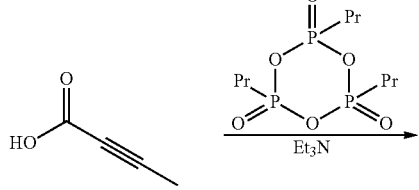

To a solution of DA-190 (60 mg, 0.163 mmol) and but-2-ynoic acid (15 mg, 0.179 mmol) in DMF (3 mL) TEA (82 mg, 0.815 mmol) followed by PPA (50% solution in AcOEt, 124 mg, 0.196 mmol) was added. Orange solution was stirred overnight, diluted with AcOEt, washed 3× with brine, dried with sodium sulfate and the solvent was removed in vacuo to give pale orange solid residue. It was purified by MPLC (silica, 0-10% MeOH in DCM) to give white solid.

1H NMR (400 MHz, MeOH-d4): 8.12 (d, 1H), 7.54 (m, 1H), 7.43-7.40 (m, 1H), 7.36 (d, 1H), 7.26 (t, 1H), 7.05 (d, 1H), 7.03 (d, 1H), 6.59 (d, 1H), 4.67 (s, 2H), 4.34 (s, 2H), 2.03 (s, 3H).

Example 4

N-(3-((3-((1H-Pyrrolo[2,3-b]pyridin-4-yl)methyl)ureido)methyl)phenyl)-3-(4-methoxyphenyl)propiolamide (E4)

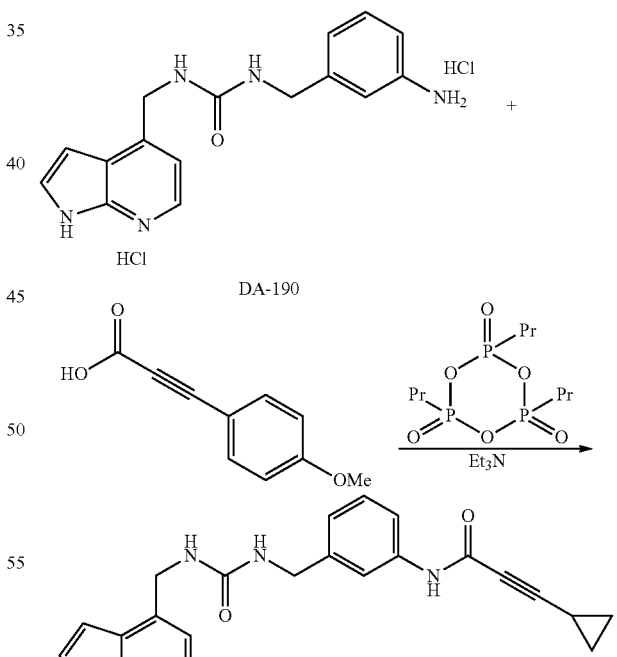

Example 2

To a solution of DA-190 (50 mg, 0.136 mmol) and 3-(4-methoxy)phenylpropiolic acid (48 mg, 0.272 mmol) in DMF (3 mL) TEA (137 mg, 1.358 mmol) followed by PPA (50% solution in AcOEt, 216 mg, 0.339 mmol) was added. Deep red solution was stirred for 4 h, diluted with AcOEt, washed 3× with brine, dried with sodium sulfate and the solvent was removed in vacuo to give brownish solid residue. It was purified by MPLC (silica, 0-10% MeOH in DCM) to give off-white solid.

1H NMR (400 MHz, DMSO-d6): 11.58 (s, 1H), 10.75 (s, 1H), 8.14 (d, 1H), 7.62-7.58 (m, 3H), 7.49 (d, 1H), 7.41 (t, 1H), 7.28 (t, 1H), 7.07-7.00 (m, 3H), 6.93 (d, 1H), 6.56-6.51 (m, 3H), 4.539 d, 2H), 4.23 (d, 2H), 3.82 (s, 3H).

Example 5

1-(((1H-Pyrrolo[2,3-b]pyridin-4-yl)methyl)-3-(2-chlorobenzyl)thiourea (E5)

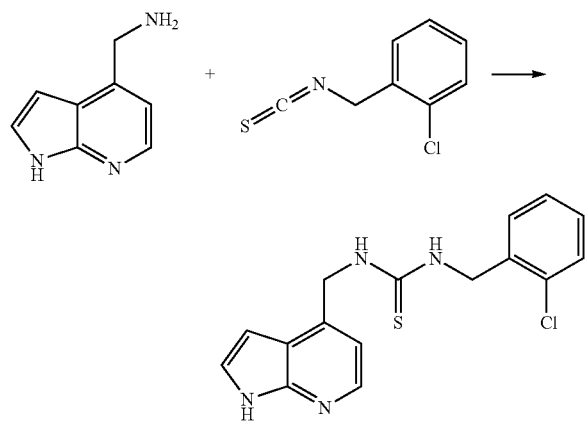

Example 5

To a solution of 1H-pyrrolo[2,3-b]pyridine-4-methanamine (74 mg, 0.5 mmol) in THF (3 mL) solution of 2-chlorobenzyl isocyanate (92 mg, 0.5 mmol) in THF (2 mL) was added. Pale orange solution was stirred overnight and solvent was removed in vacuo. Residual oil was purified by MPLC (silica, 0-10% MeOH in DCM) to give white crystalline solid.

1H NMR (400 MHz, DMSO-d6): 11.63 (s, 1H), 8.18 (bs, 1H), 8.15 (d, 1H), 8.01 (bs, 1H), 7.44 (m, 2H), 7.31 (m, 3H), 6.94 (d, 1H), 6.57 (m, 1H), 4.99 (bs, 2H), 4.76 (bs, 2H).

Example 6

N-(3-((3-(((1H-Pyrrolo[2,3-b]pyridin-4-yl)methyl)thioureido)methyl)phenyl)propiolamide (E6)

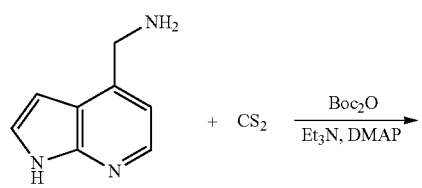

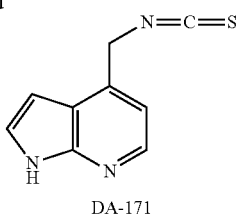

DA-171

To a cooled in an ice bath suspension of (1H-pyrrolo[2,3-b]pyridin-4-yl)methanamine (2.94 g, 20 mmol) in MeOH (10 mL) TEA (2.024 g, 20 mmol) and DMAP (49 mg, 0.4 mmol) followed by CS₂ (15.23 g, 200 mmol) was added. Bath was removed and orange solution was stirred for 30 min. at r.t. It was then cooled in an ice bath for 15 min. and boc anhydride (4.36 g, 20 mmol) in MeOH (5 mL) was added. Formed suspension was stirred for 5 min. Bath was removed and solution was stirred at r.t. for 90 min. Very dark solution was concentrated to a small volume in vacuo to give dark red suspension of crystals. Crystals were filtered off, washed with MeOH and dried in vacuo to give first crop of product as brick red crystals. Filtrate was purified by MPLC (silica, 0-5% MeOH in DCM) to give second crop of product as beige crystalline solid.

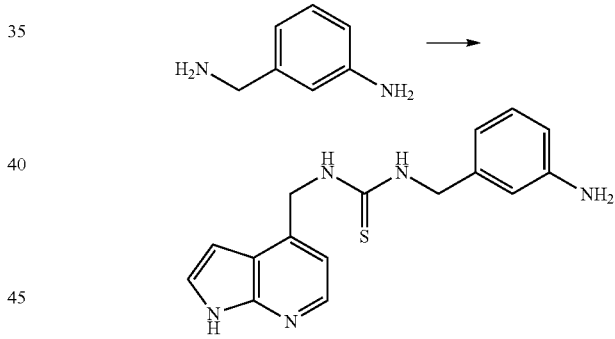

DA-149

Solution of DA-171 (189 mg, 1 mmol) and 3-aminobenzylamine (122 mg, 1 mmol) in MeOH (10 mL) was stirred for 2 days. Solvent was removed in vacuo and residue was purified by MPLC (silica, 0-10% MeOH in DCM) to give white solid.

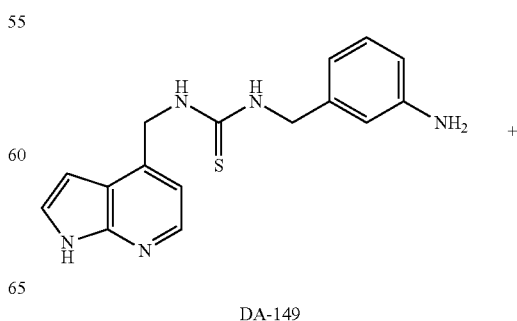

DA-149

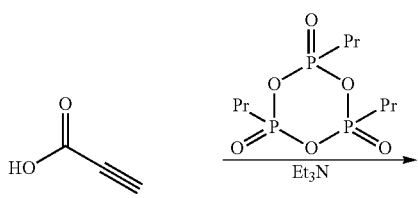

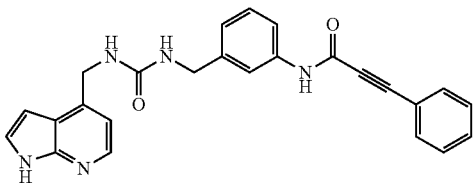

Example 7

Solution of DA-149 (50 mg, 0.161 mmol), 3-phenylpropiolic acid (26 mg, 0.177 mmol) and EDC (37 mg, 0.193 mmol) in MeCN (5 mL) was stirred overnight. Solvent was removed in vacuo and residue was purified by MPLC (silica, 0-10% MeOH in DCM) to give slightly brownish solid.

1H NMR (400 MHz, DMSO-d6): 11.62 (s, 1H), 10.88 (s, 1H), 8.14 (d, 1H), 8.05 (bs, 2H), 7.67-7.65 (m, 2H), 7.61 (s, 1H), 7.57-7.48 (m, 4H), 7.43 (t, 1H), 7.30 (t, 1H), 7.05 (d, 1H), 6.92 (bs, 1H), 6.56-6.54 (m, 1H), 4.99 (bs, 2H), 4.69 (bs, 2H).

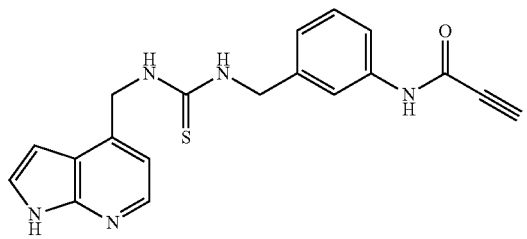

Example 6

To a solution of DA-149 (62 mg, 0.2 mmol) and propiolic acid (14 mg, 0.2 mmol) in DMF (2 mL) TEA (61 mg, 0.6 mmol) followed by PPA (50% solution in AcOEt, 153 mg, 0.24 mmol) was added. Deep red solution was stirred overnight, diluted with AcOEt, washed 3× with brine, dried with sodium sulfate and the solvent was removed in vacuo to give yellowish tar. It was purified by MPLC (silica, 0-10% MeOH in DCM) to give colorless thick oil.

1H NMR (400 MHz, MeOH-d4): 8.12 (d, 1H), 7.57 (s, 1H), 7.46 (dd, 1H), 7.37 (d, 1H), 7.28 (t, 1H), 7.09 (d, 1H), 7.01 (bs, 1H), 6.61 (d, 1H), 5.10 (bs, 2H), 4.75 (bs, 2H), 3.35 (s, 1H).

Example 7

N-(3-((3-((1H-Pyrrolo[2,3-b]pyridin-4-yl)methyl)thioureido)methyl)phenyl)-3-phenylpropiolamide (E7)

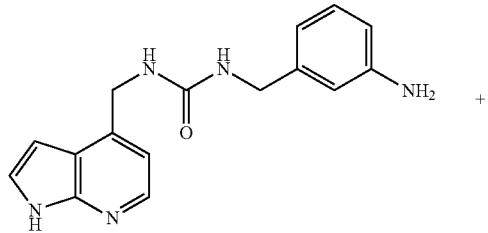

DA-149

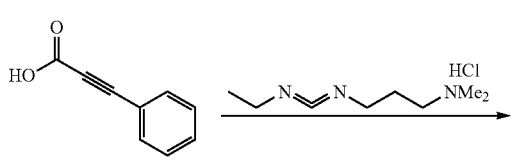

Example 8

N-(3-((3-((1H-Pyrrolo[2,3-b]pyridin-4-yl)methyl)thioureido)methyl)phenyl)but-2-ynamide (E8)

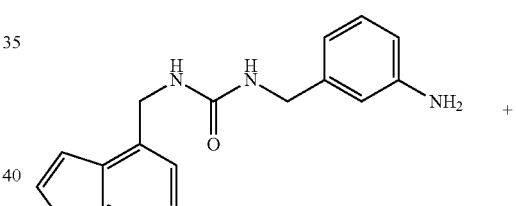

DA-149

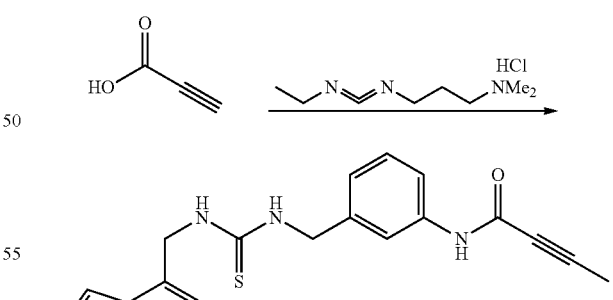

Example 8

Solution of DA-149 (52 mg, 0.167 mmol), but-2-ynoic acid (15 mg, 0.184 mmol) and EDC (38 mg, 0.2 mmol) in MeCN (5 mL) was stirred overnight. Mixture was purified by MPLC (silica, 0-10% MeOH in DCM) to give slightly violet foam.

1H NMR (400 MHz, MeOH-d4): 8.10 (d, 1H), 7.54 (s, 1H), 7.45-7.42 (m, 1H), 7.35 (d, 1H), 7.24 (t, 1H), 7.05 (d, 1H), 6.98 (bs, 1H), 6.59 (d, 1H), 5.08 (bs, 2H), 4.73 (bs, 2H), 2.01 (s, 3H).

Example 9

1-((1H-Pyrrolo[2,3-b]pyridin-4-yl)methyl)-3-(3-(aminomethyl)phenyl)thiourea (E9)

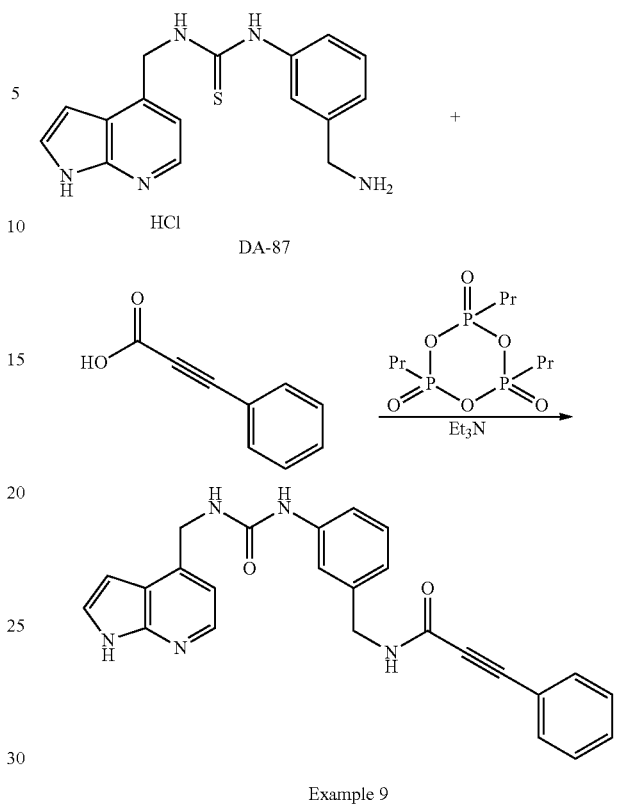

Solution of DA-171 (189 mg, 1 mmol) and tert-butyl 3-aminobenzylcarbamate (222 mg, 1 mmol) in MeOH (10 mL) was stirred for 2 days. Solvent was removed in vacuo and residue was purified by MPLC (silica, 0-10% MeOH in DCM) to give white solid of DA-76.

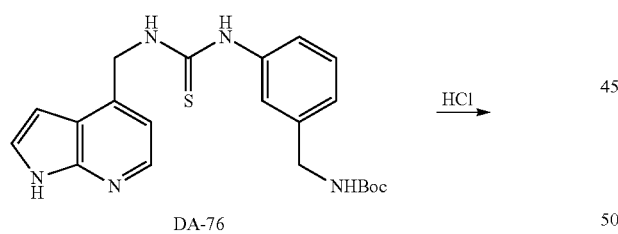

DA-76 (382 mg, 0.928 mmol) was dissolved in MeOH saturated with HCl (5 mL). Clear solution was stirred for 2 h and then diluted with diethyl ether. Formed crystals were filtered off, washed with ether and dried in vacuo to give white powder of DA-87.

To a solution of DA-87 (50 mg, 0.130 mmol) and 3-phenylpropiolic acid (21 mg, 0.143 mmol) in DMF (3 mL) TEA (66 mg, 0.650 mmol) followed by PPA (50% solution in AcOEt, 99 mg, 0.156 mmol) was added. Deep red solution was stirred overnight, diluted with AcOEt, washed 3× with brine, dried with sodium sulfate and the solvent was removed in vacuo to give pale yellow thick oil. It was purified by MPLC (silica, 0-10% MeOH in DCM) to give colorless glass.

1H NMR (400 MHz, MeOH-d4): 8.13 (d, 1H), 7.55-7.52 (m, 2H), 7.45-7.28 (m, 6H), 7.17-7.14 (m, 1H), 7.05 (d, 1H), 6.63 (d, 1H), 5.16 (s, 2H), 4.42 (s, 2H).

Example 10

N-(3-(3-((1H-Pyrrolo[2,3-b]pyridin-4-yl)methyl)thioureido)propyl)-3-phenylpropiolamide (E10)

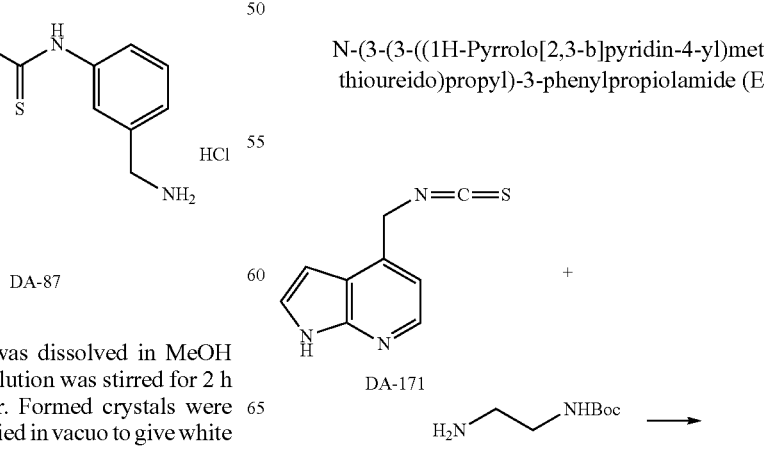

-continued

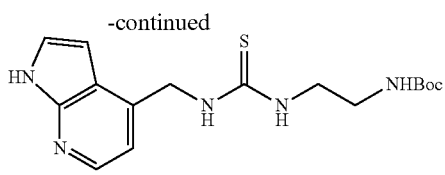

DA-77

Solution of DA-171 (378 mg, 2 mmol) and tert-butyl(2-aminoethyl)carbamate (320 mg, 2 mmol) in MeOH (20 mL) was stirred overnight. Solvent was removed in vacuo and residue was purified by MPLC (silica, 0-10% MeOH in DCM) to give colorless foam.

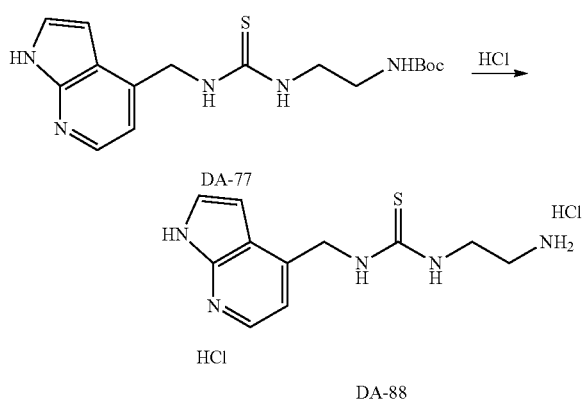

DA-77 (580 mg, 1.660 mmol) was dissolved in MeOH saturated with HCl (6 mL). Yellow solution was stirred for 2 h (after 20 min. crystals started to precipitate). It was diluted with diethyl ether, crystals were filtered off, washed several times with ether and dried in vacuo to give pale yellow powder.

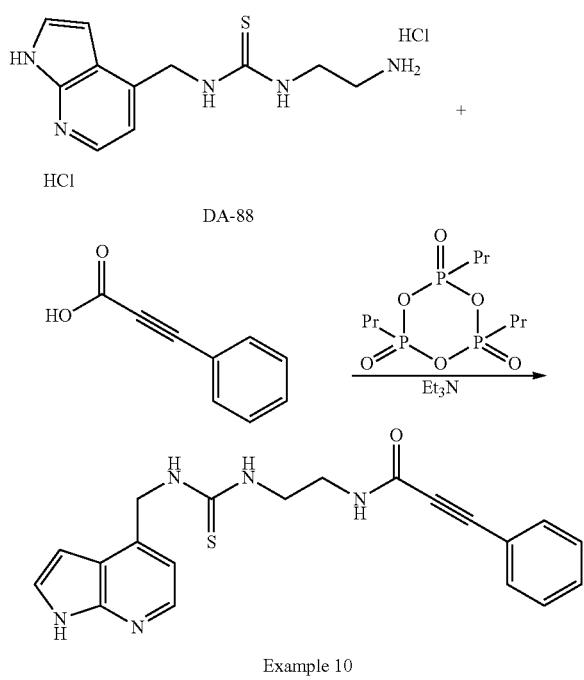

Example 10

To a solution of DA-88 (50 mg, 0.155 mmol) and 3-phenylpropiolic acid (25 mg, 0.171 mmol) in MeCN (3 mL) TEA (79 mg, 0.776 mmol) followed by PPA (50% solution in AcOEt, 118 mg, 0.186 mmol) was added. Deep red solution was stirred overnight, diluted with AcOEt, washed 3× with brine, dried with sodium sulfate and the solvent was removed in vacuo to give dark solid residue. It was purified by MPLC (silica, 0-10% MeOH in DCM) to give colorless glass.

1H NMR (400 MHz, MeOH-d4): 8.12 (d, 1H), 7.56 (m, 1H), 7.54 (m, 1H), 7.47-7.36 (m, 4H), 7.05 (d, 1H), 6.62 (d, 1H), 5.08 (bs, 2H), 3.75 (bs, 2H), 3.49 (t, 2H).

Example 11

N-(2-(3-((1H-Pyrrolo[2,3-b]pyridin-4-yl)methyl)thioureido)ethyl)-3-(4-methoxyphenyl)propiolamide (E11)

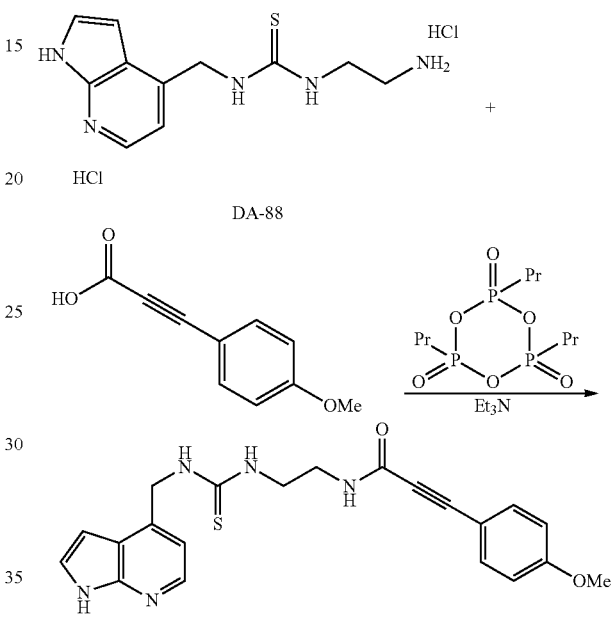

Example 11

To a solution of DA-88 (50 mg, 0.155 mmol) and 3-(4-methoxy)phenylpropiolic acid (30 mg, 0.171 mmol) in MeCN (3 mL) TEA (79 mg, 0.776 mmol) followed by PPA (50% solution in AcOEt, 118 mg, 0.186 mmol) was added. Deep red solution was stirred for 3 h, diluted with AcOEt, washed 3× with brine, dried with sodium sulfate and the solvent was removed in vacuo to give dark solid residue. It was purified by MPLC (silica, 0-10% MeOH in DCM) to give colorless glass.

1H NMR (400 MHz, MeOH-d4): 8.11 (d, 1H), 7.48 (m, 2H), 7.36 (d, 1H), 7.04 (d, 1H), 6.97-6.92 (m, 2H), 6.62 (m, 1H) 5.07 (bs, 2H), 3.82 (s, 3H), 3.73 (bs, 2H), 3.48 (t, 2H).

Example 12

N-(3-(3-((1H-Pyrrolo[2,3-b]pyridin-4-yl)methyl)thioureido)propyl)-3-phenylpropiolamide (E12)

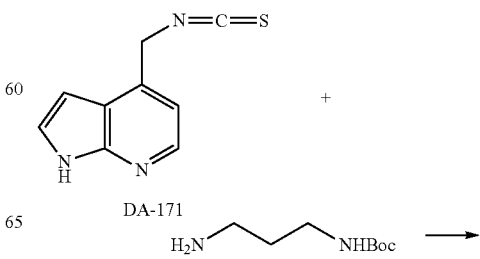

DA-171

-continued

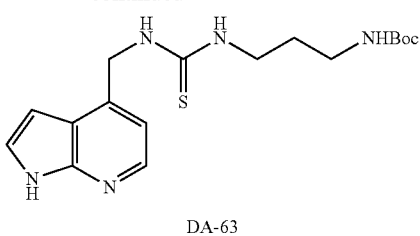

DA-63

Solution of DA-171 (378 mg, 2 mmol) and tert-butyl(3-aminopropyl)carbamate (348 mg, 2 mmol) in MeOH (20 mL) was stirred overnight. Solvent was removed in vacuo and residue was purified by MPLC (silica, 0-10% MeOH in DCM) to give yellowish glass.

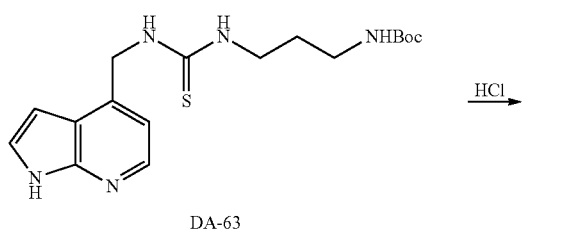

DA-63

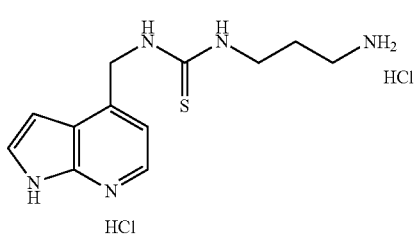

DA-65

DA-63 (631 mg, 1.736 mmol) was dissolved in MeOH saturated with HCl (10 mL). Yellow solution was stirred for 2 h (after 5 min. crystals started to precipitate). It was diluted with diethyl ether, crystals were filtered off, washed several times with ether and dried in vacuo to give white powder.

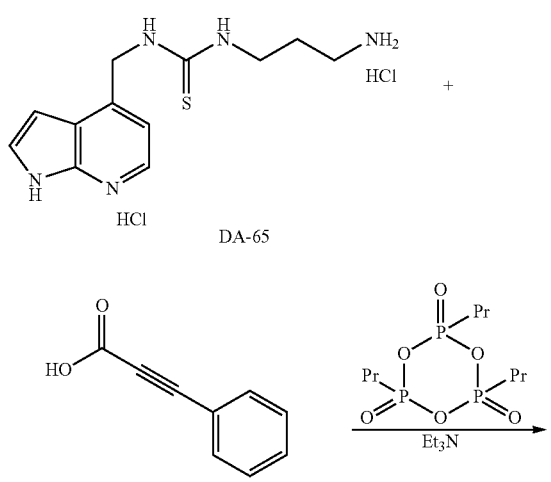

-continued

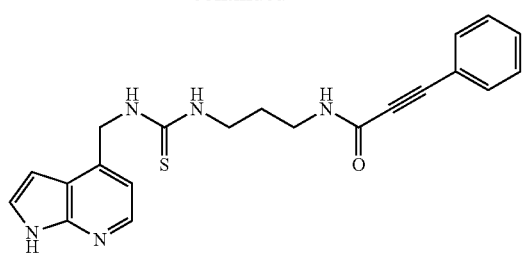

Example 12

To a solution of DA-65 (50 mg, 0.149 mmol) and 3-phenylpropiolic acid (24 mg, 0.164 mmol) in MeCN (3 mL) TEA (75 mg, 0.743 mmol) followed by PPA (50% solution in AcOEt, 114 mg, 0.178 mmol) was added. Deep red solution was stirred overnight, diluted with AcOEt, washed 3× with brine, dried with sodium sulfate and the solvent was removed in vacuo to give dark solid residue. It was purified by MPLC (silica, 0-10% MeOH in DCM) to give pinkish foam.

1H NMR (400 MHz, MeOH-d4): 8.12 (d, 1H), 7.55 (m, 1H), 7.54 (m, 1H), 7.47-7.43 (m, 1H), 7.41-7.37 (m, 3H) 7.03 (d, 1H), 6.62 (d, 1H), 5.07 (bs, 2H), 3.60 (bs, 2H), 3.30 (m, 2H), 1.81 (m, 2H).

Example 13

N-(3-((3-((1H-Pyrrolo[2,3-b]pyridin-4-yl)methyl)thioureido)methyl)benzyl)-3-phenylpropiolamide (E13)

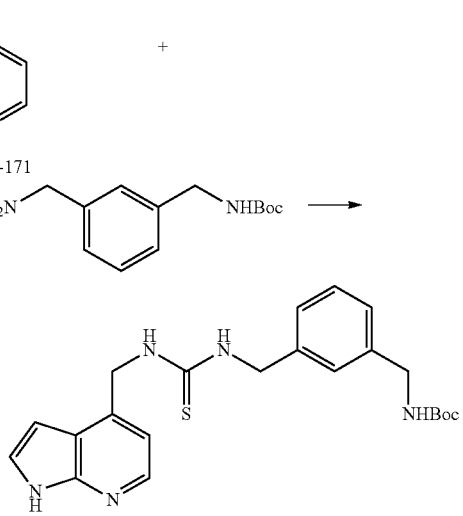

DA-74

Solution of DA-171 (189 mg, 1 mmol) and tert-butyl 3-(aminomethyl)benzylcarbamate (236 mg, 1 mmol) in MeOH (10 mL) was stirred overnight. Solvent was removed in vacuo and residue was purified by MPLC (silica, 0-10% MeOH in DCM) to give white solid.

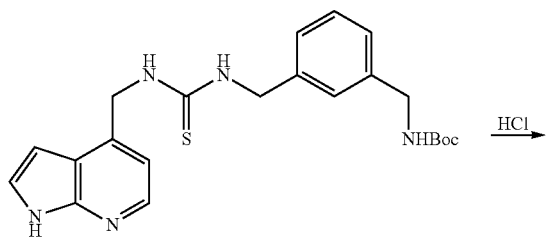

DA-74

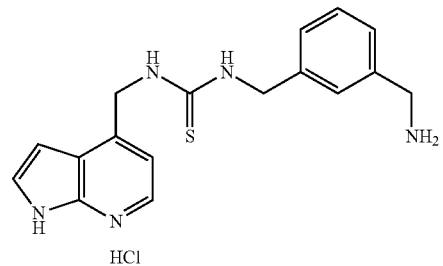

DA-75

DA-74 (294 mg, 0.691 mmol) was dissolved in MeOH saturated with HCl (10 mL). Solution was stirred for 2 h (after 1 h crystalline white solids precipitated). It was diluted with diethyl ether, crystals were filtered off, washed several times with ether and dried in vacuo to give white powder.

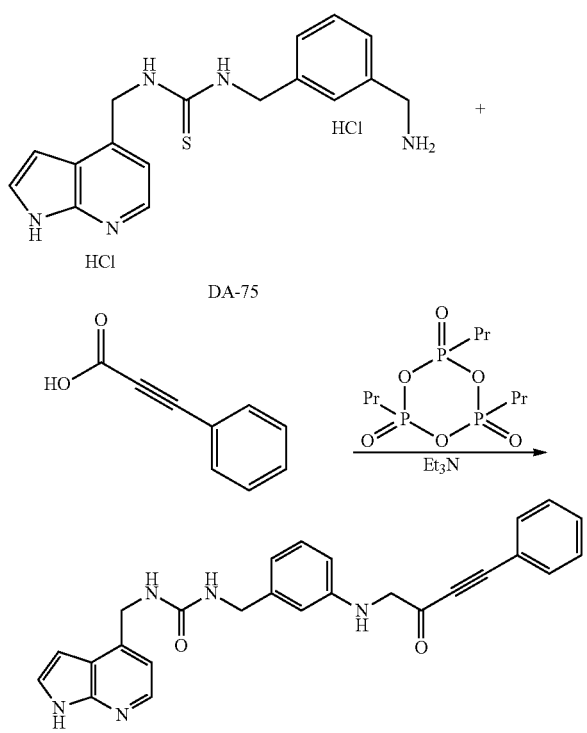

Example 13

To a solution of DA-75 (50 mg, 0.126 mmol) and 3-phenylpropiolic acid (20 mg, 0.138 mmol) in DMF (3 mL) TEA (64 mg, 0.628 mmol) followed by PPA (50% solution in AcOEt, 96 mg, 0.151 mmol) was added. Orange solution was stirred for 3 h, diluted with AcOEt, washed 3× with brine, dried with sodium sulfate and the solvent was removed in vacuo to give almost colorless semi-solid. It was purified by MPLC (silica, 0-10% MeOH in DCM) to give colorless glass.

1H NMR (400 MHz, MeOH-d4): 8.09 (d, 1H), 7.56-7.52 (m, 2H), 7.47-7.42 (m, 1H), 7.41-7.35 (m, 3H), 7.31-7.26 (m, 2H), 7.22-7.20 (m, 2H), 6.97 (bs, 1H), 6.59 (d, 1H), 5.08 (bs, 2H), 4.76 (bs, 2H), 4.42 (s, 2H).

Example 14

(E)-N-(3-((3-((1H-Pyrrolo[2,3-b]pyridin-4-yl)methyl)-2-cyanoguanidino)methyl)phenyl)but-2-ynamide (E14)

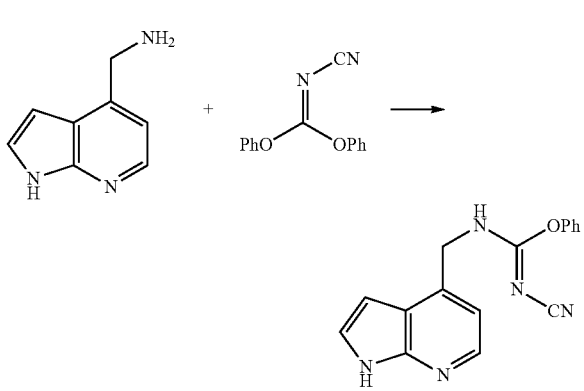

DA-164

Suspension of (1H-pyrrolo[2,3-b]pyridin-4-yl)methanamine (147 mg, 1 mmol) and diphenyl cyanocarbonimidate (238 mg, 1 mmol) in THF (5 mL) was stirred overnight. After several minutes starting materials dissolved and new solids precipitated. Suspension was stirred for 3 days and purified by MPLC (silica, 0-10% MeOH in DCM) to give white solid.

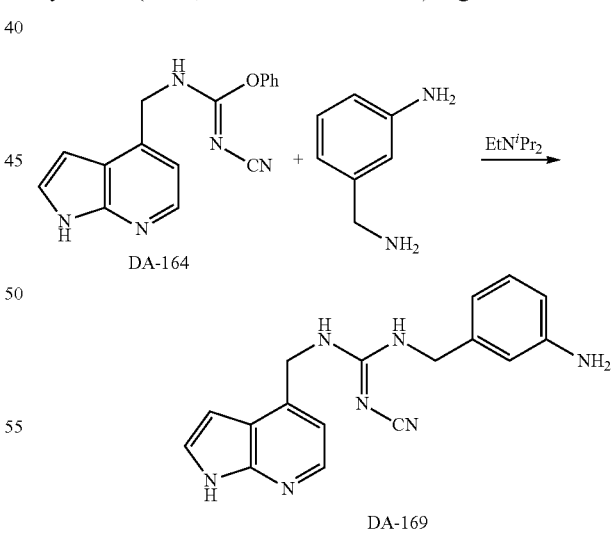

DA-169

Suspension of DA-164 (77 mg, 0.264 mmol), 3-(aminomethyl)aniline (32 mg, 0.264 mmol) and DIPEA (34 mg, 0.264 mmol) in IPA (3 mL) was MW irradiated (150° C., 2 h) to give pale yellow solution. It was diluted with AcOEt and washed with 0.1 M citric acid. Aqueous layer was basified with NaHCO₃ and extracted 5× with AcOEt. Extracts were combined, washed with brine, dried with sodium sulfate and solvent was removed in vacuo to give slightly yellowish solid. It was purified by MPLC (silica, 0-10% MeOH in DCM) to give white solid.

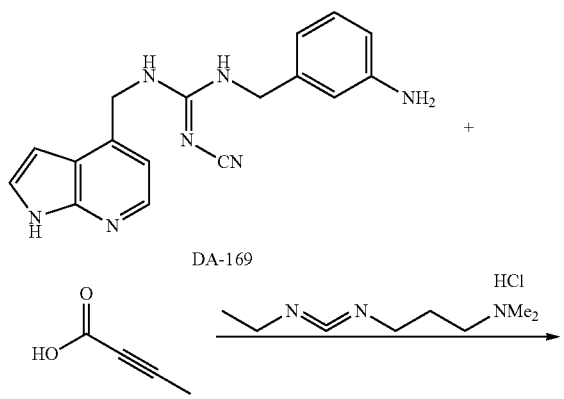

Example 14

Solution of DA-169 (60 mg, 0.188 mmol), but-2-ynoic acid (17 mg, 0.207 mmol) and EDC (43 mg, 0.225 mmol) in MeCN (5 mL) was stirred overnight. Reaction mixture was applied directly on silica gel and purified by MPLC (silica, 0-10% MeOH in DCM) to give mixture of product and unreacted DA-169 as pale violet foam. It was purified by HPLC to give fluffy white solid of TFA salt.

1H NMR (400 MHz, DMSO-d6): 11.86 (s, 1H), 10.63 (s, 1H), 8.15 (d, 1H), 7.72 (m, 2H), 7.56 (s, 1H), 7.49-7.45 (m, 2H), 7.24 (t, 1H), 6.91 (d, 1H), 6.85 (d, 1H), 6.59-6.57 (m, 1H), 4.67 (d, 2H), 4.35 (d, 2H), 2.05 (s, 3H).

Example 15

(Z)—N-(2-(3-((1H-Pyrrolo[2,3-b]pyridin-4-yl)methyl)-2-cyanoguanidino)ethyl)-3-phenylpropiolamide (E15)

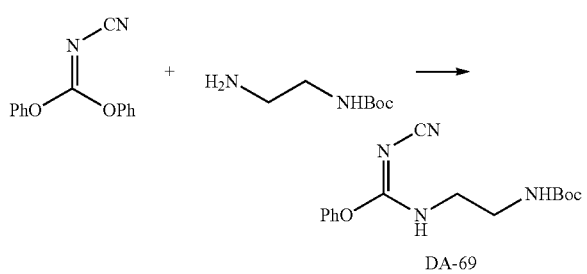

To a suspension of diphenyl cyanocarbonimidate (1.191 g, 5 mmol) in MeCN (10 mL) tert-butyl N-(2-aminoethyl)carbamate (0.801 g, 5 mmol) was added, instantly new solids precipitated. White suspension was stirred overnight and diluted with diethyl ether. Solids were filtered off, washed with ether and dried in vacuo to give white powder.

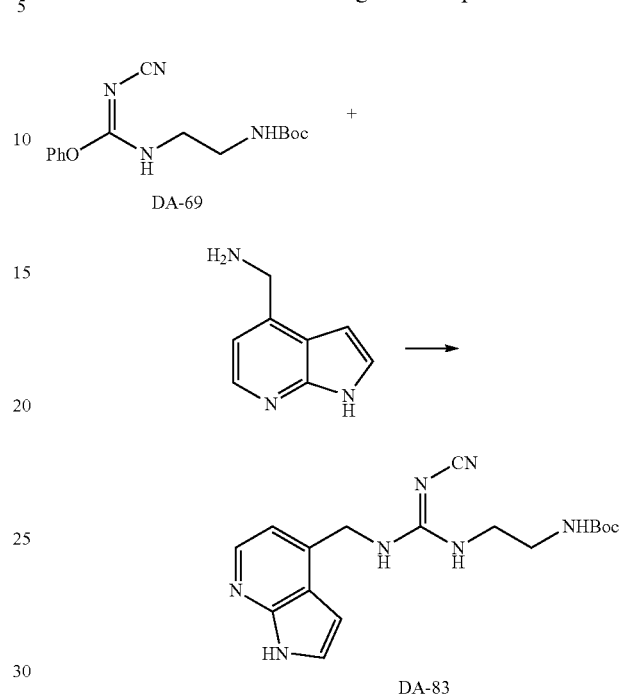

Suspension of DA-69 (304 mg, 1 mmol) and (1H-pyrrolo[2,3-b]pyridin-4-yl)methanamine (147 mg, 1 mmol) in IPA (5 mL) was MW irradiated (150° C., 1 h) to give a red solution. Solvent was removed in vacuo and residue was purified by MPLC (silica, 0-10% MeOH in DCM) to give colorless glass.

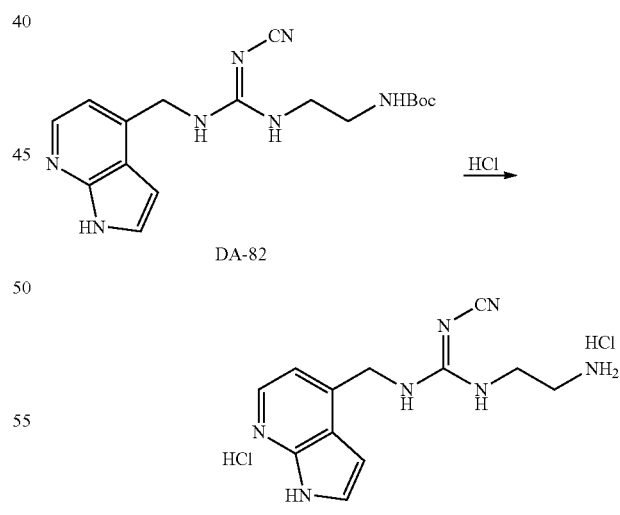

DA-83 (342 mg, 0.957 mmol) was dissolved in MeCN saturated with HCl (10 mL). Solution turned briefly green and then orange. It was stirred for 1 h and diluted with diethyl ether. Formed crystals were filtered off, washed several times with ether, then 2× with acetone, again with ether and dried in vacuo to give off-white powder.

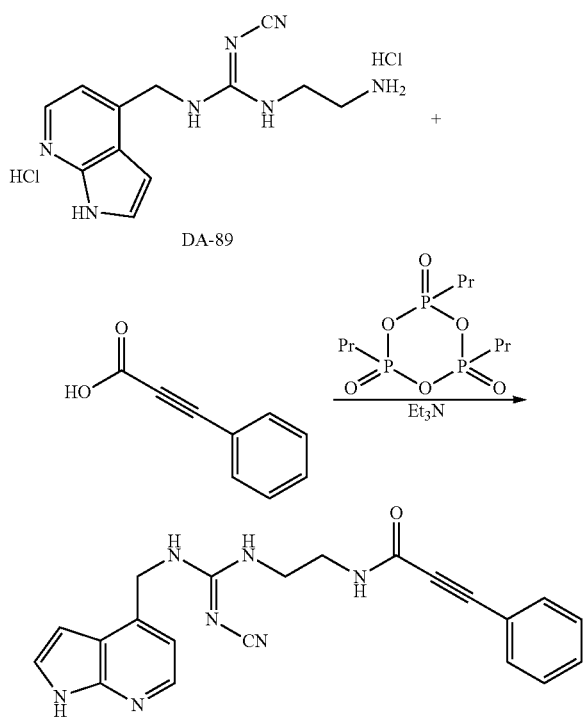

Example 15

To a solution of DA-89 (50 mg, 0.151 mmol) and 3-phenylpropiolic acid (24 mg, 0.167 mmol) in DMF (3 mL) TEA (77 mg, 0.757 mmol) followed by PPA (50% solution in AcOEt, 116 mg, 0.182 mmol) was added. Dark solution was stirred for 3 h, diluted with AcOEt, washed 3× with brine, dried with sodium sulfate and the solvent was removed in vacuo to give reddish solid. It was purified by MPLC (silica, 0-10% MeOH in DCM) to give white solid.

1H NMR (400 MHz, DMSO-d6): 11.65 (s, 1H), 8.84 (s, 1H), 8.16 (d, 1H), 7.70 (t, 1H), 7.58-7.42 (m, 6H), 7.22 (t, 1H), 6.91 (d, 1H), 6.55 (m, 1H), 4.64 (d, 2H), 3.27 (bs, 4H)

Example 16

N-(2-(3-((1H-pyrrolo[2,3-b]pyridin-4-yl)methyl)ureido)ethyl)-3-phenylpropiolamide (E16)

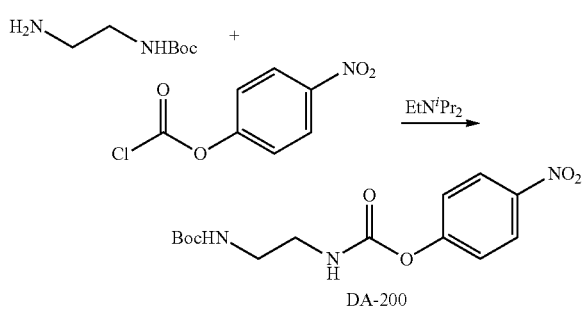

To a solution of tert-butyl(2-aminoethyl)carbamate (801 mg, 5 mmol) and 4-nitrophenyl chloroformate (1.008 g, 5 mmol) in THF (20 mL) DIPEA in THF (5 mL) was added. Mixture warmed up slightly and after several minutes white crystals precipitated. Mixture was stirred for 3 days and diluted with AcOEt, washed 2× with sat. NaHCO₃, brine, 0.1 M citric acid, brine and dried with sodium sulfate. Solvent was removed in vacuo to give yellowish solid. It was boiled in small volume of MeOH, after cooling solids were filtered off, washed with MeOH and dried in vacuo to give white powder.

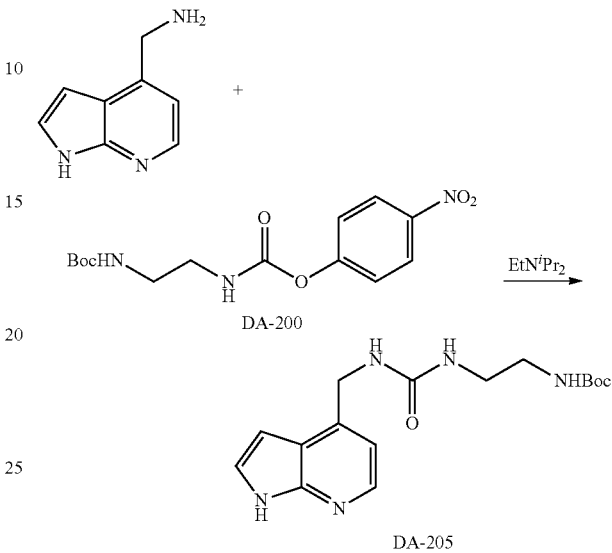

To a solution of 1H-pyrrolo[2,3-b]pyridine-4-methanamine (177 mg, 1.2 mmol) and DA-200 (325 mg, 1.0 mmol) in DMF (5 mL) DIPEA (142 mg, 1.1 mmol) was added. Mixture was stirred for 2 days. Mixture was diluted with AcOEt and washed 3× with saturated aqueous solution of NaHCO₃, once with brine and dried with sodium sulfate. Solvent was removed in vacuo to give yellowish solid. It was purified by MPLC (silica, 0-10% MeOH in DCM) to give white solid.

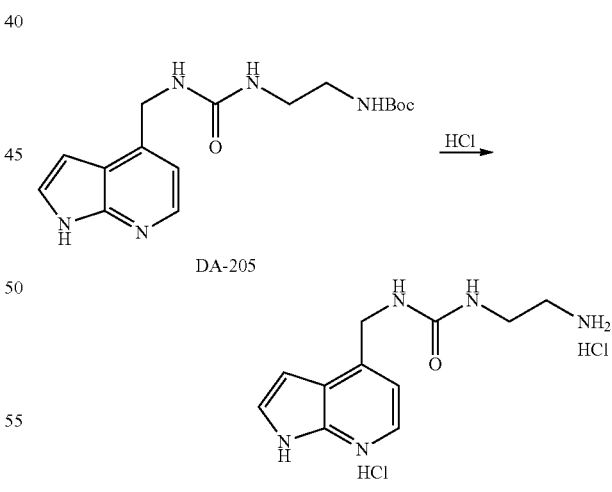

DA-205 (228 mg, 0.684 mmol) was dissolved in MeOH saturated with HCl (5 mL). After a few minutes white crystals separated. Mixture was stirred for 1 h and solvent was removed in vacuo. Residual oil was dissolved in small volume of MeOH and kept until crystallization started. It was diluted with diethyl ether, crystals were filtered off, washed with ether and dried in vacuo to give yellowish powder.

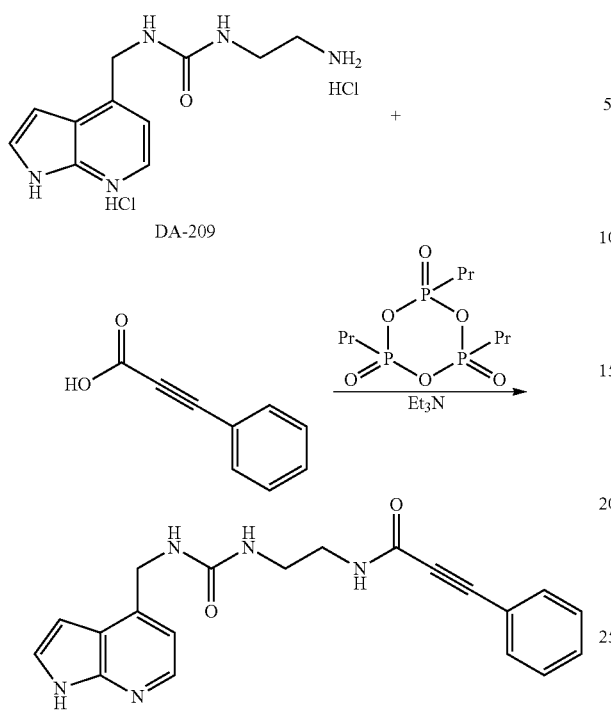

DA-209

Example 16

To a solution of DA-209 (50 mg, 0.163 mmol) and 3-phenylpropiolic acid (26 mg, 0.180 mmol) in DMF (3 mL) TEA (83 mg, 0.816 mmol) followed by PPA (50% solution in AcOEt, 125 mg, 0.196 mmol) was added. Pale violet solution was stirred overnight, diluted with AcOEt, washed 3× with brine, dried with sodium sulfate and the solvent was removed in vacuo to give solid. It was purified by MPLC (silica, 0-10% MeOH in DCM) to give white solid.

1H NMR (400 MHz, DMSO-d6): 11.59 (s, 1H), 8.81 (t, 1H), 8.13 (d, 1H), 7.58-7.38 (m, 6H), 6.92 (d, 1H), 6.58 (t, 1H), 6.53 (m, 1H), 6.15 (t, 1H), 4.50 (d, 2H), 3.17 (m, 4H)

Example 17

N-(3-(3-((1H-pyrrolo[2,3-b]pyridin-4-yl)methyl)ureido)propyl)-3-phenylpropiolamide (E17)

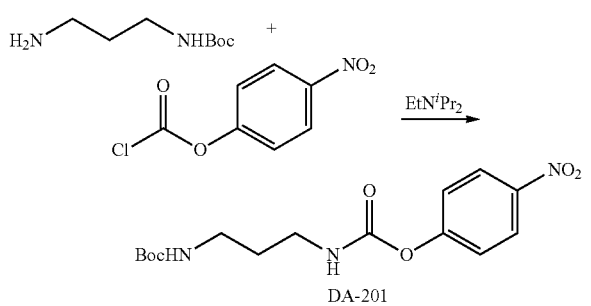

DA-201

To a solution of tert-butyl(3-aminopropyl)carbamate (871 mg, 5 mmol) and 4-nitrophenyl chloroformate (1.008 g, 5 mmol) in THF (20 mL) DIPEA in THF (5 mL) was added. Mixture warmed up slightly and after several minutes white crystals precipitated. Mixture was stirred for 3 days and diluted with AcOEt, washed 2× with sat. NaHCO₃, brine, 0.1 M citric acid, brine and dried with sodium sulfate. Solvent was removed in vacuo to give yellowish solid. It was purified by MPLC (silica, 0-10% MeOH in DCM) to give yellowish powder.

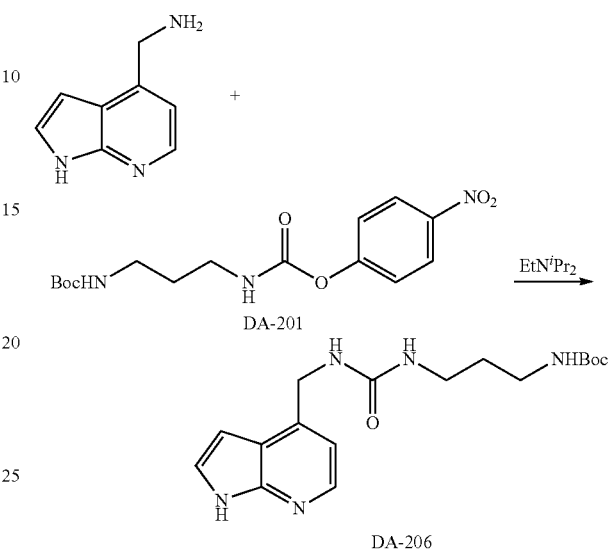

DA-206

To a solution of 1H-pyrrolo[2,3-b]pyridine-4-methanamine (177 mg, 1.2 mmol) and DA-200 (339 mg, 1.0 mmol) in DMF (5 mL) DIPEA (142 mg, 1.1 mmol) was added. Mixture was stirred for 2 days. Mixture was diluted with AcOEt and washed 3× with saturated aqueous solution of NaHCO₃, once with brine and dried with sodium sulfate. Solvent was removed in vacuo to give yellowish solid. It was purified by MPLC (silica, 0-10% MeOH in DCM) to give white solid.

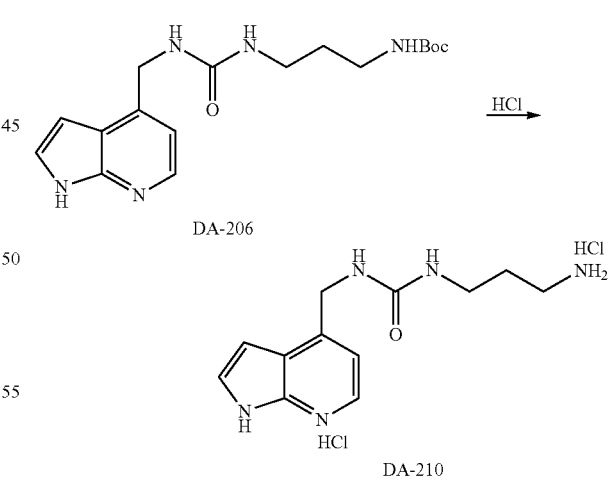

DA-210

DA-206 (229 mg, 0.684 mmol) was dissolved in MeOH saturated with HCl (5 mL). After a few minutes white crystals separated. Mixture was stirred for 1 h and solvent was removed in vacuo. Residual oil was dissolved in small volume of MeOH and kept until crystallization started. It was diluted with diethyl ether, crystals were filtered off, washed with ether and dried in vacuo to give yellowish powder.

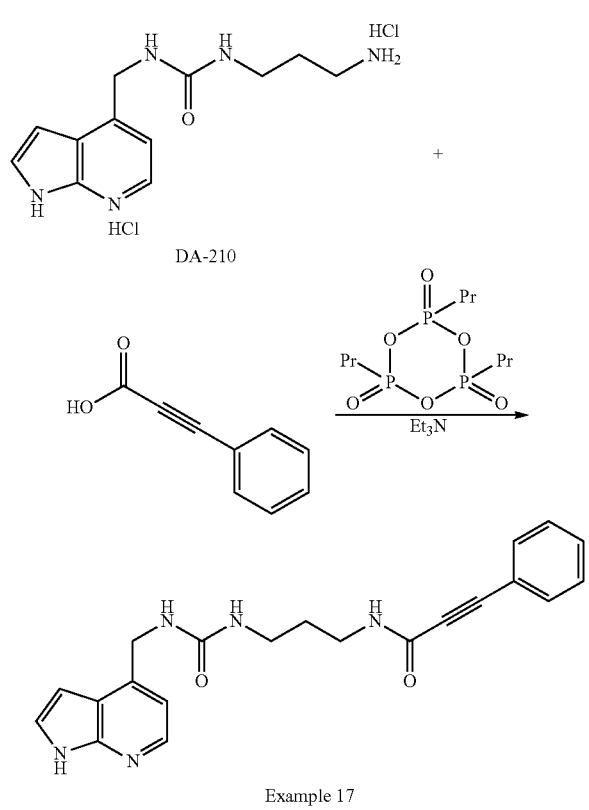

DA-210

To a solution of DA-210 (50 mg, 0.156 mmol) and 3-phenylpropiolic acid (25 mg, 0.172 mmol) in DMF (3 mL) TEA (79 mg, 0.781 mmol) followed by PPA (50% solution in AcOEt, 119 mg, 0.187 mmol) was added. Pale violet solution was stirred overnight, diluted with AcOEt, washed 3× with brine, dried with sodium sulfate and the solvent was removed in vacuo to give solid. It was purified by MPLC (silica, 0-10% MeOH in DCM) to give white solid.

1H NMR (400 MHz, DMSO-d6): 11.59 (s, 1H), 8.76 (t, 1H), 8.13 (d, 1H), 7.58-7.40 (m, 6H), 6.91 (d, 1H), 6.53 (m, 1H), 6.50 (t, 1H, 6.06 (t, 1H), 4.48 (d, 2H), 3.15 (m, 2H), 3.07 (m, 2H), 1.57 (m, 2H)

Example 18

N-((1H-pyrrolo[2,3-b]pyridin-4-yl)methyl)-4-(3-phenylpropiolamido)butanamide (E18)

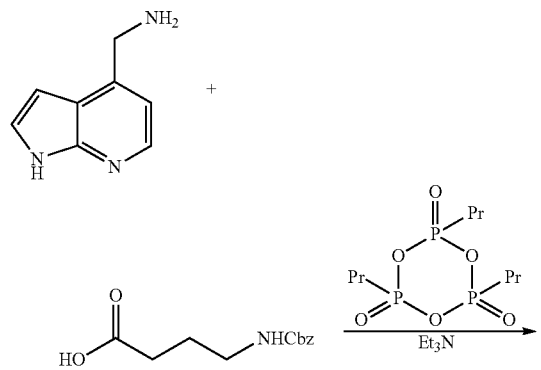

To a solution of 1H-pyrrolo[2,3-b]pyridine-4-methanamine (162 mg, 1.1 mmol) and N-Cbz-4-aminobutyric acid (237 mg, 1.0 mmol) in DMF (5 mL) TEA (304 mg, 3.0 mmol) followed by PPA (50% solution in AcOEt, 764 mg, 1.2 mmol) was added. Orange solution was stirred for 3 h, diluted with AcOEt, washed 2× with sat. NaHCO₃, once with brine, dried with sodium sulfate and the solvent was removed in vacuo to give pinkish solid. It was purified by MPLC (silica, 0-10% MeOH in DCM) to give beige solid.

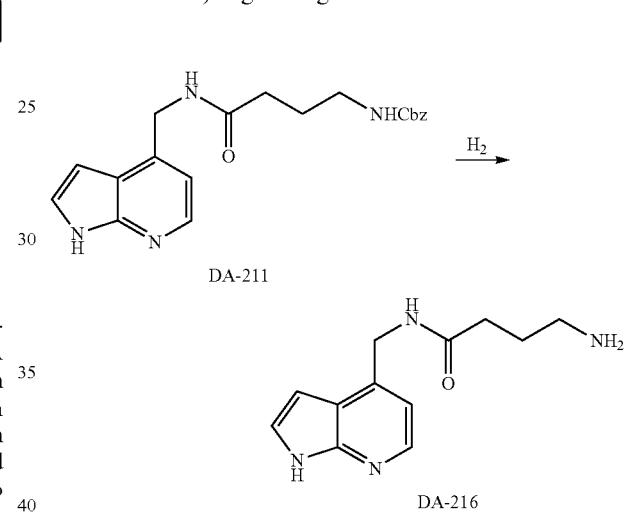

A suspension of DA-211 (170 mg, 0.464 mmol) and 10% Pd/C (170 mg) in MeOH (100 mL) was hydrogenated on Parr shaker overnight at 60 psi. Catalyst was filtered off and solvent was removed from filtrate in vacuo to give colorless oil.

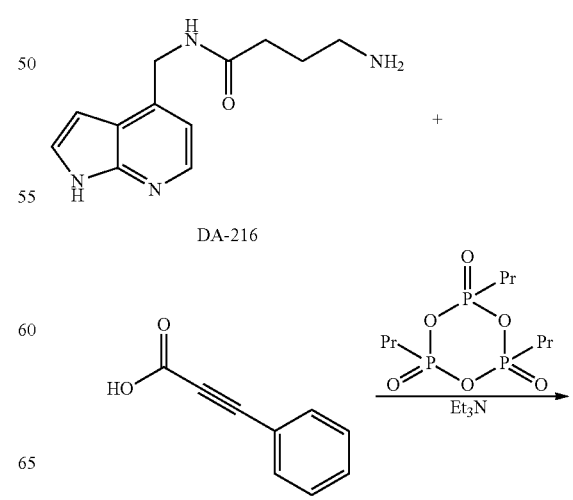

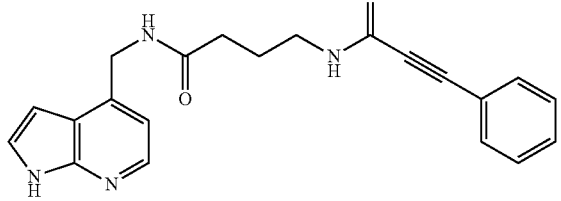

Example 18

To a solution of DA-216 (92 mg, 0.396 mmol) and 3-phenylpropiolic acid (64 mg, 0.436 mmol) in DMF (3 mL) TEA (120 mg, 1.188 mmol) followed by PPA (50% solution in AcOEt, 302 mg, 0.475 mmol) was added. Pale violet solution was stirred overnight, diluted with AcOEt, washed 3× with brine, dried with sodium sulfate and the solvent was removed in vacuo to give brownish solid. It was purified by MPLC (silica, 0-10% MeOH in DCM) to give colorless glass.

1H NMR (400 MHz, MeOH-d4): 8.13 (d, 1H), 7.56-7.52 (m, 2H), 7.46-7.36 (m, 4H), 7.02 (d, 1H), 6.58 (d, 1H), 4.69 (s, 2H), 3.31 (t, 2H), 2.35 (t, 2H), 1.89 (m, 2H)

Example 19

N-(3-(3-(((1H-pyrrolo[2,3-b]pyridin-4-yl)methyl)amino)-3-oxopropyl)phenyl)-3-phenylpropiolamide (E19)

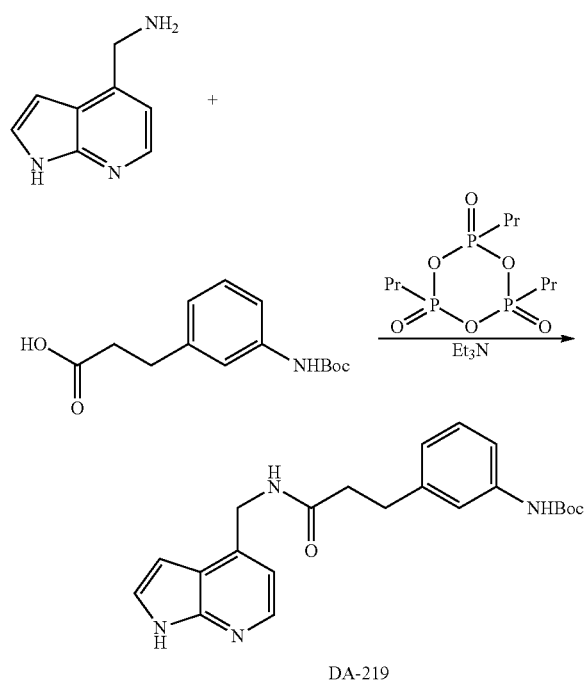

To a solution of 1H-pyrrolo[2,3-b]pyridine-4-methanamine (147 mg, 1.0 mmol) and 3-(3-((tert-butoxycarbonyl)amino)phenyl)propanoic acid (265 mg, 1.0 mmol) in DMF (5 mL) TEA (304 mg, 3.0 mmol) followed by PPA (50% solution in AcOEt, 764 mg, 1.2 mmol) was added. Orange mixture was stirred overnight, diluted with AcOEt, washed with sat. NaHCO₃, 2× with brine and dried with sodium sulfate. Solvent was removed in vacuo to give orange thick oil. It was purified by MPLC (silica, 0-10% MeOH in DCM) to give colorless thick oil.

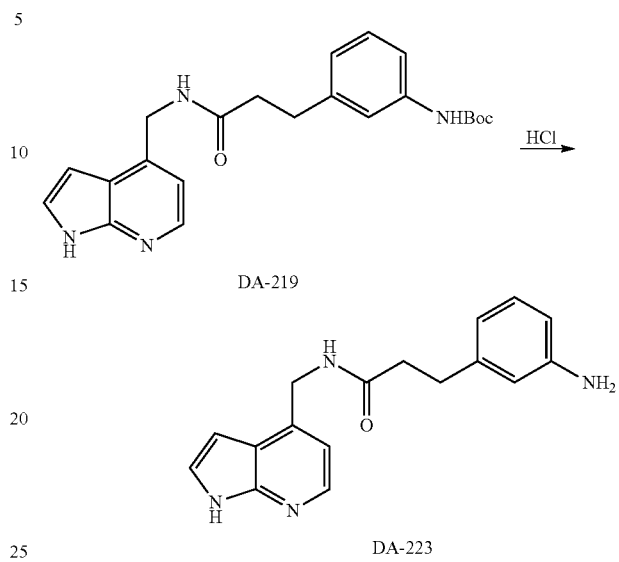

DA-219 (158 mg, 0.401 mmol) was dissolved in MeOH saturated with HCl (5 mL). Clear solution was stirred for 30 min. and solvent was removed in vacuo. Oily residue was dissolved in water, basified with NaHCO₃ and extracted 3× with AcOEt. Extracts were combined, washed with brine, dried with sodium sulfate and solvent was removed in vacuo to give almost white crystals.

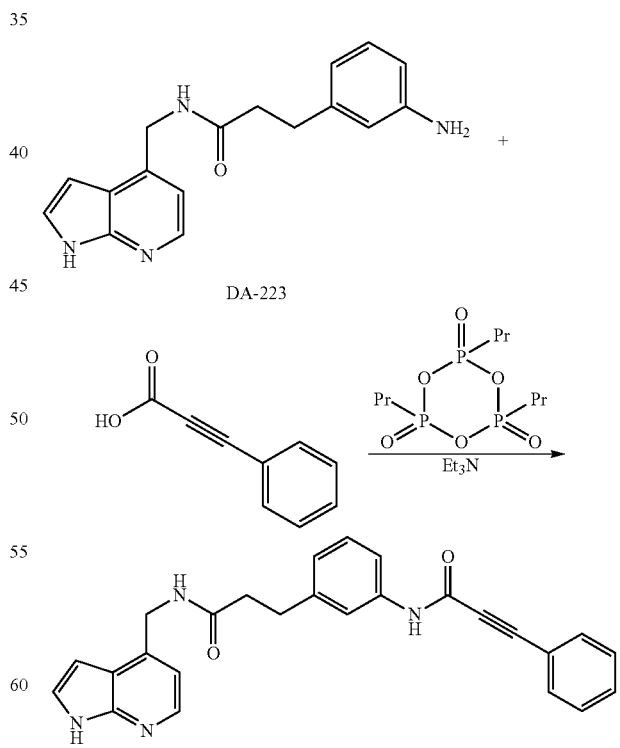

Example 19

To a solution of DA-223 (95 mg, 0.323 mmol) and 3-phenylpropiolic acid (94 mg, 0.645 mmol) in DMF (5 mL) TEA (196 mg, 1.936 mmol) followed by PPA (50% solution in AcOEt, 513 mg, 0.807 mmol) was added. Deep red solution was stirred overnight, diluted with AcOEt, washed 3× with brine, dried with sodium sulfate and the solvent was removed in vacuo to give brownish solid. It was purified by MPLC (silica, 0-10% MeOH in DCM) to give beige solid.

1H NMR (400 MHz, DMSO-d6): 11.59 (s, 1H), 10.81 (s, 1H), 8.43 (t, 1H), 8.08 (d, 1H), 7.68-7.62 (m, 2H), 7.56-7.46 (m, 5H), 7.40 (m, 1H), 7.28-7.12 (m, 2H), 6.98 (d, 1H), 6.71 (d, 1H), 6.47 (m, 1H), 4.52 (d, 2H), 2.85 (t, 2H), 2.49 (t, 2H)

Example 20

N-(2-(3-((1H-pyrrolo[2,3-b]pyridin-4-yl)methyl)ureido)ethyl)-N-methyl-3-phenylpropiolamide (E20)

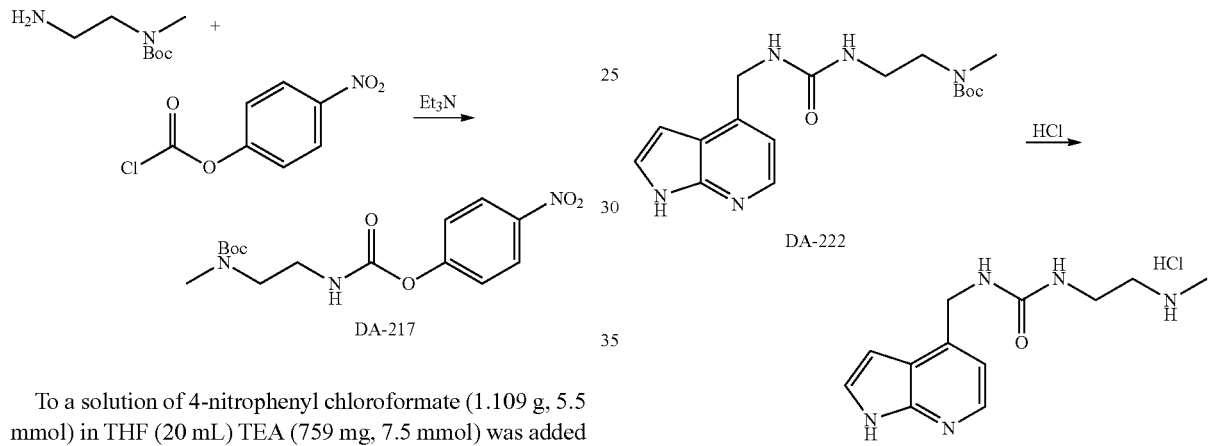

To a solution of 4-nitrophenyl chloroformate (1.109 g, 5.5 mmol) in THF (20 mL) TEA (759 mg, 7.5 mmol) was added (white solids precipitated) followed immediately with tert-butyl(2-aminoethyl)(methyl)carbamate (871 mg, 5.0 mmol) in THF (5 mL)M. Mixture boiled briefly and more solids precipitated). Yellowish suspension was stirred for 1 h. It was diluted with sat. NaHCO₃, yellow solution was extracted 3× with AcOEt, extracts were combined, washed with brine and dried with sodium sulfate. Solvent was removed in vacuo to give yellow thick oil which solidified on standing. It was purified by MPLC (silica, 0-10% MeOH in DCM) to yield thick yellowish oil which solidified on standing to give yellowish crystals.

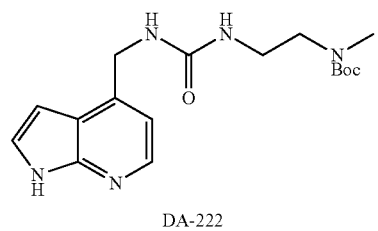

To a solution of 1H-pyrrolo[2,3-b]pyridine-4-methanamine (177 mg, 1.2 mmol) and DA-217 (339 mg, 1.0 mmol) in DMF (5 mL) TEA (152 mg, 1.5 mmol) was added and formed yellow solution was stirred for 3 days. Mixture was diluted with sat. NaHCO₃ and extracted 3× with AcOEt. Extracts were combined, washed with brine, dried with sodium sulfate and solvent was removed in vacuo to give yellowish semi-solid. It was purified by MPLC (silica, 0-10% MeOH in DCM) to give colorless oil.

DA-222 (214 mg, 0.616 mmol) was dissolved in MeOH saturated with HCl (5 mL). After a few minutes white crystals separated. Mixture was stirred for 20 min. and solvent was removed in vacuo to give almost colorless glass.

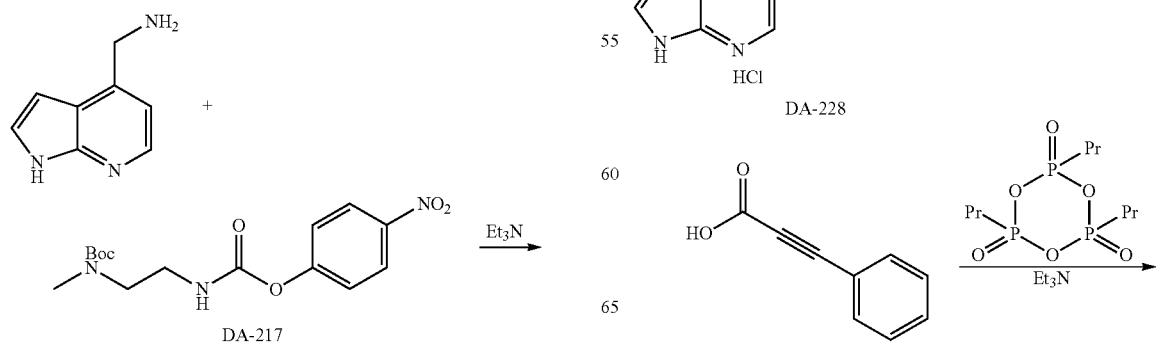

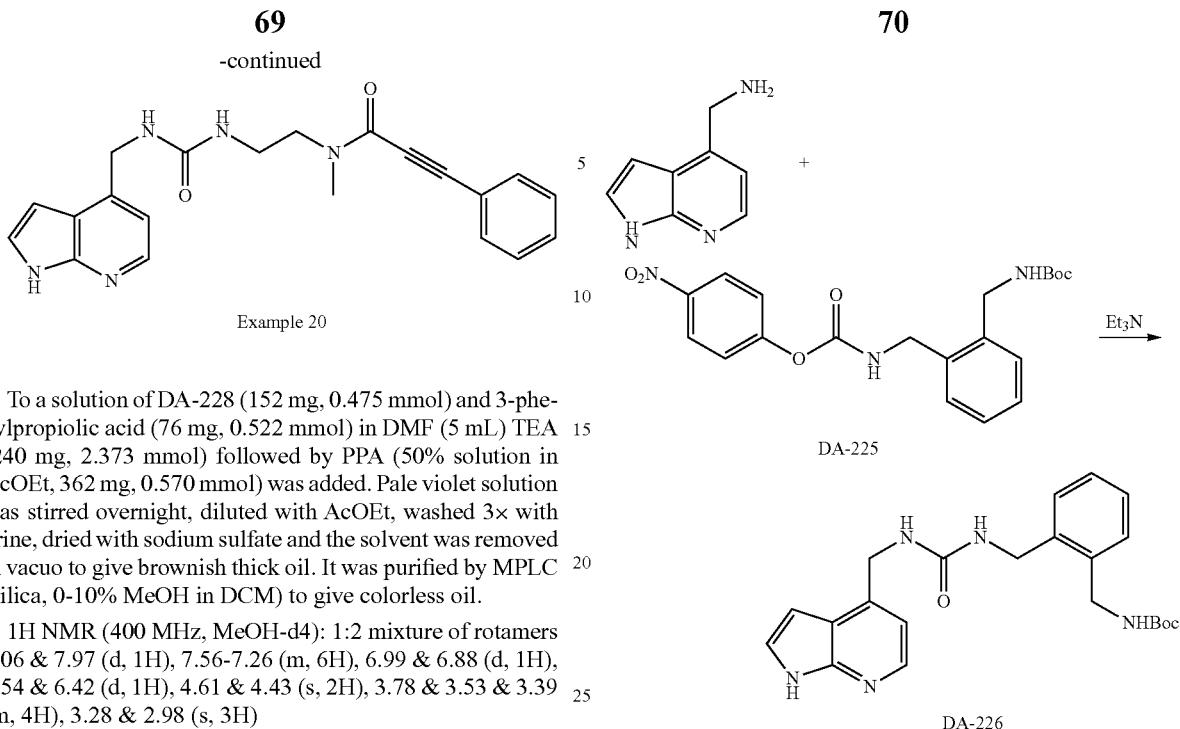

Example 20

To a solution of DA-228 (152 mg, 0.475 mmol) and 3-phenylpropiolic acid (76 mg, 0.522 mmol) in DMF (5 mL) TEA (240 mg, 2.373 mmol) followed by PPA (50% solution in AcOEt, 362 mg, 0.570 mmol) was added. Pale violet solution was stirred overnight, diluted with AcOEt, washed 3× with brine, dried with sodium sulfate and the solvent was removed in vacuo to give brownish thick oil. It was purified by MPLC (silica, 0-10% MeOH in DCM) to give colorless oil.

1H NMR (400 MHz, MeOH-d4): 1:2 mixture of rotamers 8.06 & 7.97 (d, 1H), 7.56-7.26 (m, 6H), 6.99 & 6.88 (d, 1H), 6.54 & 6.42 (d, 1H), 4.61 & 4.43 (s, 2H), 3.78 & 3.53 & 3.39 (m, 4H), 3.28 & 2.98 (s, 3H)

Example 21

N-(2-((3-((1H-pyrrolo[2,3-b]pyridin-4-yl)methyl)ureido)methyl)benzyl)-3-phenylpropiolamide (E21)

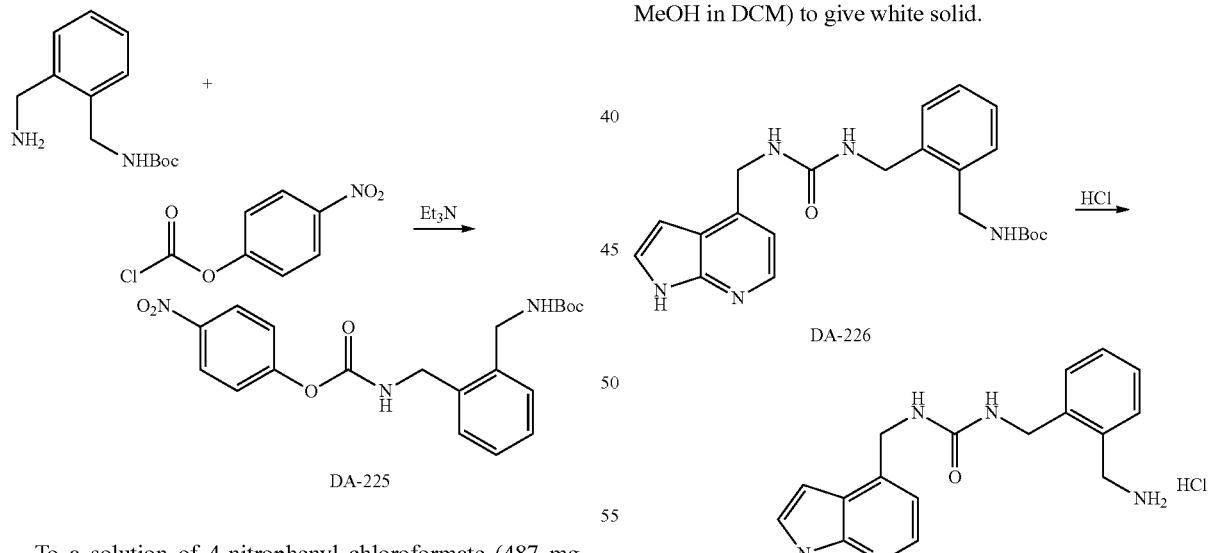

To a solution of 4-nitrophenyl chloroformate (487 mg, 2.416 mmol) in THF (10 mL) solution of tert-butyl 2-(aminomethyl)benzylcarbamate (519 mg, 2.196 mmol) and TEA (333 mg, 3.290 mmol) in THF (10 mL) was added (some solids precipitated). Yellowish suspension was stirred for 90 min. and was diluted with sat. NaHCO₃. Yellow solution was extracted 3× with AcOEt. Extracts were combined, washed with brine, 0.1 M citric acid, brine, dried with sodium sulfate and solvent was removed in vacuo to give light brown thick oil. It was purified by MPLC (silica, 0-10% MeOH in DCM) to give orange thick oil.

To a solution of 1H-pyrrolo[2,3-b]pyridine-4-methanamine (181 mg, 1.233 mmol) and DA-225 (450 mg, 1.121 mmol) in DMF (5 mL) TEA (170 mg, 1.682 mmol) was added and formed yellow solution was stirred for 3 days. Mixture was diluted with AcOEt, washed 3× with brine, dried with sodium sulfate and solvent was removed in vacuo to give yellowish solid. It was purified by MPLC (silica, 0-10% MeOH in DCM) to give white solid.

DA-226 (231 mg, 0.564 mmol) was dissolved in MeOH saturated with HCl (5 mL). After several minutes crystalline solid started to precipitate. After 1 h solvent was removed in vacuo, semisolid residue dissolved in MeOH and co-evaporated with toluene. This procedure was repeated 3× to give white solid.

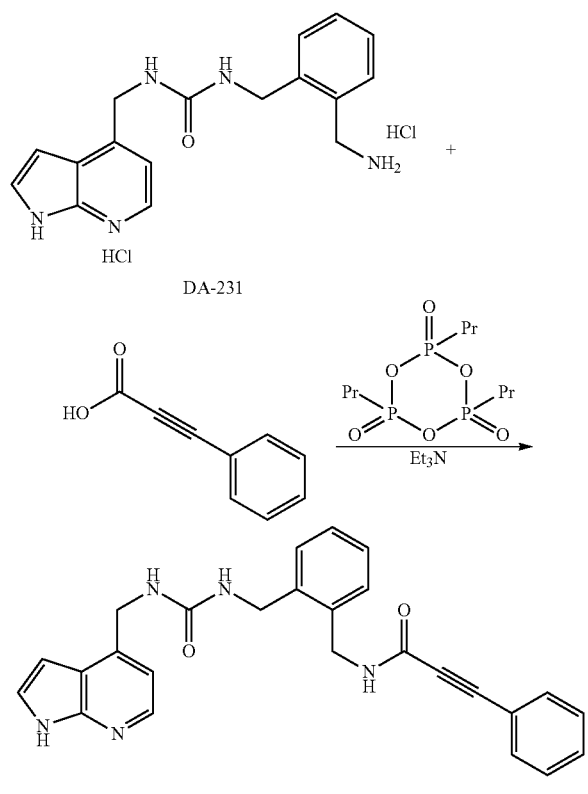

Example 21

To a solution of DA-231 (100 mg, 0.262 mmol) and 3-phenylpropiolic acid (42 mg, 0.288 mmol) in DMF (5 mL) TEA (132 mg, 1.308 mmol) followed by PPA (50% solution in AcOEt, 200 mg, 0.314 mmol) was added. Pinkish solution was stirred overnight, diluted with AcOEt, washed 3× with brine, dried with sodium sulfate and the solvent was removed in vacuo to give beige solid. It was purified by MPLC (silica, 0-10% MeOH in DCM) to give white solid.

1H NMR (400 MHz, DMSO-d6): 11.59 (s, 1H), 9.27 (t, 1H), 8.13 (d, 1H), 7.58-7.38 (m, 6H), 7.32-7.22 (m, 4H), 6.92 (d, 1H), 6.60-6.48 (m, 3H), 4.53 (d, 2H), 4.41 (d, 2H), 4.31 (d, 2H)

Example 22

N-(2-((3-((1H-pyrrolo[2,3-b]pyridin-4-yl)methyl)ureido)methyl)benzyl)but-2-ynamide (E22)

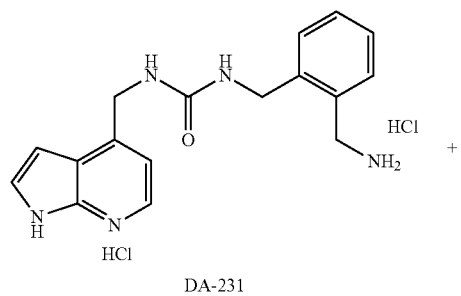

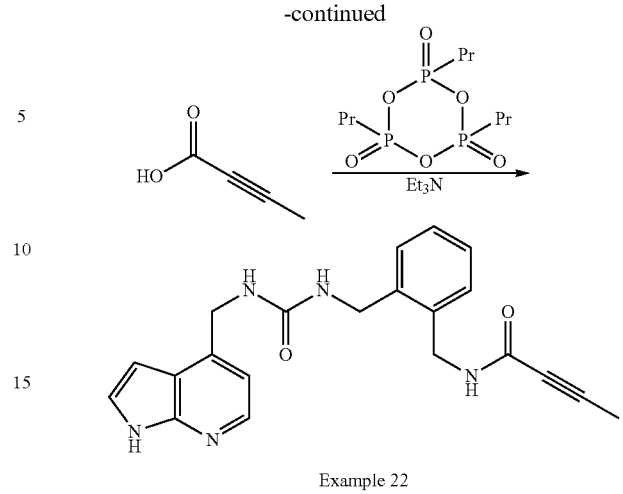

Example 22

To a solution of DA-231 (100 mg, 0.262 mmol) and but-2-ynoic acid (24 mg, 0.288 mmol) in DMF (5 mL) TEA (132 mg, 1.308 mmol) followed by PPA (50% solution in AcOEt, 200 mg, 0.314 mmol) was added. Orange solution was stirred overnight, diluted with AcOEt, washed 3× with brine, dried with sodium sulfate and the solvent was removed in vacuo to give beige solid. It was purified by MPLC (silica, 0-10% MeOH in DCM) to give white solid.

1H NMR (400 MHz, DMSO-d6): 11.59 (s, 1H), 8.95 (t, 1H), 8.13 (d, 1H), 7.44-7.41 (m, 1H), 7.28-7.16 (m, 4H), 6.92 (d, 1H), 6.56-6.52 (m, 2H), 6.46 (t, 1H), 4.52 (d, 2H), 4.31 (d, 2H), 4.27 (d, 2H), 1.95 (s, 3H)

Example 23

N-((1H-pyrrolo[2,3-b]pyridin-4-yl)methyl)-4-(3-phenylpropioloyl)piperazine-1-carboxamide (E23)

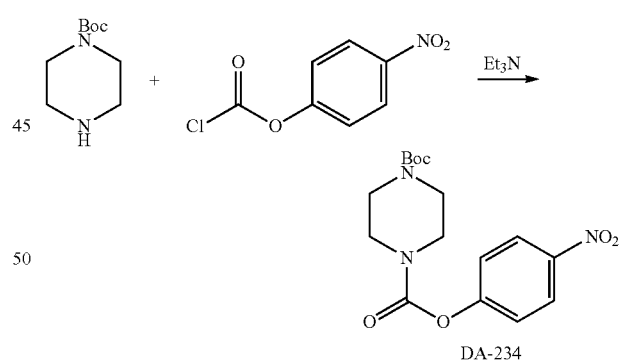

To a cooled in ice solution of 4-nitrophenyl chloroformate (1.109 g, 5.50 mmol) in THF (20 mL) solution of tert-butyl piperazine-1-carboxylate (931 mg, 5.0 mmol) and TEA (759 mg, 7.50 mmol) in THF (5 mL) was added during 20 min. Some white solids precipitated and later suspension turned yellow. Yellowish suspension was stirred at 0° C. for 20 min. Bath was removed and stirring was continued at r.t. for 20 min. Mixture was diluted with AcOEt, washed 2× with brine, 0.1 M citric acid, brine, dried with sodium sulfate and solvent was removed in vacuo to give white solid. Compound was still contaminated with about 15% of p-nitrophenol, but was used for the next step without any further purification.

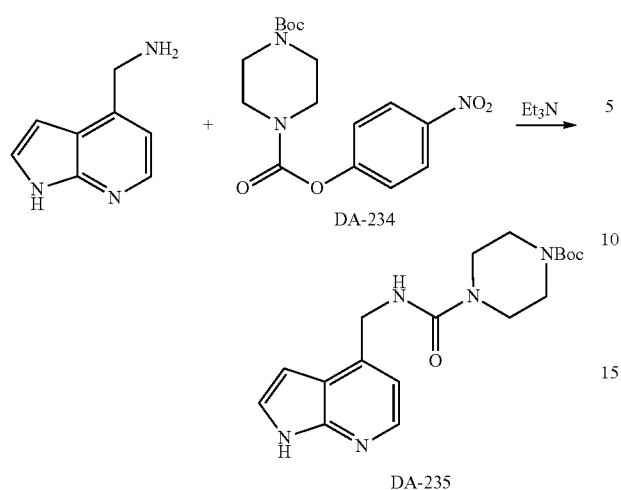

To a solution of 1H-pyrrolo[2,3-b]pyridine-4-methanamine (162 mg, 1.1 mmol) and DA-234 (413 mg, 1.0 mmol) in DMF (5 mL) TEA (202 mg, 2.0 mmol) was added and formed yellow solution was stirred for 5 days. Mixture was diluted with AcOEt, washed 3× with brine, dried with sodium sulfate and solvent was removed in vacuo to give yellowish solid. It was purified by MPLC (silica, 0-10% MeOH in DCM) to give white solid.

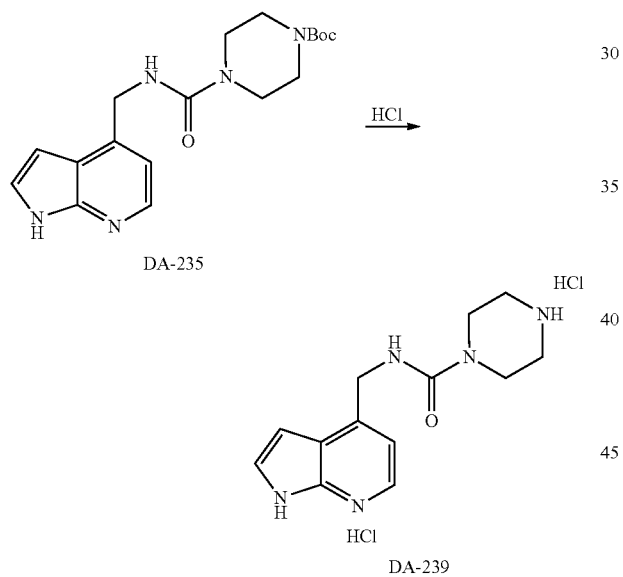

DA-235 (68 mg, 0.189 mmol) was dissolved in MeOH saturated with HCl (5 mL). After 1 h solvent was removed in vacuo, residue dissolved in MeOH and co-evaporated with toluene (3×) to give 59 mg of off-white powder.

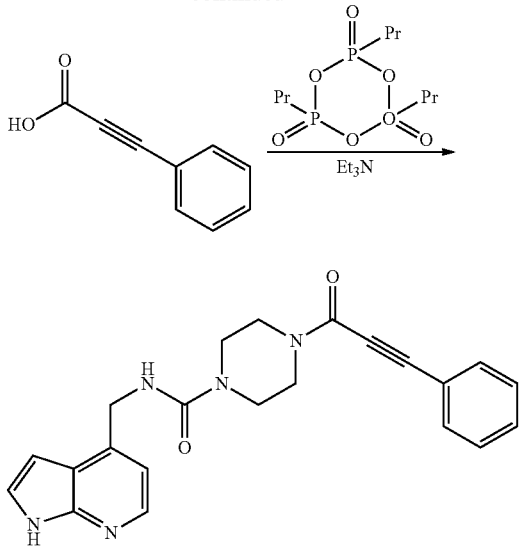

Example 23

To a solution of DA-239 (59 mg, 0.178 mmol) and 3-phenylpropiolic acid (52 mg, 0.355 mmol) in DMF (3 mL) TEA (180 mg, 1.776 mmol) followed by PPA (50% solution in AcOEt, 283 mg, 0.444 mmol) was added. Formed deep red solution was stirred overnight (it turned dark green), diluted with AcOEt, washed 3× with brine, dried with sodium sulfate and the solvent was removed in vacuo to give brown solid. It was purified by MPLC (silica, 0-10% MeOH in DCM) to give beige solid.

1H NMR (400 MHz, MeOH-d4): 8.13 (d, 1H), 7.62-7.58 (m, 2H), 7.51-7.36 (m, 4H), 7.03 (d, 1H), 6.61 (d, 1H), 4.71 (s, 2H), 3.89 (m, 2H), 3.69 (m, 2H), 3.60 (m, 2H), 3.52 (m, 2H)

Example 24

N-(3-((3-(((1H-pyrrolo[2,3-b]pyridin-4-yl)methyl)-2-nitroguanidino)methyl)phenyl)-3-phenylpropiolamide (E24)

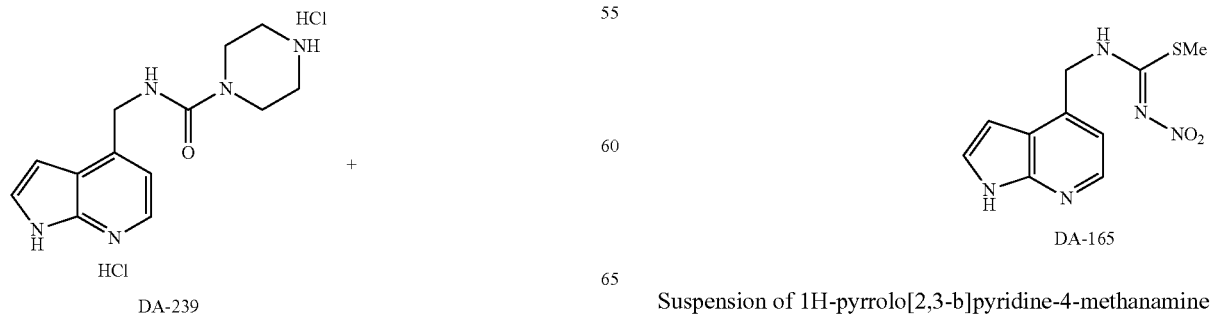

Suspension of 1H-pyrrolo[2,3-b]pyridine-4-methanamine (147 mg, 1.0 mmol) and dimethyl nitrocarbonimidodithioate (166 mg, 1.0 mmol) in THF (5 mL) was stirred overnight. After a few minutes starting materials dissolved and new solids precipitated. Suspension was stirred for 3 days. Solvent was removed in vacuo and pale yellow solid residue was boiled with small volume of MeOH. After cooling solids were filtered off, washed with MeOH and dried in vacuo to give white powder.

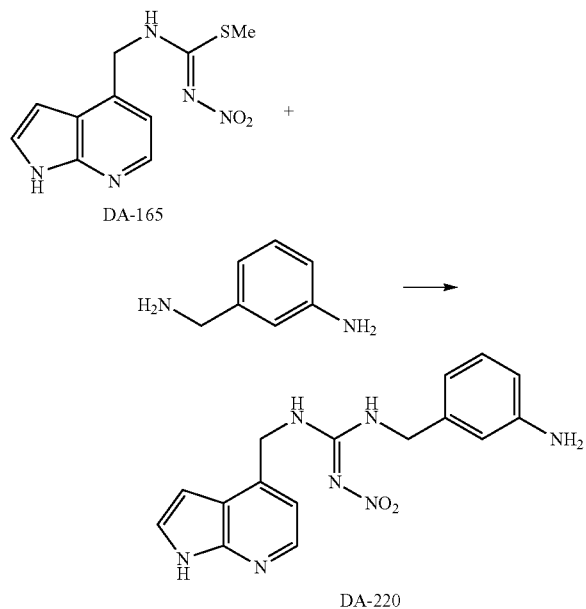

To a suspension of DA-165 (128 mg, 0.482 mmol) in DMF (1 mL) solution of 3-aminobenzylamine (71 mg, 0.579 mmol) in DMF (2 mL) was added. Everything dissolved. Straw yellow solution was stirred overnight at 60° C. (bath temp.) for 2 days. Pale orange mixture was diluted with AcOEt, washed once with water, 2× with brine and dried with sodium sulfate. Solvent was removed in vacuo to give yellowish semi-solid. It was purified by MPLC (silica, 0-10% MeOH in DCM) to give yellowish solid.

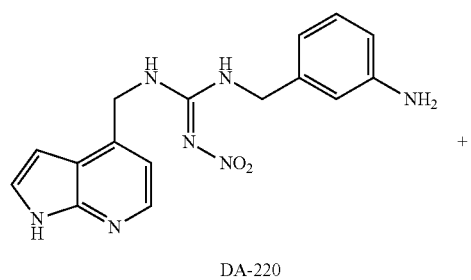

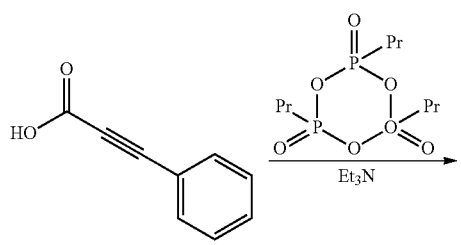

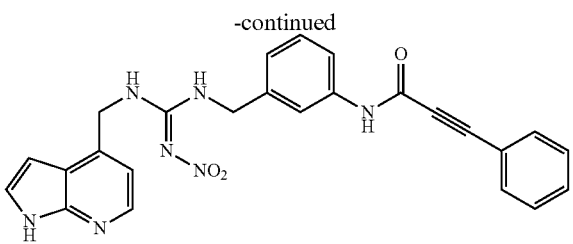

Example 24

To a solution of DA-220 (87 mg, 0.256 mmol) and 3-phenylpropiolic acid (75 mg, 0.513 mmol) in DMF (5 mL) TEA (156 mg, 1.538 mmol) followed by PPA (50% solution in AcOEt, 408 mg, 0.641 mmol) was added. Formed deep red solution was stirred for 3 h, diluted with AcOEt, washed 3× with brine, dried with sodium sulfate and the solvent was removed in vacuo to give dark solid. It was purified by MPLC (silica, 0-10% MeOH in DCM) to give off-white solid.

1H NMR (400 MHz, DMSO-d6): 11.68 (bs, 1H), 10.94 (bs, 1H), 9.77 (bs, 1H), 8.12 (bs, 1H), 7.70-7.40 (m, 7H), 7.40-6.60 (m, 5H), 6.52 (bs, 1H), 4.76 (bs, 2H), 4.53 (bs, 2H)

Example 25

N-(3-((3-((1H-pyrrolo[2,3-b]pyridin-4-yl)methyl)-2-(methylsulfonyl)guanidino)methyl)phenyl)-3-phenylpropiolamide (E25)

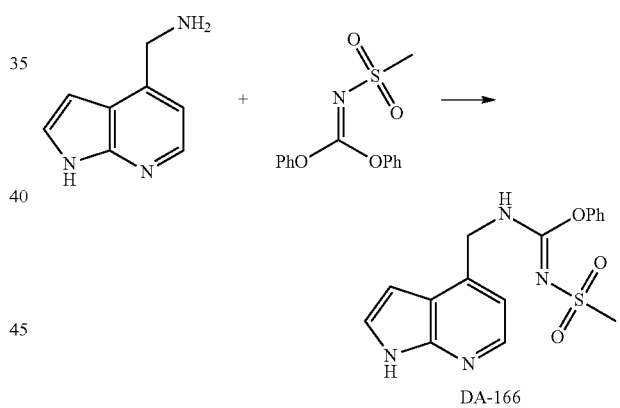

Suspension of (1H-pyrrolo[2,3-b]pyridin-4-yl)methanamine (147 mg, 1.0 mmol) and diphenyl methylsulfonylcarbonimidate (291 mg, 1.0 mmol) in THF (5 mL) was stirred for 4 days. Almost everything dissolved and after 3 h re-precipitated. Solvent was removed in vacuo and solid residue was purified by MPLC (silica, 0-10% MeOH in DCM) to give white solid.

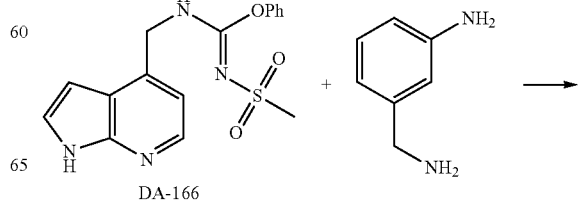

7.44 (t, 1H), 7.30 (t, 1H), 7.01 (bs, 1H), 6.83 (bs, 1H), 6.53 (m, 1H), 4.70 (bs, 2H), 4.43 (bs, 2H), 2.74 (s, 3H)

Example 26

1-((1H-pyrrolo[2,3-b]pyridin-4-yl)methyl)-3-(2-aminobenzyl)thiourea (E26)

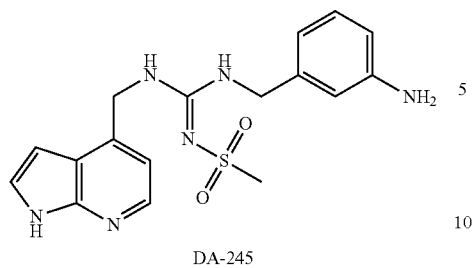

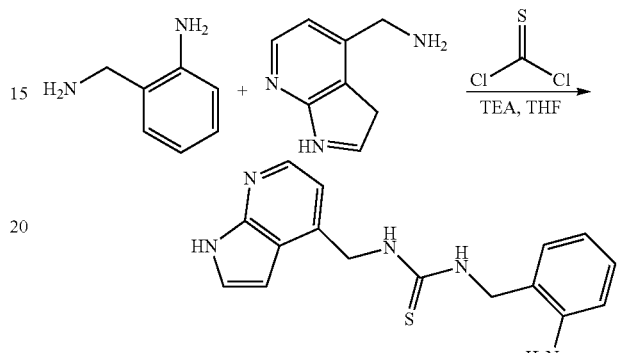

Example 26

Thiophosgene (115 uL, 1.50 mmol) was dissolved in THF (3 mL). In a separate vial, aminomethylazaindole (200 mg, 1.36 mmol) was dissolved in THF followed by the addition of TEA (228 uL, 1.20 mmol). The solution of compound 2 and TEA was then added to the vial containing thiophosgene. In another vial, 2-aminobenzylamine (199 mg, 1.63 mmol) and TEA (246 uL, 1.30 mmol) were dissolved in THF (2 mL). After the thiophosgene/azaindole mixture had been stirring for ~15 minutes, the solution of benzylamine was added. After stirring overnight, EtOAc (2 mL) was added and the resulting solution was washed three times with water (5 mL). The solvent was then stripped and the crude product purified via normal phase chromatography (DCM/MeOH, 0%→15%) to give the product as a white solid.

1H NMR (400 MHz, MeOH-d4) 8.11 (d, 1H), 7.38 (d, 1H), 7.05 (m, 3H), 6.74 (d, 1H), 6.67 (t, 1H), 6.62 (d, 1H), 5.10 (bs, 2H), 4.71 (bs, 2H)

Example 27

N-(3-((3-((1H-pyrrolo[2,3-b]pyridin-4-yl)methyl)thioureido)methyl)phenyl)acrylamide (E27)

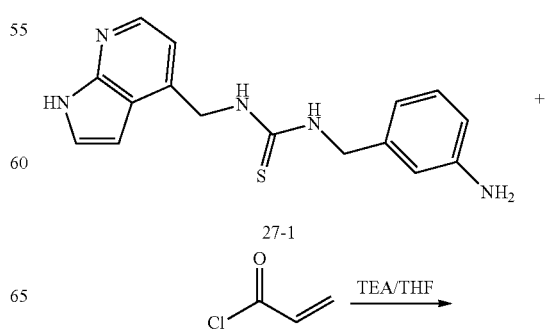

-continued

DA-245

Suspension of DA-166 (112 mg, 0.325 mmol) and 3-(aminomethyl)aniline (79 mg, 0.650 mmol) in IPA (5 mL) was MW irradiated (160° C., 1 h) to give pale yellow solution. Solvent was removed in vacuo and residue was purified by MPLC (silica, 0-10% MeOH in DCM) to give white foam.

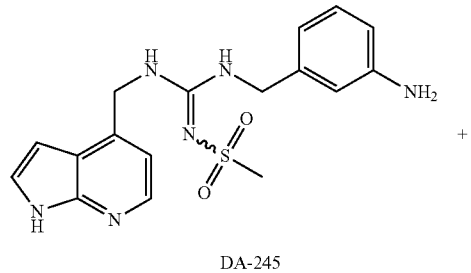

DA-245

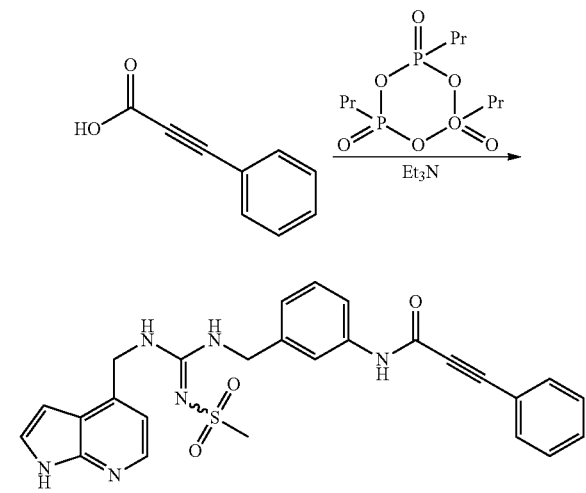

Example 25

To a solution of DA-245 (100 mg, 0.268 mmol) and 3-phenylpropiolic acid (78 mg, 0.537 mmol) in DMF (5 mL) TEA (163 mg, 1.611 mmol) followed by PPA (50% solution in AcOEt, 427 mg, 0.671 mmol) was added. Formed dark orange solution was stirred overnight (dark color faded), diluted with AcOEt, washed 3× with brine, dried with sodium sulfate and the solvent was removed in vacuo to give beige solid. It was purified by MPLC (silica, 0-10% MeOH in DCM) to give white solid.

1H NMR (400 MHz, DMSO-d6): 11.65 (s, 1H), 10.91 (s, 1H), 8.13 (bs, 1H), 7.68-7.65 (m, 4H), 7.60-7.48 (m, 4H),

-continued

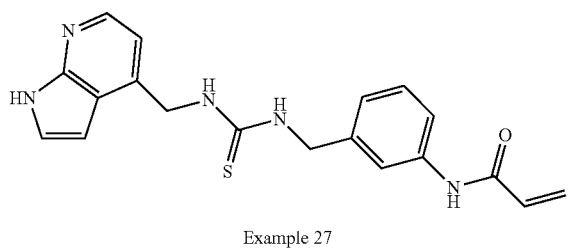

Example 27

Compound 27-1 (50 mg, 0.161 mmol) was dissolved in THF (1.5 mL) then TEA (34 uL, 0.241 mmol) was added followed by acryloyl chloride (13 uL, 0.161 mmol). After stirring for 30 minutes the solvent was removed in vacuo and the product isolated by normal phase chromatography (DCM/MeOH, 0%→10%).

1H NMR (400 MHz, MeOH-d4) 8.12 (d, 1H), 7.64 (s, 1H), 7.56 (d, 1H), 7.38 (d, 1H), 7.30 (t, 1H), 7.10 (d, 1H), 7.01 (bs, 1H), 6.63 (d, 1H), 6.42 (m, 2H), 5.79 (dd, 1H), 5.12 (bs, 2H), 4.78 (bs, 2H)

Example 28

N-(2-((3-(((1H-pyrrolo[2,3-b]pyridin-4-yl)methyl) thioureido)methyl)phenyl)acetamide (E28)

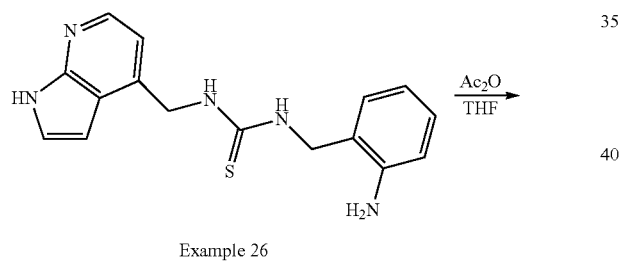

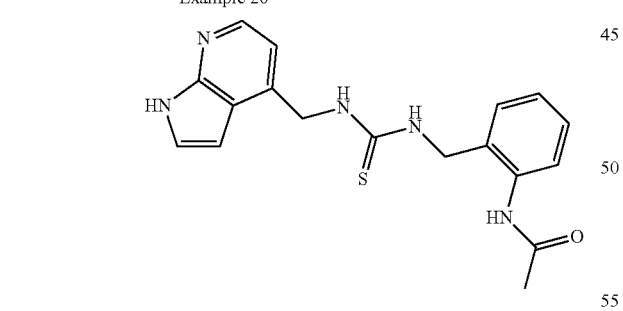

Example 28

Example 26 (50 mg, 0.161 mmol) was dissolved in THF (1.5 mL) then acetic anhydride (16.7 uL, 0.177 mmol) was added. After stirring overnight the solvent was removed in vacuo and the product isolated by normal phase chromatography (DCM/MeOH, 0%→10%).

1H NMR (400 MHz, MeOH-d4) 8.10 (d, 1H), 7.56 (bs, 1H), 7.37 (m, 2H), 7.30 (t, 1H), 7.12 (m, 1H), 6.95 (bs, 1H), 6.61 (d, 1H), 5.09 (bs, 2H), 4.80 (bs, 2H), 2.15 (s, 3H)

Example 29

N-(2-((3-(((1H-pyrrolo[2,3-b]pyridin-4-yl)methyl) thioureido)methyl)phenyl)acrylamide (E29)

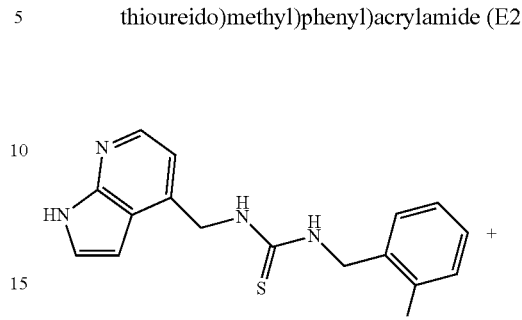

Example 26

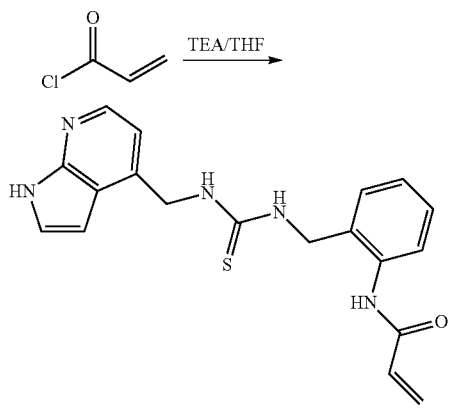

Example 29

Compound 1 (50 mg, 0.161 mmol) was dissolved in THF (1.5 mL) then TEA (34 uL, 0.241 mmol) was added followed by acryloyl chloride (13 uL, 0.161 mmol). After stirring for 30 minutes the solvent was removed in vacuo and the product isolated by normal phase chromatography (DCM/MeOH, 0%→10%).

1H NMR (400 MHz, MeOH-d4) 8.08 (d, 1H), 7.70 (bs, 1H), 7.37 (m, 2H), 7.32 (t, 1H), 6.96 (bs, 1H), 6.61 (d, 1H), 6.55 (m, 1H), 6.34 (m, 1H), 5.76 (d, 1H), 5.09 (bs, 2H), 4.82 (bs, 2H)

Example 30

1-((1H-pyrrolo[2,3-b]pyridin-4-yl)methyl)-3-(2-amino-5-nitrobenzyl)thiourea (E30)

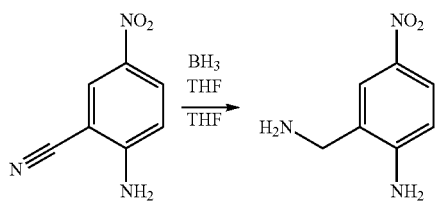

30-2

Borane in THF (40 ml, 40.0 mmol) is added dropwise to 2-amino-5-nitrobenzonitrile (6000 mg, 37 mmol) in THF (60 ml) at 0 DEG C. The mixture is allowed to warm to room temperature and is stirred for 16 hours. The resulting mixture is cooled to 0 DEG C and 20 ml of absolute ethanol that is saturated with HCl is added. After stirring for 2 h, diethyl ether (30 mL) is added and the product (30-2) removed via filtration.

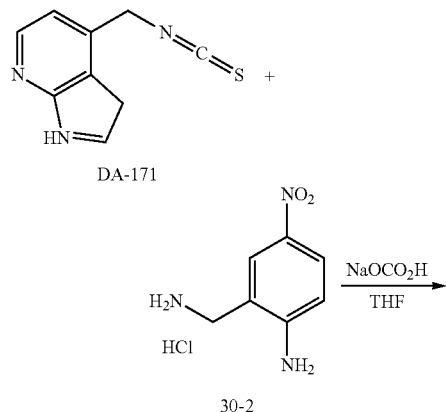

Compounds DA-171 (250 mg, 1.32 mmol) and 30-2 (269 mg, 1.32 mmol) were combined with sodium bicarbonate (2.77 mg, 3.30 mmol) and THF (4 mL) was added. The resulting mixture was stirred overnight, then the solvent was stripped in vacuo and the product isolated by normal phase chromatography (DCM/MeOH, 0%→15%).

1H NMR (400 MHz, MeOH-d4) 8.09 (d, 1H), 8.02 (s, 1H) 7.91 (dd, 1H), 7.34 (d, 1H), 7.01 (d, 1H), 6.65 (d, 1H), 6.59 (d, 1H), 5.07 (bs, 2H), 4.77 (bs, 2H)

Example 31

1-((1H-pyrrolo[2,3-b]pyridin-4-yl)methyl)-3-((1-(2-chloropyrimidin-4-yl)piperidin-3-yl)methyl)thiourea (E31)

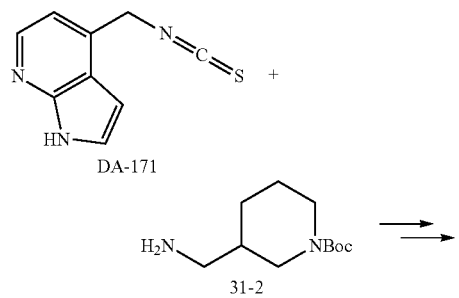

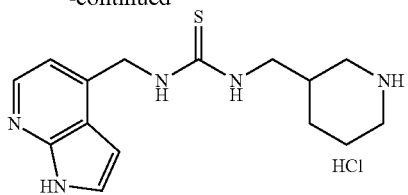

Compounds DA-171 (70 mg, 0.370 mmol) and 31-2 (79 mg, 0.370 mmol) were combined and THF (4 mL) was added. The resulting mixture was stirred overnight, then the solvent was stripped in vacuo and the boc protected product isolated by normal phase chromatography (DCM/MeOH, 0%→10%). The purified boc protected product was then dissolved in EtOH/HCl (5 mL) and the resulting solution stirred for 1 h. Diethyl ether (30 mL) was then added and the product collected by filtration as a white solid of 1-((1H-pyrrolo[2,3-b]pyridin-4-yl)methyl)-3-(piperidin-3-ylmethyl)thiourea.

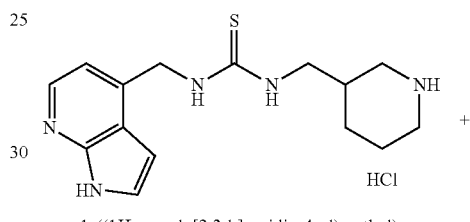

1-((1H-pyrrolo[2,3-b]pyridin-4-yl)methyl)-3-(piperidin-3-ylmethyl)thiourea

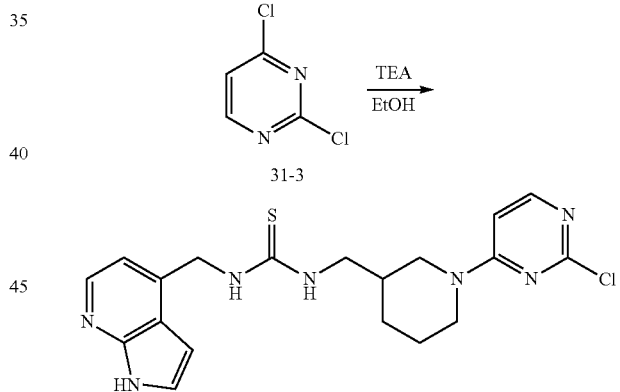

Example 31

1-((1H-pyrrolo[2,3-b]pyridin-4-yl)methyl)-3-(piperidin-3-ylmethyl)thiourea (40 mg, 0.106 mmol) and 31-3 (17.4 mg, 0.117 mmol) were dissolved in EtOH (1 mL) and TEA (52 uL, 0.372 mmol) was added. The reaction mixture was then heated to reflux overnight. EtOAc (2 mL) was added and the reaction extracted 3 times with water (2 mL). The solvent was stripped in vacuo and the product isolated by normal phase chromatography (DCM/MeOH, 0%→15%). Two regioisomers were identified with the major isomer being the desired product Example 31.

1H NMR (400 MHz, MeOH-d4) 8.11 (d, 1H), 7.88 (d, 1H), 7.34 (d, 1H), 7.03 (d, 1H), 6.62 (d, 1H), 6.54 (bs, 1H), 5.05 (bs, 2H), 4.19 (bs, 2H), 3.48 (bs, 2H), 3.03 (t, 1H), 2.83 (t, 1H), 1.85 (m, 2H), 1.75 (m, 1H), 1.46 (m, 1H), 1.31 (m, 1H)

Example 32

1-((1H-pyrrolo[2,3-b]pyridin-4-yl)methyl)-3-(2-amino-5-(trifluoromethyl)benzyl)thiourea (E32)

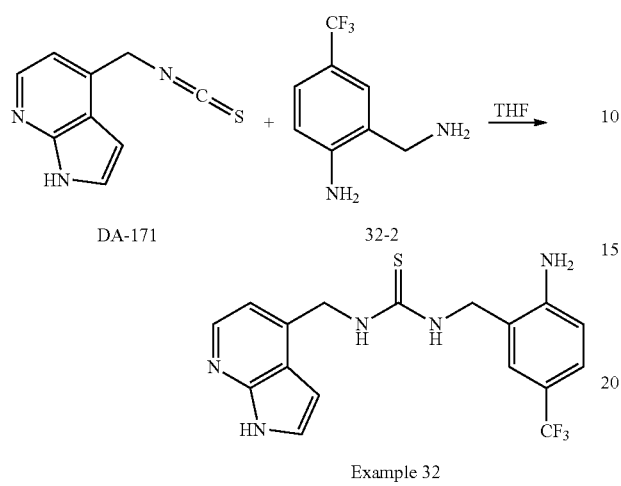

Example 32

Compounds DA-171 (60 mg, 0.317 mmol) and 32-2 (66 mg, 0.349 mmol) were dissolved in THF and stirred overnight. The solvent was then stripped in vacuo and the product isolated by normal phase chromatography (DCM/MeOH, 0%→10%).

1H NMR (400 MHz, MeOH-d4) 8.08 (d, 1H), 7.33 (m, 2H), 7.24 (d, 1H), 6.99 (d, 1H), 6.73 (d, 1H), 6.59 (d, 1H), 5.07 (bs, 2H), 4.75 (bs, 2H)

Example 33

N-(2-((3-((1H-pyrrolo[2,3-b]pyridin-4-yl)methyl)thioureido)methyl)-4-(trifluoromethyl)phenyl)acrylamide (E33)

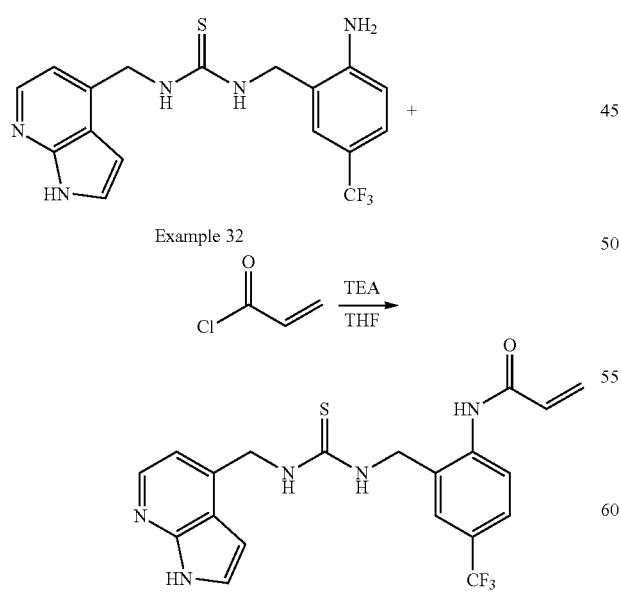

Example 33

Example 32 (47 mg, 0.124 mmol) was dissolved in THF (1.5 mL) then TEA (26 uL, 0.186 mmol) was added followed by acryloyl chloride (15 uL, 0.186 mmol). After stirring for 60 minutes EtOAc (2 mL) was added and the mixture washed three times with water (2 mL). The solvent was then removed in vacuo and the product isolated by normal phase chromatography (DCM/MeOH, 0%→10%).

1H NMR (400 MHz, DMSO-d6) 11.96 (s, 1H), 9.83 (s, 1H), 8.16 (m, 2H), 7.90 (d, 1H), 7.59 (d, 1H), 7.48 (nt, 1H), 7.23 (m, 1H), 6.98 (bs, 1H), 6.65 (m, 2H), 6.55 (m, 1H), 6.26 (m, 1H), 5.77 (dd, 1H), 5.03 (bs, 2H), 4.76 (bs, 2H)

Example 34

1-((1H-pyrrolo[2,3-b]pyridin-4-yl)methyl)-3-((1-(2-chloropyrimidin-4-yl)pyrrolidin-3-yl)methyl)thiourea (E34)

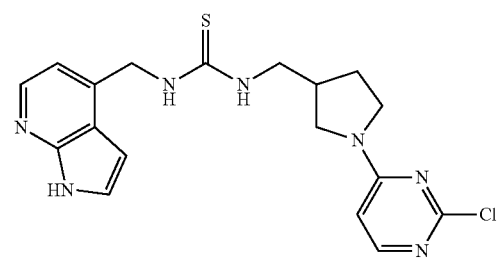

Example 34

Example 34 (E34) was prepared in the same manner described in the synthesis of Example 31 (E31).

1H NMR (400 MHz, MeOH-d4) 8.11 (d, 1H), 791 (d, 1H), 7.35 (d, 1H), 7.02 (d, 1H), 6.62 (d, 1H), 6.4-6.2 (m, 1H), 5.04 (bs, 2H), 3.78-3.35 (m, 5H), 3.11 (m, 1H), 2.65 (m, 1H), 2.03 (m, 1H), 1.76 (m, 1H)

Example 35

N-(3-((3-((1H-pyrrolo[2,3-b]pyridin-4-yl)methyl)thioureido)methyl)-5-(trifluoromethyl)phenyl)acrylamide (E35)

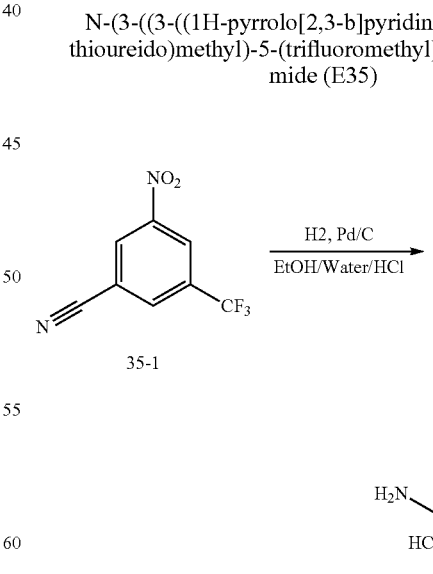

In a Parr shaker flask, compound 35-1 (1 g, 4.63 mmol) was dissolved in EtOH and concentrated HCl (2 mL) was added. The reaction mixture was flushed with nitrogen, Pd/C (0.5 g) was added and the reaction was placed on the Parr shaker at 45 psi hydrogen pressure overnight. The solids were removed by filtration and the solids stripped in vacuo. The product was then taken up in MeOH (10 mL) and diethyl ether was added (100 mL). The product (35-2) was then isolated by filtration.

1H NMR (400 MHz, MeOH-d4) 8.08 (d, 1H), 7.96 (s, 1H), 7.77 (s, 1H), 7.35 (s, 1H), 7.33 (d, 1H), 6.99 (d, 1H), 6.58 (d, 1H), 6.39 (m, 2H), 5.79 (dd, 1H), 5.08 (bs, 2H), 4.83 (bs, 2H)

Example 36

N-(3-((3-((1H-pyrrolo[2,3-b]pyridin-4-yl)methyl)thioureido)methyl)phenyl)-3-bromopropanamide (E36)

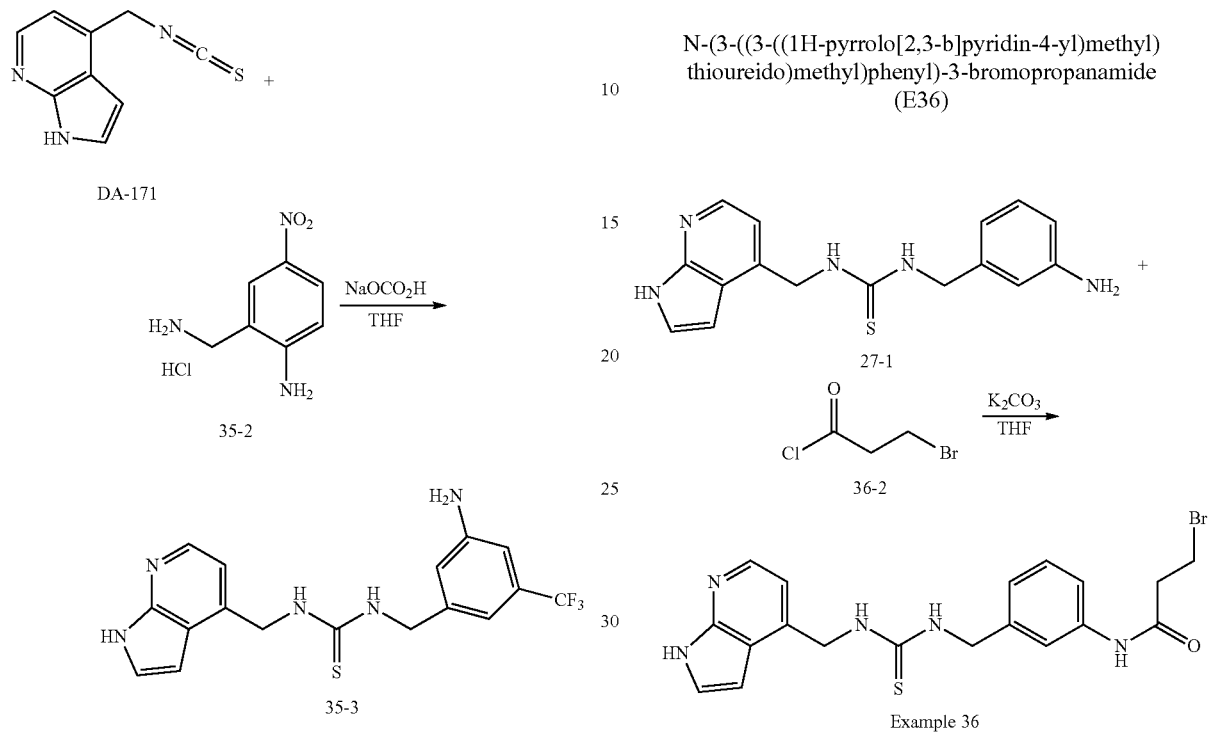

1-((1H-pyrrolo[2,3-b]pyridin-4-yl)methyl)-3-(3-amino-5-(trifluoromethyl)benzyl)thiourea was synthesized in the same manner as described in the synthesis of Example 30 (E30) using 35-3 in place of 30-2.

Compound 27-1 (75 mg, 0.241 mmol) was dissolved in THF (2 mL). Potassium Carbonate (67 mg, 0.482 mmol) was then added followed by compound 36-2 (41 mg, 0.241 mmol). The mixture was stirred for 1 h then the solvent was stripped in vacuo and the product purified by normal phase chromatography (DCM/MeOH, 0%→10%).

1H NMR (400 MHz, MeOH-d4) 8.09 (d, 1H), 7.53 (s, 1H), 7.43 (d, 1H), 7.34 (d, 1H), 7.24 (t, 1H), 7.04 (d, 1H), 6.97 (bs, 1H), 6.58 (d, 1H), 5.08 (bs, 2H), 4.72 (bs, 2H), 3.69 (t, 2H), 2.95 (t, 2H)

Example 37 methyl(2-((3-((1H-pyrrolo[2,3-b]pyridin-4-yl)methyl)thioureido)methyl)phenyl)carbamate (E37)

Example 35 (E35) was synthesized in the same manner as described in the synthesis of Example 29 (E29) using 35-3 in place of E26.

87
-continued

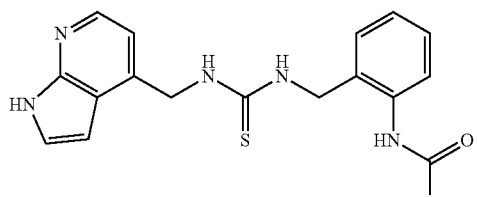

Example 37

Example 26 (50 mg, 0.161 mmol) was dissolved in THF (1.5 mL). Triethylamine (22.4 uL, 0.161 mmol) was then added followed by methyl chloroformate (12.4 uL, 0.161 mmol). The reaction was stirred overnight then EtOAc (2 mL) was added and the mixture washed three times with water (2 mL). The solvent was then stripped in vacuo and the product purified by normal phase chromatography (DCM/MeOH, 0%→10%).

1H NMR (400 MHz, MeOH-d4) 8.15 (d, 1H), 7.49 (d, 1H), 7.37 (m, 1H), 7.27 (d, 1H), 7.19 (m, 2H), 7.07 (m, 1H), 6.79 (d, 1H), 5.13 (bs, 2H), 4.64 (bs, 2H), 3.62 (s, 3H)

Example 38

1-((7H-pyrrolo[2,3-d]pyrimidin-4-yl)methyl)-3-(2-amino-5-nitrobenzyl)thiourea (E38)

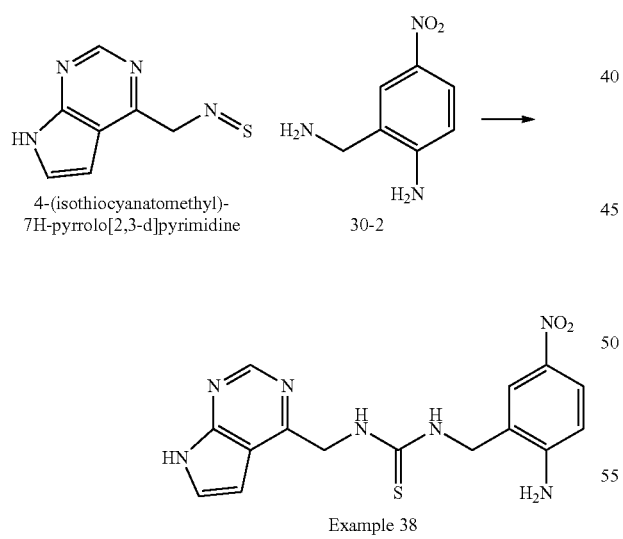

Example 38 (E38) was synthesized in the same manner as described in the synthesis of Example 30 (E30) using 4-(isothiocyanatomethyl)-7H-pyrrolo[2,3-d]pyrimidine in place of DA-171.

1H NMR (400 MHz, MeOH-d4) 8.78 (s, 1H), 7.94 (nd, 1H) 7.85 (dd, 1H), 7.65 (nd, 1H), 6.92 (s, 1H), 6.59 (d, 1H), 5.19 (bs, 2H), 4.65 (bs, 2H)

88

Example 39

N-(2-(((N-((1H-pyrrolo[2,3-b]pyridin-4-yl)methyl)sulfamoyl)amino)methyl)phenyl)acrylamide (E39)

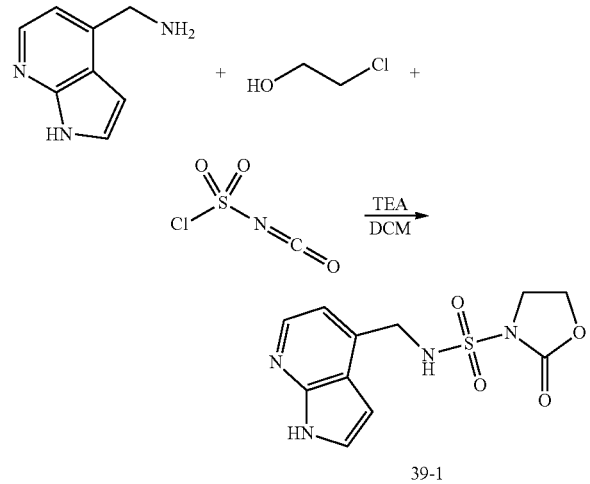

2-Chloroethanol (683 uL, 10.2 mmol) was added dropwise to a solution of chlorosulfonyl isocyanatein (887 uL, 10.2 mmol) in dichloromethane (10 mL) at −20 degrees C. The reaction mixture was warmed to 0 degrees C. and maintained at that temperature 1.5 h. The solution was then transferred to a suspension of aminomethylazaindole (1.50 g, 10.2 mmol) and triethylamine (5 mL, 36 mmol) in dichloromethane (15 mL) at −10 degrees C. The reaction mixture was then warmed to room temperature and stirred for 17 h under nitrogen. Water was added to the reaction mixture and the solids removed by filtration. The precipitate was washed with water to give the desired product 39-1.

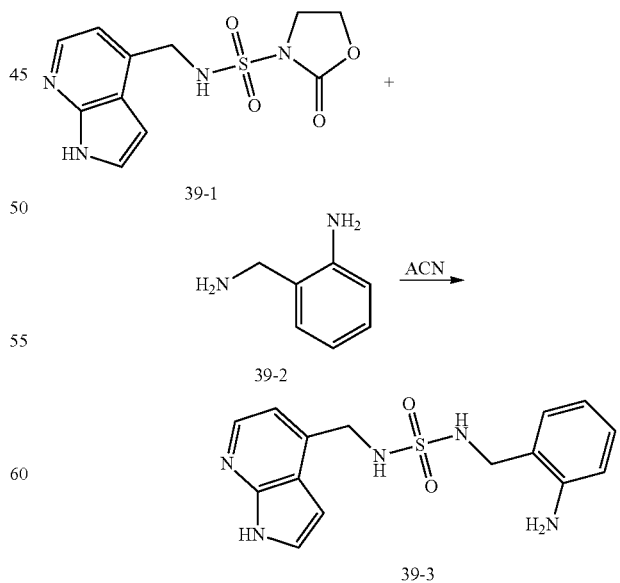

Compound 39-1 (600 mg, 2.03 mmol) and compound 39-2 (247 mg, 2.03 mmol) were combined and acetonitrile (5 mL)

was added forming a slurry. The mixture was heated to 70° C. for 16 h. The solvent was then stripped in vacuo and the product isolated by column chromatography (DCM/MeOH 0%→10%) to give compound 39-3.

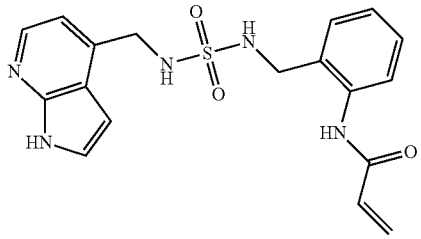

Example 39

Starting from compound 39-3, Example 39 (E39) was synthesized in the same manner as described in the synthesis of Example 29 (E29).

1H NMR (400 MHz, MeOH-d4) 8.18 (d, 1H), 7.52 (d, 1H), 7.42 (d, 1H), 7.38 (d, 1H), 7.28 (d, 1H), 7.22 (t, 1H), 7.11 (t, 1H), 6.81 (d, 1H), 6.29 (m, 2H), 5.70 (d, 1H), 4.45 (s, 2H), 4.06 (s, 1H)

Example 40

N-(3-(((N-((1H-pyrrolo[2,3-b]pyridin-4-yl)methyl)sulfamoyl)amino)methyl)phenyl)acrylamide (E40)

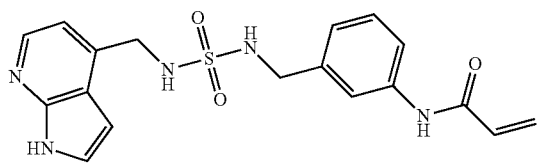

Example 40

Example 40 (E40) was synthesized in the same manner as described in the synthesis of Example 39 (E39) using as starting material 3-aminobenzylamine in place of 39-2.

1H NMR (400 MHz, MeOH-d4) 8.03 (d, 1H), 7.58 (s, 1H), 7.39 (d, 1H), 7.28 (d, 1H), 7.17 (t, 1H), 7.02 (d, 1H), 6.96 (d, 1H), 6.53 (d, 1H), 6.29 (m, 2H), 5.66 (dd, 1H), 4.32 (s, 2H), 4.03 (s, 1H)

Example 41

N-(3-((3-((1H-pyrrolo[2,3-b]pyridin-4-yl)methyl)thioureido)methyl)phenyl)-4-methoxybut-2-ynamide (E41)

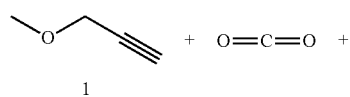

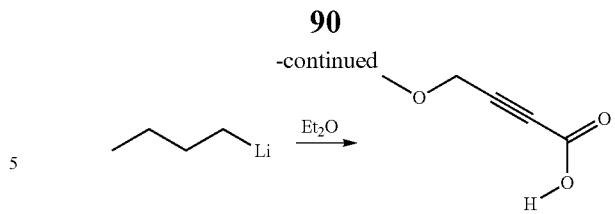

Dissolved compound 1 (2 mL, 23.6 mmol) in ether (20 mL) then cooled to −78° C. in a dry ice acetone bath. Added n-butyl lithium (13.3 mL, 21.2 mmol) and stirred for 10 min. Bubbled CO2 through the reaction for 30 min then warmed to room temp. Extracted with water (10 mL) and kept the aq. layer. Acidified the aq. layer then extracted twice with ether (15 mL). The organic extracts from the acidified water were combined and the solvent stripped in vacuo to give the product as light brown oil.

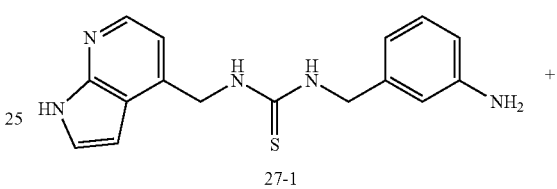

27-1

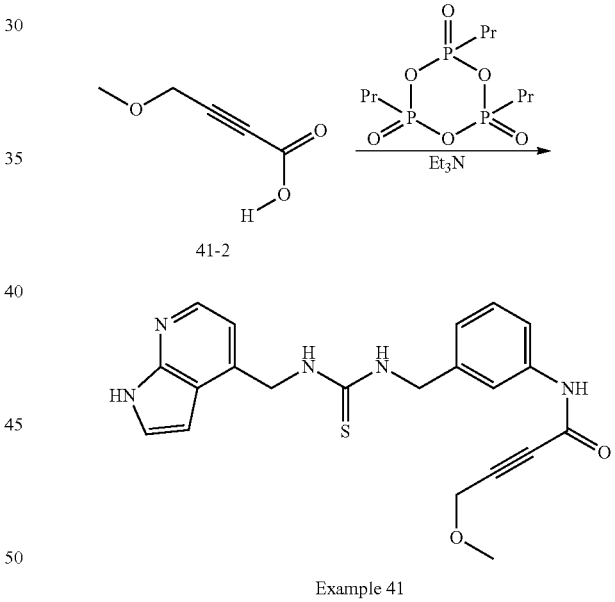

Example 41

Compound 27-1 (50 mg, 0.163 mmol) and compound 41-2 (20 mg, 0.179 mmol) in DMF (3 mL) TEA (82 mg, 0.815 mmol) followed by PPA (50% solution in AcOEt, 124 mg, 0.196 mmol) was added. The reaction was stirred overnight then diluted with AcOEt and washed three times with water. The solvent was then stripped in vacuo and the product purified by normal phase chromatography (DCM/MeOH, 0%→10%).

1H NMR (400 MHz, MeOH-d4) 8.01 (d, 1H), 7.47 (s, 1H), 7.37 (d, 1H), 7.27 (d, 1H), 7.18 (t, 1H), 6.99 (d, 1H), 6.89 (bs, 1H), 6.51 (d, 1H), 5.00 (bs, 2H), 4.65 (bs, 2H), 4.21 (s, 2H), 3.11 (s, 3H)

Example 42

N-(2-(((N-((1H-pyrrolo[2,3-b]pyridin-4-yl)methyl)sulfamoyl)amino)methyl)phenyl)but-2-ynamide (E42)

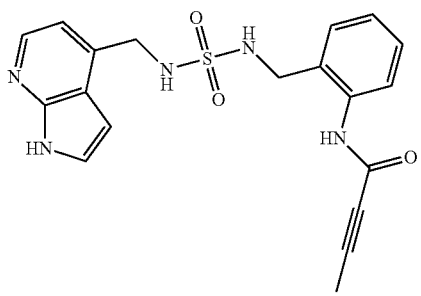

Example 42

Example 42 (E42) was synthesized in the same manner as described in the synthesis of Example 22 using 39-3 in place of DA-231.

1H NMR (400 MHz, MeOH-d4) 8.18 (d, 1H), 7.54 (d, 1H), 7.40 (d, 1H), 7.28 (m, 2H), 7.20 (t, 1H), 7.11 (t, 1H), 6.83 (d, 1H), 4.46 (s, 2H), 4.05 (s, 2H), 1.93 (s, 3H)

Example 43

N-(3-((N-((1H-pyrrolo[2,3-b]pyridin-4-yl)methyl)sulfamoyl)amino)phenyl)but-2-ynamide (E43)

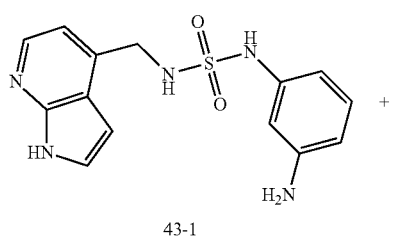

43-1

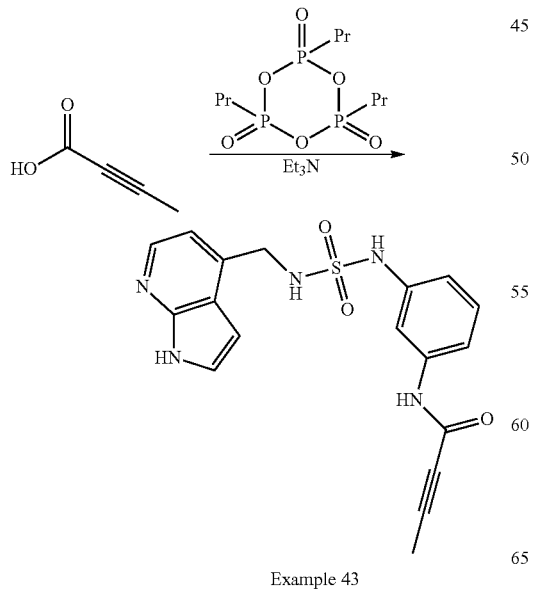

Example 43

Example 43 (E43) was synthesized in the same manner as described in the synthesis of Example 22, but using 43-1 in place of DA-231 as starting material.

1H NMR (400 MHz, MeOH-d4) 8.16 (d, 1H), 7.54 (d, 1H), 7.40 (s, 1H), 7.34 (d, 1H), 7.12 (t, 1H), 7.04 (d, 1H), 6.83 (m, 2H), 4.60 (s, 2H), 2.61 (s, 3H)

Example 44

N-(4-((N-((1H-pyrrolo[2,3-b]pyridin-4-yl)methyl)sulfamoyl)amino)phenyl)acrylamide (E44)

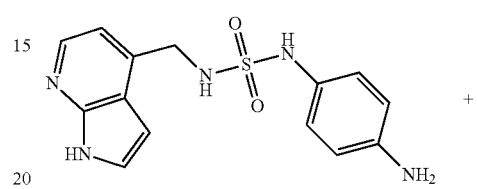

44-1

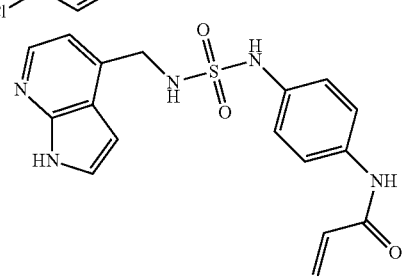

Example 44

Example 44 (E44) was synthesized in the same manner as described in the synthesis of Example 27 (E27), using 44-1 as starting material in place of 27-1.

1H NMR (400 MHz, MeOH-d4) 7.95 (d, 1H), 7.42 (d, 2H), 7.22 (d, 1H), 7.02 (d, 2H), 6.91 (d, 1H), 6.41 (d, 1H), 6.29 (m, 2H), 5.66 (m, 1H), 4.35 (s, 2H)

Example 45

N-(3-((N-((1H-pyrrolo[2,3-b]pyridin-4-yl)methyl)sulfamoyl)amino)phenyl)acrylamide (E45)

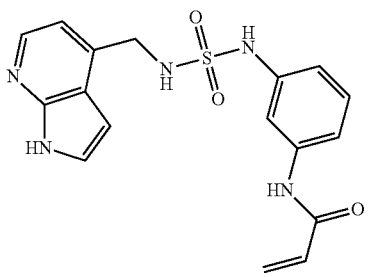

Example 45

Example 45 (E45) was synthesized in the same manner as described in the synthesis of Example 27 (E27), using 43-1 as starting material in place of 27-1.

1H NMR (400 MHz, MeOH-d4) 8.16 (d, 1H), 7.53 (m, 2H), 7.35 (d, 1H), 7.15 (m, 2H), 6.38 (m, 2H), 5.75 (dd, 1H), 4.61 (s, 2H)

Example 46

6-(3-((1H-pyrrolo[2,3-b]pyridin-4-yl)methyl)thioureido)-2-aminohexanoic acid (E46)

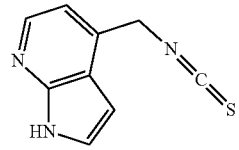

DA-171

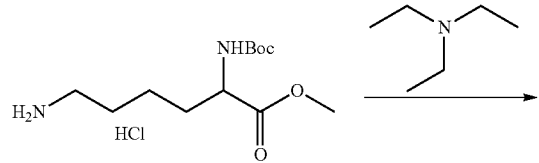

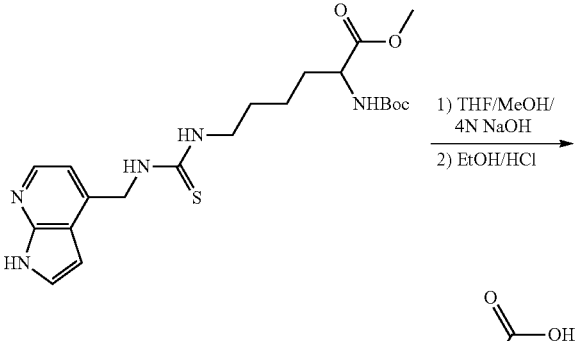

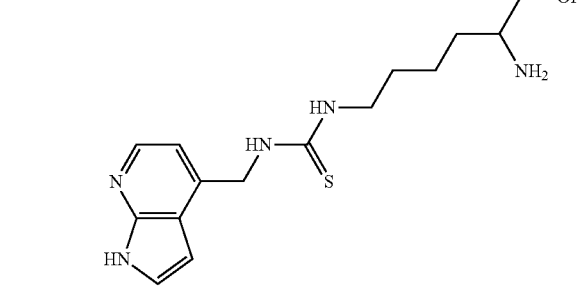

Example 46

Dissolved the isothiocyanate DA-171 (70 mg, 0.37 mmol) and the aminoacid (115 mg, 0.39 mmol) in THF and stirred overnight. Isolated the product via normal phase MPLC (DCM/MeOH, 0→10%). Dissolved the purified, boc protected product in Methanol/THF/4N NaOH (1/1/1) and stirred for 2 h. Acidified with acetic acid then extracted with EtOAc. The crude mixture was then dissolved in EtOH/HCl and stirred for 1 h. Diethyl ether was added causing the product to precipitate from solution. The product was collected by filtration and purified by reverse phase HPLC (ACN/water, 0.05% TFA).

1H NMR (400 MHz, MeOH-d4) 8.28 (d, 1H), 7.62 (d, 1H), 7.37 (d, 1H), 6.92 (d, 1H), 5.22 (s, 2H), 3.95 (t, 1H), 3.54 (bs, 2H), 1.94 (m, 2H), 1.66 (m, 2H), 1.50 (m, 2H)

Example 47

1-((1H-pyrrolo[2,3-b]pyridin-4-yl)methyl)-3-((1-(3-phenylpropioloyl)piperidin-2-yl)methyl)thiourea (E47)

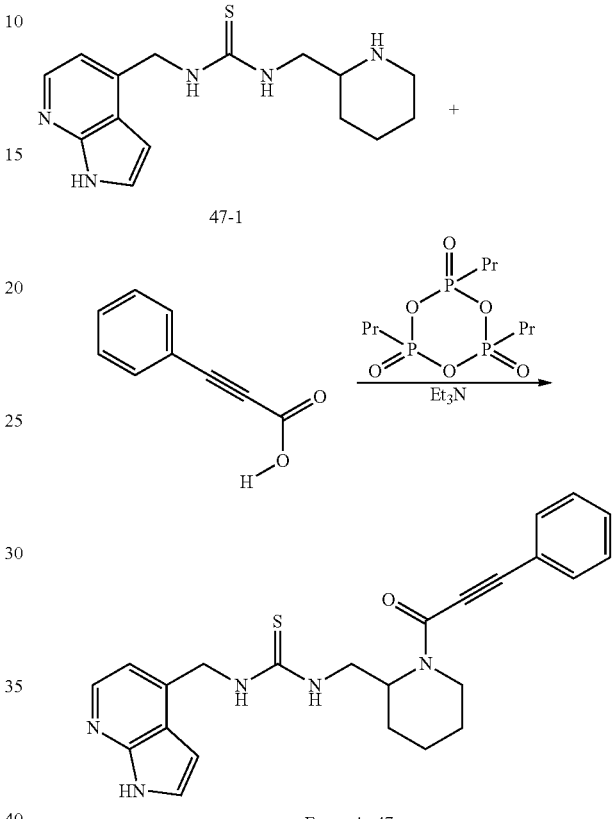

Example 47

Example 47 (E47) was synthesized in the same general manner as described in the synthesis of Example 41 (E41), but using the above illustrated starting materials.

1H NMR (400 MHz, MeOH-d4) Rotamers 8.09+7.98 (d, 1H), 7.60-7.23 (m, 6H), 7.17 (d, 1H), 6.83+6.72 (d, 1H), 5.20-4.88 (m, 3H), 4.41 (m, 1H), 3.99 (m, 1H), 3.84 (m, 1H), 3.61, m, 1H), 2.97 (t, 1H), 1.91-1.10 (m, 5H)

Example 48

1-((1H-pyrrolo[2,3-b]pyridin-4-yl)methyl)-3-((1-(3-phenylpropioloyl)piperidin-3-yl)methyl)sulfuric diamide (E48)

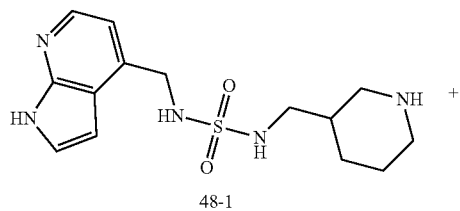

48-1

-continued

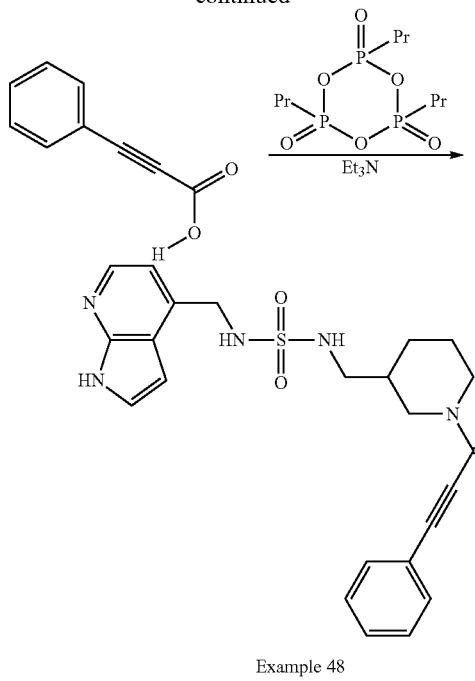

Example 48

Compound 48-1 was synthesized in the same manner as described in the synthesis of 39-3. Example 48 (E48) was then synthesized in the same manner as described in the synthesis of Example 41 (E41) using 48-1 as starting material.

1H NMR (400 MHz, MeOH-d4) Rotamers 8.14+8.11 (d, 1H), 7.62-7.54 (m, 2H), 7.50-7.3 (m, 4H), 7.17+7.12 (d, 1H), 6.66+6.58 (d, 1H), 4.57-4.20 (m, 4H), 2.95-2.55 (m, 4H), 1.80-1.20 (m, 5H)

Example 49

N-(3-((N-((1H-pyrrolo[2,3-b]pyridin-4-yl)methyl)sulfamoyl)amino)propyl)-3-phenylpropiolamide (E49)

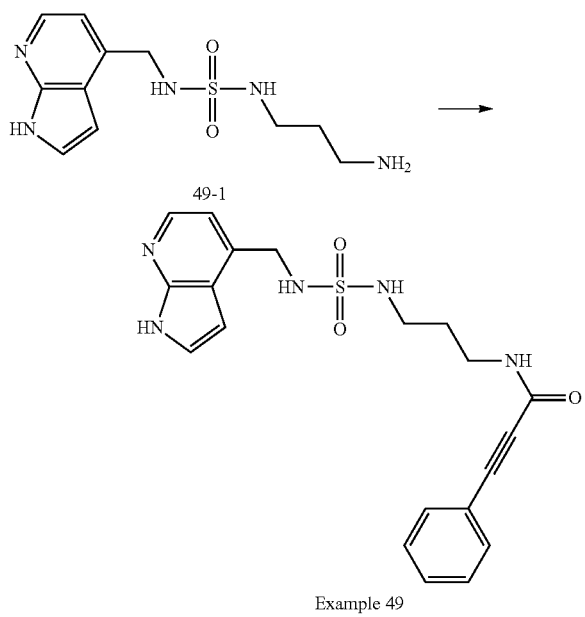

Example 49

Example 49 (E49) was synthesized in the same manner as described in the synthesis of Example 48 (E48) using 49-1 in place of 48-1.

1H NMR (400 MHz, MeOH-d4) 8.14 (d, 1H), 7.53 (m, 2H), 7.48-7.33 (m, 4H), 7.17 (d, 1H), 6.65 (d, 1H), 4.45 (s, 2H), 3.28 (t, 2H), 3.00 (t, 2H), 1.71 (m, 2H)

Example 50

N-(2-((N-((1H-pyrrolo[2,3-b]pyridin-4-yl)methyl)sulfamoyl)amino)ethyl)-3-phenylpropiolamide (E50)

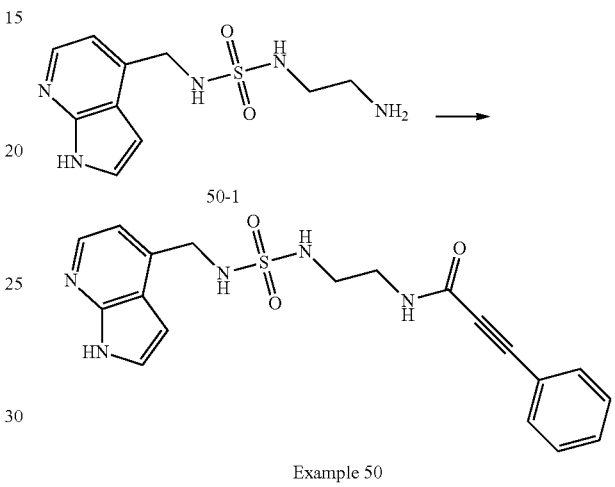

Example 50

Example 50 (E50) was synthesized in the same manner as described in the synthesis of Example 48 (E48) using 50-1 in place of 48-1.

1H NMR (400 MHz, MeOH-d4) 8.13 (d, 1H), 7.50 (m, 2H), 7.48-7.31 (m, 4H), 7.17 (d, 1H), 6.40 (d, 1H), 4.47 (s, 2H), 3.37 (t, 2H), 3.11 (t, 2H)

Example 51

1-((1H-pyrrolo[2,3-b]pyridin-4-yl)methyl)-3-(1-(3-phenylpropioloyl)piperidin-3-yl) sulfuric diamide (E51)

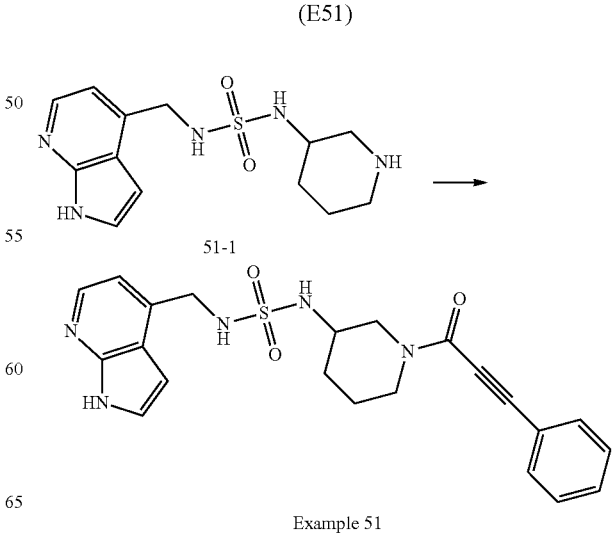

Example 51

Example 51 (E51) was synthesized in the same manner as described in the synthesis of Example 48 (E48) using 51-1 in place of 48-1

Example 52

1-(3-aminobenzyl)-3-((3-chloro-1H-pyrrolo[2,3-b]pyridin-4-yl)methyl)urea (E52)

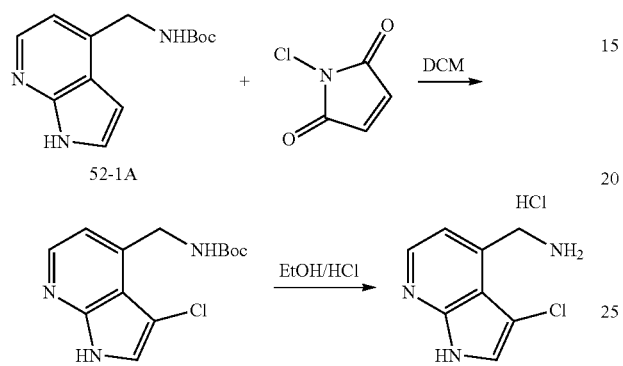

Compound 52-1A (1.0 g, 4.04 mmol) was dissolved in DCM and NCS (580 mg, 4.41 mmol) was then added. The reaction was stirred at room temperature for 5 h. The solvent was then stripped in vacuo and the boc protected product purified by normal phase chromatography (hexanes/EtOAc, 0%→100%). The boc protected product was then dissolved in EtOH/HCl and stirred for 1 h. Diethyl ether was added causing the product to precipitate from solution. The product was collected by filtration.

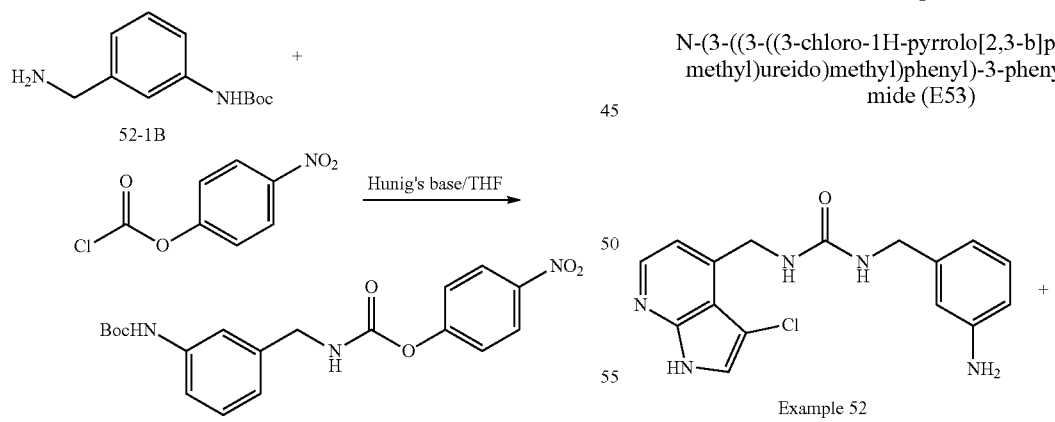

Compound 52-1B (2.0 g, 9.0 mmol) was combined with 4-nitrophenylchloroformate (1.8 g, 9.0 mmol) then the mixture was suspended in THF (20 mL) and cooled in an ice water bath. Hunig's base (1.9 mL, 13 mmol) was then diluted with THF (5 mL) and added dropwise. The reaction mixture was stirred for 3 h then diluted with EtOAc and washed with water three times. The product was then isolated by normal phase chromatography (DCM/MeOH 0%→5%).

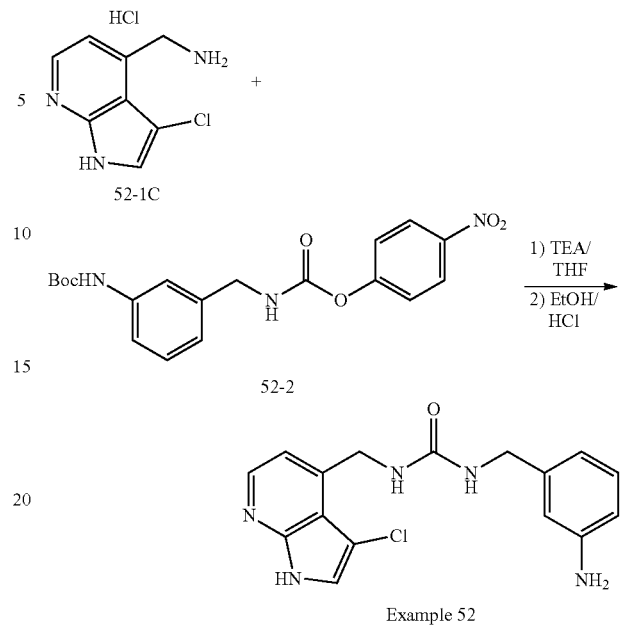

Compound 52-1C (74 mg, 0.29 mmol) and compound 52-2 (113 mg, 0.29 mmol) were combined in THF (1.5 mL) and TEA (142 uL, 1.0 mmol) was added. The reaction was stirred overnight then diluted with EtOAc and washed three times with water. The solvent was the stripped in vacuo and the boc protected product isolated by normal phase chromatography (DCM/MeOH, 0%→10%). The boc protected product was then dissolved in EtOH/HCl and stirred for 1 h. Diethyl ether was then added and the product collected by filtration.

1H NMR (400 MHz, MeOH-d4) 8.41 (d, 1H), 7.73 (s, 1H), 7.48 (m, 3H), 7.35 (s, 1H), 7.26 (d, 1H), 5.13 (s, 2H), 4.40 (s, 2H)

Example 53

N-(3-((3-((3-chloro-1H-pyrrolo[2,3-b]pyridin-4-yl)methyl)ureido)methyl)phenyl)-3-phenylpropiolamide (E53)

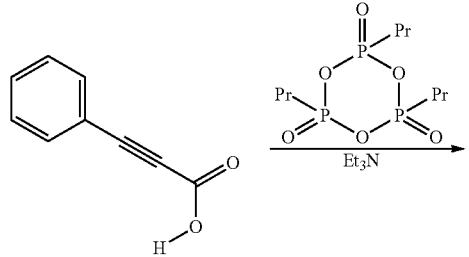

-continued

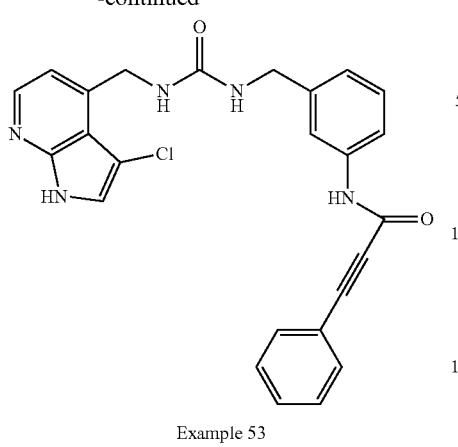

Example 53

Example 53 (E53) was synthesized from Example 52 (E52) in the same manner as described in the synthesis of Example 41 (E41).

1H NMR (400 MHz, MeOH-d4) 8.15 (d, 1H), 7.58 (m, 3H), 7.44 (m, 4H), 7.22 (t, 1H), 6.97 (m, 2H), 4.79 (s, 2H), 4.21 (s, 2H)

Example 54

1-((1H-pyrrolo[2,3-b]pyridin-4-yl)methyl)-3-(2-(((4-chloropyrimidin-2-yl)amino)methyl)benzyl)thiourea (E54)

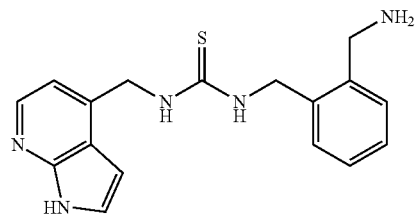

54-1

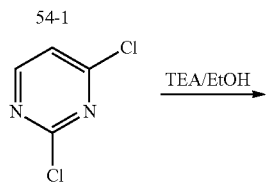

Example 54

Example 54 (E54) was synthesized in the same manner as described in the synthesis of Example 31 (E31) except the minor product was obtained as the desired product.

1H NMR (400 MHz, MeOH-d4) 8.25 (d, 1H), 8.13 (d, 1H), 7.63 (d, 1H), 7.36 (m, 3H), 7.24 (m, 2H), 6.96 (d, 1H), 6.61 (d, 1H), 5.27 (s, 2H), 4.81 (bs, 2H), 4.61 (s, 2H)

Example 55

N-(2-(((N-((1H-pyrrolo[2,3-b]pyridin-4-yl)methyl)sulfamoyl)amino)methyl)benzyl)-3-phenylpropiolamide (E55)

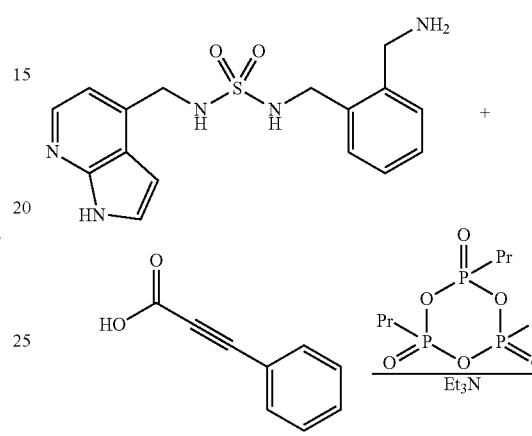

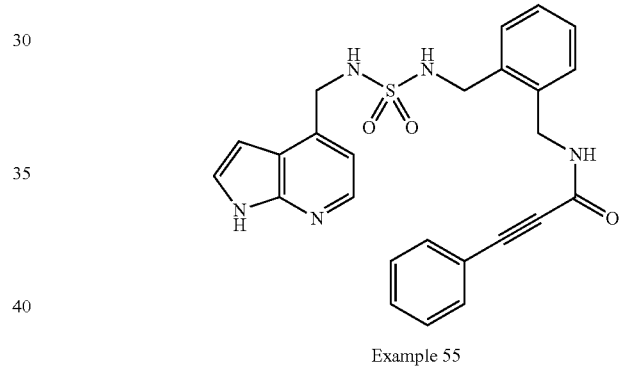

Example 55

Example 55 (E55) was synthesized in the same manner as described in the synthesis of Example 42 (E42).

1H NMR (400 MHz, MeOH-d4) 8.12 (d, 1H), 7.52 (d, 2H), 7.49-7.19 (m, 8H), 7.13 (d, 1H), 6.62 (d, 1H), 4.49 (s, 2H), 4.43 (s, 2H), 4.19 (s, 2H)

Example 56

N-(2-((3-((1H-pyrrolo[2,3-b]pyridin-4-yl)methyl)thioureido)methyl)benzyl)-3-phenylpropiolamide (E56)

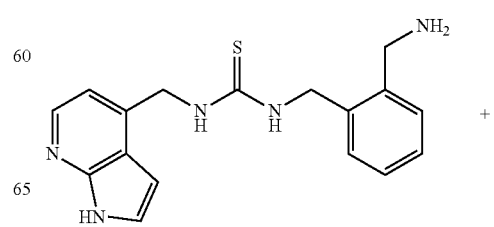

-continued

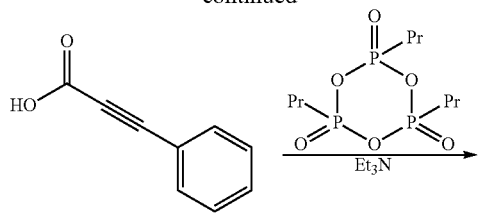

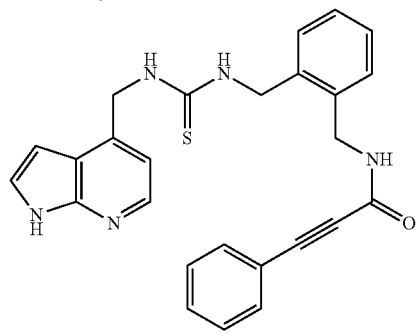

Example 56

Example 56 (E56) was synthesized in the same manner as described in the synthesis of Example 41 (E41).

1H NMR (400 MHz, MeOH-d4) 8.06 (d, 1H), 7.50 (d, 2H), 7.46-7.19 (m, 8H), 6.95 (bs, 1H), 6.58 (d, 1H), 5.07 (s, 2H), 4.81 (s, 2H), 4.49 (s, 2H)

Example 57

1-((1H-pyrrolo[2,3-b]pyridin-4-yl)methyl)-3-(1-(3-phenylpropioloyl)azetidin-3-yl)urea (E57)

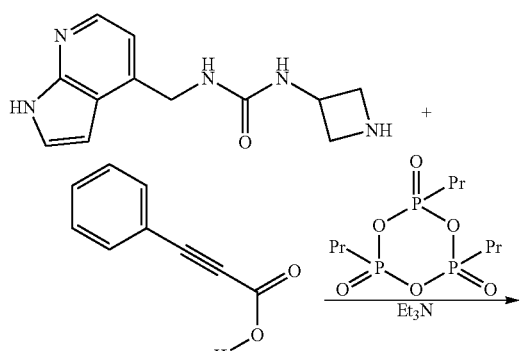

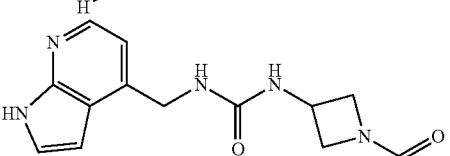

Example 57

Example 57 (E57) was synthesized in the manner described in the synthesis of Example 52 (E52) and Example 47 (E47).

1H NMR (400 MHz, MeOH-d4) 8.11 (d, 1H), 7.54 (d, 2H), 7.48-7.31 (m, 4H), 7.01 (d, 1H), 6.58 (d, 1H), 4.63 (s, 2H), 4.57 (m, 2H), 4.32 (m, 1H), 4.14 (m, 1H), 3.89 (m, 1H)

Example 58

1-((1H-pyrrolo[2,3-b]pyridin-4-yl)methyl)-3-(1-(3-phenylpropioloyl)pyrrolidin-3-yl)urea (E58)

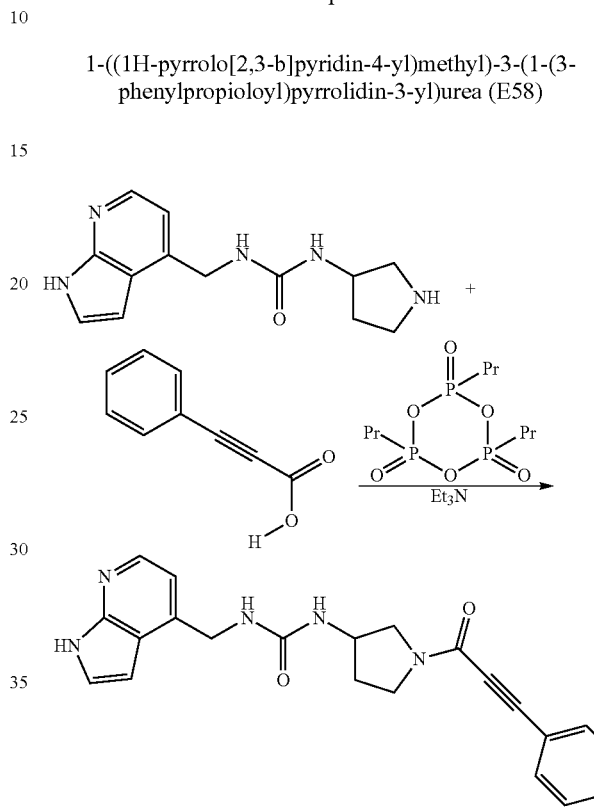

Example 58

Example 58 (E58) was synthesized in the same manner as described in the synthesis of Example 57 (E57).

1H NMR (400 MHz, MeOH-d4) rotamers 8.11+8.07 (d, 1H), 7.56 (m, 2H), 7.46 (d, 1H), 7.41 (m, 2H), 7.35+7.32 (d, 1H), 7.00 (m, 1H), 6.58 (m, 1H), 4.64 (s, 2H), 4.32 (m, 1H), 3.96 (m, 1H), 3.85 (m, 1H), 3.70 (m, 1H), 3.58 (m, 1H), 2.25 (m, 1H), 1.95 (m, 1H)

Example 59

1-((1H-pyrrolo[2,3-b]pyridin-4-yl)methyl)-3-(1-(3-phenylpropioloyl)piperidin-3-yl)urea (E59)

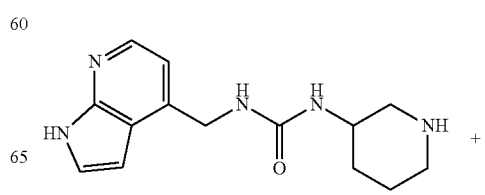

-continued

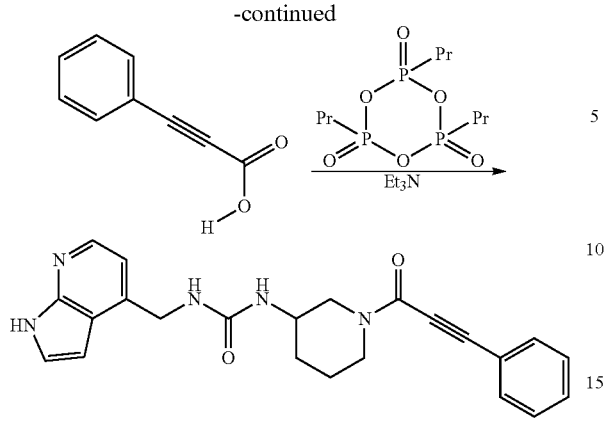

Example 59

Example 59 (E59) was synthesized in the same manner as described in the synthesis of Example 57 (E57).

1H NMR (400 MHz, MeOH-d4) rotamers 8.11+7.95 (d, 1H), 7.53 (m, 2H), 7.38 (m, 2H), 7.28 (m, 2H), 7.01+6.91 (d, 1H), 6.57+6.46 (d, 1H), 4.63+4.52 (s, 2H), 3.95 (m, 1H), 3.84 (m, 2H), 3.38 (m, 1H), 2.0-1.5 (m, 5H)

Example 60

1-((1H-pyrrolo[2,3-b]pyridin-4-yl)methyl)-3-(1-(3-phenylpropioloyl)azetidin-3-yl) sulfuric diamide (E60)

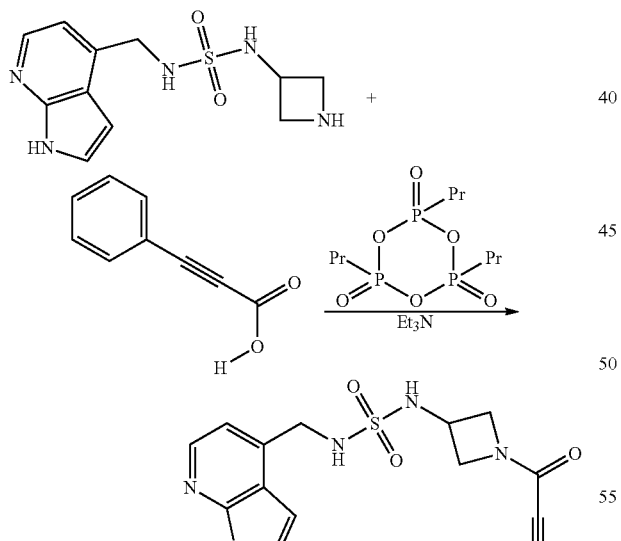

Example 60

Example 60 (E60) was synthesized in the same manner as described in the synthesis of Example 48 (E48).

1H NMR (400 MHz, MeOH-d4) 8.15 (d, 1H), 7.52 (dd, 2H), 7.46 (d, 1H), 7.40 (m, 3H), 7.14 (d, 1H), 6.65 (d, 1H), 4.46 (s, 2H), 4.41 (m, 1H), 4.16 (m, 2H), 4.04 (m, 1H), 3.79 (m, 1H)

Example 61

1-((1H-pyrrolo[2,3-b]pyridin-4-yl)methyl)-3-(1-(3-phenylpropioloyl)pyrrolidin-3-yl) sulfuric diamide (E61)

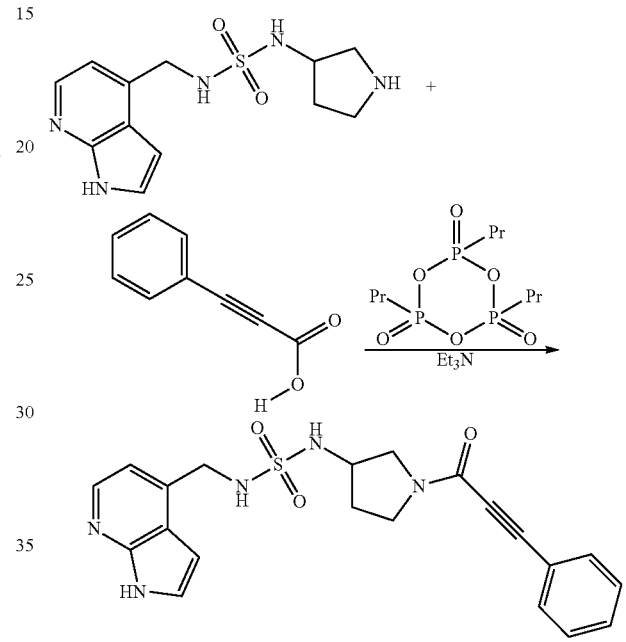

Example 61

Example 61 (E61) was synthesized in the same manner as described in the synthesis of Example 48 (E48).

1H NMR (400 MHz, MeOH-d4) rotamers 8.15+8.11 (d, 1H), 7.56 (d, 1H), 7.51-7.32 (m, 5H), 7.17+7.16 (d, 1H), 6.66+6.64 (d, 1H), 4.47+4.46 (s, 2H), 3.91 (m, 2H), 3.68 (m, 2H), 3.40 (m, 1H), 2.10 (m, 1H), 1.91 (m, 1H)

Example 62

N-(3-((3-((3-fluoro-1H-pyrrolo[2,3-b]pyridin-4-yl)methyl)ureido)methyl)phenyl)-3-phenylpropiolamide (E62)

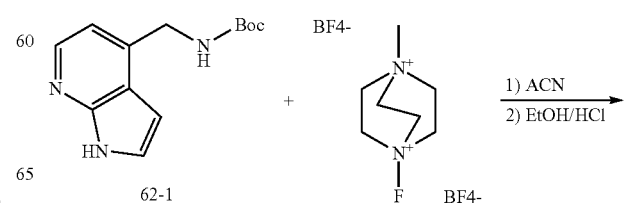

105
-continued

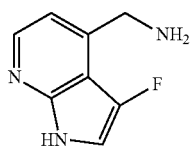

Compound 62-1 (500 mg, 2.02 mmol) was dissolved in acetonitrile (4 mL) and cooled in an ice water bath. Selectfluor 11 (647 mg, 2.02 mmol) was then dissolved in acetonitrile (4 mL) and added to the reaction mixture. After 2 h the reaction mixture was warmed to room temperature, then after an additional 2 h the solvent was stripped off in vacuo and the product isolated by normal phase chromatography (DCM/MeOH, 0%→5%) as a 50/50 mixture of the desired product and starting material. This mixture was carried forward as is.

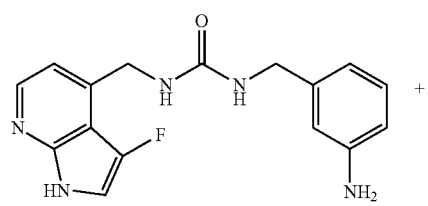

Example 62

Example 62 (E62) was synthesized in the same manner as described in the synthesis of Example 41 (E41) except that reverse phase purification on prep. HPLC (water/ACN, 0.05% TFA) was required to separate the desired fluorinated product from the unfluorinated impurity.

1H NMR (400 MHz, MeOH-d4) 8.16 (d, 1H), 7.61 (m, 3H), 7.44 (m, 4H), 7.28 (t, 1H), 7.15 (d, 1H), 7.06 (m, 2H), 4.76 (s, 2H), 4.34 (s, 2H)

106
Example 63

N-(3-((3-((3-bromo-1H-pyrrolo[2,3-b]pyridin-4-yl)methyl)ureido)methyl)phenyl)-3-phenylpropiolamide (E63)

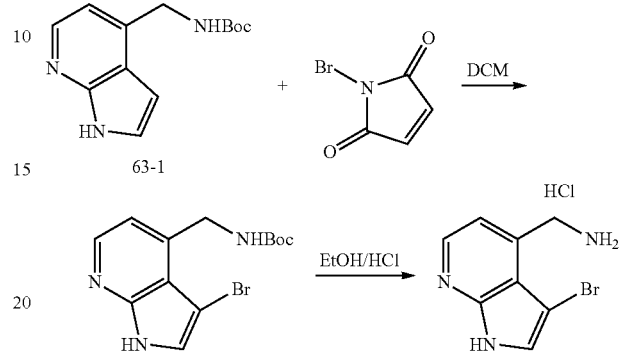

Compound 63-1 (1.0 g, 4.04 mmol) was dissolved in DCM and NBS (775 mg, 4.41 mmol) was then added. The reaction was stirred at room temperature for 5 h. The solvent was then stripped in vacuo and the boc protected product purified by normal phase chromatography (hexanes/EtOAc, 0%→100%). The boc protected product was then dissolved in EtOH/HCl and stirred for 1 h. Diethyl ether was added causing the product to precipitate from solution. The product was collected by filtration.

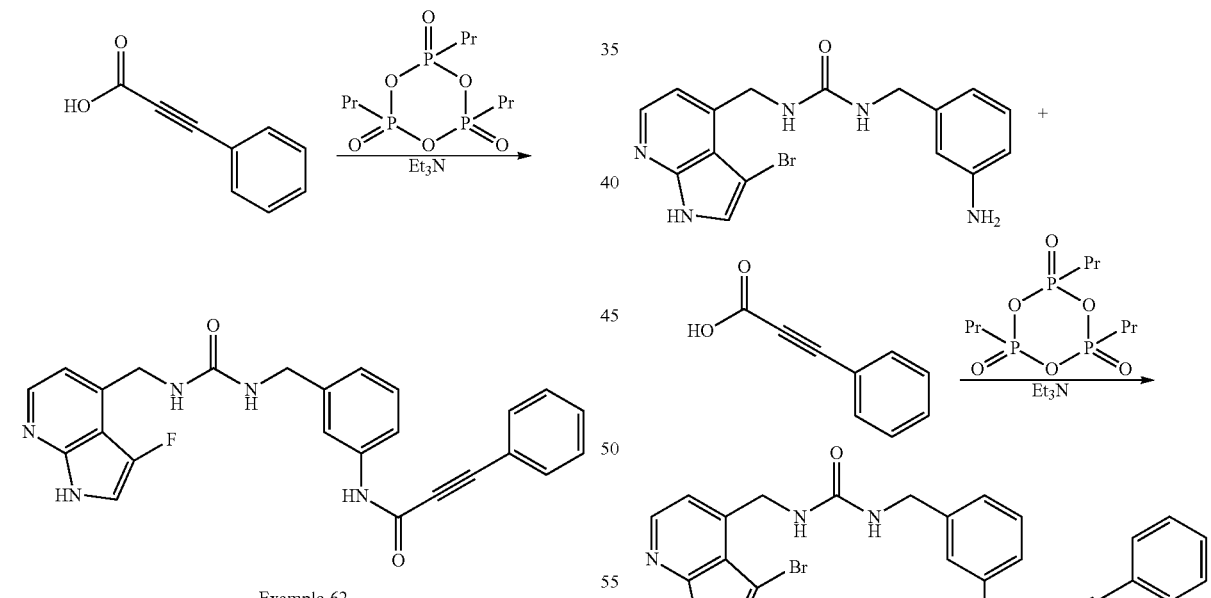

Example 63

Example 63 (E63) was synthesized in the same manner as described in the synthesis of Example 41 (E41).

1H NMR (400 MHz, MeOH-d4) 8.18 (d, 1H), 7.62 (m, 3H), 7.47 (m, 4H), 7.26 (t, 1H), 6.98 (d, 1H), 6.48 (m, 2H), 4.83 (d, 2H), 4.20 (d, 2H)

Example 64

1-((3-chloro-1H-pyrrolo[2,3-b]pyridin-4-yl)methyl)-3-(1-(3-phenylpropioloyl)pyrrolidin-3-yl)urea (E64)

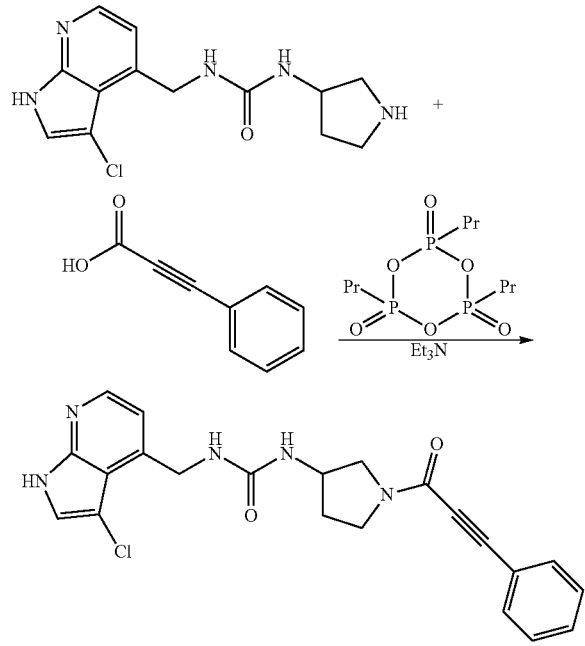

Example 64

Example 64 (E64) was synthesized in the same manner as described in the synthesis of Example 52 (E52) and Example 57 (E57).

1H NMR (400 MHz, MeOH-d4) rotamers 8.17+8.11 (d, 1H), 7.56 (m, 2H), 7.50-7.35 (m, 4H), 7.05 (m, 1H), 4.92 (s, 2H), 4.31 (m, 1H), 3.96 (m, 1H), 3.85 (m, 1H), 3.70 (m, 1H), 3.58 (m, 1H), 2.24 (m, 1H), 1.95 (m, 1H)

Example 65

E65

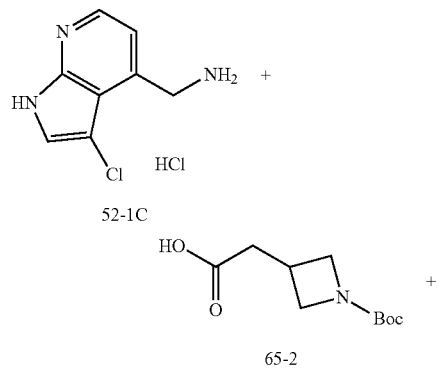

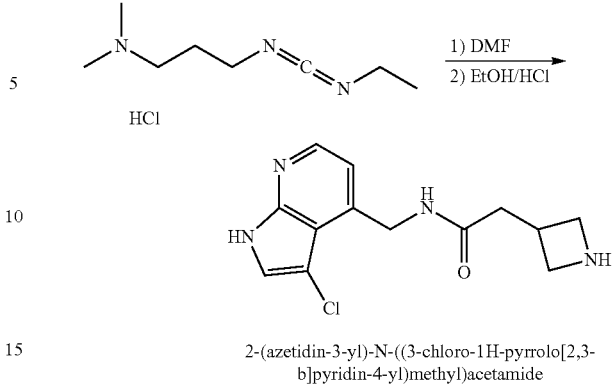

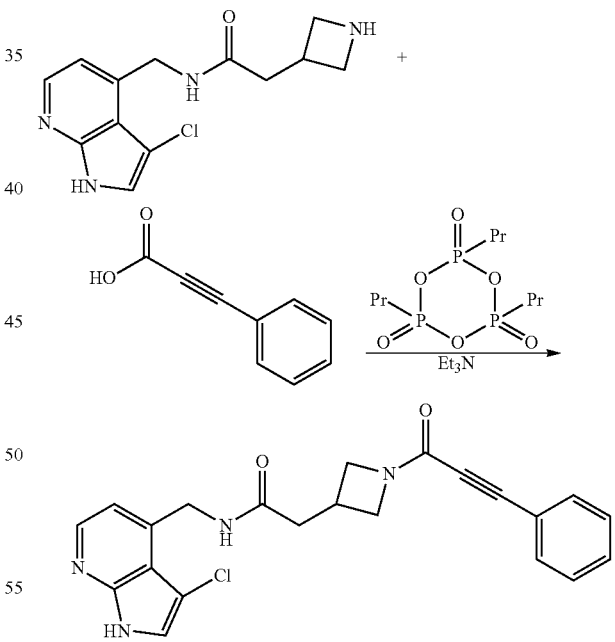

2-(azetidin-3-yl)-N-((3-chloro-1H-pyrrolo[2,3-b]pyridin-4-yl)methyl)acetamide

Compound 52-1C (130 mg, 0.51 mmol), and compound 65-2 (121 mg, 0.56 mmol) were dissolved in DMF. NMM (281 uL, 2.6 mmol) was then added followed by EDC (108 mg, 0.56 mmol). The reaction was stirred for 3 hours then diluted with EtOAc and washed with water three times. The solvent was then removed in vacuo and the boc protected product isolated by normal phase chromatography (DCM/MeOH 0%→10%). The boc protected product was then dissolved in EtOH/HCl and stirred for 30 min. Diethyl ether was added and the product was collected by filtration to give 2-(azetidin-3-yl)-N-((3-chloro-1H-pyrrolo[2,3-b]pyridin-4-yl)methyl)acetamide.

Example 65

Example 65 (E65) was synthesized in the same manner as described in the synthesis of Example 48 (E48).

1H NMR (400 MHz, MeOH-d4) 8.54 (m, 1H), 8.19 (d, 1H), 7.55 (m, 2H), 7.50-7.38 (m, 3H), 7.05 (m, 1H), 4.97 (d, 2H), 4.47 (t, 1H), 4.21 (t, 1H), 4.08 (m, 1H), 3.80 (m, 1H), 3.10 (m, 1H), 2.69 (d, 2H)

Example 66

N-((3-chloro-1H-pyrrolo[2,3-b]pyridin-4-yl)methyl)-2-(1-(3-phenylpropioloyl)azetidin-3-yl)acetamide (E66)

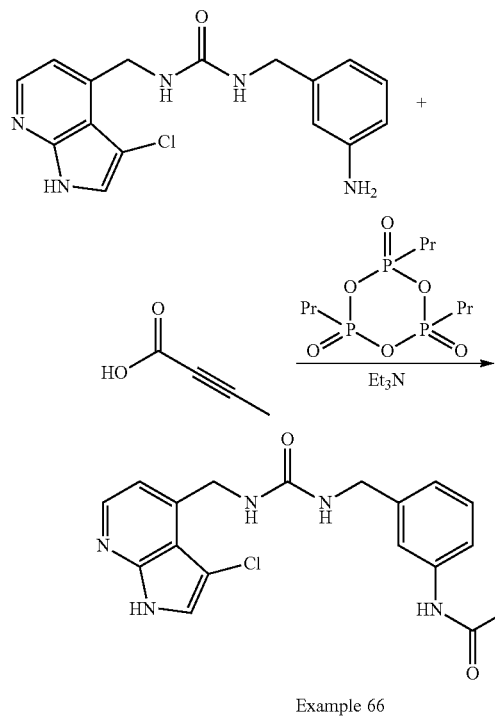

Example 66

Example 66 (E66) was synthesized in the same manner as Example 53 (E53).

1H NMR (400 MHz, MeOH-d4) 8.16 (d, 1H), 7.53 (s, 1H), 7.39 (d, 1H), 7.36 (s, 1H), 7.25 (t, 1H), 7.06 (m, 2H), 4.95 (s, 2H), 4.32 (s, 2H)

Example 67

N-(3-((3-((3-chloro-1H-pyrrolo[2,3-b]pyridin-4-yl)methyl)ureido)methyl)phenyl)acrylamide (E67)

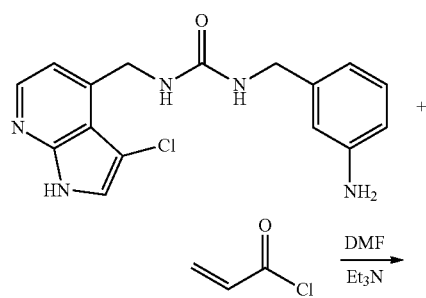

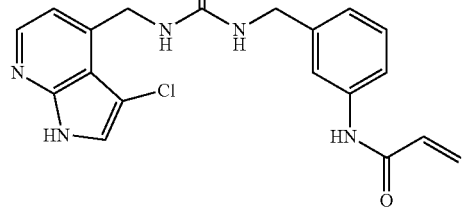

Example 67

Example 67 (E67) was synthesized in the same manner as described in the synthesis of Example 52 (E52) and Example 29 (E29).

1H NMR (400 MHz, MeOH-d4) 8.15 (d, 1H), 7.60 (s, 1H), 7.48 (d, 1H), 7.36 (s, 1H), 7.27 (t, 1H), 7.07 (m, 2H), 6.38 (m, 2H), 5.74 (dd, 1H), 4.95 (s, 2H), 4.34 (s, 2H)

Example 68

N-((1H-pyrrolo[2,3-b]pyridin-4-yl)methyl)-2-(1-(3-phenylpropioloyl)azetidin-3-yl)acetamide (E68)

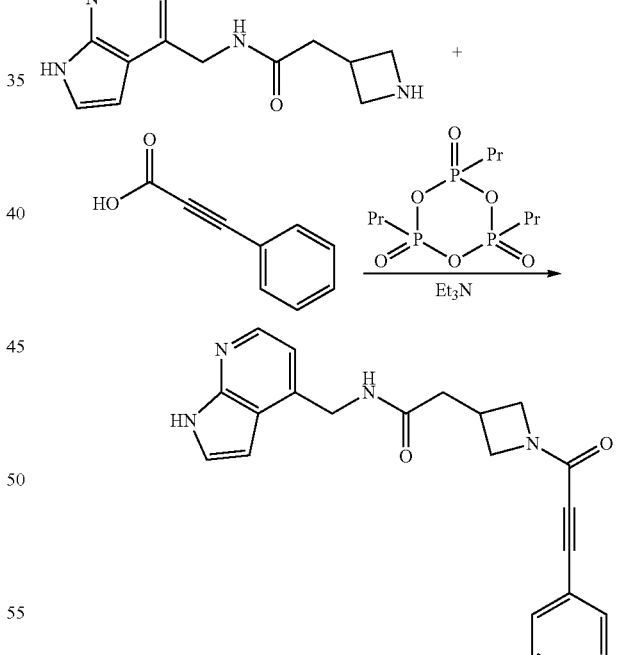

Example 68

Example 68 (E68) was synthesized in the same manner as described in the synthesis of Example 65 (E65).

1H NMR (400 MHz, MeOH-d4) 8.12 (d, 1H), 7.56-7.34 (m, 6H), 7.00 (d, 1H), 6.56 (d, 1H), 4.67 (d, 2H), 4.44 (t, 1H), 4.18 (t, 1H), 4.04 (m, 1H), 3.77 (m, 1H), 3.08 (m, 1H), 2.64 (d, 2H)

Example 69

N-((3-fluoro-1H-pyrrolo[2,3-b]pyridin-4-yl)methyl)-2-(1-(3-phenylpropioloyl)azetidin-3-yl)acetamide (E69)

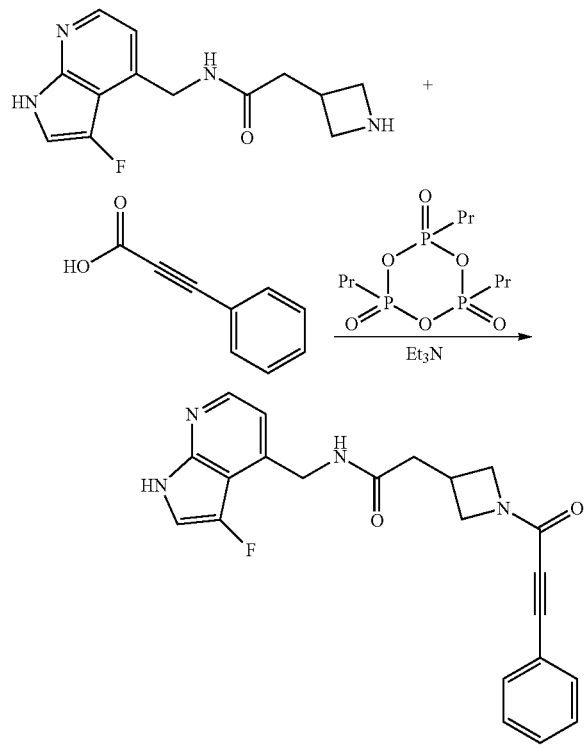

Example 69

Example 69 (E69) was synthesized in the same manner as described in the synthesis of Example 62 (E62) and Example 65 (E65).

1H NMR (400 MHz, MeOH-d4) 8.62 (m, 1H), 8.21 (d, 1H), 7.54 (m, 2H), 7.50-7.38 (m, 3H), 7.26 (m, 1H), 7.10 (d, 1H), 4.79 (d, 2H), 4.46 (t, 1H), 4.20 (t, 1H), 4.07 (m, 1H), 3.79 (m, 1H), 3.09 (m, 1H), 2.69 (d, 2H)

Example 70

3-phenyl-N-(3-((3-((3-(pyrrolidin-1-ylmethyl)-1H-pyrrolo[2,3-b]pyridin-4-yl)methyl)ureido)methyl)phenyl)propiolamide (E70)

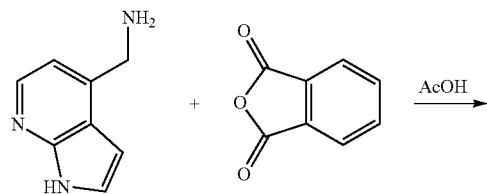

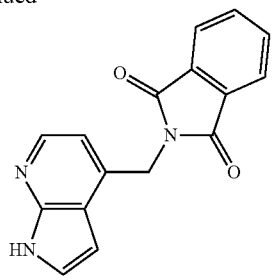

(1H-pyrrolo[2,3-b]pyridin-4-yl)methanamine (2.92 g, 19.8 mmol) and phthalic anhydride (2.94 g, 19.8 mmol) were dissolved in acetic acid and heated to 80° C. for 6 h. The reaction was then diluted with EtOAc and washed with saturated potassium carbonate solution twice and water once. The organic layer was then stripped in vacuo and the product purified by normal phase chromatography (hexanes/EtOAc, 0→100%).

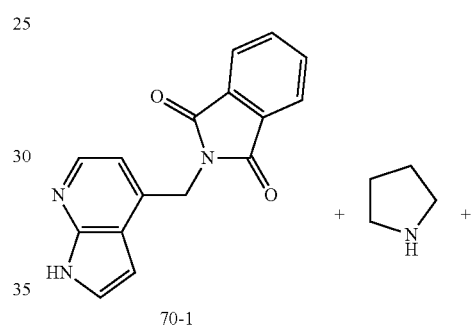

70-1

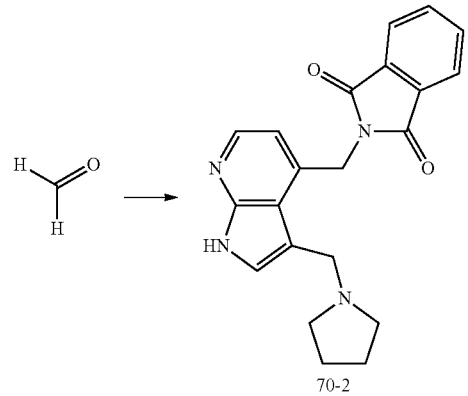

70-2

To a solution of pyrrolidine (326 uL, 3.97 mmol) in AcOH (5 mL) was added formaldehyde (38% aqueous) (144 uL, 1.98 mmol). After stirring for 15 min a solution of compound 70-1 (500 mg, 1.8 mmol) in acetic acid (3 mL). The reaction was stirred overnight at 75° C. then cooled to room temperature and diluted with EtOAc and washed with saturated potassium carbonate solution twice and water once. The organic layer was then stripped in vacuo and the product purified by normal phase chromatography (DCM/MeOH, 0→20%).

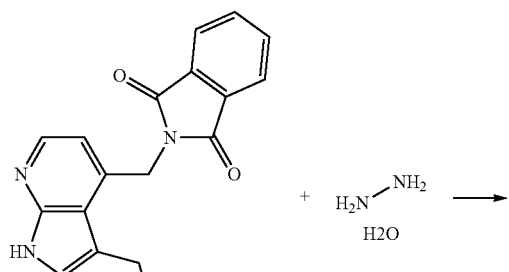

70-2

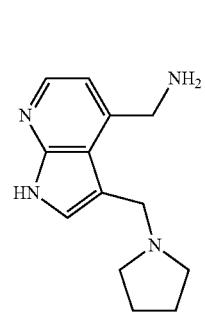

Compound 70-2 (700 mg, 1.94 mmol) was dissolved in chloroform/methanol (5 mL of a 3/1 mixture) and hydrazine hydrate (486 mg, 9.7 mmol) was added. The reaction mixture was stirred at 50° C. for 5 h then the solvent was stripped in vacuo. The crude product was taken on as is to the next step.

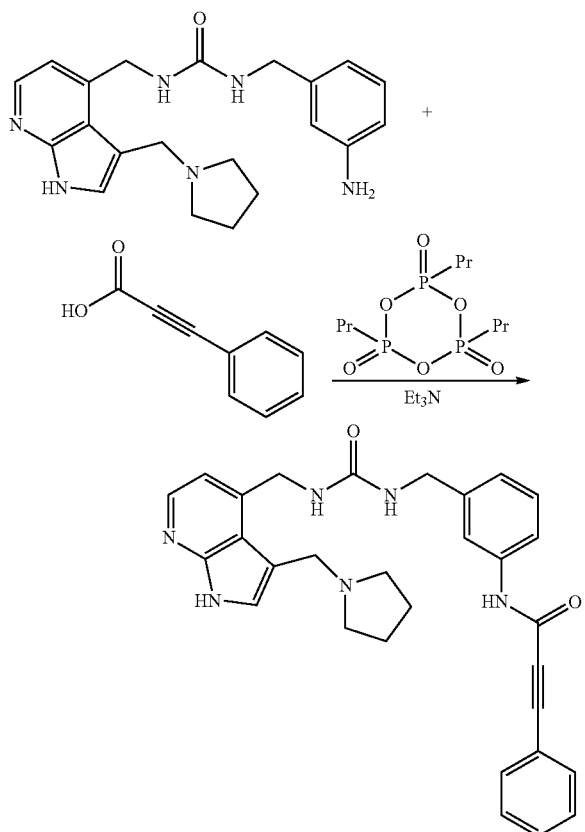

Example 70

Example 70 (E70) was synthesized in the same manner as described in the synthesis of Example 62 (E62).

1H NMR (400 MHz, MeOH-d4) 8.24 (d, 1H), 7.66 (d, 2H), 7.61 (d, 2H), 7.45 (m, 3H), 7.26 (m, 2H), 7.17 (d, 1H), 6.98 (d, 1H), 4.60 (s, 2H), 4.53 (s, 2H), 4.21 (s, 2H), 2.77 (m, 6H), 2.05 (m, 1H) 1.82 (m, 1H)

Example 71

N-(1-(3-((1H-pyrrolo[2,3-b]pyridin-4-yl)methyl)thioureido)pent-4-en-2-yl)-3-phenylpropiolamide (E71)

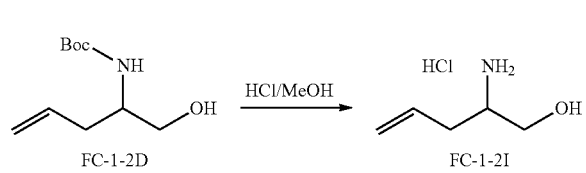

To a stirred solution of compound FC-1-2D (1.0 g, 5 mmol) in EtOAc (10 mL) was added solution of EtOAc/HCl (2N, 20 mL). The reaction mixture was stirred at 25° C. for 18 hrs. The white precipitate was collected by filtration, dried in vacuum to afford the product as white solid (700 mg, crude).

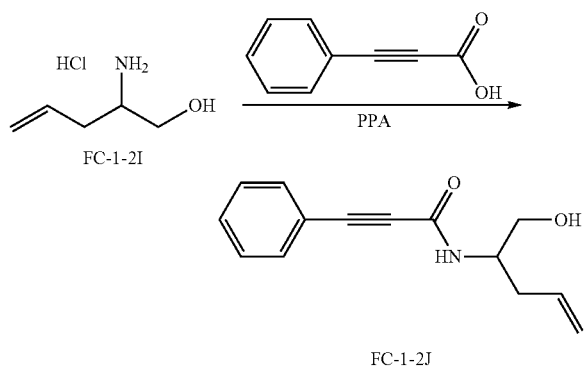

FC-1-2J

To a stirred solution of compound FC-1-2I (1.6 g, 11.8 mmol) in DMF (5 mL) was added phenylpropiolic acid (2.06 g, 14.1 mmol), TEA (4.76 g, 47.2 mmol) and PPA (1-propanphosphonic acid cyclic anhydride, 6.32 g, 23.6 mmol). The reaction mixture was stirred at 25° C. for 18 hrs.

The analysis of TLC showed no change of SM and formation of desired product, it was quenched by addition of H₂O (20 mL), extracted with EtOAc (2×50 mL), the organic layer was washed with H₂O, brine dried over Na₂SO₄ and concentrated. The residue was purified by flash chromatography to afford the product as white solid (1.2 g, yield: 44.4%).

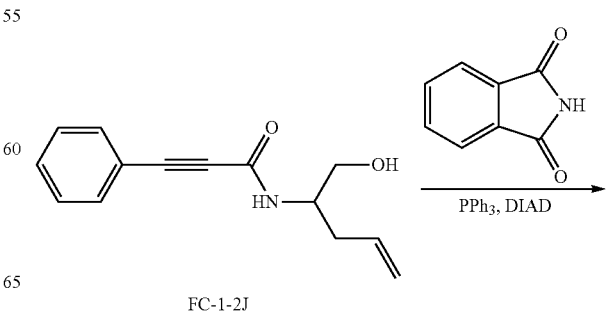

FC-1-2J

-continued

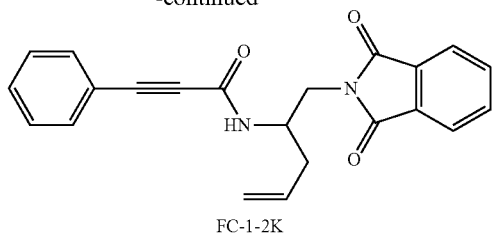
FC-1-2K

To a stirred solution of compound FC-1-2K (0.23 g, 1 mmol) in THF (5 mL) was added phthalimide (0.22 g, 1.5 mmol), PPh$_3$ (0.39 g, 1.5 mmol) and DIAD (0.4 g, 2.0 mmol) at 0° C., then the reaction mixture was warmed to 25° C. for 18 hrs. The analysis of LC/MS showed completion of the reaction and formation of desired product, it was quenched by addition of H$_2$O (10 mL), extracted with DCM (50 mL), concentrated and purified by flash chromatography to afford the product as white solid (230 mg, yield: 64.6%).

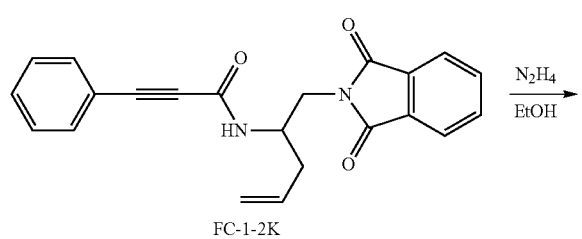
FC-1-2K $\xrightarrow{N_2H_4}{EtOH}$

FC-1-2L

To a stirred solution of compound FC-1-2K (0.23 g, 0.6 mmol) in EtOH (5 mL) was added hydrazine hydrate (1.2 mmol, 60 mg). The reaction mixture was stirred at 25° C. for 1 hr. The analysis of TLC showed completion of the reaction, it was concentrated directly and purified by flash chromatography to afford the product as white solid (80 mg, yield: 58.5%).

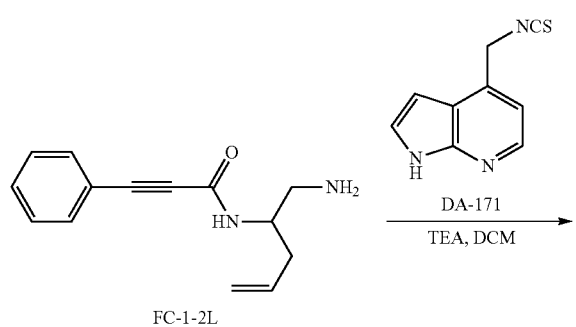
FC-1-2L

DA-171
TEA, DCM

-continued

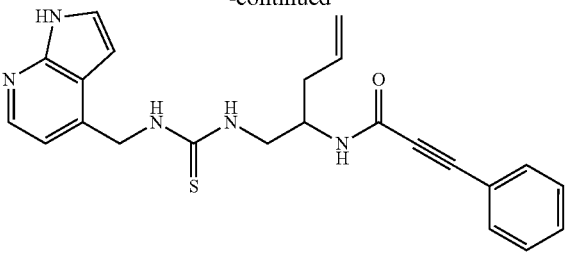
Example 71

To a stirred solution of compound FC-1-2L (80 mg, 0.35 mmol) in dichloromethane (2 mL) was added DA-171 (66.3 mg, 0.35 mmol) and TEA (110 mg, 1.05 mmol). The reaction mixture was stirred at 25° C. for 18 hrs. The analysis of LC/MS showed completion of the reaction and formation of desired product, it was concentrated directly and purified by Pre-HPLC to afford the product as white solid (46 mg, yield: 31.5%).

$^1$H NMR: 400 MHz MeOD δ 8.11 (d, J=5.2 Hz, 1H), 7.52 (d, J=7.6 Hz, 2H), 7.37-7.45 (m, 4H), 7.07 (d, J=5.2 Hz, 1H), 6.64 (d, J=3.2 Hz, 1H), 5.77-5.87 (m, 1H), 5.08-5.16 (m, 4H), 4.23 (d, J=4.8 Hz, 1H), 3.78 (s, 1H), 3.59-3.65 (m, 1H), 2.22-2.38 (m, 2H).

Example 72

N-(3-(3-((1H-pyrrolo[2,3-b]pyridin-4-yl)methyl) thioureido)-2-methylpropyl)-3-phenylpropiolamide (E72)

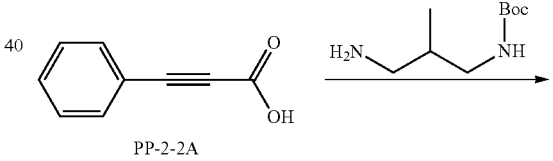
PP-2-2A

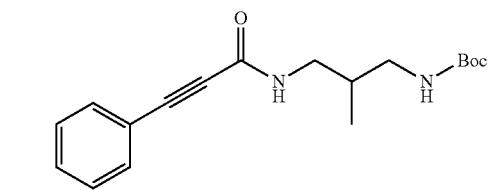
FC-1-4A

To a stirred solution of phenylpropiolic acid (156 mg, 1.1 mmol) in THF (2 mL) was added N-(tert-butoxycarbonyl)-2-methyl-1,3-diaminopropane (200 mg, 1.1 mmol), HATU (613 mg, 1.6 mmol) and TEA (0.3 mL). The reaction mixture was stirred at 25° C. for 12 hrs.

The analysis of LCMS showed completion of reaction and formation of desired product, it was quenched by addition of H$_2$O (20 mL), extracted with EtOAc (2×50 mL), the organic layer was washed with H$_2$O, brine dried over Na$_2$SO$_4$ and concentrated. The residue was purified by column chromatography on silica gel (DCM/MeOH=10:1) to afford the product as a white solid (0.28 g, yield: 82%).

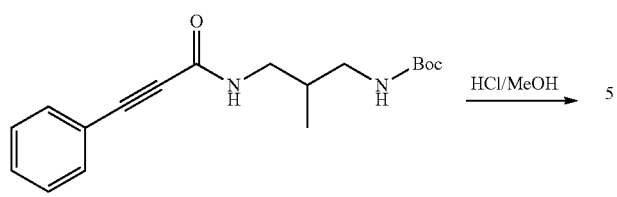

FC-1-4A

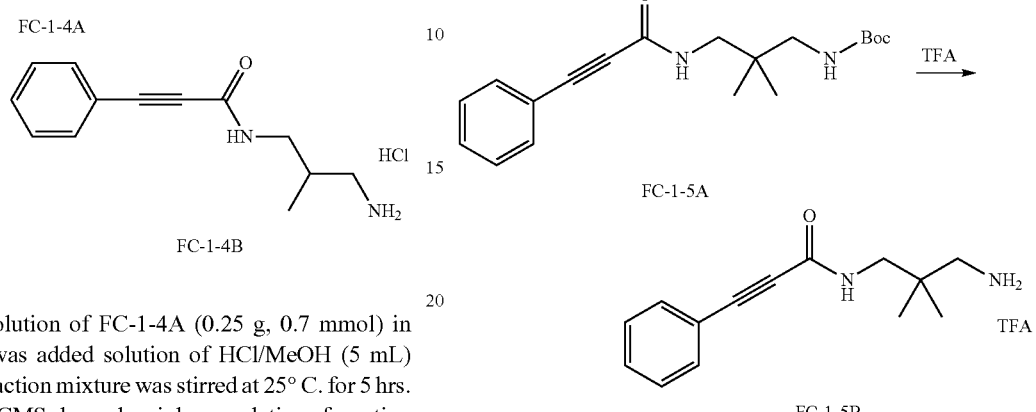

Example 73

N-(3-(3-((1H-pyrrolo[2,3-b]pyridin-4-yl)methyl)thioureido)-2,2-dimethylpropyl)-3-phenylpropiolamide (E73)

To a stirred solution of FC-1-4A (0.25 g, 0.7 mmol) in MeOH (5 mL) was added solution of HCl/MeOH (5 mL) dropwise. The reaction mixture was stirred at 25° C. for 5 hrs. The analysis of LCMS showed mainly completion of reaction and formation of desired product, it was concentrated directly to afford the product as pall-yellow solid (150 mg, crude).

To a stirred solution of compound FC-1-5A (0.28 g, 0.85 mmol) in DCM (5 mL) was added trifluoroacetic acid (2 mL) dropwise slowly and the reaction mixture was stirred at 25° C. for 1 hr. The analysis of LCMS showed completely consumption of starting material, it was diluted with EtOAc (15 mL) and adjusted to pH>7 by addition of TEA, then concentrated under reduced pressure. The residue was purified by column chromatography on silica gel (DCM/MeOH=15:1) to afford the product as pale-yellow solid (0.14 g, yield: 74%).

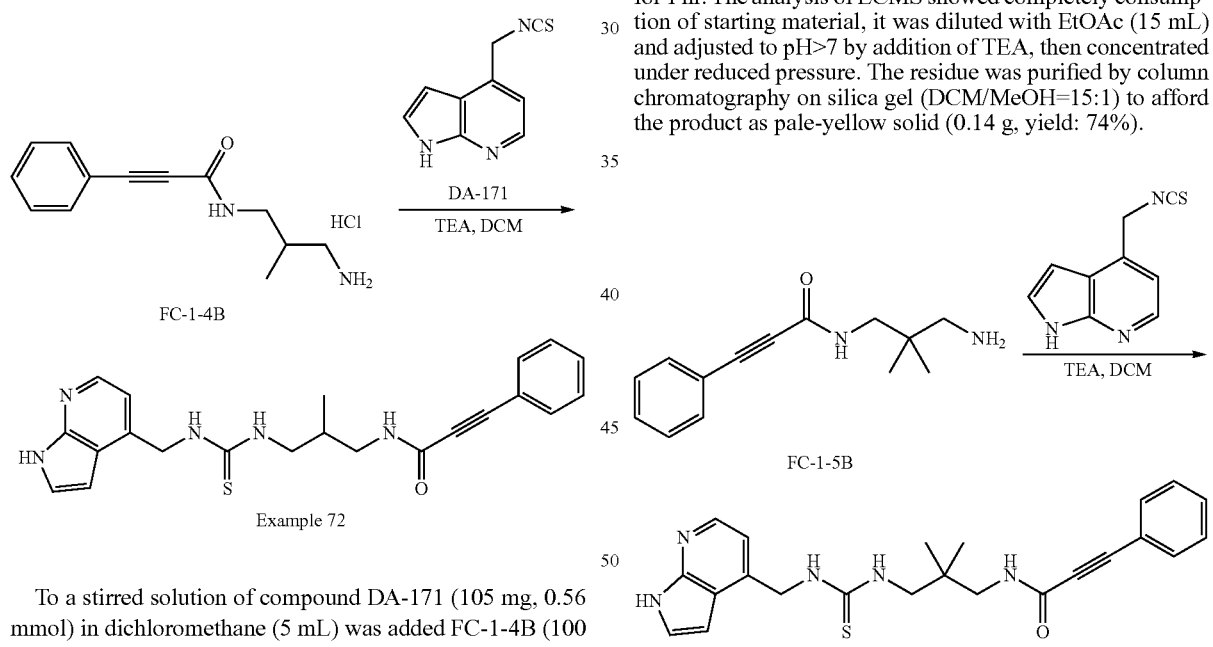

To a stirred solution of compound DA-171 (105 mg, 0.56 mmol) in dichloromethane (5 mL) was added FC-1-4B (100 mg, 0.46 mmol) and TEA (170 mg, 1.68 mmol). The reaction mixture was stirred at 25° C. for 18 hrs. The analysis of LC/MS showed completion of the reaction and formation of desired product, it was concentrated directly and purified by Pre-HPLC to afford the product as white solid (46 mg, TFA salt).

$^1$H NMR: 400 MHz DMSO

δ 12.19 (brs, 1H), 8.76 (t, J=7 Hz, 1H), 8.25 (d, J=5.2 Hz, 1H), 8.13 (s, 1H), 7.77 (brs, 1H), 7.40-7.57 (m, 6H), 7.08 (d, J=6.8 Hz, 1H), 6.72 (d, J=3.2 Hz, 1H), 5.10 (s, 2H), 3.34 (m, 2H), 2.97-3.14 (m, 2H), 1.92-1.94 (m, 1H), 0.83 (d, J=6.8 Hz, 3H).

To a stirred solution of compound FC-1-5B (140 mg, 0.6 mmol) in dichloromethane (2 mL) was added solution of DA-171 (110 mg, 0.6 mmol) and TEA (180 mg, 1.8 mmol). The reaction mixture was stirred at 25° C. for 4 hrs. The analysis of LC/MS showed completion of the reaction and formation of desired product, it was concentrated directly and purified by Pre-HPLC to afford the product as white solid (46 mg, free base).

$^1$H NMR: 400 MHz MeOD

δ 8.15 (d, J=5.2 Hz, 1H), 7.58 (d, J=6.8 Hz, 2H), 7.40-7.51 (m, 4H), 7.08 (d, J=4.8 Hz, 1H), 6.67 (d, J=3.2 Hz, 1H), 5.08 (s, 2H), 4.15 (s, 2H), 3.51 (s, 2H), 2.99-3.03 (m, 2H), 0.90 (s, 6H).

Example 74

N-(3-((3-((1H-pyrrolo[2,3-b]pyridin-4-yl)methyl)thioureido)methyl)-4-fluorophenyl)acrylamide (E74)

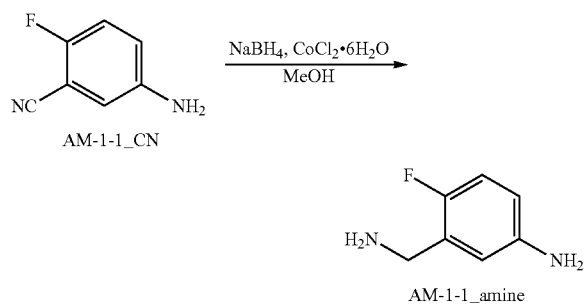 [SMILES: "MeOH" ; N#Cc1cc(N)ccc1F ; NCc1cc(N)ccc1F]

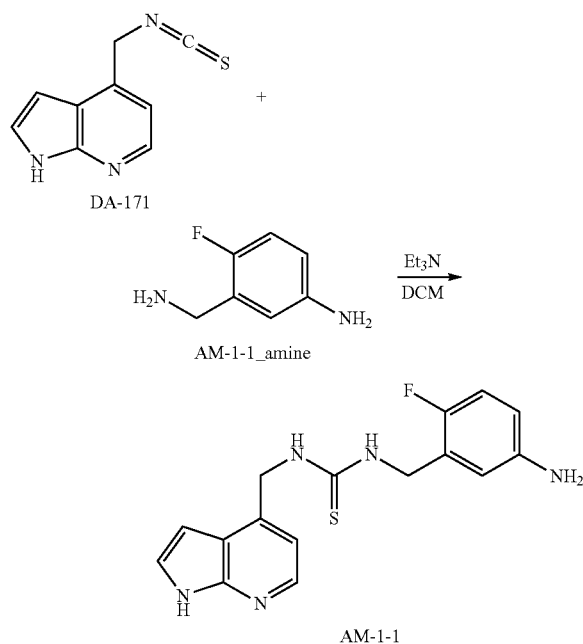

To a solution of AM-1-1_CN (1.36 g, 10 mmol) in MeOH (50 mL) was added CoCl$_2$.6H$_2$O (4.7 g, 20 mmol). NaBH$_4$ (1.13 g, 30 mmol) was added in portions to the above mixture at 0° C. The reaction mixture was warmed to r.t. and continued stirring for 12 hrs. The reaction mixture was made pH=13 with NH$_3$.H$_2$O and extracted with EA. The combined organic layer was washed with brine, dried over Na$_2$SO$_4$ and concentrated. The crude was purified by column chromatography on silica gel (DCM/MeOH, 9:1) to give the product (0.6 g, 43%).

To a solution of AM-1-1_amine (210 mg, 1.5 mmol) and DA-171 (285 mg, 1.5 mmol) in dry DCM (10 mL) was added Et$_3$N (0.6 mL, 4.5 mmol). The reaction mixture was stirred at r.t. for 12 hrs. The solvent was removed under reduced pressure. The residue was purified by column chromatography on silica gel (DCM/MeOH, 20:1) to give the product as a white solid (210 mg, 42.7%). For delivery, the product was further purified by prep-HPLC.

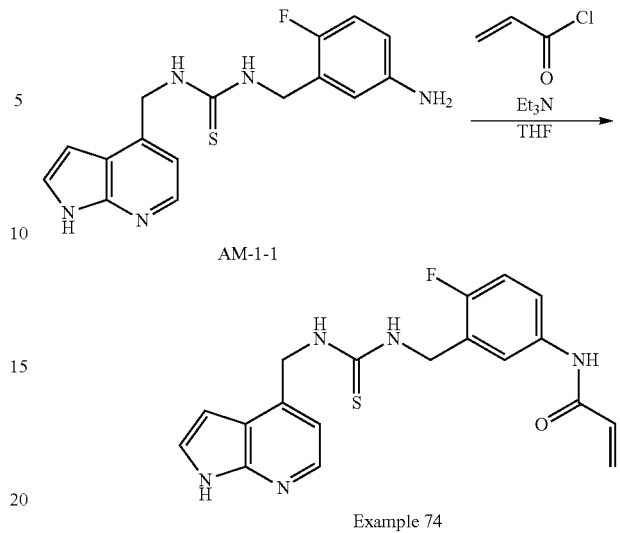

Acryloyl chloride (57 mg, 0.63 mmol) was added dropwise to a solution of AM-1-1 (140 mg, 0.42 mmol) and Et$_3$N (0.18 mL, 1.27 mmol) in dry THF (5 mL) at −70° C. under N$_2$ atmosphere. The mixture was warmed to r.t. and continued stirring for 10 mins. Water was added and the mixture was extracted with EtOAc repeatedly. The combined organic layer was dried over Na$_2$SO$_4$ and concentrated under reduced pressure. The residue was purified by Prep. HPLC under acidic conditions to give Example 74 (E74) (31 mg, FTA salt) as a pale yellow solid.

$^1$H NMR: 400 MHz MeOD

δ 8.25 (d, J=6.0 Hz, 1H), 7.77 (d, J=4.4 Hz, 1H), 7.59 (d, J=3.6 Hz, 1H), 7.48 (d, J=4.0 Hz, 1H), 7.41 (d, J=5.2 Hz, 1H), 7.06 (d, J=9.2 Hz, 1H), 6.91 (d, J=3.6 Hz, 1H), 6.42 (m, 2H), 5.78 (m, 1H), 5.26 (s, 2H), 4.81 (s, 2H).

Example 75

N-(3-((3-((1H-pyrrolo[2,3-b]pyridin-4-yl)methyl)thioureido)methyl)-4-methoxyphenyl)acrylamide (E75)

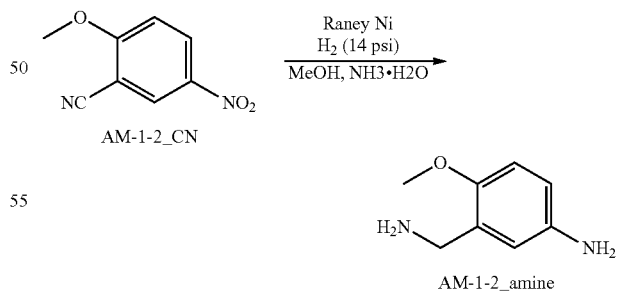

To a solution of AM-1-2_CN (630 mg, 3.5 mmol) in MeOH (40 mL) and NH$_3$.H$_2$O (4 mL) was added Raney Ni (300 mg). The reaction mixture was stirred at room temperature for three hrs under H$_2$ (14 psi) atmosphere. After filtered, the filtrate was concentrated and the residue was purified by column chromatography on silica gel (DCM/MeOH, 9:1) to give the product (250 mg, 47.2%).

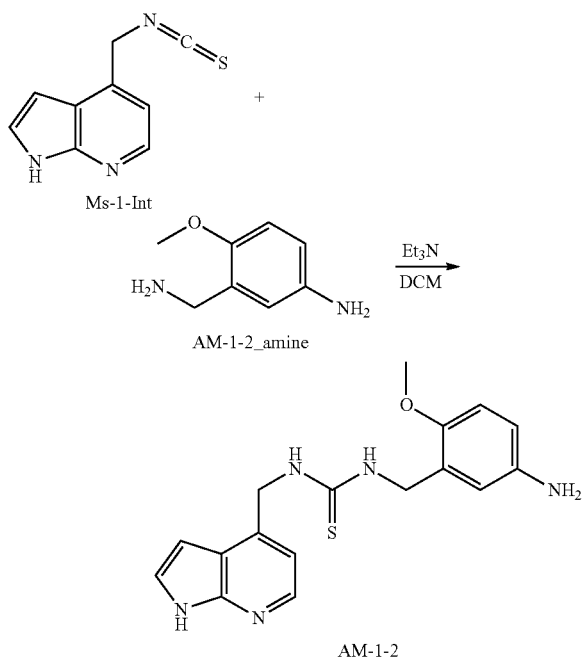

To a solution of AM-1-2_amine (250 mg, 1.64 mmol) and Ms-1-Int (310 mg, 1.64 mmol) in dry DCM (10 mL) was added Et$_3$N (0.68 mL, 4.92 mmol). The reaction mixture was stirred at r.t. for 12 hrs. The solvent was removed under reduced pressure. The residue was purified by column chromatography on silica gel (DCM/MeOH, 20:1) to give the product as a pale yellow solid (360 mg, 64.3%). For delivery, the product was further purified by prep-HPLC.

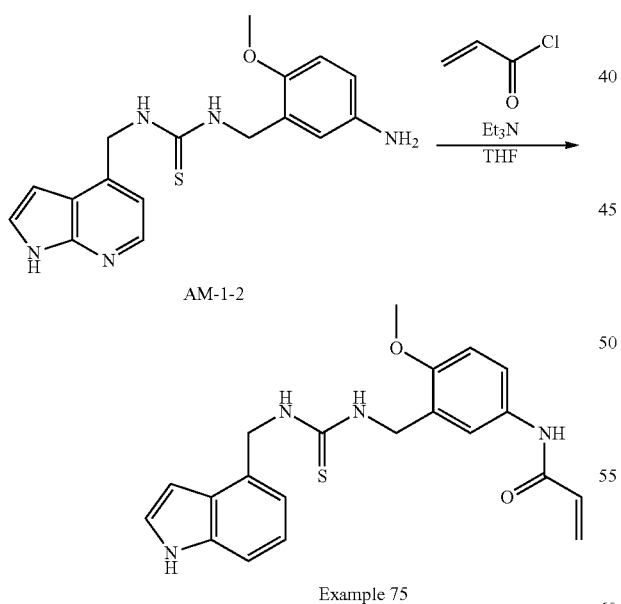

Acryloyl chloride (36 mg, 0.43 mmol) was added dropwise to a solution of AM-1-2 (90 mg, 0.29 mmol) and Et$_3$N (0.11 mL, 0.9 mmol) in dry THF (3 mL) at −70° C. under N$_2$ atmosphere. The mixture was warmed to r.t. and continued stirring for 10 mins. Water was added and the mixture was extracted with EtOAc repeatedly. The combined organic layer was dried over Na$_2$SO$_4$ and concentrated under reduced pressure. The residue was purified by Prep. HPLC under acid condition to give Example 75 (E75) (25 mg, TFA salt) as a white solid.

$^1$H NMR: 400 MHz MeOD

δ 8.21 (d, J=5.6 Hz, 1H), 7.55 (d, J=3.6 Hz, 2H), 7.49 (d, J=8.4 Hz, 1H), 7.32 (s, 1H), 6.92 (d, J=8.8 Hz, 1H), 6.84 (d, J=3.6 Hz, 1H), 6.35 (m, 2H), 5.74 (m, 1H), 5.22 (m, 2H), 4.69 (m, 2H), 3.81 (m, 3H).

Example 76

N-(5-((3-((1H-pyrrolo[2,3-b]pyridin-4-yl)methyl)thioureido)methyl)-2-chlorophenyl)acrylamide (E76)

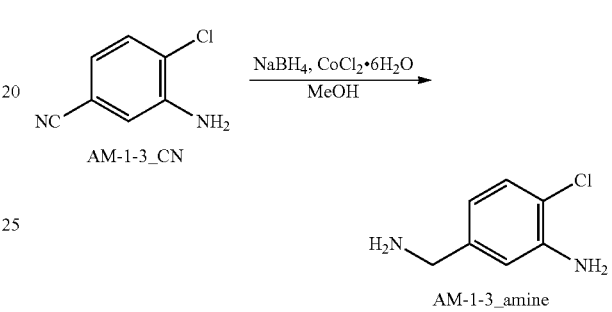

To a solution of AM-1-3_CN (1.5 g, 10 mmol) in MeOH (50 ml) was added CoCl$_2$.6H$_2$O (4.7 g, 20 mmol). NaBH$_4$ (1.13 g, 30 mmol) was added in portions to the above mixture at 0° C. The reaction mixture was warmed to r.t. and continued stirring for 12 hrs. The reaction mixture was made pH=13 with NH$_3$.H$_2$O and extracted with EA. The combined organic layer was washed with brine, dried over Na$_2$SO$_4$ and concentrated. The crude was purified by column chromatography on silica gel (DCM/MeOH, 9:1) to give the product (0.3 g, 20%).

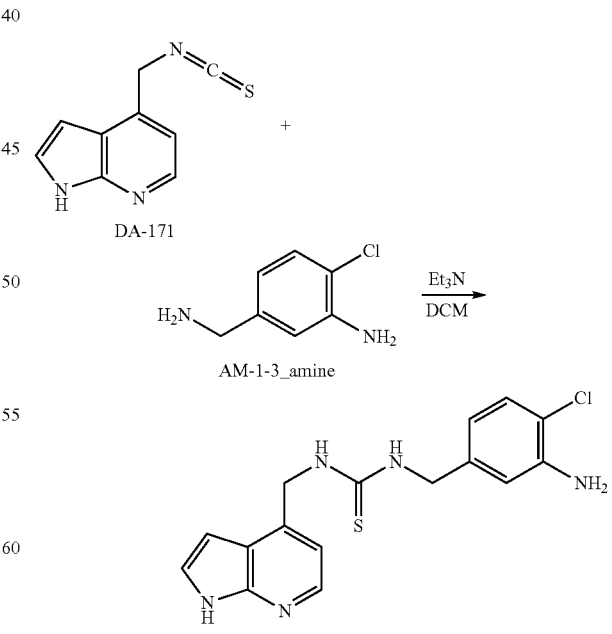

To a solution of AM-1-3_amine (310 mg, 2 mmol) and DA-171 (380 mg, 2 mmol) in dry DCM (15 mL) was added Et₃N (0.83 mL, 6 mmol). The reaction mixture was stirred at r.t. for 12 hrs. The solvent was removed under reduced pressure. The residue was purified by column chromatography on silica gel (DCM/MeOH, 20:1) to give the product as a white solid (341 mg, 50.0%).

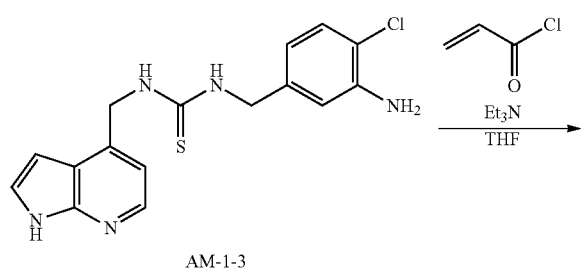

AM-1-3

Acryloyl chloride (39 mg, 0.44 mmol) was added dropwise to a solution of AM-1-3 (100 mg, 0.29 mmol) and Et₃N (0.12 mL, 0.88 mmol) in dry THF (5 mL) at −70° C. under N₂ atmosphere. The mixture was warmed to r.t. and continued stirring for 10 mins. Water was added and the mixture was extracted with EtOAc repeatedly. The combined organic layer was dried over Na₂SO₄ and concentrated under reduced pressure. The residue was purified by Prep. HPLC under acid condition to give Example 76 (E76) (21 mg, TFA salt) as a pale yellow solid.

¹H NMR: 400 MHz MeOD

δ 8.25 (d, J=6.0 Hz, 1H), 7.84 (s, 1H), 7.59 (d, J=3.6 Hz, 1H), 7.41 (d, J=8.4 Hz, 1H), 7.35 (d, J=4.0 Hz, 1H), 7.16 (d, J=8.0 Hz, 1H), 6.90 (d, J=3.6 Hz, 1H), 6.57 (m, 1H), 6.40 (m, 1H), 5.83 (m, 1H), 5.25 (s, 2H), 4.76 (m, 2H).

Example 77

N-(5-((3-((1H-pyrrolo[2,3-b]pyridin-4-yl)methyl)thioureido)methyl)-2-hydroxyphenyl)acrylamide (E77)

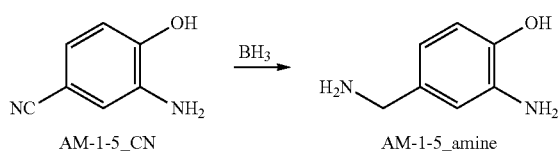

To a solution of AM-1-5_CN (400 mg, 3 mmol) in dry THF (20 mL) was added BH₃.Me₂S (0.85 mL, 9.0 mmol) dropwise under nitrogen atmosphere at 0° C. The reaction mixture was warmed to r.t. and continued stirring for half an hour. Then the reaction mixture was heated at reflux for three hrs. The mixture was cooled to r.t. and quenched by 2 N HCl (1 mL). Then the mixture was heated at reflux for an hour. The solvent was removed under reduced pressure to give the crude product as HCl salt (0.6 g).

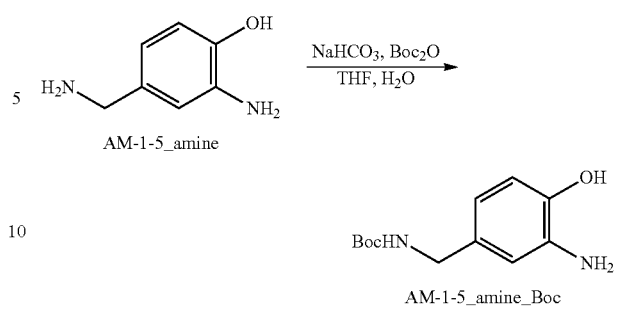

To a solution of AM-1-5_amine (150 mg, 1.08 mmol) in THF (16 mL) and H₂O (4 mL) was added NaHCO₃ (316 mg, 3.78 mmol). A solution of Boc₂O (260 mg, 1.19 mmol) in THF (2 mL) was added dropwise. The reaction mixture was stirred at r.t. for two hrs. Water (20 mL) was added and extracted with EtOAc (50 mL×2). The combined organic layer was washed with brine, dried over Na₂SO₄ and concentrated. The crude (260 mg) was used to the next step without further purification.

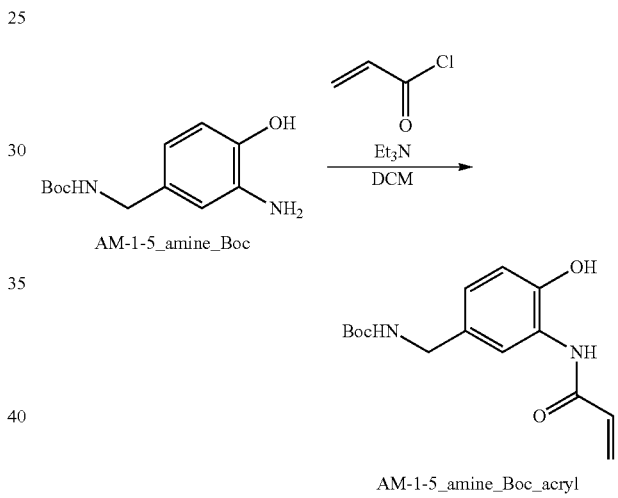

Acryloyl chloride (146 mg, 1.62 mmol) was added dropwise to a solution of AM-1-5_amine_Boc (260 mg, 1.08 mmol) and Et₃N (0.15 mL, 1.08 mmol) in dry DCM (10 mL) at 0° C. under N₂ atmosphere. The mixture was warmed to r.t. and continued stirring for half an hour. Water was added and the mixture was extracted with DCM repeatedly. The combined organic layer was dried over Na₂SO₄ and concentrated under reduced pressure. The residue was purified by column chromatography on silica gel (PE/EA, 4:1) to give AM-1-5_amine_Boc_acryl (100 mg, 35.7%).

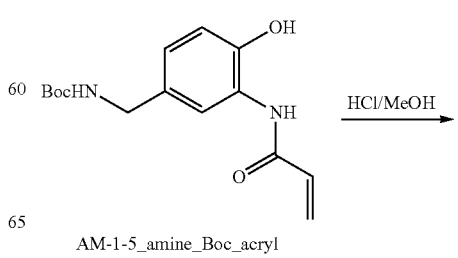

125
-continued

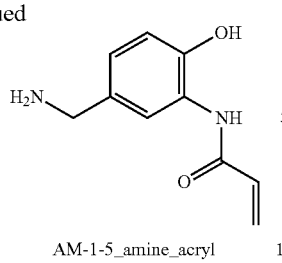

AM-1-5_amine_acryl

A solution of AM-1-5_amine_Boc_acryl (100 mg, 0.34 mmol) in HCl/MeOH (5 mL) was stirred at room temperature for half an hour. The solvent was removed under reduced pressure to give the crude product as HCl salt (40 mg) which was used to the next step without further purification.

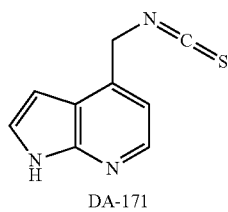

DA-171

+

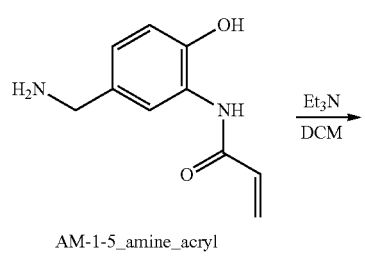

AM-1-5_amine_acryl

Et₃N / DCM →

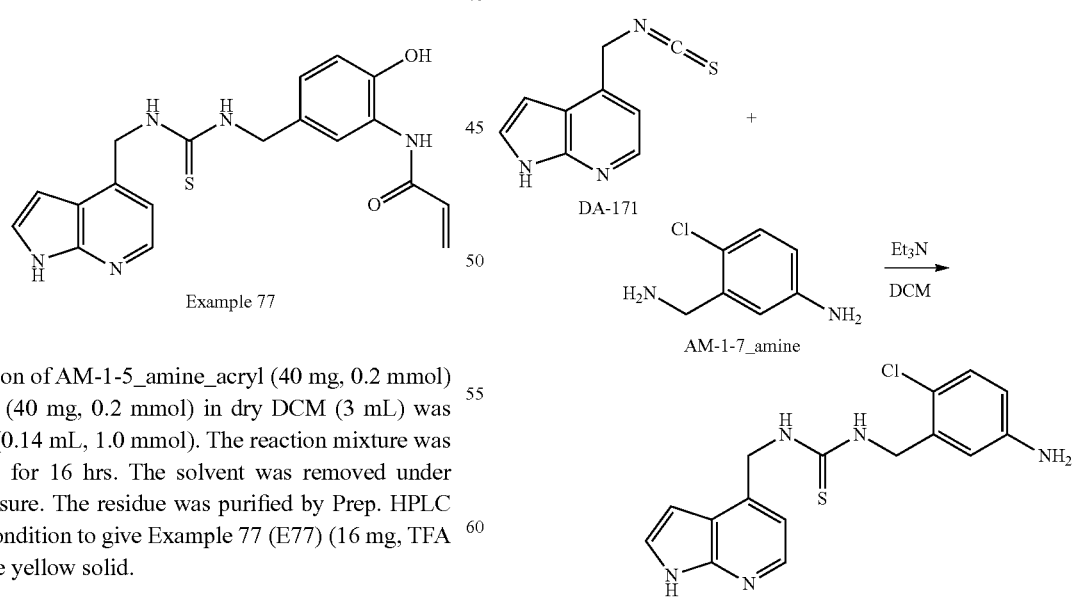

Example 77

To a solution of AM-1-5_amine_acryl (40 mg, 0.2 mmol) and DA-171 (40 mg, 0.2 mmol) in dry DCM (3 mL) was added Et₃N (0.14 mL, 1.0 mmol). The reaction mixture was stirred at r.t. for 16 hrs. The solvent was removed under reduced pressure. The residue was purified by Prep. HPLC under acid condition to give Example 77 (E77) (16 mg, TFA salt) as a pale yellow solid.

¹H NMR: 400 MHz MeOD

δ 8.22 (d, J=5.6 Hz, 1H), 7.76 (s, 1H), 7.36 (s, 1H), 7.57 (d, J=3.6 Hz, 1H), 7.30 (s, 1H), 7.00 (m, 1H), 6.98 (m, 1H), 6.85 (m, 1H), 6.36 (m, 1H), 5.77 (m, 1H), 5.23 (s, 2H), 4.62 (s, 2H).

126
Example 78

N-(3-((3-((1H-pyrrolo[2,3-b]pyridin-4-yl)methyl) thioureido)methyl)-4-chlorophenyl)acrylamide (E78)

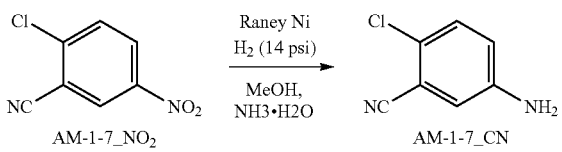 [SMILES: N#Cc1cc([N+](=O)[O-])ccc1Cl ; N#Cc1cc(N)ccc1Cl]

AM-1-7_NO₂ → AM-1-7_CN

Raney Ni
H₂ (14 psi)
MeOH, NH₃·H₂O

To a solution of AM-1-7_NO₂ (917 mg, 5 mmol) in MeOH (20 mL) and NH₃·H₂O (2 mL) was added Raney Ni (500 mg). The reaction mixture was stirred at room temperature for five hrs under H₂ (14 psi) atmosphere. After filtered, the filtrate was concentrated and the residue was purified by column chromatography on silica gel (DCM/MeOH, 30:1) to give the product (400 mg, 51.3%).

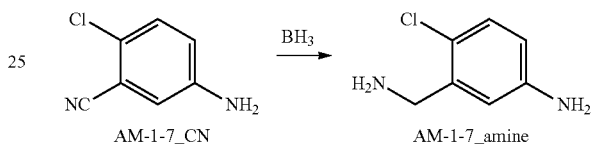

AM-1-7_CN → AM-1-7_amine

BH₃

To a solution of AM-1-7_CN (400 mg, 2.6 mmol) in dry THF (20 ml) was added BH₃·Me₂S (0.49 mL, 5.2 mmol) dropwise under nitrogen atmosphere at 0° C. The reaction mixture was warmed to r.t. and continued stirring for half an hour. Then the reaction mixture was heated at reflux for two hrs. The mixture was cooled to r.t. and quenched by 2 N HCl (1 mL). Then the mixture was heated at reflux for an hour. The solvent was removed under reduced pressure to give the crude product as HCl salt (0.62 g).

To a solution of AM-1-7_amine (400 mg, 1.76 mmol) and DA-171 (330 mg, 1.76 mmol) in dry DCM (20 mL) was added Et₃N (0.73 mL, 5.28 mmol). The reaction mixture was stirred at r.t. for three hrs. The solvent was removed under reduced pressure. The residue was purified by column chromatography on silica gel (DCM/MeOH, 15:1) to give AM-1-7 (470 mg, 82.4%) as a white solid.

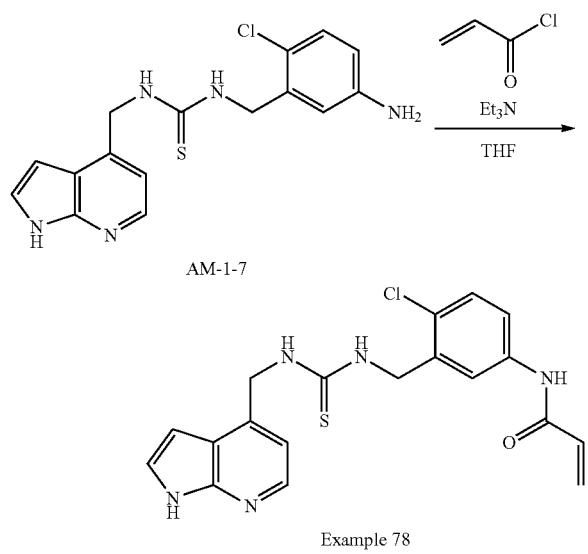

Acryloyl chloride (59 mg, 0.64 mmol) was added dropwise to a solution of AM-1-7 (150 mg, 0.43 mmol) and Et₃N (0.36 mL, 1.29 mmol) in dry THF (5 mL) at −70° C. under N₂ atmosphere. The mixture was warmed to r.t. and continued stirring for 10 mins. Water was added and the mixture was extracted with EtOAc repeatedly. The combined organic layer was dried over Na₂SO₄ and concentrated under reduced pressure. The residue was purified by Prep. HPLC for two times under acid condition to give Example 78 (E78) (10.5 mg, TFA salt) as a pale yellow solid.

¹H NMR: 400 MHz MeOD

δ 8.25 (d, J=6.0 Hz, 1H), 7.83 (d, J=7.2 Hz, 1H), 7.59 (d, J=4.0 Hz, 1H), 7.47 (m, 1H), 7.43 (m, 1H), 7.34 (d, J=8.4 Hz, 1H), 6.90 (d, J=4.0 Hz, 1H), 6.41 (m, 2H), 5.79 (m, 1H), 5.26 (s, 2H), 4.84 (s, 2H).

Example 79

1-((1H-pyrrolo[2,3-b]pyridin-4-yl)methyl)-3-(3-amino-2-chlorobenzyl)thiourea (E79)

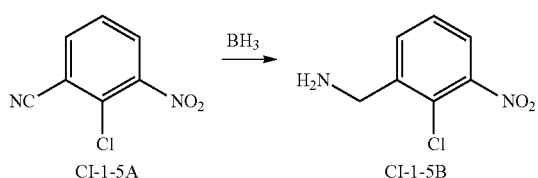

To a solution of 2-chloro-3-nitrobenzonitrile (200 mg, 1.3 mmol) in absolute THF (20 mL) was added dropwise BH₃SMe₂ (0.2 mL, 2.6 mmol) under nitrogen atmosphere protection. The mixture was stirred at reflux for 2 hrs. Then 2 N HCl (1.5 mL) was added to the mixture and the mixture was stirred at reflux for 1 hour. The mixture was condensed to crude compound CI-1-5B (248 mg) as yellow solid.

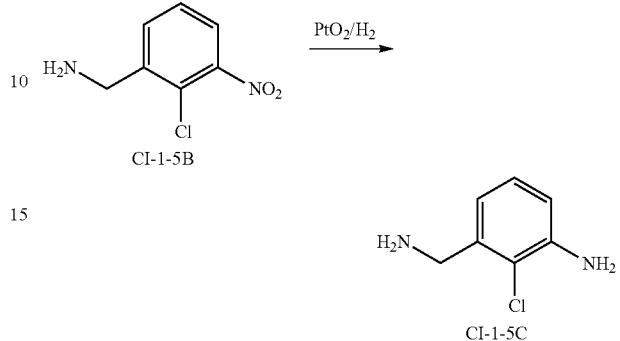

To a solution of compound CI-1-5B (200 mg, 0.9 mmol) in EtOAC (20 mL) was added PtO₂ (50 mg), then H₂ was accessed. The mixture was stirred at room temperature for 48 hrs.

Then the mixture was filtered and condensed to give crude CI-1-5C (103 mg) as yellow solid.

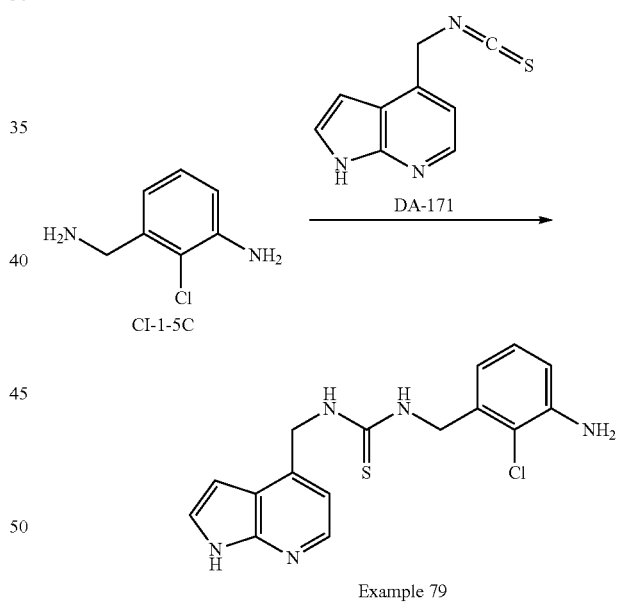

To a solution of CI-1-5C (103 mg, 0.67 mmol) and compound DA-171 (127 mg, 0.67 mmol) in CH₂Cl₂ (10 mL) was added TEA (102 mg, 1.01 mmol). The mixture was stirred at room temperature for 2 hrs. Then the mixture washed with NaHCO₃ solution (20 mL×2), dried over Na₂SO₄ and condensed. The residue was purified by prep-HPLC to give Example 79 (E79) (4.5 mg, HCl salt) as yellow solid.

¹H NMR: 400 MHz MeOD

δ 8.38 (d, J=6.4 Hz, 1H), 7.73 (d, J=3.6 Hz, 1H), 7.53 (d, J=6.4 Hz, 1H), 7.41-7.34 (m, 3H), 7.06 (d, J=3.6 Hz, 1H), 5.34 (s, 2H), 4.92 (s, 2H).

Example 80

N-(2-((3-((1H-pyrrolo[2,3-b]pyridin-4-yl)methyl)thioureido)methyl)-3-chlorophenyl)acrylamide (E80)

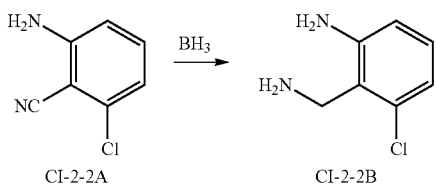

To a solution of 2-amino-6-chlorobenzonitrile (1 g, 6.6 mmol) in absolute THF (100 mL) was added dropwise BH$_3$SMe$_2$ (1.2 mL, 13.2 mmol) under nitrogen atmosphere protection. The mixture was stirred at reflux for 2 hrs. Then 2 N HCl (10 mL) was added to the mixture and the mixture was stirred at reflux for 1 hour. The mixture was condensed to crude compoundCl-2-2B (1.4 g) as yellow solid.

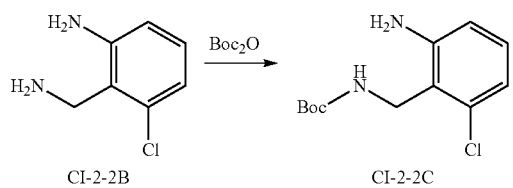 [SMILES: "Boc2O" ; NCc1c(N)cccc1Cl ; CC(C)(C)OC(=O)NCc1c(N)cccc1Cl]

To a solution of CI-2-2B (1 g, 6.4 mmol) in absolute THF (100 mL) and H$_2$O (25 mL) was added AcOK (3.14 g, 32 mmol) and Boc2O (1.4 g, 6.4 mmol). The mixture was stirred at room temperature for 2 hrs and condensed, dissolved in H$_2$O (100 mL), extracted with EtOAC (100 mL×2). The organic phase was separated, dried over Na$_2$SO$_4$ and condensed. The residue was purified by flash chromatography (petroleum ether/EtOAc=5:1) to give compoundCl-2-2C (0.6 g, 36.5%) as white solid.

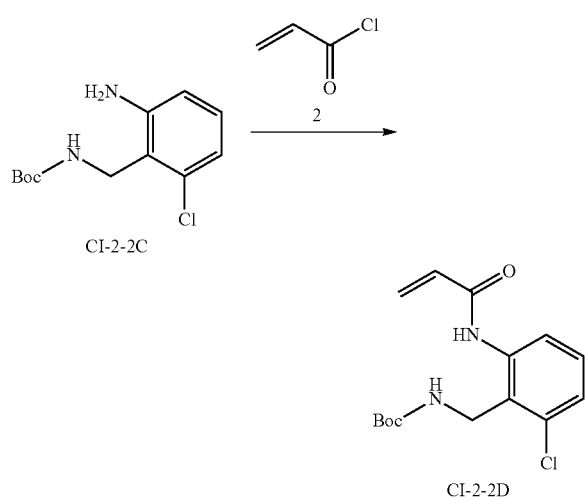

To a solution of CI-2-2C (200 mg, 0.78 mmol) in absolute CH$_2$Cl$_2$ (20 mL) was added TEA (119 mg, 1.17 mmol) and acryloyl chloride (71 mg, 0.78 mmol) at 0° C. The mixture was stirred at 0° C. for 10 minute and quenched with Na$_2$CO$_3$ solution (10 mL). The organic phase was separated, dried over Na$_2$SO$_4$ and condensed. The residue was purified by flash chromatography (petroleum ether/EtOAc=5:1) to give compoundCl-2-2D (114 mg, 47.1%) as white solid.

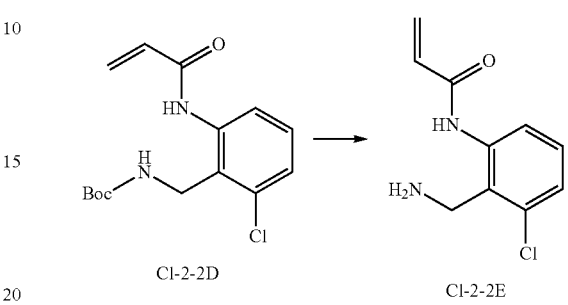

To a solution of CI-2-2D (114 mg, 0.37 mmol) in absolute CH$_2$Cl$_2$ (10 mL) was added TFA (2 mL). The mixture was stirred at room temperature for 30 minutes and condensed to crude compoundCl-2-2E (93 mg) as yellow slurry.

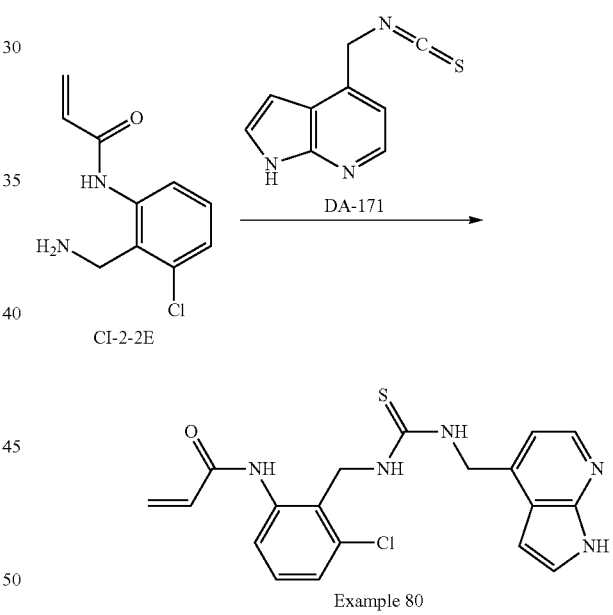

Example 80

To a solution of CI-2-2E (93 mg, 0.44 mmol) and compound DA-171 (84 mg, 0.44 mmol) in CH$_2$Cl$_2$ (10 mL) was added TEA (67 mg, 0.66 mmol). The mixture was stirred at room temperature overnight. Then the mixture washed with NaHCO$_3$ solution (10 mL×2), dried over Na$_2$SO$_4$ and condensed. The residue was purified by prep-HPLC to give Example 80 (E80) (18 mg, HCl salt) as white solid.

$^1$H NMR: 400 MHz MeOD

δ 8.32 (d, J=6 Hz, 1H), 7.81-7.78 (m, 1H), 7.67 (d, J=3.6 Hz, 1H), 7.44 (d, J=6 Hz, 1H), 7.38-7.32 (m, 2H), 6.98 (d, J=3.6 Hz, 1H), 6.52-6.45 (m, 1H), 6.40-6.35 (m, 1H), 5.79-5.76 (m, 1H), 5.28 (s, 2H), 4.98 (s, 2H).

Example 81

N-(2-((3-((1H-pyrrolo[2,3-b]pyridin-4-yl)methyl)thioureido)methyl)-5-chlorophenyl)acrylamide (E81)

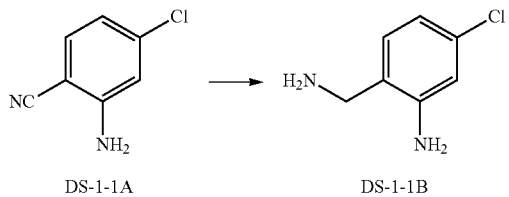 [SMILES: N#Cc1ccc(Cl)cc1N ; NCc1ccc(Cl)cc1N]

DS-1-1A → DS-1-1B

To a solution of 2-amino-4-chlorobenzonitrile (4 g, 26 mmol) in absolute THF (150 mL) was added dropwise BH$_3$SMe$_2$ (4.8 mL, 5.2 mmol) under nitrogen atmosphere protection.

The mixture was stirred at reflux for 2 hrs. Then 2 N HCl (8 mL) was added to the mixture and the mixture was stirred at reflux for 1 hour. The mixture was condensed to crude compound DS-1-1B (3.9 g).

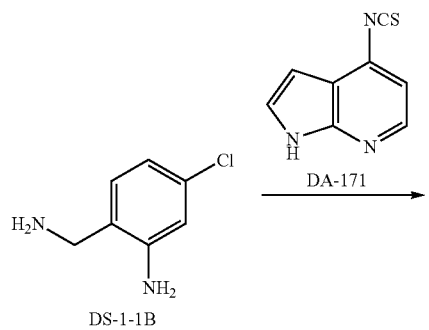

DS-1-1B + DA-171 →

To a solution of compound DS-1-1B (2 g, 11 mmol) and compound DA-171 (2.03 g, 11 mmol) in CH$_2$Cl$_2$ (100 mL) was added TEA (1.6 g, 16 mmol). The mixture was stirred at room temperature for 1 hour. Then the mixture was washed with NaHCO$_3$ solution (100 mL×2), dried over Na$_2$SO$_4$ and condensed. The residue was purified by flash chromatography (100% CH$_2$Cl$_2$ to CH$_2$Cl$_2$:CH$_3$OH=20:1) to give compound DS-1-1 (1.3 g, 35.6%) as yellow solid.

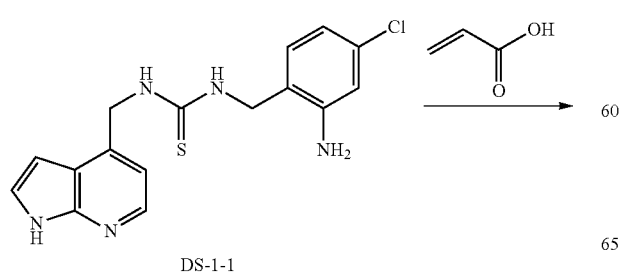

DS-1-1 →

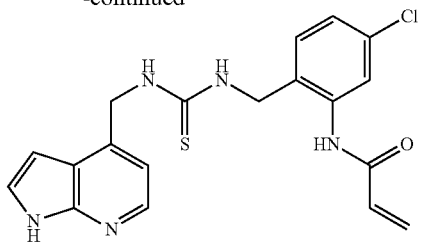

Example 81

To a solution of acrylic acid (105 mg, 1.45 mmol) in CH$_2$Cl$_2$ (10 mL) was added HATU (717 mg, 1.89 mmol) and TEA (382 mg, 3.78 mmol) at 0° C. The mixture was stirred at room temperature for 0.5 hour. And then compound DS-1-1 (100 mg, 0.29 mmol) was added to, the mixture was stirred at room temperature overnight. After stirring overnight, the mixture washed with NaHCO$_3$ solution (20 mL×2), dried over Na$_2$SO$_4$ and condensed. The residue was purified by prep-HPLC to give Example 81 (E81) (5.1 mg, TFA salt) as white solid.

$^1$H NMR: 400 MHz MeOD

δ 8.28 (d, J=6 Hz, 1H), 7.95-7.86 (m, 1H), 7.64 (d, J=3.6 Hz, 1H), 7.41-7.36 (m, 2H), 7.22-7.20 (m, 1H), 6.94 (d, J=3.6 Hz, 1H), 6.52-6.46 (m, 1H), 6.38-6.34 (m, 1H), 5.74 (d, J=10.8 Hz, 1H), 5.26 (s, 2H), 4.82 (s, 2H).

Example 82

N-(2-((3-((1H-pyrrolo[2,3-b]pyridin-4-yl)methyl)thioureido)methyl)-5-chlorophenyl)but-2-ynamide (E82)

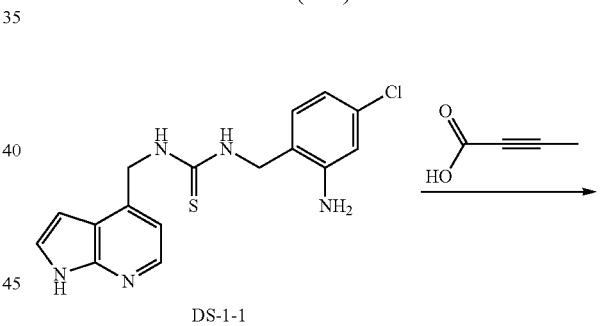

DS-1-1 →

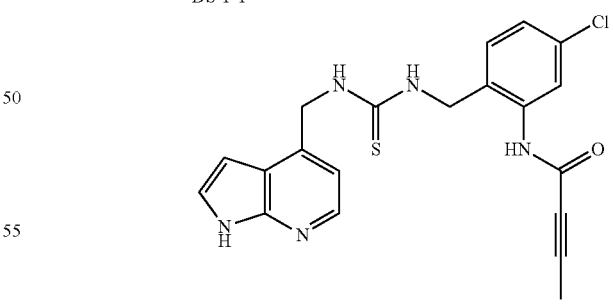

Example 82

To a solution of 2-butynoic acid (29 mg, 0.35 mmol) in DMF (1 mL) was added DCC (91 mg, 0.44 mmol) and TEA (88 mg, 0.87 mmol) at 0° C. The mixture was stirred at room temperature for 0.5 hour. And then compound DS-1-1 (100 mg, 0.29 mmol) was added to, the mixture was stirred at room temperature for 4 hour. After stirring for 4 hour, the mixture washed with NaHCO$_3$ solution (20 mL×2), dried over Na₂SO₄ and condensed. The residue was purified by prep-HPLC to give Example 82 (E82) (5 mg TFA salt) as yellow solid.

¹H NMR: 400 MHz MeOD

δ 8.24 (d, J=9.2 Hz, 1H), 7.70 (s, 1H), 7.57 (d, J=3.6 Hz, 1H), 7.34-7.28 (m, 2H), 7.18-7.16 (m, 1H), 6.86 (d, J=3.6 Hz, 1H), 5.2 (s, 2H), 4.74 s, 2H), 1.93 (s, 3H).

Example 83

N-(2-((3-((1H-pyrrolo[2,3-b]pyridin-4-yl)methyl)thioureido)methyl)phenyl)-2-hydroxyacetamide (E83)

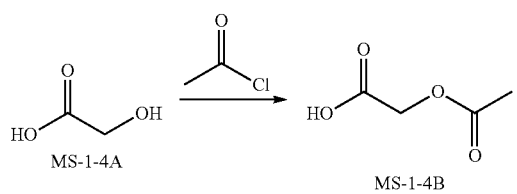

To a solution of glycolic acid (500 mg, 6.58 mmol) in CH₂Cl₂ (50 mL) was added TEA (1 g, 9.87 mmol) and acetyl chloride (770 mg, 9.87 mmol) at 0° C. The mixture was stirred at room temperature for 48 hrs and condensed to crude compound MS-1-4B (700 mg).

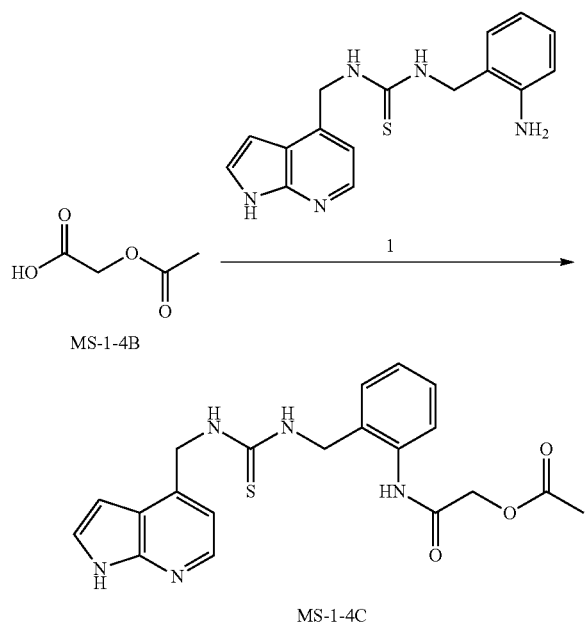

To a solution of compound MS-1-4B (51 mg, 0.48 mmol) and compound 1 (150 mg, 0.48 mmol) in CH₂Cl₂ (15 mL) was added TEA (73 mg, 0.72 mmol) and HATU (274 mg, 0.72 mmol). The mixture was stirred at room temperature overnight. Then the mixture was washed with NaHCO₃ solution (20 mL×2), dried over Na₂SO₄ and condensed. The residue was purified by flash chromatography (100% CH₂Cl₂ to CH₂Cl₂:CH₃OH=20:1) to give crude MS-1-4C (192 mg) as white solid.

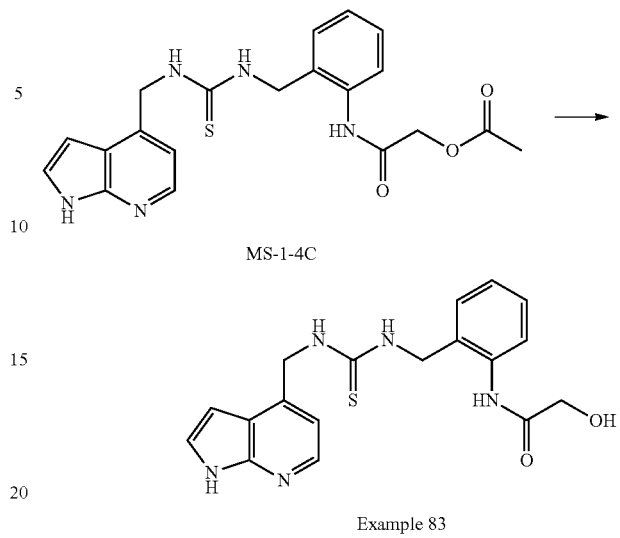

A solution of MS-1-4C (100 mg, 0.24 mmol) in NH₃/CH₃OH (10 mL) was stirred at room temperature overnight and condensed. The residue was purified by prep-HPLC to give Example 83 (E83) (10 mg TFA salt) as white solid.

¹H NMR: 400 MHz MeOD

δ 8.25 (d, J=6 Hz, 1H), 7.61 (d, J=3.6 Hz, 1H), 7.51 (d, J=7.6 Hz, 1H), 7.44 (d, J=7.2 Hz, 1H), 7.37-7.33 (m, 1H), 7.29-7.26 (m, 2H), 6.90 (d, J=3.6 Hz, 1H), 5.25 (s, 2H), 4.71 (s, 2H), 3.72 (s, 2H).

Example 84

N-(2-(2-(3-((1H-pyrrolo[2,3-b]pyridin-4-yl)methyl)thioureido)ethyl)phenyl)acrylamide (E84)

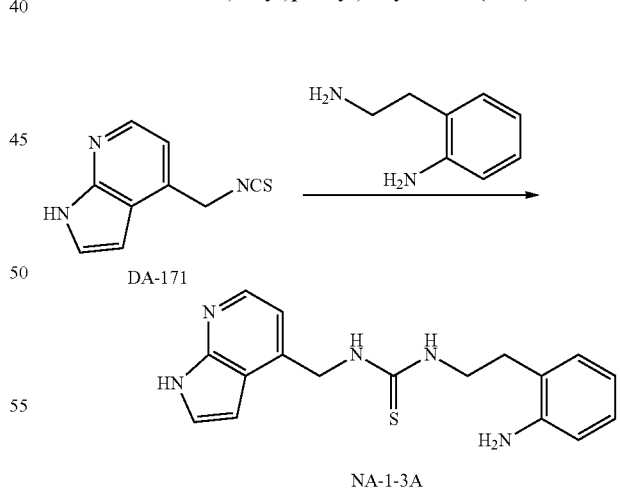

2-(2-Amino-ethyl)-phenylamine (82 mg, 0.53 mmol) was added to the mixture of DA-171 (100 mg, 0.53 mmol) and TEA (110 mg, 1.06 mmol) in CH₂Cl₂ (2 mL). The mixture was stirred for 5 hrs and concentrated in vacuo. The residue was purified by flash chromatography (MeOH/CH₂Cl₂, 0%~100%) to give the desired product as solid (80 mg, 46.5%).

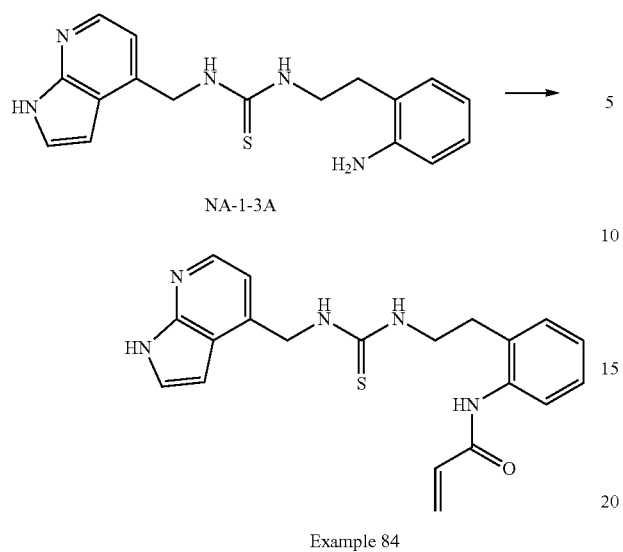

Example 84

Acryloyl chloride was added to a solution of NA-1-3A (80 mg, 0.25 mmol) and TEA (50 mg, 0.5 mmol) at 0° C. and stirred for 1 h. The reaction was quenched with MeOH and concentrated in vacuo. The residue was purified by pre. HPLC to give the product (13 mg, TFA salt)

$^1$H NMR: 400 MHz MeOH

δ 8.24 (d, J=5.6 Hz, 1H), 7.58 (d, J=3.6 Hz, 1H), 7.52-7.17 (m, 5H), 6.88 (d, J=3.6 Hz, 1H), 6.52-6.44 (m, 1H), 6.33-6.29 (m, 1H), 5.73 (d, J=11.2 Hz, 1H), 5.14 (s, 2H), 3.67 (m, J=7.2 Hz, 2H), 2.93 (t, J=7.2 Hz, 2H).

Example 85

N-(2-(3-((1H-pyrrolo[2,3-b]pyridin-4-yl)methyl)thioureido)ethyl)-3-(4-fluorophenyl)propiolamide (E85)

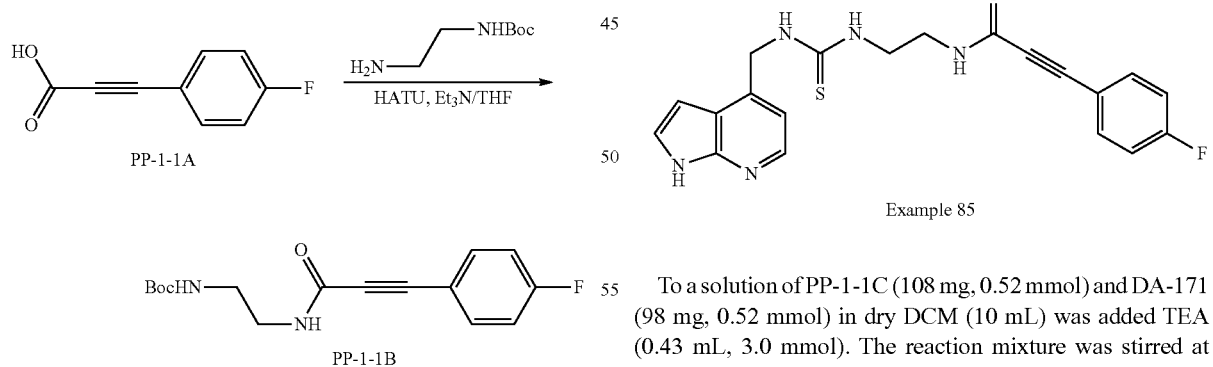

To a solution of (2-amino-ethyl)-carbamic acid tert-butyl ester (160 mg, 1.0 mmol), PP-1-1A (164 mg, 1.0 mmol) and TEA (0.42 mL, 3.0 mmol) in dry THF (15 mL) was added HATU (456 mg, 1.2 mmol) at room temperature. The reaction mixture was stirred at room temperature for three hours. EA was added and the mixture was washed with sat. NaHCO$_3$ (10 mL×2). The organic phase was separated, dried over Na$_2$SO$_4$ and concentrated. The residue was purified by flash chromatography (PE/EA=2:1) to give PP-1-1B (160 mg, 52.3%) as white solid.

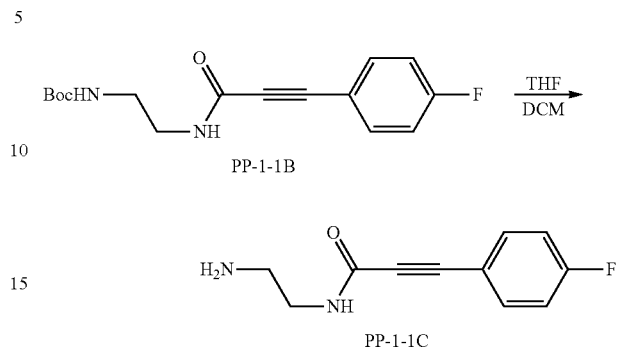

To a solution of PP-1-1B (160 mg, 0.52 mmol) in dry DCM (8 mL) was added TFA (2 mL) dropwise. The reaction mixture was stirred at room temperature for an hour. The solvent was removed under reduced pressure and the crude PP-1-1C (108 mg) was used to the next step without further purification.

To a solution of PP-1-1C (108 mg, 0.52 mmol) and DA-171 (98 mg, 0.52 mmol) in dry DCM (10 mL) was added TEA (0.43 mL, 3.0 mmol). The reaction mixture was stirred at room temperature for 16 hours. The solvent was removed under reduced pressure and the residue was purified by prep-HPLC under acid condition for two times to yield Example 85 (E85) (30 mg, TFA salt) as white solid.

$^1$H NMR: 400 MHz MeOD

δ 8.28 (d, J=6 Hz, 1H), 7.62 (m, 3H), 7.42 (t, J=3.2 Hz, 1H), 7.19 (t, J=8.8 Hz, 2H), 6.94 (t, J=2.4 Hz, 1H), 5.26 (s, 2H), 3.75 (m, 2H), 3.52 (t, J=6.4 Hz, 2H).

Example 86

N-(2-(3-((1H-pyrrolo[2,3-b]pyridin-4-yl)methyl)thioureido)ethyl)-3-(3-fluorophenyl)propiolamide (E86)

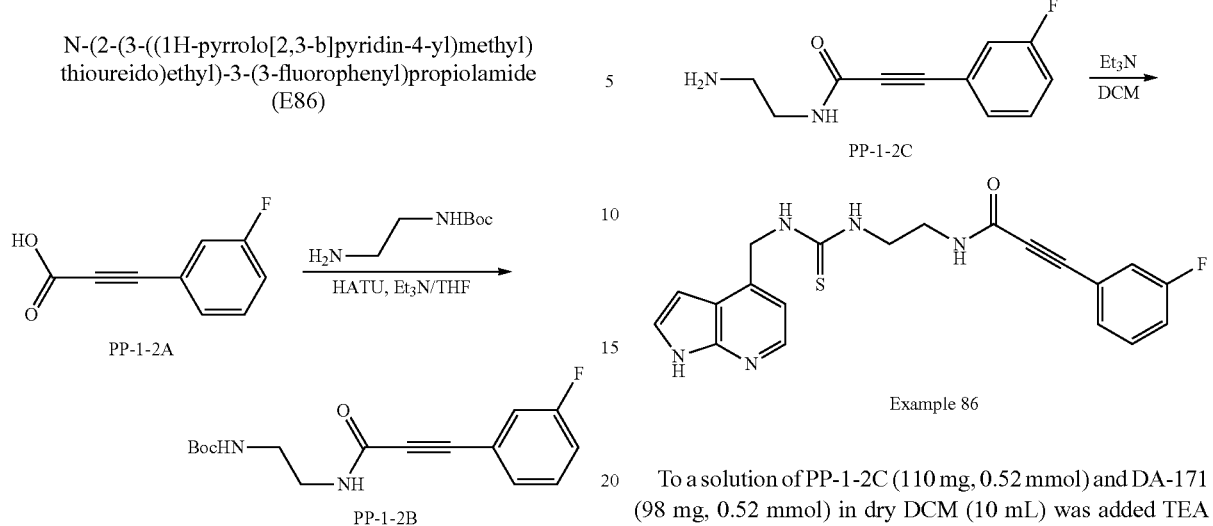

To a solution of (2-amino-ethyl)-carbamic acid tert-butyl ester (160 mg, 1.0 mmol), PP-1-2A (164 mg, 1.0 mmol) and TEA (0.42 mL, 3.0 mmol) in dry THF (15 mL) was added HATU (456 mg, 1.2 mmol) at room temperature. The reaction mixture was stirred at room temperature for three hours. EA was added and the mixture was washed with sat. NaHCO$_3$ (10 mL×2). The organic phase was separated, dried over Na$_2$SO$_4$ and concentrated. The residue was purified by flash chromatography (PE/EA=2:1) to give PP-1-2B (158 mg, 52.1%) as white solid.

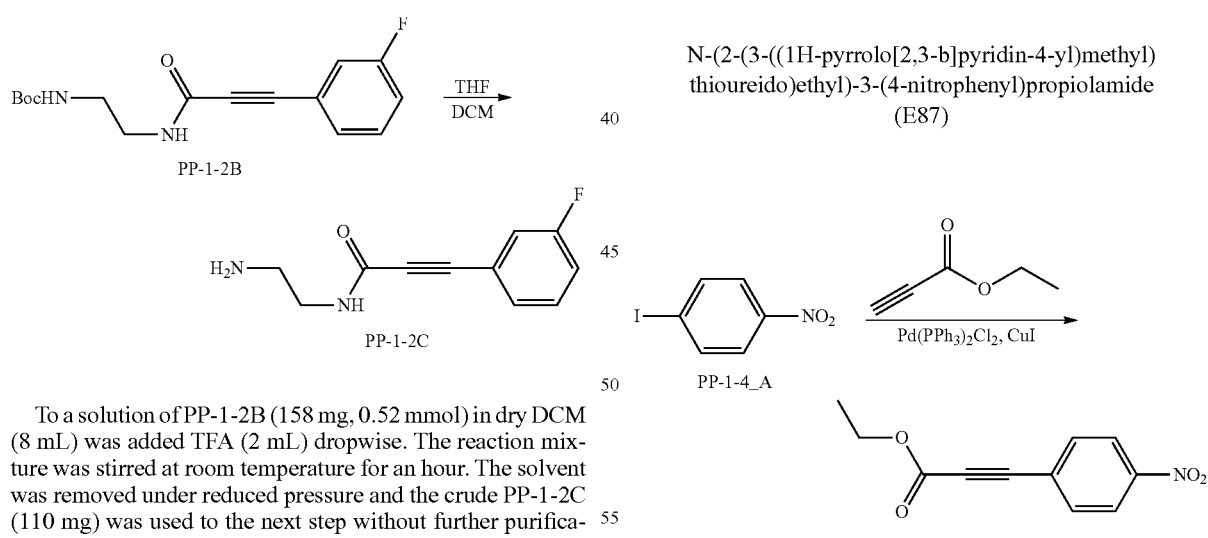

To a solution of PP-1-2B (158 mg, 0.52 mmol) in dry DCM (8 mL) was added TFA (2 mL) dropwise. The reaction mixture was stirred at room temperature for an hour. The solvent was removed under reduced pressure and the crude PP-1-2C (110 mg) was used to the next step without further purification.

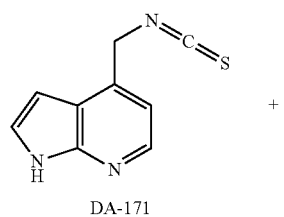

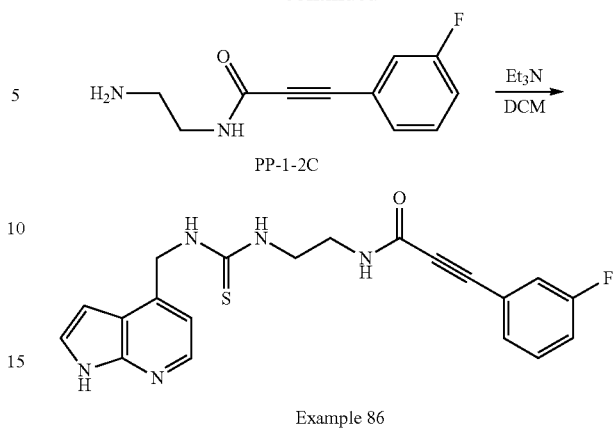

To a solution of PP-1-2C (110 mg, 0.52 mmol) and DA-171 (98 mg, 0.52 mmol) in dry DCM (10 mL) was added TEA (0.43 mL, 3.0 mmol). The reaction mixture was stirred at room temperature for 16 hours. The solvent was removed under reduced pressure and the residue was purified by prep-HPLC under acid condition for two times to yield Example 86 (E86) (25 mg, TFA salt) as white solid.

$^1$H NMR: 400 MHz MeOD

δ 8.29 (d, J=6 Hz, 1H), 7.64 (d, J=3.6 Hz, 1H), 7.44 (m, 3H), 7.32 (m, 2H), 6.95 (d, J=3.6 Hz, 1H), 5.27 (s, 2H), 3.76 (s, 2H), 3.53 (d, J=6.0 Hz, 2H).

Example 87

N-(2-(3-((1H-pyrrolo[2,3-b]pyridin-4-yl)methyl)thioureido)ethyl)-3-(4-nitrophenyl)propiolamide (E87)

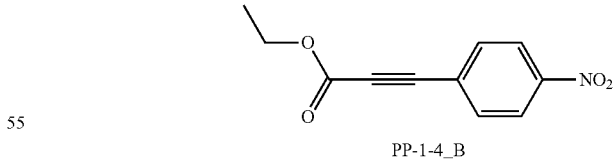

To a solution of PP-1-4_A (2.49 g, 10 mmol), propynoic acid ethyl ester (1.27 g, 13 mmol), TEA (4.2 mL, 30 mmol) and CuI (0.19 g, 1.0 mmol) in dry DMF (30 mL) was added Pd(PPh$_3$)$_2$Cl$_2$ (0.35 g, 0.5 mmol) under N$_2$ atmosphere. The reaction mixture was stirred at room temperature for 12 hours. The solvent was removed under reduced pressure and the residue was purified by flash chromatography (PE/EA=10:1) to give PP-1-4_B (1.2 g, 54.8%) as yellow solid.

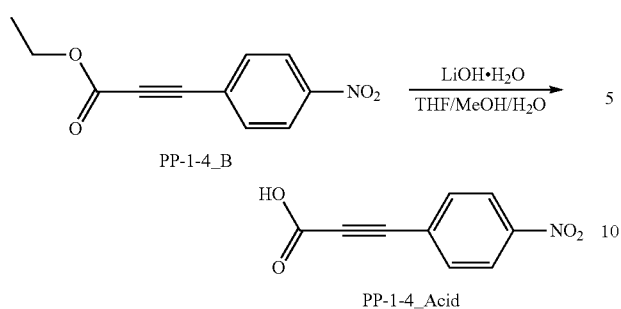

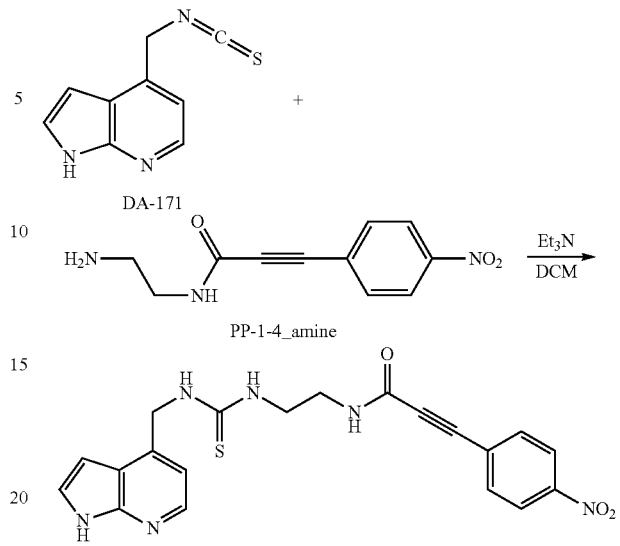

To a solution of PP-1-4_B (438 mg, 2.0 mmol) in THF/MeOH/H$_2$O (8 mL/2 mL/2 mL) was added LiOH H$_2$O (116 mg, 2.8 mmol). The reaction mixture was stirred at room temperature for 16 hours. The organic solvent was removed under reduced pressure and the aqueous was made pH=4 with 1N HCl slowly. After filtered, the solid was collected which was PP-1-4_Acid (180 g, 50%) as yellow solid.

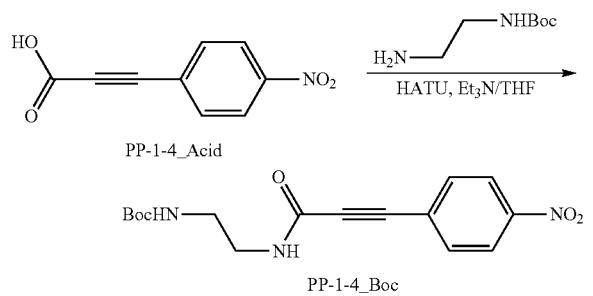

To a solution of (2-amino-ethyl)-carbamic acid tert-butyl ester (96 mg, 0.6 mmol), PP-1-4_Acid (120 mg, 0.6 mmol) and TEA (0.18 mL, 1.2 mmol) in dry THF (5 mL) was added HATU (266 mg, 0.7 mmol) at room temperature. The reaction mixture was stirred at room temperature for three hours. EA was added and the mixture was washed with sat. NaHCO$_3$ (10 mL×2). The organic phase was separated, dried over Na$_2$SO$_4$ and concentrated. The residue was purified by flash chromatography (PE/EA=3:1) to give PP-1-4_Boc (190 mg, 95%) as white solid.

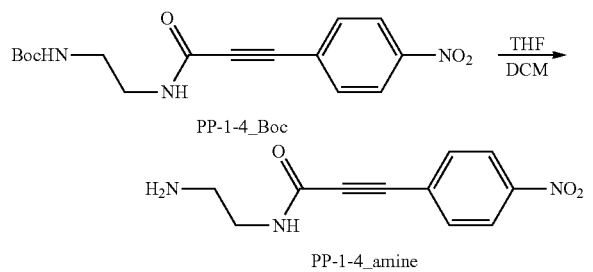

To a solution of PP-1-4_Boc (190 mg, 0.57 mmol) in dry DCM (8 mL) was added TFA (2 mL) dropwise. The reaction mixture was stirred at room temperature for an hour. The solvent was removed under reduced pressure and the crude PP-1-4_amine (140 mg) was used to the next step without further purification.

To a solution of PP-1-4_amine (120 mg, 0.6 mmol) and DA-171 (114 mg, 0.6 mmol) in dry DCM (5 mL) was added TEA (0.45 mL, 3.0 mmol). The reaction mixture was stirred at room temperature for three hours. The solvent was removed under reduced pressure and the residue was purified by prep-HPLC under acid condition to afford Example 87 (E87) (35 mg, TFA salt) as white solid.

$^1$H NMR: 400 MHz MeOD

δ 8.31 (m, 3H), 7.80 (m, 2H), 7.65 (d, J=3.2 Hz, 1H), 7.45 (d, J=5.6 Hz, 1H), 6.96 (d, J=3.6 Hz, 1H), 5.27 (s, 2H), 3.76 (m, 2H), 3.54 (t, J=6.0 Hz, 2H).

Example 88

N-(2-(3-((1H-pyrrolo[2,3-b]pyridin-4-yl)methyl)thioureido)ethyl)-3-(p-tolyl)propiolamide (E88)

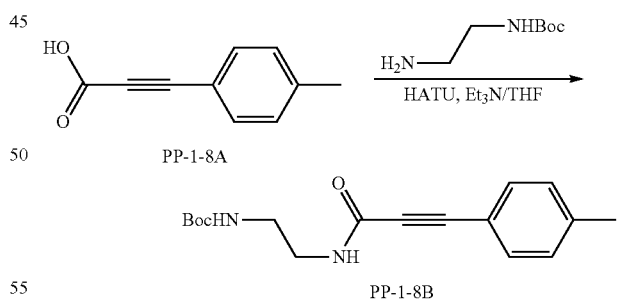

To a solution of (2-amino-ethyl)-carbamic acid tert-butyl ester (160 mg, 1.0 mmol), PP-1-8A (160 mg, 1.0 mmol) and TEA (0.42 mL, 3.0 mmol) in dry THF (15 mL) was added HATU (456 mg, 1.2 mmol) at room temperature. The reaction mixture was stirred at room temperature for three hours. EA was added and the mixture was washed with sat. NaHCO$_3$ (10 mL×2). The organic phase was separated, dried over Na$_2$SO$_4$ and concentrated. The residue was purified by flash chromatography (PE/EA=3:1) to give PP-1-8B (180 mg, 46.1%) as white solid.

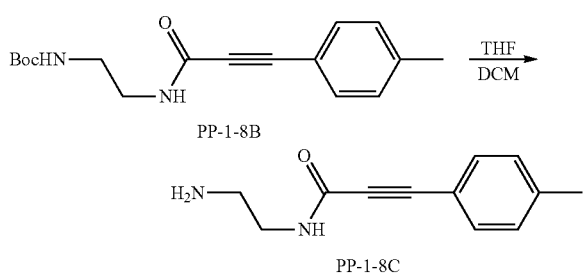

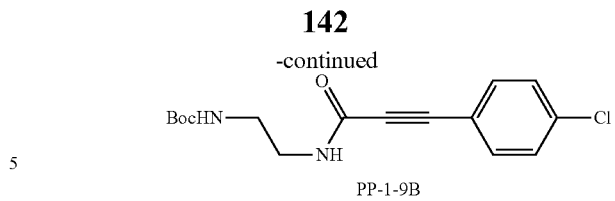

To a solution of PP-1-8B (180 mg, 0.46 mmol) in dry DCM (8 mL) was added TFA (2 mL) dropwise. The reaction mixture was stirred at room temperature for an hour. The solvent was removed under reduced pressure and the crude PP-1-8C (140 mg) was used to the next step without further purification.

To a solution of (2-amino-ethyl)-carbamic acid tert-butyl ester (160 mg, 1.0 mmol), PP-1-9A (180 mg, 1.0 mmol) and TEA (0.42 mL, 3.0 mmol) in dry THF (15 mL) was added HATU (456 mg, 1.2 mmol) at room temperature. The reaction mixture was stirred at room temperature for three hours. EA was added and the mixture was washed with sat. NaHCO₃ (10 mL×2). The organic phase was separated, dried over Na₂SO₄ and concentrated. The residue was purified by flash chromatography (PE/EA=3:1) to give PP-1-9B (250 mg, 59%) as white solid.

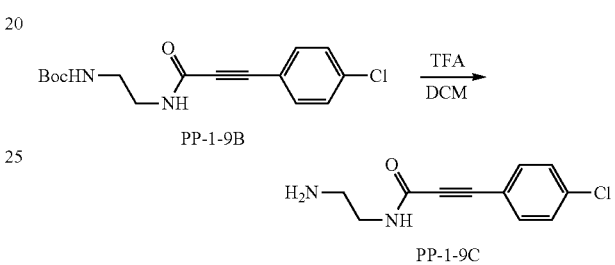

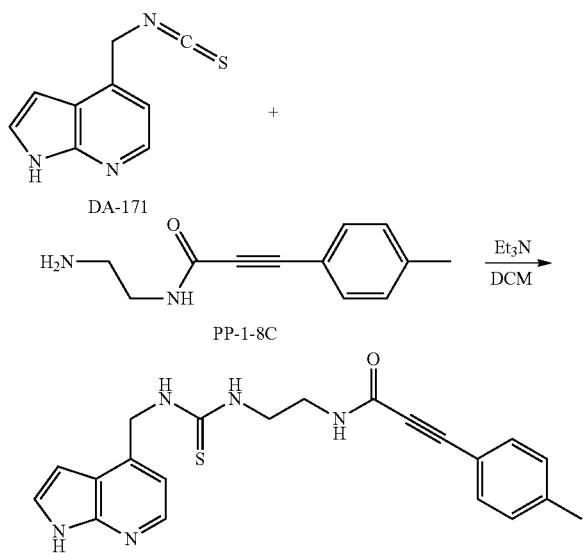

To a solution of PP-1-9B (250 mg, 0.59 mmol) in dry DCM (8 mL) was added TFA (2 mL) dropwise. The reaction mixture was stirred at room temperature for an hour. The solvent was removed under reduced pressure and the crude PP-1-9C (204 mg) was used to the next step without further purification.

To a solution of PP-1-8C (140 mg, 0.46 mmol) and DA-171 (90 mg, 0.46 mmol) in dry DCM (10 mL) was added TEA (0.34 mL, 2.4 mmol). The reaction mixture was stirred at room temperature for 16 hours. The solvent was removed under reduced pressure and the residue was purified by prep-HPLC under acid condition to yield Example 88 (E88) (40 mg, TFA salt) as white solid.

¹H NMR: 400 MHz MeOD

δ 8.29 (d, J=6.0 Hz, 1H), 7.64 (d, J=3.6 Hz, 1H), 7.45 (m, 3H), 7.25 (d, J=8.4 Hz, 2H), 6.96 (d, J=3.6 Hz, 1H), 5.27 (s, 2H), 3.75 (m, 2H), 3.52 (t, J=6.4 Hz, 2H), 2.40 (s, 3H).

Example 89

N-(2-(3-((1H-pyrrolo[2,3-b]pyridin-4-yl)methyl)thioureido)ethyl)-3-(4-chlorophenyl)propiolamide (E89)

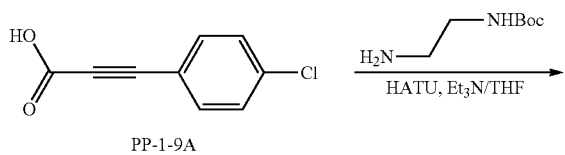

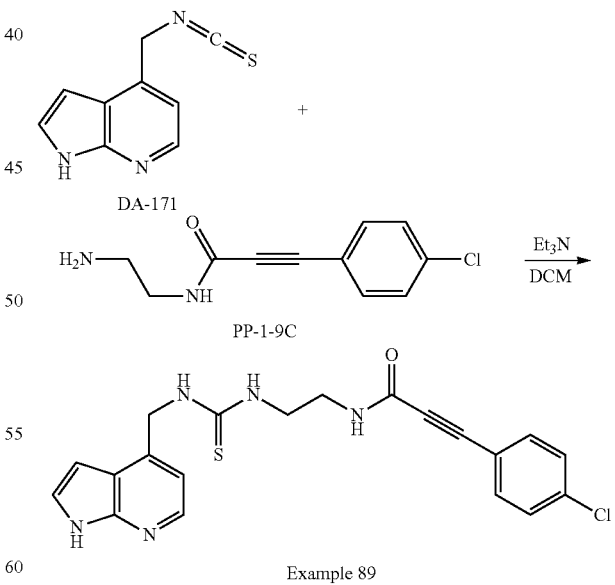

To a solution of PP-1-9C (204 mg, 0.6 mmol) and DA-171 (120 mg, 0.6 mmol) in dry DCM (10 mL) was added TEA (0.5 mL, 3.6 mmol). The reaction mixture was stirred at room temperature overnight. The solvent was removed under reduced pressure and the residue was purified by prep-HPLC under acid condition for two times to obtain Example 89 (E89) (40 mg, TFA salt) as white solid.

¹H NMR: 400 MHz MeOD

δ 8.29 (d, J=6.0 Hz, 1H), 7.63 (d, J=3.6 Hz, 1H), 7.55 (m, 2H), 7.47 (m, 2H), 7.42 (m, 1H), 6.94 (d, J=3.6 Hz, 1H), 5.26 (s, 2H), 3.76 (s, 2H), 3.53 (d, J=6.0 Hz, 2H).

Example 90

N-(2-(3-((1H-pyrrolo[2,3-b]pyridin-4-yl)methyl)thioureido)ethyl)-3-(2-fluorophenyl)propiolamide (E90)

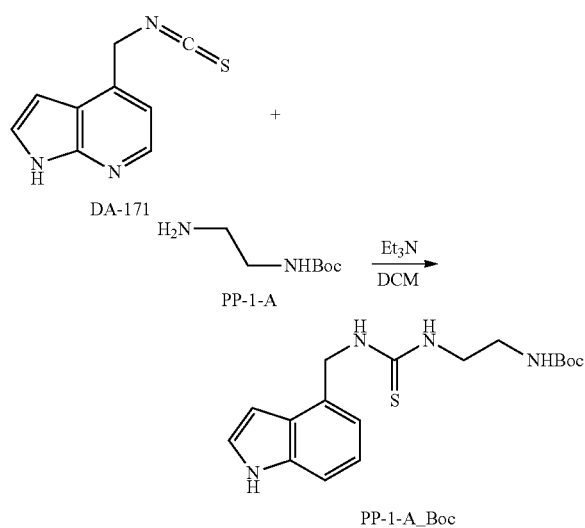

To a solution of PP-1-A (1.6 g, 10 mmol) and DA-171 (1.89 g, 10 mmol) in dry DCM (100 mL) was added TEA (4.2 mL, 30 mmol). The reaction mixture was stirred at room temperature for two hours. The solvent was removed under reduced pressure and the residue was purified by flash chromatography (DCM/MeOH=30:1) to give PP-1-A_Boc (2.0 g, 57.1%) as white solid.

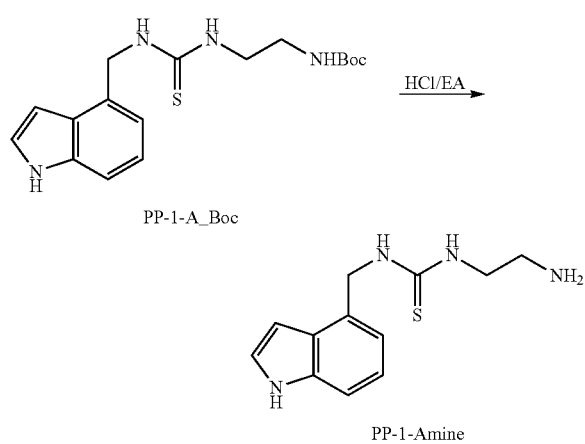

A solution of PP-1-A_Boc (2.0 g, 5.3 mmol) in HCl/EA (10 mL) was stirred at room temperature for 16 hrs. After filtered, the solid (2.4 g) was collected which was used to the next step without further purification.

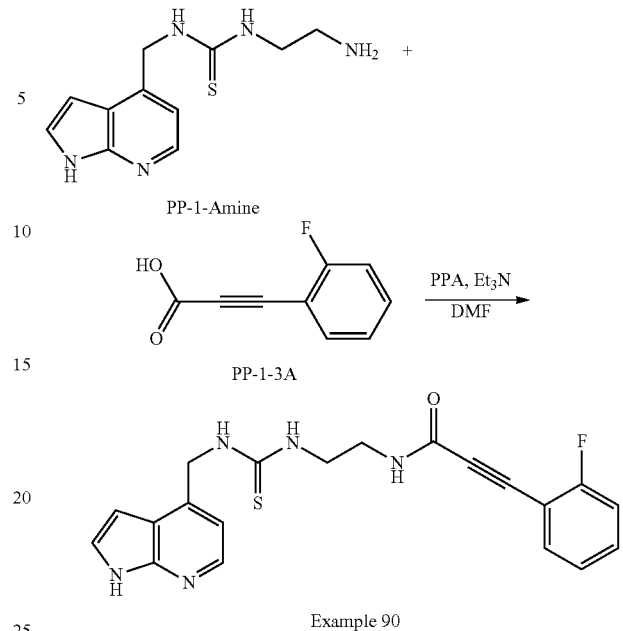

To a solution of PP-1-Amine (125 mg, 0.5 mmol) and PP-1-3A (82 mg, 0.5 mmol) in dry DMF (3 mL) was added PPA (190 mg, 0.6 mmol) and TEA (0.18 mL, 1.5 mmol) at r.t. The mixture was stirred at this temperature for three hours. After filtered, the filtrate was purified by prep-HPLC under acid condition and then purified by prep-HPLC under basic condition to yield Example 90 (E90) (20 mg, free base) as white solid.

¹H NMR: 400 MHz MeOD

δ 8.11 (d, J=5.2 Hz, 1H), 7.56 (m, 1H), 7.49 (m, 1H), 7.35 (d, J=3.2 Hz, 1H), 7.21 (m, 2H), 7.03 (d, J=5.2 Hz, 1H), 6.60 (d, J=3.6 Hz, 1H), 5.06 (s, 2H), 3.71 (s, 2H), 3.48 (d, J=604 Hz, 2H).

Example 91

N-(2-(3-((1H-pyrrolo[2,3-b]pyridin-4-yl)methyl)thioureido)ethyl)-3-(3-methoxyphenyl)propiolamide (E91)

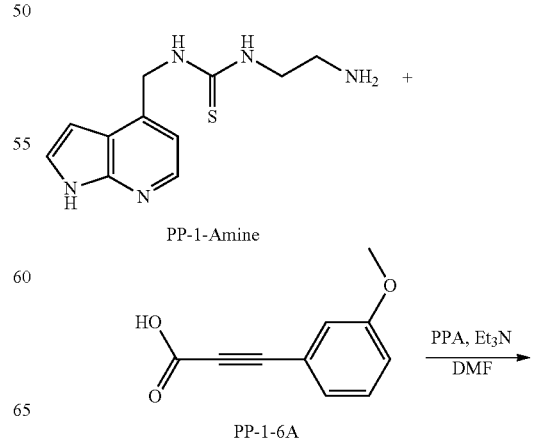

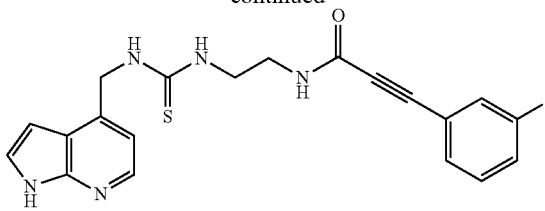

Example 91

To a solution of PP-1-Amine (124 mg, 0.5 mmol) and PP-1-6A (88 mg, 0.5 mmol) in dry DMF (3 mL) was added PPA (260 mg, 0.6 mmol) and TEA (0.18 mL, 1.5 mmol) at r.t. The reaction mixture was stirred at this temperature for three hours. After filtered, the filtrate was purified by prep-HPLC under acid condition and then purified by prep-HPLC under basic condition to obtain Example 91 (E91) (20 mg, free base) as white solid.

$^1$H NMR: 400 MHz MeOD
δ 8.10 (d, J=5.2 Hz, 1H), 7.35 (d, J=3.6 Hz, 1H), 7.30 (m, 1H), 7.10 (m, 2H), 7.01 (m, 2H), 6.60 (d, J=3.6 Hz, 1H), 5.06 (s, 2H), 3.78 (s, 3H), 3.73 (m, 2H), 3.47 (t, J=6.0 Hz, 2H).

Example 92

N-(2-(3-((1H-pyrrolo[2,3-b]pyridin-4-yl)methyl)thioureido)ethyl)-3-(3,4-dimethoxyphenyl)propiolamide (E92)

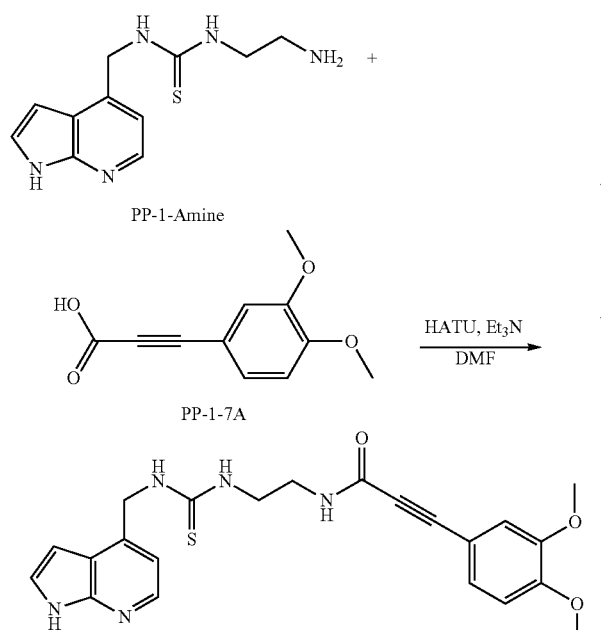

Example 92

To a solution of PP-1-Amine (120 mg, 0.5 mmol) and PP-1-7A (103 mg, 0.5 mmol) in dry DMF (3 mL) was added HATU (228 mg, 0.6 mmol) and TEA (0.35 mL, 2.5 mmol) at r.t. The mixture was stirred at this temperature for two hours. After filtered, the filtrate was purified by prep-HPLC under acid condition for two times to obtain Example 92 (E92) (30 mg, TFA salt) as white solid.

$^1$H NMR: 400 MHz MeOD
δ 8.24 (d, J=6.0 Hz, 1H), 7.59 (d, J=3.2 Hz, 1H), 7.38 (d, J=6.0 Hz, 1H), 7.14 (m, 1H), 7.07 (d, J=2.0 Hz, 1H), 6.95 (d, J=8.4 Hz, 1H), 6.90 (d, J=3.6 Hz, 1H), 5.22 (s, 2H), 3.84 (s, 3H), 3.80 (s, 3H), 3.70 (m, 2H), 3.48 (t, J=6.4 Hz, 2H).

Example 93

N-(2-(3-((1H-pyrrolo[2,3-b]pyridin-4-yl)methyl)thioureido)ethyl)-3-(benzo[d][1,3]dioxol-5-yl)propiolamide (E93)

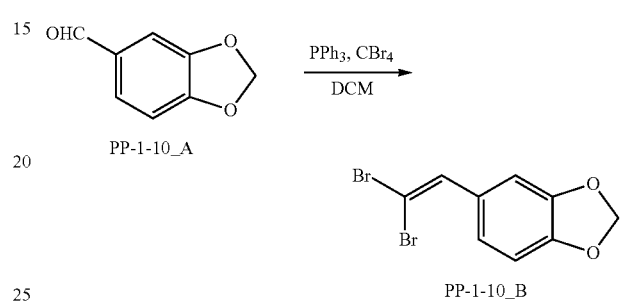

To a solution of CBr$_4$ (9.9 g, 30 mmol) in DCM (100 mL) was added PPh$_3$ (15.7 g, 60 mmol) in portions under N$_2$ atmosphere. The reaction mixture was stirred at room temperature for an hour. Then the mixture was cooled to 0° C. and a solution of PP-1-10_A (3.0 g, 20 mmol) in DCM (50 mL) was added dropwise at this temperature. The reaction mixture was continued stirring for two hours. Water was added and the mixture was extracted with DCM (50 mL×2). The combined organic layer was washed with brine, dried over Na$_2$SO$_4$ and concentrated. The residue was purified by flash chromatography (PE/DCM=20:1) to give PP-1-10_B (3.3 g, 54.1%) as white solid.

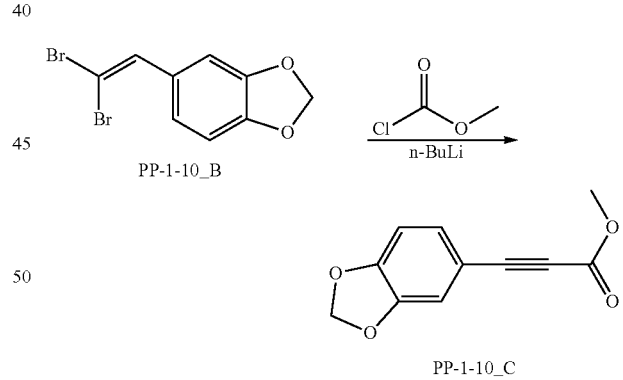

To a solution of PP-1-10_B (3.3 g, 10.8 mmol) in dry THF (100 mL) was added n-BuLi (2.5 M, 9.5 mL) at −78° C. The reaction mixture was warmed to r.t. and stirred at room temperature for an hour. The reaction mixture was cooled to −78° C. and chloro formic acid methyl ester (1.2 g, 13 mmol) was added. The reaction mixture was warmed to r.t. and stirred at room temperature for two hours. The mixture was quenched by cold water and extracted with ethyl acetate. The combined organic phase was washed with brine, dried over Na$_2$SO$_4$ and concentrated. The residue was purified by flash chromatography (PE/EA=20:1) to give PP-1-10_C (1.58 g, 72.7%) as white solid.

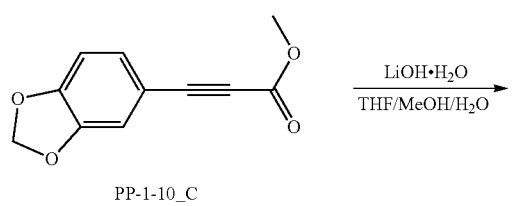

PP-1-10_C

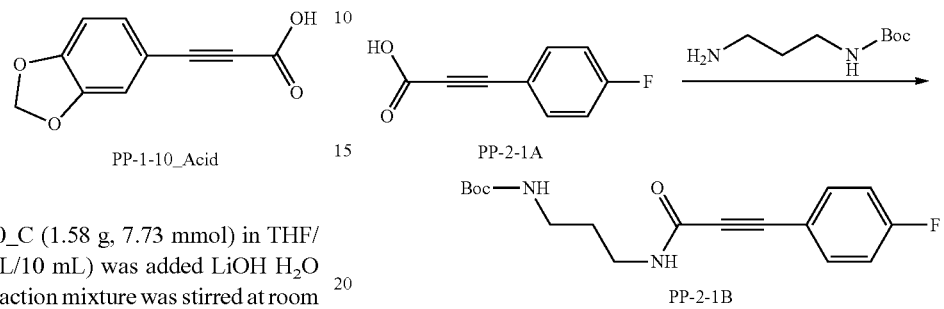

Example 94

N-(3-(3-((1H-pyrrolo[2,3-b]pyridin-4-yl)methyl)thioureido)propyl)-3-(4-fluorophenyl)propiolamide (E94)

To a solution of PP-1-10_C (1.58 g, 7.73 mmol) in THF/MeOH/H₂O (40 mL/10 mL/10 mL) was added LiOH·H₂O (0.46 g, 10.8 mmol). The reaction mixture was stirred at room temperature for 16 hours. The organic solvent was removed under reduced pressure and the aqueous was made pH=4 with 1N HCl slowly. After filtered, the solid was collected which was PP-1-10_Acid (1.1 g, 78.6%) as white solid.

To a solution of N-Boc-diaminopropane (140 mg, 0.8 mmol), 3-(4-flurophenyl)prop-2-ynoic acid (158 mg, 0.96 mmol) and HATU (456 mg, 1.2 mmol) in CH₂Cl₂ (15 mL) was added TEA (243 mg, 2.4 mmol) at 0° C. The mixture was stirred at room temperature overnight. Then the mixture was washed with NaHCO₃ solution (10 mL×2). The organic phase was separated, dried over Na₂SO₄ and condensed. The residue was purified by flash chromatography (petroleum ether/EtOAc=2:1) to give compound PP-2-1B (140 mg, 54.5%) as yellow solid.

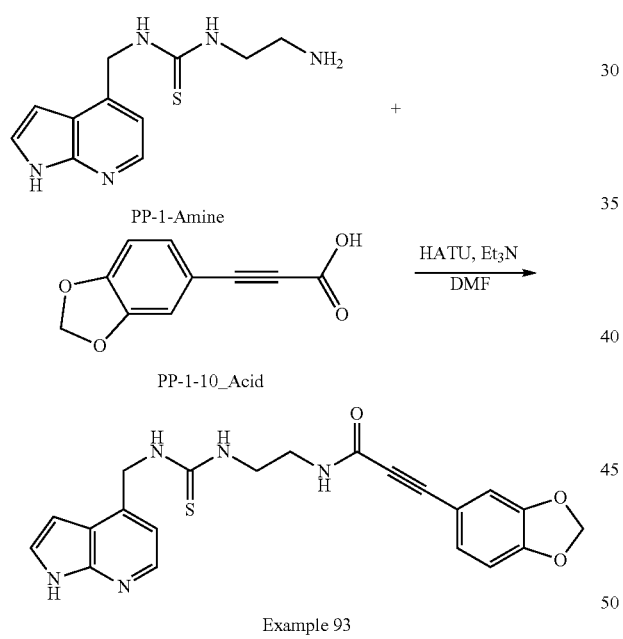

Example 93

To a solution of PP-1-Amine (120 mg, 0.5 mmol) and PP-1-10 Acid (90 mg, 0.5 mmol) in dry DMF (3 mL) was added HATU (228 mg, 0.6 mmol) and TEA (0.26 mL, 1.9 mmol) at r.t. The mixture was stirred at this temperature for 16 hours. After filtered, the filtrate was purified by prep-HPLC under acid condition for two times to obtain Example 93 (E93) (40 mg, TFA salt) as white solid.

¹H NMR: 400 MHz MeOD

δ 8.28 (d, J=5.6 Hz, 1H), 7.64 (s, 1H), 7.43 (m, 1H), 7.12 (m, 1H), 7.00 (s, 1H), 6.95 (m, 1H), 6.88 (d, J=8.0 Hz, 1H), 6.05 (s, 2H), 5.26 (s, 2H), 3.75 (m, 2H), 3.51 (d, J=6.4 Hz, 2H).

To a solution of compound PP-2-1B (140 mg, 0.44 mmol) in absolute CH₂Cl₂ (10 mL) was added TFA (2 mL). The mixture was stirred at room temperature for 30 minutes and condensed to crude compound PP-2-1C (124 mg) as yellow oil.

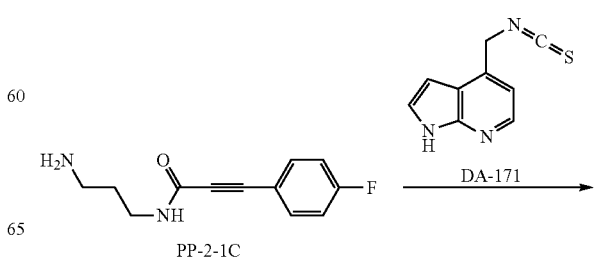

-continued

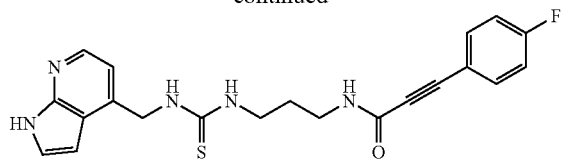

Example 94

To a solution of compound PP-2-1C (124 mg, 0.56 mmol) and compound DA-171 (106 mg, 0.56 mmol) in CH$_2$Cl$_2$ (10 mL) was added TEA (170 mg, 1.68 mmol). The mixture was stirred at room temperature for 0.5 hour. Then the mixture washed with NaHCO$_3$ solution (10 mL×2), dried over Na$_2$SO$_4$ and condensed. The residue was purified by prep-HPLC to give compound Example 94 (E94) (30 mg, 13%) as white solid.

$^1$H NMR: 400 MHz MeOD

δ 8.28 (d, J=6 Hz, 1H), 7.62-7.56 (m, 3H), 7.39 (d, J=6 Hz, 1H), 7.17-7.12 (m, 2H), 6.92 (d, J=3.6 Hz, 1H), 5.23 (s, 2H), 3.58 (s, 2H), 3.32-3.31 (m, 2H), 1.86-1.79 (m, 2H).

Example 95

N-(3-(3-((1H-pyrrolo[2,3-b]pyridin-4-yl)methyl)thioureido)propyl)-3-(2-fluorophenyl)propiolamide (E95)

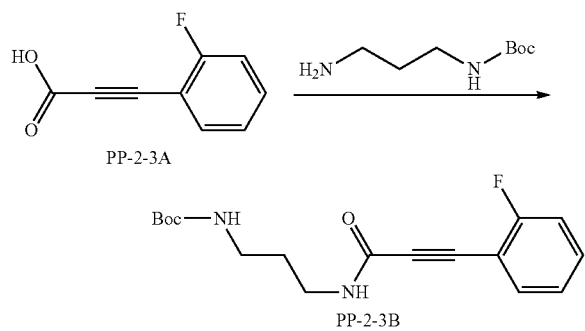

To a solution of N-Boc-diaminopropane (140 mg, 0.8 mmol), (2-fluro-phenyl)propynoic acid (158 mg, 0.96 mmol) and HATU (456 mg, 1.2 mmol) in CH$_2$Cl$_2$ (15 mL) was added TEA (243 mg, 2.4 mmol) at 0° C. The mixture was stirred at room temperature overnight. Then the mixture was washed with NaHCO$_3$ solution (10 mL×2). The organic phase was separated, dried over Na$_2$SO$_4$ and condensed. The residue was purified by flash chromatography (petroleum ether/EtOAc=2:1) to give compound PP-2-3B (120 mg, 46.7%) as yellow solid.

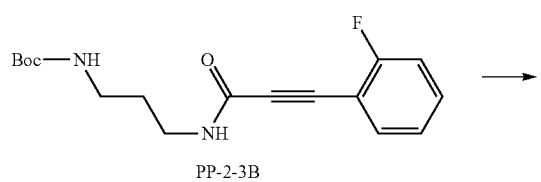

-continued

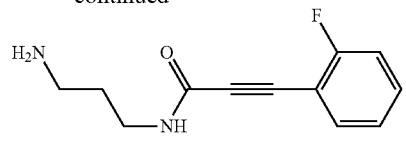

To a solution of compound PP-2-3B (120 mg, 0.38 mmol) in absolute CH$_2$Cl$_2$ (10 mL) was added TFA (2 mL). The mixture was stirred at room temperature for 30 minutes and condensed to crude compound PP-2-3C (93 mg) as yellow oil.

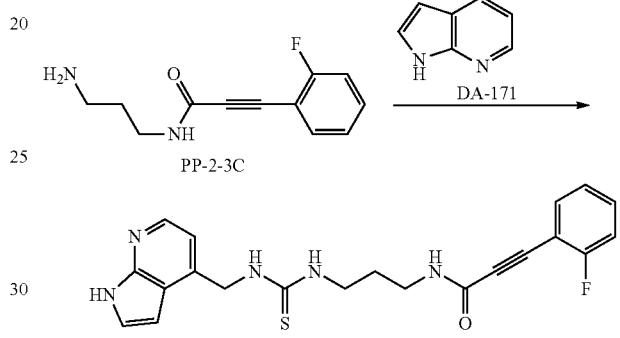

To a solution of compound PP-2-3C (93 mg, 0.42 mmol) and compound DA-171 (80 mg, 0.42 mmol) in CH$_2$Cl$_2$ (10 mL) was added TEA (128 mg, 1.26 mmol). The mixture was stirred at room temperature for 0.5 hour. Then the mixture washed with NaHCO$_3$ solution (10 mL×2), dried over Na$_2$SO$_4$ and condensed. The residue was purified by prep-HPLC to give compound Example 95 (E95) (50 mg TFA salt) as white solid.

$^1$H NMR: 400 MHz MeOD

δ 8.32-8.30 (m, 1H), 8.05-7.51 (m, 4H), 7.50-7.41 (m, 1H), 7.27-7.21 (m, 2H), 6.97-6.94 (m, 1H), 5.26 (s, 2H), 3.65-3.59 (m, 2H), 3.37-3.53 (m, 2H), 1.90-1.83 (m, 2H).

Example 96

N-(3-(3-((1H-pyrrolo[2,3-b]pyridin-4-yl)methyl)thioureido)propyl)-3-(4-nitrophenyl)propiolamide (E96)

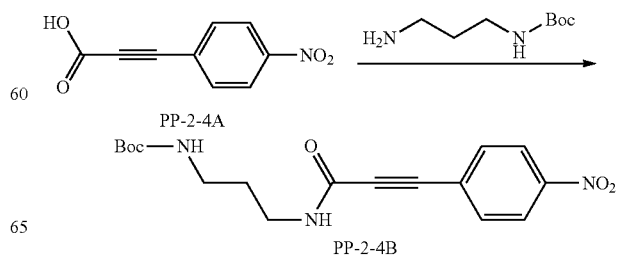

To a solution of N-Boc-diaminopropane (140 mg, 0.8 mmol), compound PP-2-4A (184 mg, 0.96 mmol) and HATU (456 mg, 1.2 mmol) in CH$_2$Cl$_2$ (15 mL) was added TEA (243 mg, 2.4 mmol) at 0° C. The mixture was stirred at room temperature overnight. Then the mixture was washed with NaHCO$_3$ solution (10 mL×2). The organic phase was separated, dried over Na$_2$SO$_4$ and condensed. The residue was purified by flash chromatography (petroleum ether/EtOAc=2:1) to give compound PP-2-4B (120 mg, 43%) as yellow solid.

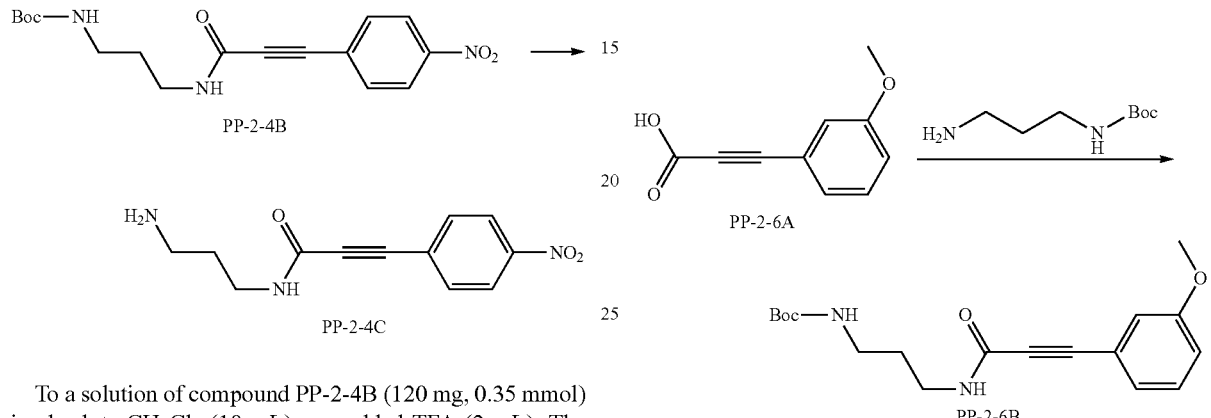

To a solution of compound PP-2-4B (120 mg, 0.35 mmol) in absolute CH$_2$Cl$_2$ (10 mL) was added TFA (2 mL). The mixture was stirred at room temperature for 30 minutes and condensed to crude compound PP-2-4C (93 mg) as yellow oil.

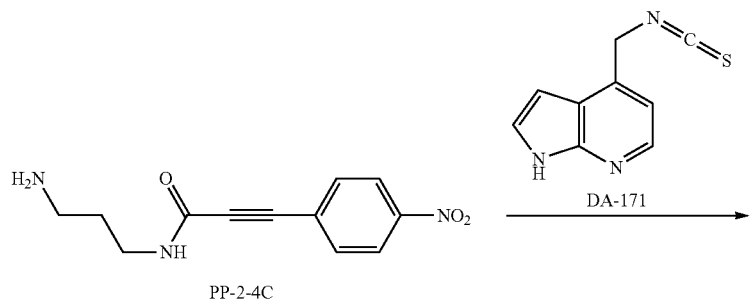

To a solution of compound PP-2-4C (93 mg, 0.38 mmol) and compound DA-171 (72 mg, 0.38 mmol) in CH$_2$Cl$_2$ (10 mL) was added TEA (115 mg, 1.14 mmol). The mixture was stirred at room temperature for 0.5 hour. Then the mixture washed with NaHCO$_3$ solution (10 mL×2), dried over Na$_2$SO$_4$ and condensed. The residue was purified by prep-HPLC to give compound Example 96 (E96) (25 mg, TFA salt) as white solid.

$^1$H NMR: 400 MHz MeOD
δ 8.33-8.28 (m, 3H), 7.81-7.79 (m, 2H), 7.66 (d, J=3.6 Hz, 1H), 7.44 (d, J=5.6 Hz, 1H), 6.97 (d, J=3.6 Hz, 1H), 5.28 (s, 2H), 3.65-3.58 (m, 2H), 3.38-3.35 (m, 2H), 1.91-1.84 (m, 2H).

Example 97

N-(3-(3-((1H-pyrrolo[2,3-b]pyridin-4-yl)methyl)thioureido)propyl)-3-(3-methoxyphenyl)propiolamide (E97)

To a solution of N-Boc-diaminopropane (140 mg, 0.8 mmol), compound PP-2-6A (169 mg, 0.96 mmol) and HATU (456 mg, 1.2 mmol) in CH$_2$Cl$_2$ (15 mL) was added TEA (243 mg, 2.4 mmol) at 0° C. The mixture was stirred at room temperature overnight. Then the mixture was washed with NaHCO$_3$ solution (10 mL×2). The organic phase was separated, dried over Na$_2$SO$_4$ and condensed. The residue was purified by flash chromatography (petroleum ether/EtOAc=2:1) to give compound PP-2-6B (150 mg, 55%) as yellow solid.

154

Example 98

N-(3-(3-((1H-pyrrolo[2,3-b]pyridin-4-yl)methyl)thioureido)propyl)-3-(p-tolyl)propiolamide (E98)

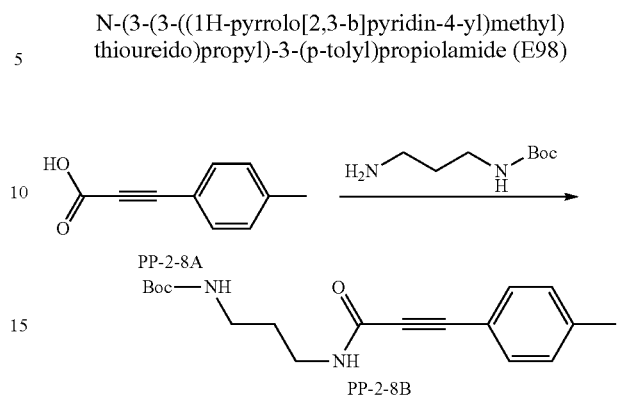

To a solution of N-Boc-diaminopropane (140 mg, 0.8 mmol), compound PP-2-8A (154 mg, 0.96 mmol) and HATU (456 mg, 1.2 mmol) in CH₂Cl₂ (15 mL) was added TEA (243 mg, 2.4 mmol) at 0° C. The mixture was stirred at room temperature overnight. Then the mixture was washed with NaHCO₃ solution (10 mL×2). The organic phase was separated, dried over Na₂SO₄ and condensed. The residue was purified by flash chromatography (petroleum ether/EtOAc=2:1) to give compound PP-2-8B (130 mg, 51.2%) as yellow solid.

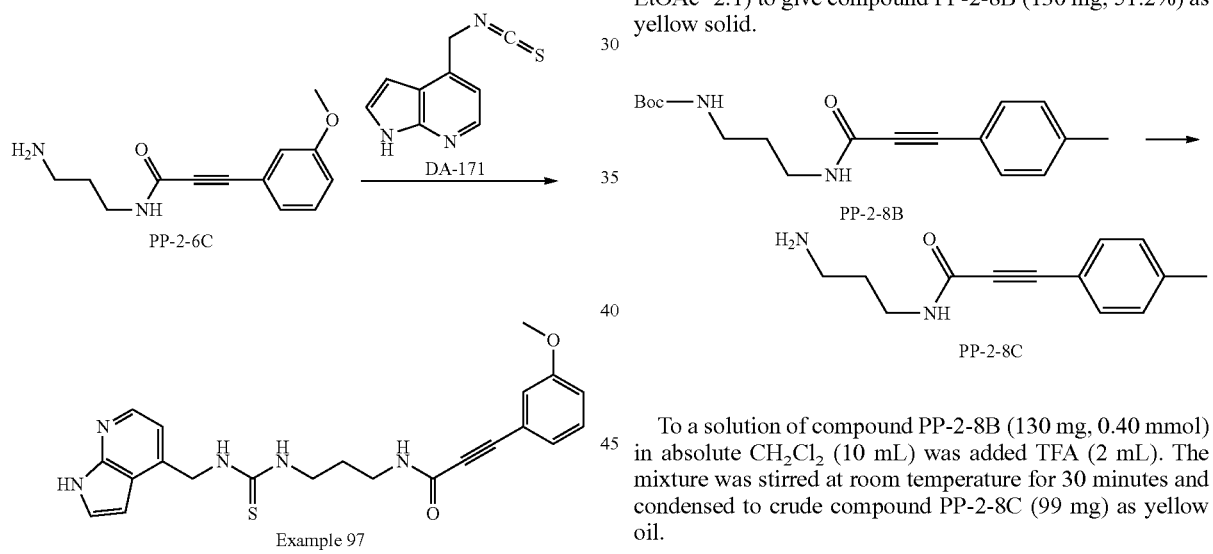

To a solution of compound PP-2-8B (130 mg, 0.40 mmol) in absolute CH₂Cl₂ (10 mL) was added TFA (2 mL). The mixture was stirred at room temperature for 30 minutes and condensed to crude compound PP-2-8C (99 mg) as yellow oil.

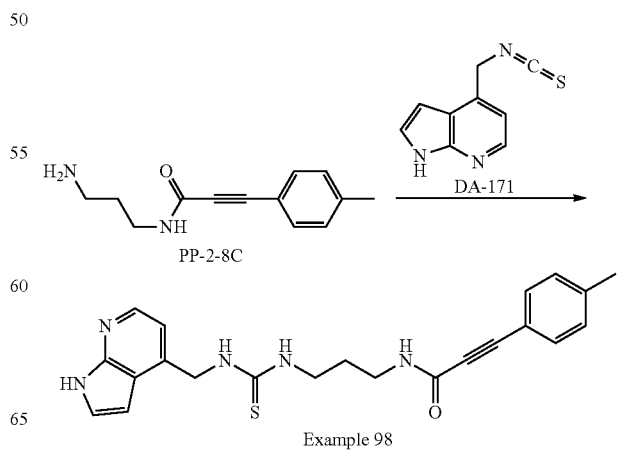

153

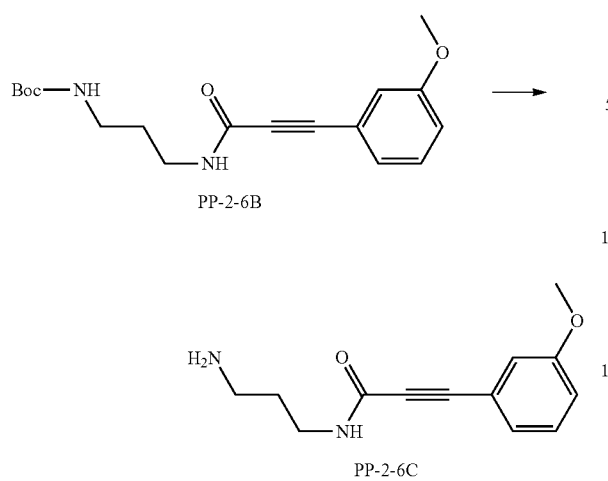

To a solution of compound PP-2-6B (150 mg, 0.45 mmol) in absolute CH₂Cl₂ (10 mL) was added TFA (2 mL). The mixture was stirred at room temperature for 30 minutes and condensed to crude compound PP-2-6C (117 mg) as yellow oil.

To a solution of compound PP-2-6C (117 mg, 0.50 mmol) and compound DA-171 (95 mg, 0.50 mmol) in CH₂Cl₂ (10 mL) was added TEA (152 mg, 1.50 mmol). The mixture was stirred at room temperature for 0.5 hour. Then the mixture washed with NaHCO₃ solution (10 mL×2), dried over Na₂SO₄ and condensed. The residue was purified by prep-HPLC to give compound Example 97 (E97) (45 mg TFA salt) as white solid.

¹H NMR: 400 MHz MeOD

δ 8.27 (d, J=6 Hz, 1H), 7.61 (d, J=3.6 Hz, 1H), 7.38 (d, J=5.6 Hz, 1H), 7.31-7.26 (m, 1H), 7.11-7.09 (m, 1H), 7.07-7.06 (m, 1H), 7.03-7.00 (m, 1H), 6.92-6.91 (m, 1H), 5.22 (s, 2H), 3.78 (s, 3H), 3.58 (s, 2H), 3.23-3.30 (m, 2H), 1.86-1.79 (m, 2H).

To a solution of compound PP-2-8C (99 mg, 0.46 mmol) and compound DA-171 (87 mg, 0.46 mmol) in CH$_2$Cl$_2$ (10 mL) was added TEA (140 mg, 1.38 mmol). The mixture was stirred at room temperature for 0.5 hour. Then the mixture washed with NaHCO$_3$ solution (10 mL×2), dried over Na$_2$SO$_4$ and condensed. The residue was purified by prep-HPLC to give compound Example 98 (E98) (35 mg TFA salt) as white solid.

$^1$H NMR: 400 MHz MeOD

δ 8.27 (d, J=6 Hz, 1H), 7.61 (d, J=3.6 Hz, 1H), 7.43-7.38 (m, 3H), 7.22-7.19 (m, 2H), 6.92 (d, J=3.2 Hz, 1H), 5.23 (s, 2H), 3.58 (s, 2H), 3.32-3.30 (m, 2H), 2.35 (s, 3H), 1.85-1.78 (m, 2H).

Example 99

N-(3-(3-((1H-pyrrolo[2,3-b]pyridin-4-yl)methyl)thioureido)propyl)-3-(4-chlorophenyl)propiolamide (E99)

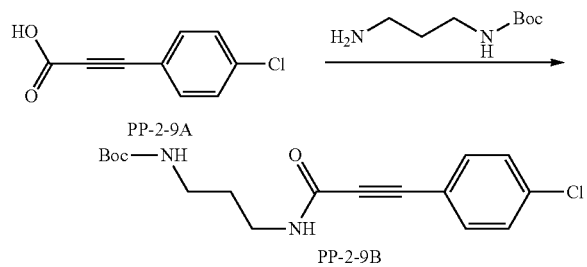

To a solution of N-Boc-diaminopropane (140 mg, 0.8 mmol), compound PP-2-9A (174 mg, 0.96 mmol) and HATU (456 mg, 1.2 mmol) in CH$_2$Cl$_2$ (15 mL) was added TEA (243 mg, 2.4 mmol) at 0° C. The mixture was stirred at room temperature overnight. Then the mixture was washed with NaHCO$_3$ solution (10 mL×2). The organic phase was separated, dried over Na$_2$SO$_4$ and condensed. The residue was purified by flash chromatography (petroleum ether/EtOAc=2:1) to give compound PP-2-9B (120 mg, 44.4%) as white solid.

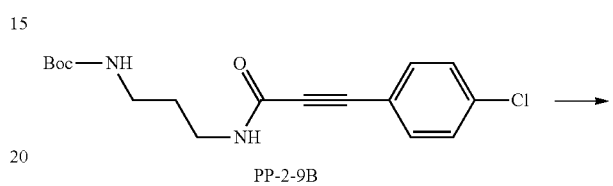

PP-2-9B

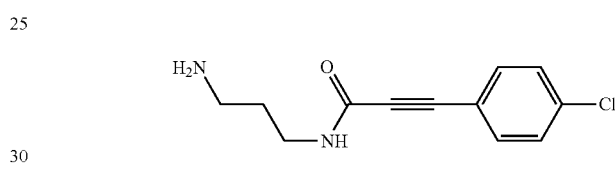

PP-2-9C

To a solution of compound PP-2-9B (120 mg, 0.36 mmol) in absolute CH$_2$Cl$_2$ (10 mL) was added TFA (2 mL). The mixture was stirred at room temperature for 30 minutes and condensed to crude compound PP-2-9C (95 mg) as yellow oil.

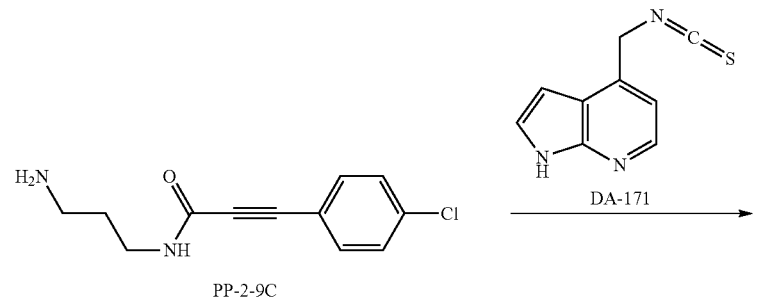

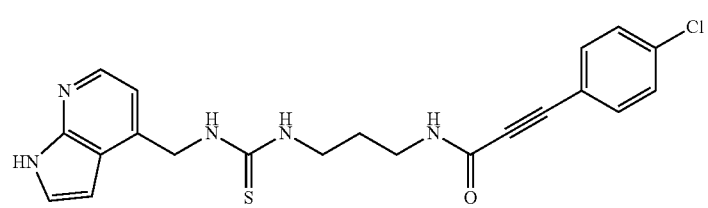

Example 99

To a solution of compound PP-2-9C (95 mg, 0.40 mmol) and compound DA-171 (76 mg, 0.40 mmol) in CH$_2$Cl$_2$ (10 mL) was added TEA (121 mg, 1.20 mmol). The mixture was stirred at room temperature for 0.5 hour. Then the mixture washed with NaHCO$_3$ solution (10 mL×2), dried over Na$_2$SO$_4$ and condensed. The residue was purified by prep-HPLC to give compound Example 99 (E99) (30 mg, TFA salt) as white solid.

$^1$H NMR: 400 MHz MeOD

δ 8.31 (d, J=6 Hz, 1H), 7.65 (d, J=3.6 Hz, 1H), 7.57-7.55 (m, 2H), 7.47-7.42 (m, 3H), 6.96 (d, J=3.6 Hz, 1H), 5.27 (s, 2H), 3.65-3.56 (m, 2H), 3.36-3.35 (m, 2H), 1.90-1.38 (m, 2H).

Example 100

N-(3-(3-((1H-pyrrolo[2,3-b]pyridin-4-yl)methyl)thioureido)propyl)-3-(2-methoxyphenyl)propiolamide (E100)

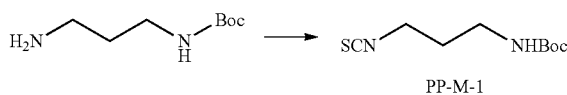

PP-M-1

To a solution of N-Boc-diaminopropane (10.44 g, 60 mmol) in absolute CH$_3$CH$_2$OH (180 mL) was added CS$_2$ (45.6 g, 600 mmol) and TEA (6.06 g, 60 mmol). The mixture was stirred at room temperature for 0.5 hour. Then Boc2O (13.08 g, 60 mmol) in absolute CH$_3$CH$_2$OH (20 mL) and DMAP (1 g) was added to the mixture at 0° C. After stirring at 0° C. for 5 minutes, the temperature was slowly warmed up to room temperature. The mixture was stirred for 1 hour and condensed to crude compound PP-M-1 (14 g) as yellow solid.

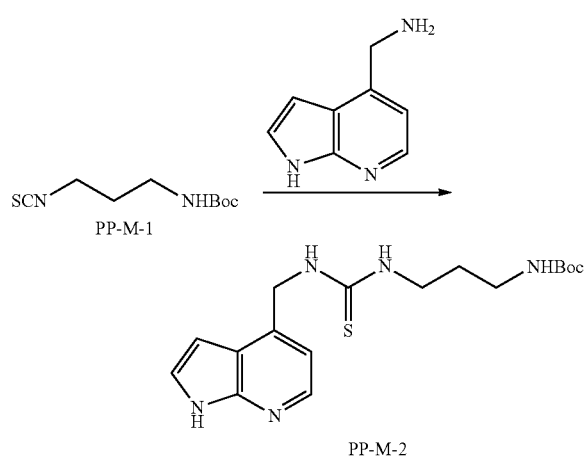

To a solution of compound PP-M-1 (2.16 g, 10 mmol) and (1H-pyrrolo[2,3-b]pyridin-4-yl)methanamine (1.56 g, 10 mmol) in absolute CH$_2$Cl$_2$ (100 mL) was added TEA (1.52 g, 15 mmol). The mixture was stirred at room temperature for 2 hrs. Then the mixture washed with NaHCO$_3$ solution (50 mL×2), dried over Na$_2$SO$_4$ and condensed. The residue was purified by flash chromatography (100% CH$_2$Cl$_2$ to CH$_2$Cl$_2$:MeOH=10:1) to give compound PP-M-2 (2.1 g, 64.4%) as yellow solid.

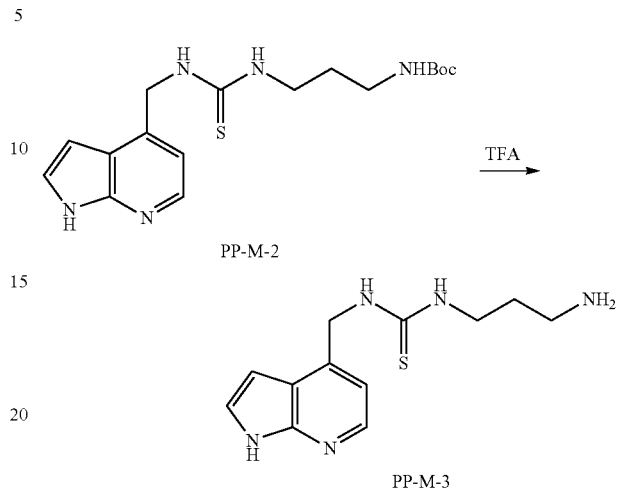

To a solution of compound PP-M-2 (2.1 g, 5.8 mmol) in absolute CH$_2$Cl$_2$ (100 mL) was added TFA (20 mL). The mixture was stirred at room temperature for 30 minutes and condensed to crude compound PP-M-3 (1.8 g) as yellow oil.

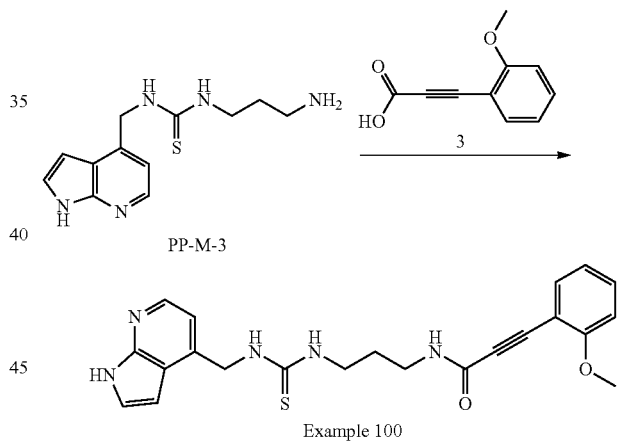

To a solution of compound 3 (106 mg, 0.6 mmol) in CH$_2$Cl$_2$ (10 mL) was added HATU (285 mg, 0.75 mmol) and TEA (152 mg, 1.5 mmol) at 0° C. The mixture was stirred at 0° C. for 30 minutes, then compound PP-M-3 (131 mg, 0.5 mmol) was added to. The mixture was stirred at room temperature overnight and washed with NaHCO$_3$ solution (10 mL×2). The organic phase was separated, dried over Na$_2$SO$_4$ and condensed. The residue was purified by prep-HPLC to give compound Example 100 (E100) (16 mg, free base) as white solid.

$^1$H NMR: 400 MHz MeOD

δ 8.11 (d, J=5.2 Hz, 1H), 7.46-7.39 (m, 2H), 7.36 (d, J=3.6 Hz, 1H), 7.03-6.95 (m, 2H), 6.95-6.91 (m, 1H), 6.61 (d, J=3.6 Hz, 1H), 5.05 (s, 2H), 3.86 (s, 3H), 3.58-3.54 (m, 2H), 3.30-3.29 (m, 2H), 1.85-1.76 (m, 2H).

Example 101

N-(3-(3-((1H-pyrrolo[2,3-b]pyridin-4-yl)methyl)thioureido)propyl)-3-(benzo[d][1,3]dioxol-5-yl)propiolamide (E101)

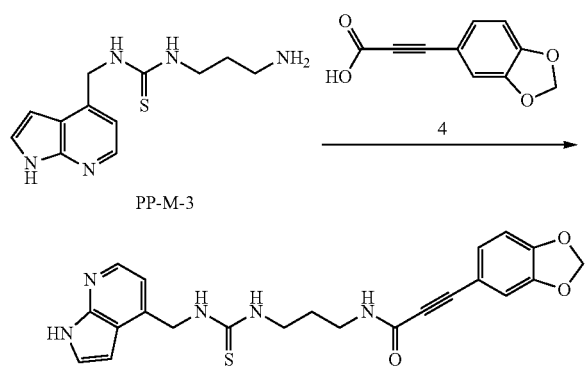

Example 101

To a solution of PP-M-3 (140 mg, 0.53 mmol) and compound 4 (121 mg, 0.64 mmol) in CH$_2$Cl$_2$ (15 mL) was added HATU (302 mg, 0.8 mmol) and TEA (161 mg, 1.59 mmol) at 0° C. The mixture was stirred at room temperature overnight and washed with NaHCO$_3$ solution (10 mL×2). The organic phase was separated, dried over Na$_2$SO$_4$ and condensed. The residue was purified by prep-HPLC to give compound Example 101 (E101) (15 mg, TFA salt) as white solid.

$^1$H NMR: 400 MHz MeOD

δ 18.30 (d, J=6 Hz, 1H), 7.64 (d, J=4 Hz, 1H), 7.40 (d, J=6 Hz, 1H), 7.14-7.12 (m, 1H), 7.00 (d, J=2 Hz, 1H), 6.95 (d, J=3.2 Hz, 1H), 6.88 (d, J=8 Hz, 1H), 6.04 (s, 2H), 5.26 (s, 2H), 3.64-3.60 (m, 2H), 3.35-3.34 (m, 2H), 1.89-1.82 (m, 2H).

Example 102

1-((1H-pyrrolo[2,3-b]pyridin-4-yl)methyl)-3-(2-(thiazol-4-yl)benzyl)thiourea (E102)

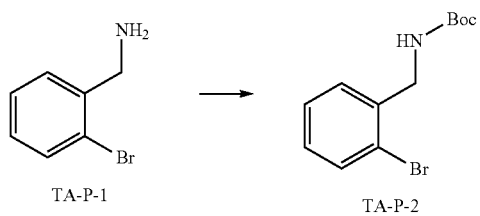 [SMILES: NCc1ccccc1Br ; CC(C)(C)OC(=O)NCc1ccccc1Br]

To a solution of 2-bromobenzylamine (10 g, 54 mmol) in absolute CH$_2$Cl$_2$ (100 mL) was added TEA (8.18 g, 81 mmol) and Boc$_2$O (14.2 g, 65 mmol). The mixture was stirred at room temperature overnight. Then the mixture was washed with critic acid (200 mL×2). The organic phase was separated, dried over Na$_2$SO$_4$ and condensed to crude compound TA-P-2 (9.6 g).

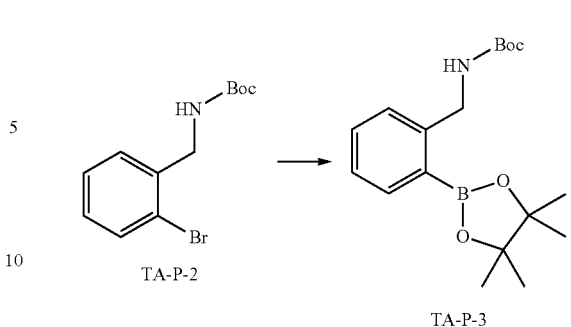

To a solution of compound TA-P-2 (7 g, 27.3 mmol) and bis(pinacolato)diboron (6.95 g, 27.3 mmol) in DMF (100 mL) was added AcOK (5.35 g, 54.6 mmol) and Pd(dppf)Cl$_2$ (2 g, 2.73 mmol) under nitrogen atmosphere protection. The mixture was stirred at 80° C. overnight. Then the mixture was dissolved in H$_2$O (1000 mL), extracted with EtOAc (200 mL×2). The combined organic phase was dried over Na$_2$SO$_4$ and condensed. The residue was purified by flash chromatography (petroleum ether/EtOAc=5:1) to give compound TA-P-3 (4 g, 43.96%) as white solid.

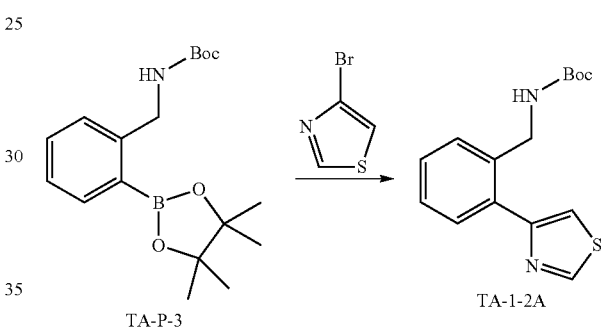

To a solution of compound TA-P-3 (333 mg, 1 mmol) and 4-bromothiazole (163 mg, 1 mmol) in dioxane (8 mL) and H$_2$O (2 mL) was added K$_2$CO$_3$ (276 mg, 2 mmol) and Pd(PPh$_3$)$_4$ (115.6 mg, 0.1 mmol) under nitrogen atmosphere protection. The mixture was heated to 120° C. by microwave and stirred for 0.5 hour. Then the mixture was condensed and dissolved in H$_2$O (100 mL) and extracted with EtOAc (50 mL×2). The combined organic phase was dried over Na$_2$SO$_4$ and condensed. The residue was purified by flash chromatography (petroleum ether/EtOAc=5:1) to give compound TA-1-2A (170 mg, 58.6%) as white solid.

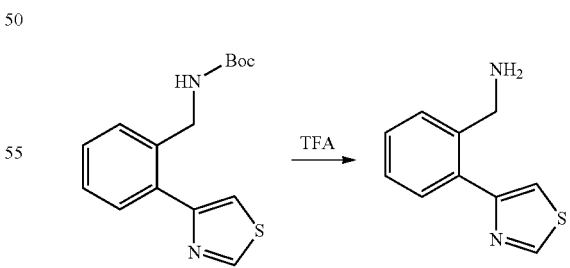

To a solution of compound TA-1-2A (170 mg, 0.59 mmol) in absolute CH$_2$Cl$_2$ (10 mL) was added TFA (2 mL). The mixture was stirred at room temperature for 30 minutes and condensed to give crude compound TA-1-2B (139 mg) as yellow oil.

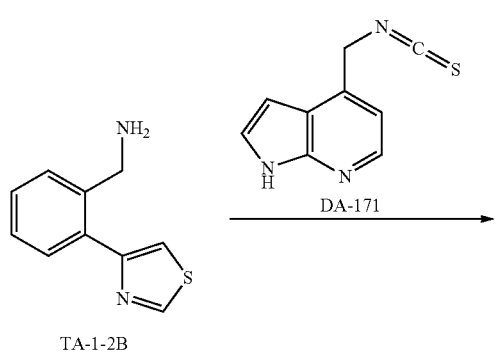

TA-1-2B     DA-171

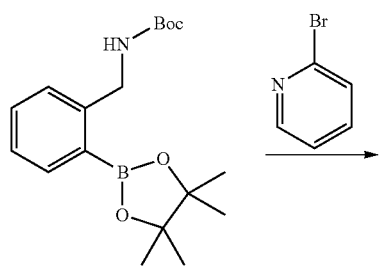

Example 102

To a solution of compound TA-1-2B (139 mg, 0.73 mmol) and compound DA-171 (138 mg, 0.73 mmol) in CH$_2$Cl$_2$ (10 mL) was added TEA (111 mg, 1.1 mmol). The mixture was stirred at room temperature for 2 hrs. Then the mixture washed with NaHCO$_3$ solution (20 mL×2), dried over Na$_2$SO$_4$ and condensed. The residue was purified by prep-HPLC to give compound Example 102 (E102) (40 mg, HCl salt) as yellow solid.

$^1$H NMR: 400 MHz DMSO(D$_2$O)

δ 9.18 (s, 1H), 8.37 (s, 1H), 7.85 (s, 1H), 7.71 (s, 1H), 7.58-7.56 (m, 1H), 7.45 (s, 1H), 7.38-7.29 (m, 2H), 7.24 (s, 1H), 6.92 (s, 1H), 5.15 (s, 2H), 4.81-4.78 (m, 2H).

Example 103

1-((1H-Pyrrolo[2,3-b]pyridin-4-yl)methyl)-3-(2-(pyridin-2-yl)benzyl)thiourea (E103)

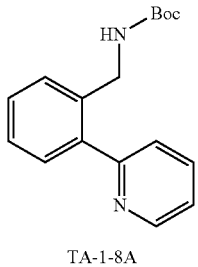

TA-P-3

To a solution of compound TA-P-3 (333 mg, 1 mmol) and 2-bromopyridine (157 mg, 1 mmol) in dioxane (8 mL) and H$_2$O (2 mL) was added K$_2$CO$_3$ (276 mg, 2 mmol) and Pd(PPh$_3$)$_4$ (115.6 mg, 0.1 mmol) under nitrogen atmosphere protection. The mixture was heated to 120° C. by microwave and stirred for 0.5 hour. Then the mixture was condensed and dissolved in H$_2$O (100 mL) and extracted with EtOAc (50 mL×2). The combined organic phase was dried over Na$_2$SO$_4$ and condensed. The residue was purified by flash chromatography (petroleum ether/EtOAc=5:1) to give compound TA-1-8A (137 mg, 48.2%) as white solid.

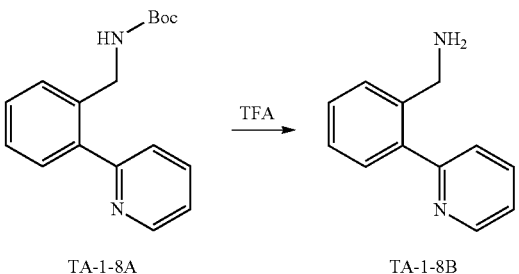 [SMILES: CC(C)(C)OC(=O)NCc1ccccc1-c1ccccn1 ; NCc1ccccc1-c1ccccn1]

TA-1-8A     TA-1-8B

To a solution of compound TA-1-2A (137 mg, 0.48 mmol) in absolute CH$_2$Cl$_2$ (10 mL) was added TFA (2 mL). The mixture was stirred at room temperature for 30 minutes and condensed to crude compound TA-1-8B (99 mg) as yellow oil.

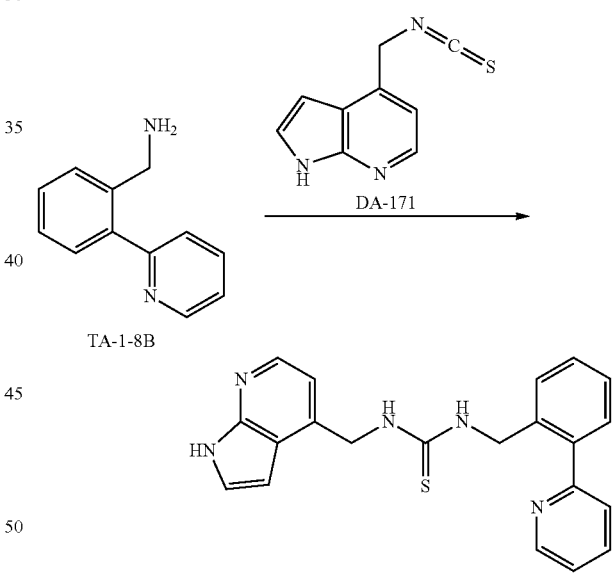

Example 103

To a solution of compound TA-1-8B (99 mg, 0.54 mmol) and compound DA-171 (102 mg, 0.54 mmol) in CH$_2$Cl$_2$ (10 mL) was added TEA (82 mg, 0.81 mmol). The mixture was stirred at room temperature for 2 hrs. Then the mixture washed with NaHCO$_3$ solution (20 mL×2), dried over Na$_2$SO$_4$ and condensed. The residue was purified by prep-HPLC to give compound Example 103 (E103) (40 mg, free base) as yellow solid.

$^1$H NMR: 400 MHz DMSO(D$_2$O) δ 8.49-8.48 (m, 1H), 8.06 (d, J=4.8 Hz, 1H), 7.87-7.83 (m, 1H), 7.53-7.49 (m, 2H), 7.41-7.31 (m, 5H), 6.82-6.81 (m, 1H), 6.49 (d, J=3.6 Hz, 1H), 4.93 (s, 2H), 4.66 (s, 2H).

Example 104

1-((1H-Pyrrolo[2,3-b]pyridin-4-yl)methyl)-3-(3-((2-chloropyrimidin-4-yl)amino)propyl)thiourea; and

Example 105

1-((1H-Pyrrolo[2,3-b]pyridin-4-yl)methyl)-3-(3-((4-chloropyrimidin-2-yl)amino)propyl)thiourea (E104 and E105)

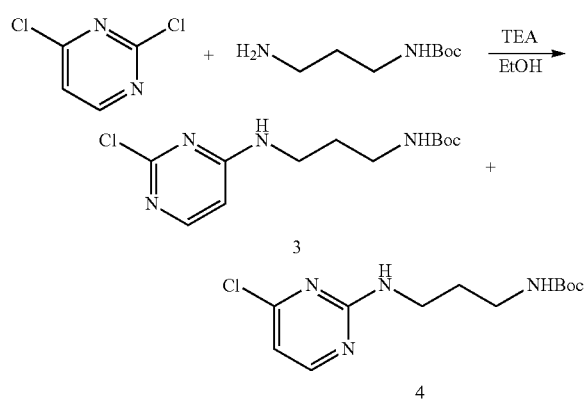

The mono boc protected propylene diamine (3.5 mL, 20 mmol) was added to a solution of 2,4-dichloropyrimidine (3.0 g, 20 mmol) in ethanol (20 mL). Triethylamine (3.4 mL, 24 mmol) was added and the reaction mixture heated to reflux for 16 h. The reaction mixture was then cooled to rt and the solvent removed in vacuo. The crude product was then purified via normal phase MPLC (DCM/MeOH 0-10%) to give the mixture of isomers 3 and 4.

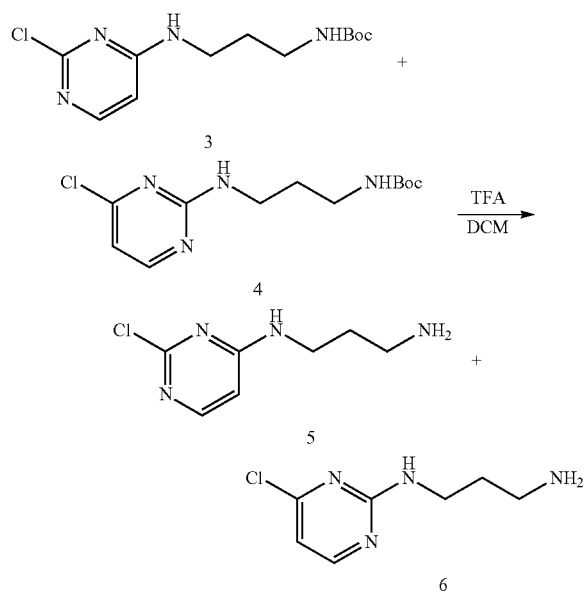

The purified mixture of Intermediates 3 and 4 was dissolved in 10 mL of DCM. TFA (5 mL) was added. After 60 min 25 mL of 4N HCl in dioxane was added. The reaction mixture was then poured into 300 mL of diethyl ether. The solids were removed via filtration to give a mixture of Intermediates 5 and 6 as their bis HCl salts. $^1$H NMR (400 MHz MeOH-$d_4$) 8.01 (d, 1H), 6.77 (d, 1H), 3.64 (t, 2H), 3.03 (t, 2H), 2.02 (m, 2H).

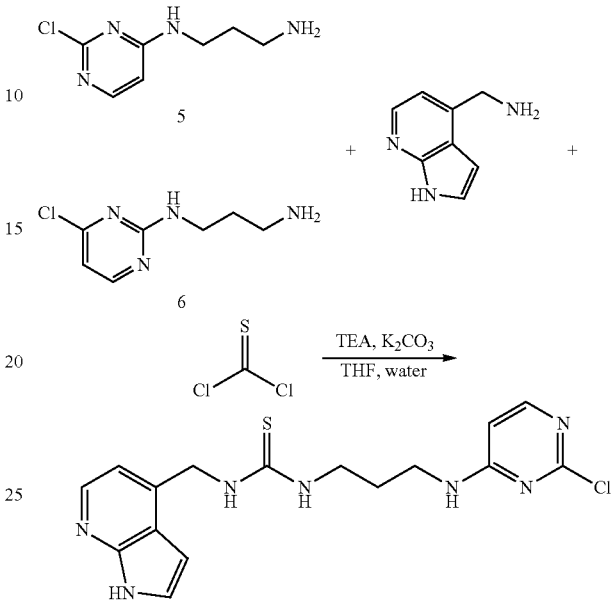

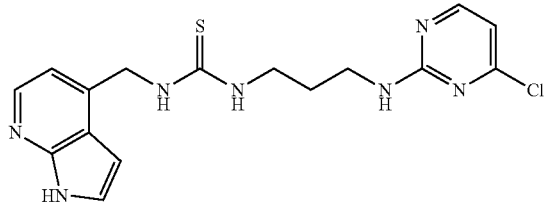

Example 105

Thiophosgene (57 μL, 0.75 mmol) was added to 2 mL of THF. In a separate vial 1H-pyrrolo[2,3-b]pyridin-4-yl) methanamine (100 mg, 0.68 mmol) was suspended in a mixture of THF (3 mL) and triethylamine (104 μL, 0.75 mmol). The suspension 1H-pyrrolo[2,3-b]pyridin-4-yl)methanamine was then added to the thiophosgene solution. An additional 2 mL of THF was used to wash in the remaining solids. After 30 min, a solution of the regioisomer Intermediates 5 and 6 (212 mg, 0.82 mmol) and potassium carbonate (329 mg, 2.38 mmol) in 3 mL of water was added. The resulting biphasic mixture was then stirred for 16 h. The organic layer was then separated and the solvent removed in vacuo to give the crude product mixture, which was then purified by normal phase MPLC (DCM/MeOH, 0-15%) to give EXAMPLES 104 and 105.

Example 104: 1H NMR (400 MHz, DMSO-d6) 11.58 (s, 1H), 8.10 (d, 1H), 7.86 (m, 3H), 7.61 (bs, 1H), 7.39 (s, 1H), 6.87 (d, 1H), 6.52 (s, 1H), 6.39 (d, 1H), 4.92 (s, 2H), 3.43 (m, 2H), 3.26 (m, 2H), 1.72 (m, 2H)

Example 105: 1H NMR (400 MHz, DMSO-d6) 11.58 (s, 1H), 8.19 (s, 1H), 8.10 (d, 1H), 7.91 (bs, 1H), 7.62 (m, 2H), 7.39 (s, 1H), 6.87 (d, 1H), 6.62 (d, 1H), 6.52 (s, 1H), 4.92 (s, 2H), 3.41 (m, 2H), 3.23 (m, 2H), 1.71 (m, 2H)

Example 106

1-((1H-Pyrrolo[2,3-b]pyridin-4-yl)methyl)-3-(3-((2-chloropyrimidin-4-yl)amino)propyl)urea (E106)

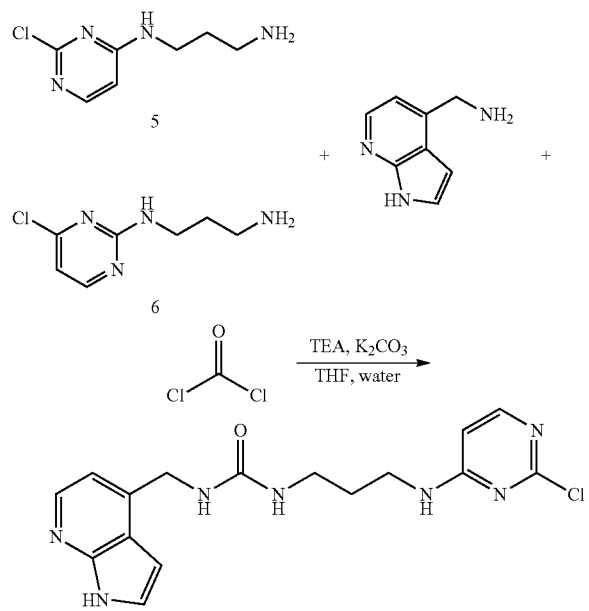

Example 106

A solution of 20% phosgene in toluene (400 µL, 0.75 mmol) was added to 2 mL of THF. In a separate vial, 1H-pyrrolo[2,3-b]pyridin-4-yl)methanamine (100 mg, 0.68 mmol) was suspended in a mixture of THF (3 mL) and triethylamine (104 µL, 0.75 mmol). The suspension of 1H-pyrrolo[2,3-b]pyridin-4-yl)methanamine was then added to the phosgene solution. An additional 2 mL of THF was used to wash in the remaining solids. After 15 min, a solution of the regioisomer Intermediates 5 and 6 (212 mg, 0.82 mmol) and potassium carbonate (329 mg, 2.38 mmol) in 3 mL of water was added. The resulting biphasic mixture was then stirred for 3 h. The organic layer was then separated and the solvent removed in vacuo to give the crude product mixture, which was then purified by normal phase MPLC (DCM/MeOH, 0-15%) to give Example 106. The minor isomer was not obtained in sufficient purity or quantity for testing.

1H NMR (400 MHz, DMSO-d6) 11.60 (s, 1H), 8.13 (d, 1H), 7.88 (m, 2H), 7.41 (t, 1H), 6.90 (d, 1H), 6.52 (s, 1H), 6.46 (m, 2H), 6.11 (t, 1H), 4.49 (d, 2H), 3.27 (m, 2H), 3.08 (m, 2H), 1.64 (m, 2H)

Example 107

1-((1H-Pyrrolo[2,3-b]pyridin-4-yl)methyl)-3-(4-((2-chloropyrimidin-4-yl)amino)butyl)thiourea (E107)

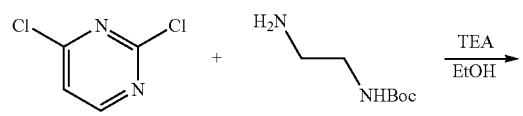

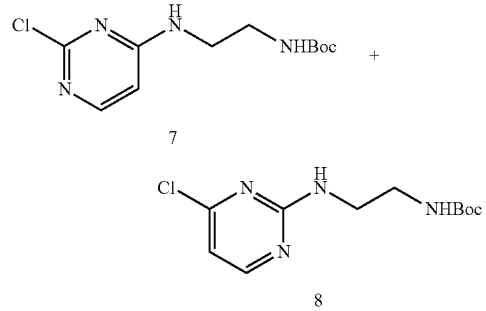

The mono boc protected ethylene diamine (3.2 mL, 20 mmol) was added to a solution of 2,4-dichloropyrimidine (3.0 g, 20 mmol) in ethanol (20 mL). Triethylamine (3.4 mL, 24 mmol) was added and the reaction mixture heated to reflux for 16 h. The reaction mixture was then cooled to rt and the solvent removed in vacuo. The crude product was then purified via normal phase MPLC (DCM/MeOH 0-10%) to give the mixture of isomer Intermediates 7 and 8.

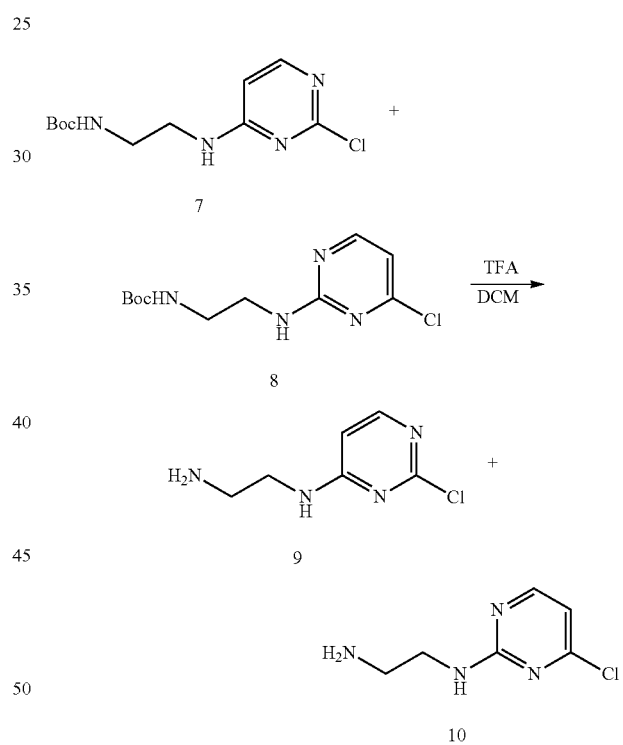

The purified mixture of Intermediates 7 and 8 was dissolved in 10 mL of DCM. TFA (5 mL) was added. After 60 min, 25 mL of 4N HCl in dioxane was added. The reaction mixture was then poured into 300 mL of diethyl ether. The solids were removed via filtration to give a mixture of Intermediates 9 and 10 as their bis HCl salts. 1H NMR (400 MHz MeOH-d4) 8.11 (d, 1H), 6.85 (d, 1H), 3.87 (t, 2H), 3.23 (t, 2H).

-continued

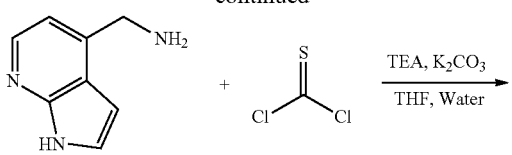

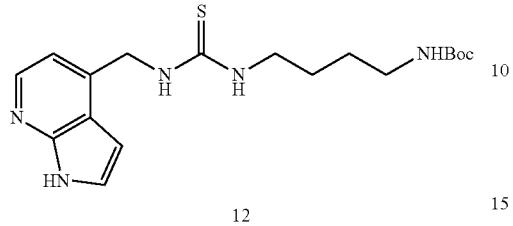

12

Thiophosgene (180 μL, 2.34 mmol) was added to 4 mL of THF. In a separate vial, 1H-pyrrolo[2,3-b]pyridin-4-yl)methanamine (300 mg, 2.04 mmol) was suspended in a mixture of THF (4 mL) and triethylamine (313 μL, 2.24 mmol). The suspension of 1H-pyrrolo[2,3-b]pyridin-4-yl)methanamine was then added to the thiophosgene solution. An additional 2 mL of THF was used to wash in the remaining solids. After 30 min the mono boc protected butylenediamine (649 μL, 2.45 mmol) was added followed immediately by a solution of potassium carbonate (704 mg, 5.10 mmol) in 3 mL of water. The resulting biphasic mixture was then stirred for 16 h. The organic layer was then separated and the solvent removed in vacuo to give the crude product, which was then purified by normal phase MPLC (DCM/MeOH, 0-10%) to give Intermediate 12 as a light brown foam.

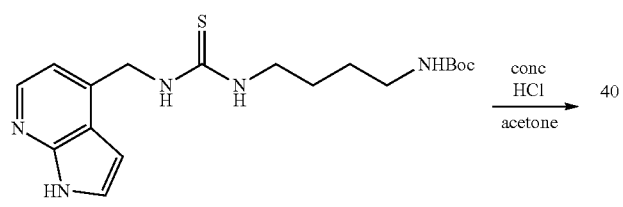

Intermediate 12 was dissolved in 5 mL of acetone. Concentrated HCl (1 mL) was then added and the reaction stirred for 60 min. The solvents were then removed in vacuo to give the crude product, which was dissolved in about 1 mL of methanol. The methanolic solution was then slowly poured into 30 mL of diethyl ether causing the product to precipitate from solution as a white solid. The precipitate was isolated by filtration and dried to give Intermediate 13. $^1$H NMR (400 MHz, MeOH-d$_4$) 8.18 (d, 1H), 7.77 (s, 1H), 7.52 (d, 1H), 7.03 (s, 1H) 5.35 (s, 2H), 3.61 (m, 2H), 2.98 (m, 2H), 1.88 (m, 4H).

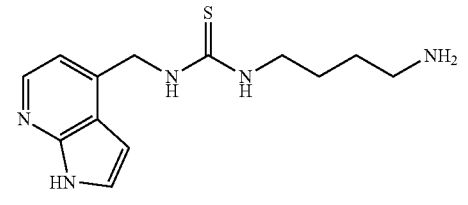

Example 107

Potassium carbonate (237 mg, 1.7 mmol), Intermediate 13 (150 mg, 0.43 mmol) and 2,4-dichloropyrimidine (64 mg, 0.43 mmol) were added to 5 mL of ethanol. The reaction mixture was heated to reflux for 3 h, after which it was cooled to rt and the solvent removed in vacuo. The crude product was then purified via normal phase chromatography (0-10% MeOH in DCM) to give Example 107 as a white solid.

1H NMR (400 MHz, DMSO-d6) 11.63 (s, 1H), 8.13 (d, 1H), 7.88 (m, 3H), 7.61 (bs, 1H), 7.43 (t, 1H), 6.90 (d, 1H), 6.54 (s, 1H), 6.42 (d, 1H), 4.96 (s, 2H), 3.43 (m, 2H), 3.27 (m, 2H), 1.53 (m, 4H)

Example 108

1-((1H-Pyrrolo[2,3-b]pyridin-4-yl)methyl)-3-(2-((2-chloropyrimidin-4-yl)amino)ethyl)thiourea (E108); and Example 109

1-((1H-Pyrrolo[2,3-b]pyridin-4-yl)methyl)-3-(2-((4-chloropyrimidin-2-yl)amino)ethyl)thiourea (E109)

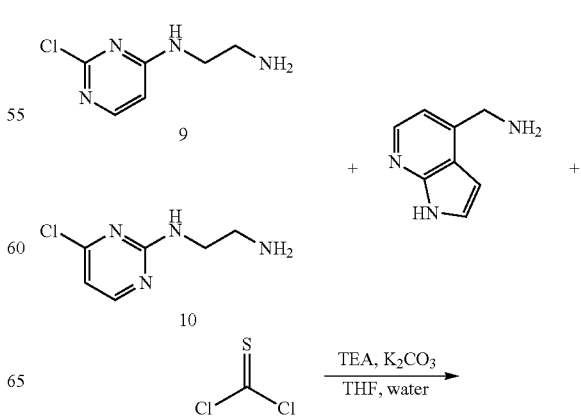

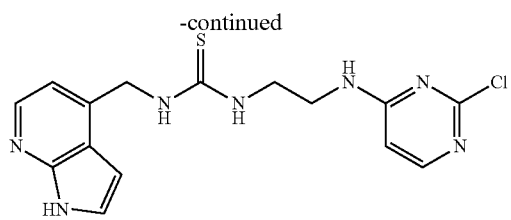

Example 108

+

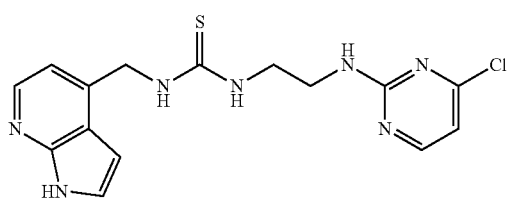

Example 109

(01) Thiophosgene (115 μL, 1.50 mmol) was added to 4 mL of THF. In a separate vial, Intermediate 1H-pyrrolo[2,3-b]pyridin-4-yl)methanamine (200 mg, 1.36 mmol) was suspended in a mixture of THF (4 mL) and triethylamine (189 μL, 1.36 mmol). The suspension of 1H-pyrrolo[2,3-b]pyridin-4-yl)methanamine was then added to the thiophosgene solution. An additional 2 mL of THF was used to wash in the remaining solids. After 30 min, a solution of the regioisomer Intermediates 9 and 10 (281 mg, 1.63 mmol) and potassium carbonate (939 mg, 6.79 mmol) in 4 mL of water was added. The resulting biphasic mixture was then stirred for 16 h. The organic layer was then separated and the solvent removed in vacuo to give the crude product mixture, which was then purified by normal phase MPLC (DCM/MeOH, 0-15%) to give Example 109 as a white powder. After chromatography, Example 108 was still not sufficiently pure. The fractions containing Example 108 were combined and the solvent removed in vacuo. The enriched material was then purified via preparatory TLC using acetone/chloroform/methanol (42/56/2) as the eluent, giving Example 108 as a pure white powder.

Example 108: 1H NMR (400 MHz, DMSO-d6) 11.80 (s, 1H), 8.18 (d, 1H), 8.04 (m, 2H), 7.90 (d, 1H), 7.77 (bs, 1H), 7.48 (t, 1H), 6.96 (d, 1H), 6.60 (s, 1H), 6.45 (d, 1H), 4.99 (bs, 2H), 3.59 (m, 2H), 3.45 (m, 2H)

Example 109: 1H NMR (400 MHz, DMSO-d6) 11.63 (s, 1H), 8.22 (d, 1H), 8.13 (d, 1H), 8.01 (bs, 1H), 7.71 (m, 2H), 7.42 (t, 1H), 6.90 (d, 1H), 6.69 (d, 1H), 6.54 (s, 1H), 4.97 (bs, 2H), 3.61 (m, 2H), 3.42 (m, 2H)

Example 110

N-(2-((3-(((1H-Pyrrolo[2,3-b]pyridin-4-yl)methyl)thioureido)methyl)-4-nitrophenyl)acrylamide (E110)

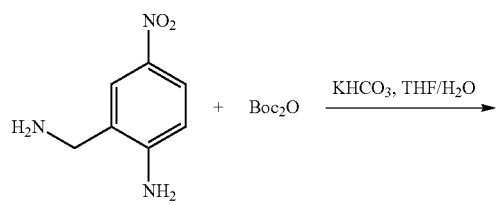

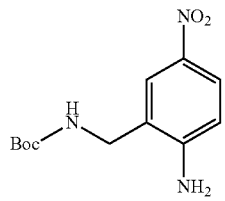

2-(Aminomethyl)-4-nitroaniline (500 mg, 2.99 mmol, see Example 30 for preparation) was dissolved in a mixture of THF and water. Potassium biocarbonate (449 mg, 4.49 mmol) was then added followed by di-tert-butyl dicarbonate (718 mg, 0.29 mmol). The mixture was stirred at rt for 16 h. The organic layer was extracted with diethyl ether, dried and evaporated. The crude oil was purified by normal phase MPLC (0-10% MeOH in DCM) to yield tert-butyl 2-amino-5-nitrobenzylcarbamate as a light orange oil.

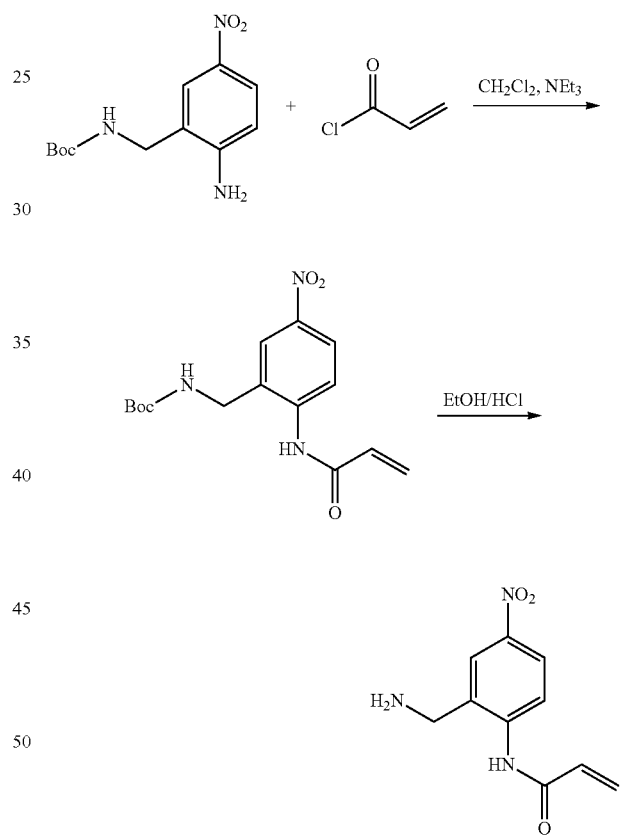

To a mixture of tert-butyl 2-amino-5-nitrobenzylcarbamate (200 mg, 0.75 mmol) and triethylamine (76 mg, 0.75 mmol) in DCM was added acryloyl chloride (102 mg, 1.12 mmol). The mixture was stirred at rt for 48 h, and purified with column chromatography to give tert-butyl 2-acrylamido-5-nitrobenzylcarbamate. The tert-butyl 2-acrylamido-5-nitrobenzylcarbamate was dissolved in EtOH/HCl and stirred at rt for 1 h. Diethyl ether was then added and the solid formed was collected by filtration to yield the HCl salt of N-(2-(aminomethyl)-4-nitrophenyl)acrylamide (46 mg, 0.18 mmol).

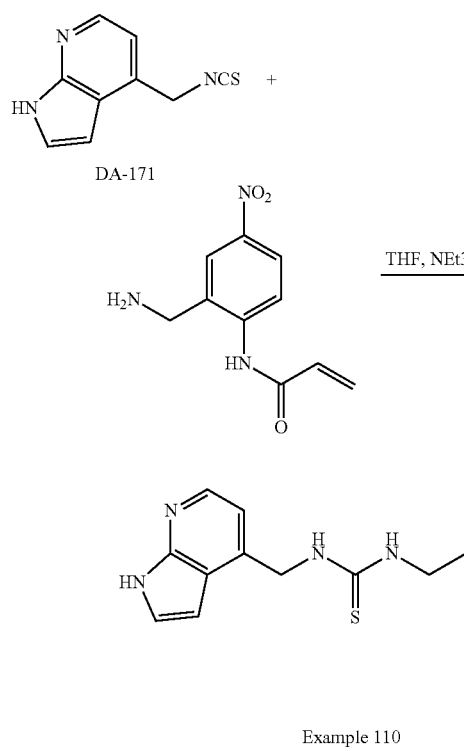

Example 110

A combined mixture of DA-171 (34 mg, 0.18 mmol), N-(2-(aminomethyl)-4-nitrophenyl)acrylamide (46 mg, 0.18 mmol), and triethylamine (27 mg, 0.27 mmol) in THF was stirred at rt for 16 h. Ethyl acetate was added and washed with 2× with water. The organic layer was dried and evaporated. Crude product was purified by normal phase MPLC (0-10% MeOH in DCM) to yield Example 110, N-(2-((3-((1H-pyrrolo[2,3-b]pyridin-4-yl)methyl)thioureido)methyl)-4-nitrophenyl)acrylamide.

1H NMR (400 MHz, MeOH-d4) 8.30 (m, 2H), 8.18 (m, 1H), 8.10 (d, 1H), 7.36 (d 1H), 7.01 (d, 1H), 6.65 (m, 1H), 6.61 (d, 1H), 6.43 (m, 1H), 5.81 (d, 1H), 5.10 (bs, 2H), 5.01 (s, 2H)

Example 111

1-((1H-Pyrrolo[2,3-b]pyridin-4-yl)methyl)-3-(2-(thiazol-2-yl)benzyl)thiourea (E111)

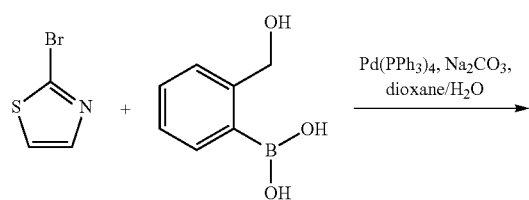

To a stirred solution of 2-bromothiazole (1.0 g, 6.1 mmol) in dioxane/water (20/5 mL) was added (2-(hydroxymethyl)phenyl)boronic acid (1.4 g, 9.1 mmol), sodium carbonate (1.29 g, 12.2 mmol), and Pd(PPh3)4 under nitrogen. The mixture was heated at reflux for 18 h. After cooling to rt, water (50 mL) was added and aqueous was extracted with DCM (3×50 mL). The combined organic layer was dried and evaporated. The residue was purified by column chromatography to yield (2-(thiazol-2-yl)phenyl)methanol (0.95 g, 5.1 mmol).

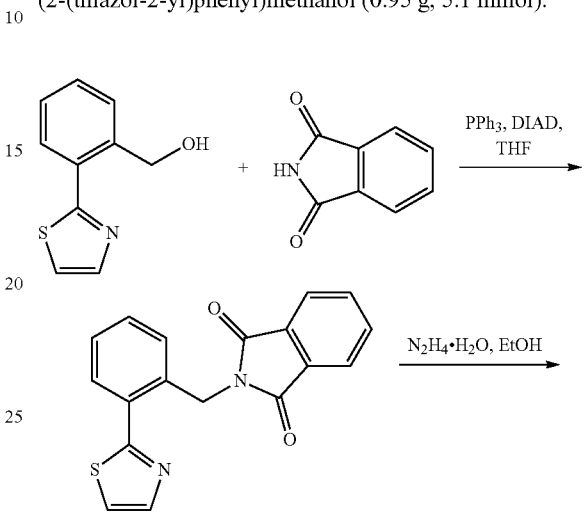

To a stirred solution of (2-(thiazol-2-yl)phenyl)methanol (0.95 g, 5.1 mmol) in THF (15 mL) was added phthalimide (1.12 g, 7.65 mmol), triphenylphosphine (2.0 g, 7.65 mmol). The mixture was cooled in an ice-water bath and diisopropyl azodicarboxylate (3.1 g, 15.3 mmol) was added dropwise. After the addition, the mixture was stirred at 0° C. for 30 min, and at rt for 18 h. The mixture was then filtered and the filtrate was evaporated. The residue was purified by column chromatography to yield 2-(2-(thiazol-2-yl)benzyl)isoindoline-1,3-dione (1.1 g) as a white solid. To a stirred solution of 2-(2-(thiazol-2-yl)benzyl)isoindoline-1,3-dione (400 mg, 1.25 mmol) in ethanol (10 mL) was added dropwise hydrazine hydrate (160 mg, 3.1 mmol). The mixture was heated at 70° C. for 1 h. After cooling to rt, the mixture was filtered, and the filtrate was evaporated. The residue was purified by column chromatography to yield (2-(thiazol-2-yl)phenyl)methanamine (190 mg) as a white solid.

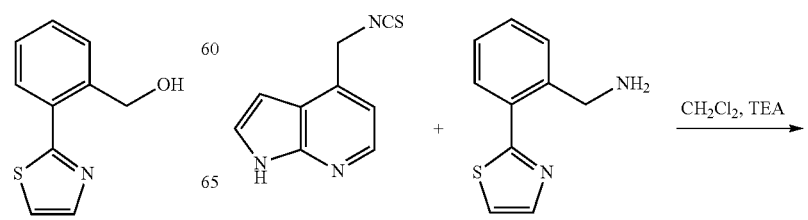

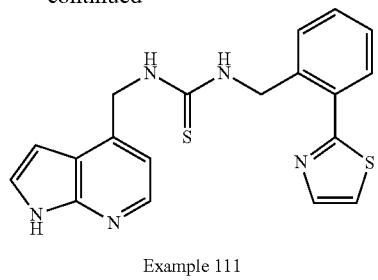

Example 111

Example 111 (E111) 1-((1H-pyrrolo[2,3-b]pyridin-4-yl)methyl)-3-(2-(thiazol-2-yl)benzyl)thiourea was synthesized in the same manner as described for the synthesis of Example 102 (E102) substituting (2-(thiazol-2-yl)phenyl)methanamine for TA-1-8B.

1H NMR (400 MHz, MeOH-d4) 8.25 (d, 1H), 7.88 (bs, 1H), 7.65 (m, 4H), 7.46 (m, 2H), 7.31 (bs, 1H), 6.93 (s, 1H), 5.26 (bs, 2H), 4.92 (bs, 1H)

Example 112

N-(3-((3-((1H-Pyrrolo[2,3-b]pyridin-4-yl)methyl)thioureido)methyl)phenyl)-2-aminoacetamide (E112)

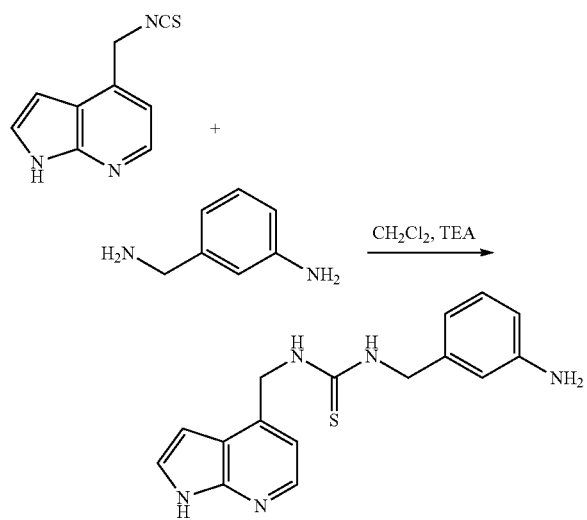

Compound 27-1 was prepared in a similar manner as in Example 102, substituting 3-aminobenzylamine for TA-1-8B.

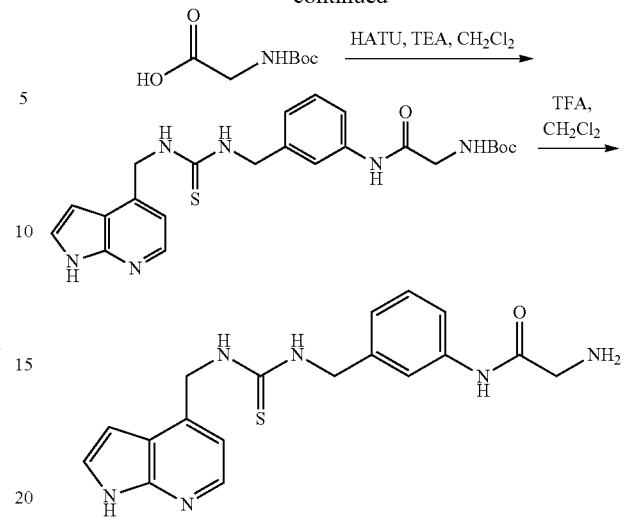

Example 112

To a solution of 27-1 (100 mg, 0.32 mmol) and Boc-glycine (68 mg, 0.39 mmol) in DCM (10 mL) was added TEA (98 mg, 0.96 mmol) and HATU (184 mg, 0.48 mmol). the mixture was stirred at rt for 16 h. The mixture then washed with saturated sodium bicarbonate solution (aq), and the organic layer was dried and evaporated. The residue was purified by column chromatography to yield tert-butyl(2-((3-((3-((1H-pyrrolo[2,3-b]pyridin-4-yl)methyl)thioureido)methyl)phenyl)amino)-2-oxoethyl)carbamate (120 mg, 0.26 mmol). To a solution of tert-butyl(2-((3-((3-((1H-pyrrolo[2,3-b]pyridin-4-yl)methyl)thioureido)methyl)phenyl)amino)-2-oxoethyl)carbamate (120 mg, 0.26 mmol) in DCM (10 mL) was added TFA (2 mL). The mixture was stirred at rt for 0.5 h. Solvent was evaporated and the residue was purified by semi-prep HPLC to yield Example 112, N-(3-((3-((1H-pyrrolo[2,3-b]pyridin-4-yl)methyl)thioureido)methyl)phenyl)-2-aminoacetamide (13 mg).

1H NMR (400 MHz, MeOH-d4) 8.34 (d, 1H), 7.68 (d, 1H), 7.62 (s, 1H), 7.48 (m, 2H), 7.29 (t, 1H), 7.11 (d, 1H), 7.00 (d, 1H), 5.30 (s, 2H), 4.75 (bs, 2H), 3.88 (s, 2H)

Example 113

N-(2-((3-((1H-Pyrrolo[2,3-b]pyridin-4-yl)methyl)thioureido)methyl)phenyl)-2-methoxyacetamide (E113)

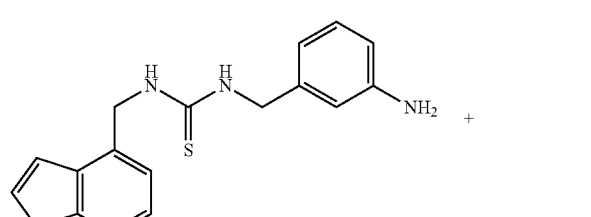

27-1

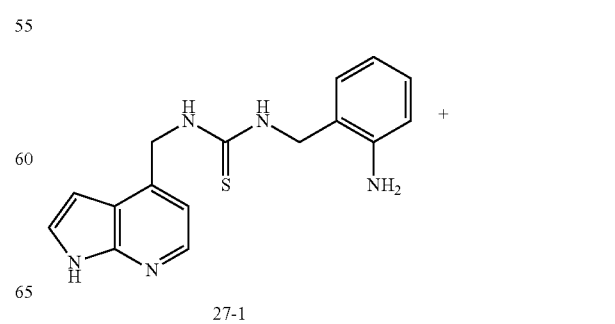

27-1

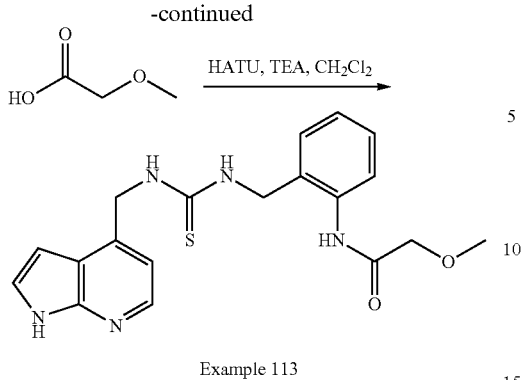

Example 113

Example 113 N-(2-((3-((1H-pyrrolo[2,3-b]pyridin-4-yl)methyl)thioureido)methyl)phenyl)-2-methoxyacetamide was prepared with similar procedures as in Example 112.

1H NMR (400 MHz, MeOH-d4) 8.28 (d, 1H), 7.65 (d, 1H), 7.46 (m, 2H), 7.30 (m, 3H), 6.94 (s, 1H), 5.27 (s, 2H), 4.70 (bs, 2H), 4.09 (s, 2H), 3.50 (s, 3H)

Example 114

N-(2-((3-((1H-Pyrrolo[2,3-b]pyridin-4-yl)methyl)thioureido)methyl)phenyl)-2-aminoacetamide (E114)

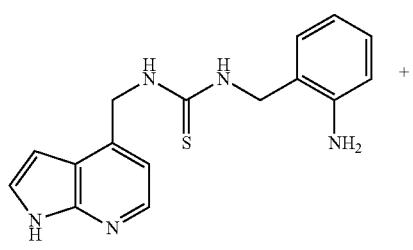

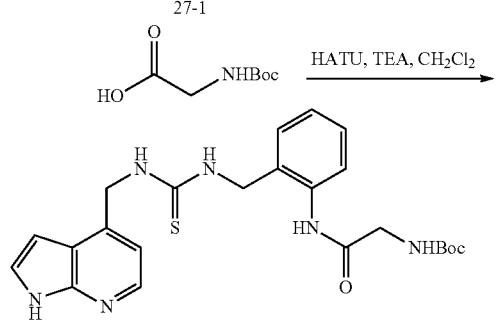

Example 114

Example 114 N-(2-((3-((1H-pyrrolo[2,3-b]pyridin-4-yl)methyl)thioureido)methyl)phenyl)-2-aminoacetamide was prepared with similar procedures as in Example 112.

1H NMR (400 MHz, MeOH-d4) 8.29 (d, 1H), 7.64 (m, 2H), 7.50-7.20 (m, 4H), 6.92 (s, 1H), 5.27 (s, 2H), 4.83 (bs, 2H), 3.96 (s, 2H)

Example 115

1-((1H-pyrrolo[2,3-b]pyridin-4-yl)methyl)-3-(2-(oxazol-4-yl)benzyl)thiourea

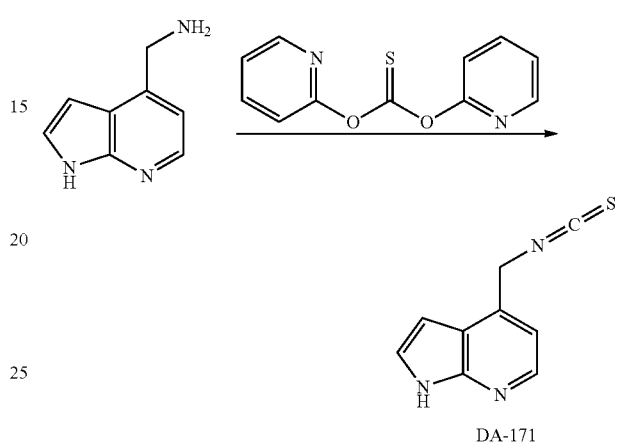

DA-171

Alternate synthesis of DA-171 (Example 6).

O,O-di-2-pyridinyl thiocarbonate (1136 mg, 4.89 mmol) was added to a solution of (1H-pyrrolo[2,3-b]pyridin-4-yl)methanamine (720 mg, 4.89 mmol) in tetrahydrofuran (THF) (60 mL). Let stir at RT for 30 minutes and concentrated. The residue was purified via Biotage (0% to 50% gradient EtOAc: Hex; 25 g-HP-silica gel column) to obtain 690 mg of 4-(isothiocyanatomethyl)-1H-pyrrolo[2,3-b]pyridine. $^1$H NMR (400 MHz, DMSO-d$_6$) δ ppm 5.26 (s, 2H) 6.57 (dd, J=3.54, 1.77 Hz, 1H) 7.07 (d, J=4.80 Hz, 1H) 7.50-7.63 (m, 1H) 8.26 (d, J=4.80 Hz, 1H) 11.86 (br. s., 1H); MS [MH]$^+$=190.0

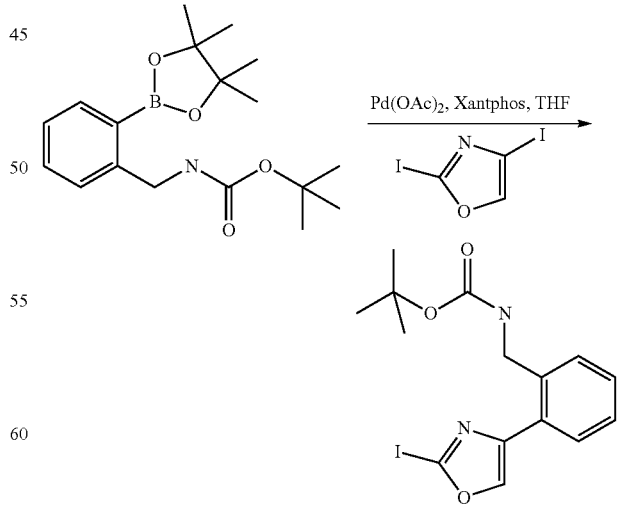

Palladium(II) acetate (35.0 mg, 0.156 mmol) and Xantphos (90 mg, 0.156 mmol) was added to degassed THF (3 ml) and let stir for 5 minutes then transferred to a separate rxn vessel that contained tert-butyl 2-(4,4,5,5-tetramethyl-1,3,2-dioxaborolan-2-yl)benzylcarbamate (1142 mg, 3.43 mmol), 2,4-diiodooxazole (1000 mg, 3.12 mmol), Potassium phosphate (1985 mg, 9.35 mmol) and degassed Tetrahydrofuran (THF) (12 mL). The rxn vessel was capped and heated to 80° for 16 hours. Filtered and the residue was purified via Biotage (0% to 100% DCM:Hex; 50 g-HP-silica gel column) to obtain 460 mg of tert-butyl 2-(2-iodooxazol-4-yl)benzylcarbamate. $^1$H NMR (400 MHz, CHLOROFORM-d) δ ppm 1.47 (s, 9H) 4.39 (d, J=5.31 Hz, 2H) 5.40 (br. s., 1H) 7.31-7.45 (m, 2H) 7.53 (dd, J=19.45, 7.07 Hz, 2H) 7.94 (s, 1H); MS [MH]$^+$=401.1

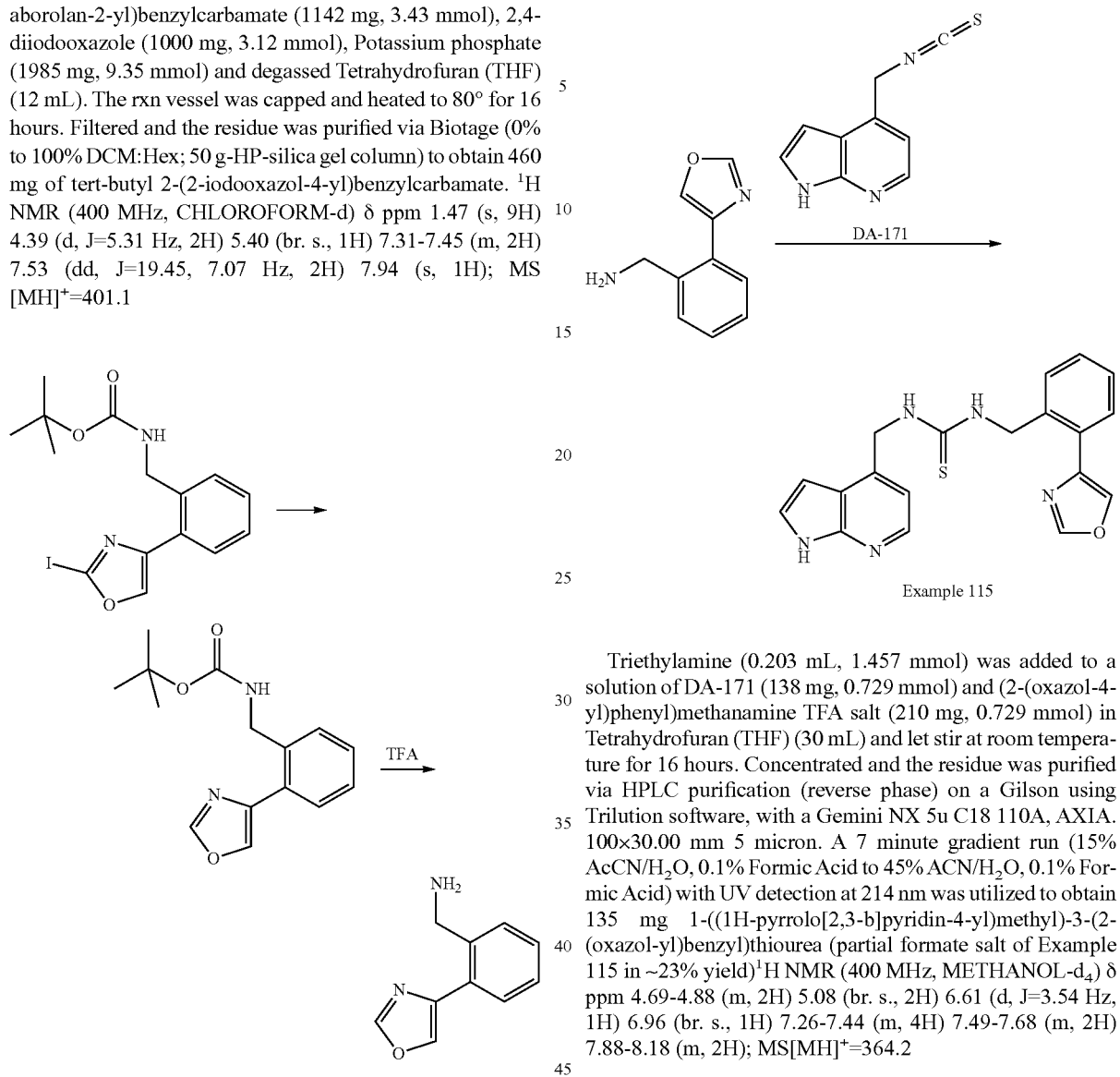

Example 115

Hydrogenolysis of the tert-butyl 2-(2-iodooxazol-4-yl)benzylcarbamate was performed using H-Cube, 10% Pd/C, full H2 Mode, at 25° in EtOH. Following completion the reaction was concentrated and the residue was purified via Biotage (0% to 10% gradient; EtOAc:Hex; 50 g-HP-silica gel column). Obtained 200 mg of tert-butyl 2-(oxazol-4-yl)benzylcarbamate. $^1$H NMR (400 MHz, CHLOROFORM-d) δ ppm 1.47 (s, 9H) 4.39 (s, 2H) 7.36 (ddd, J=7.26, 5.37, 1.77 Hz, 2H) 7.48-7.65 (m, 2H) 7.89 (d, J=1.01 Hz, 1H) 8.00 (s, 1H); MS[MH]$^+$=275.2

Added trifluoroacetic acid (5 mL, 64.9 mmol) to a solution of tert-butyl 2-(oxazol-4-yl)benzylcarbamate (200 mg, 0.729 mmol) in Dichloromethane (DCM) (5 mL) and let stir at room temperature for 1 hour. Concentrated to dryness. Obtained 300 mg of (2-(oxazol-4-yl)phenyl)methanamine trifluoroacetate. $^1$H NMR (400 MHz, CHLOROFORM-d) δ ppm 3.88-4.50 (m, 2H) 7.38-7.60 (m, 4H) 8.00 (s, 1H) 8.10 (s, 1H) 8.19-8.56 (m, 2H). MS[MH]$^+$=175.1

Triethylamine (0.203 mL, 1.457 mmol) was added to a solution of DA-171 (138 mg, 0.729 mmol) and (2-(oxazol-4-yl)phenyl)methanamine TFA salt (210 mg, 0.729 mmol) in Tetrahydrofuran (THF) (30 mL) and let stir at room temperature for 16 hours. Concentrated and the residue was purified via HPLC purification (reverse phase) on a Gilson using Trilution software, with a Gemini NX 5u C18 110A, AXIA. 100×30.00 mm 5 micron. A 7 minute gradient run (15% AcCN/H$_2$O, 0.1% Formic Acid to 45% ACN/H$_2$O, 0.1% Formic Acid) with UV detection at 214 nm was utilized to obtain 135 mg 1-((1H-pyrrolo[2,3-b]pyridin-4-yl)methyl)-3-(2-(oxazol-yl)benzyl)thiourea (partial formate salt of Example 115 in ~23% yield)$^1$H NMR (400 MHz, METHANOL-d$_4$) δ ppm 4.69-4.88 (m, 2H) 5.08 (br. s., 2H) 6.61 (d, J=3.54 Hz, 1H) 6.96 (br. s., 1H) 7.26-7.44 (m, 4H) 7.49-7.68 (m, 2H) 7.88-8.18 (m, 2H); MS[MH]$^+$=364.2

Example 116

1-((1H-pyrrolo[2,3-b]pyridin-4-yl)methyl)-3-(2-(piperidin-3-yl)benzyl)thiourea

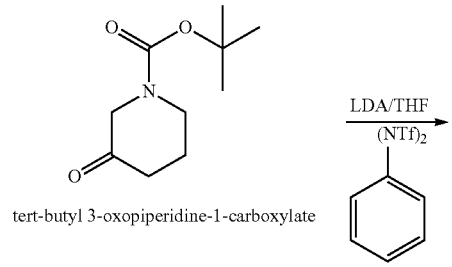

tert-butyl 3-oxopiperidine-1-carboxylate

-continued

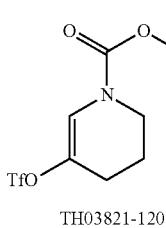
TH03821-120

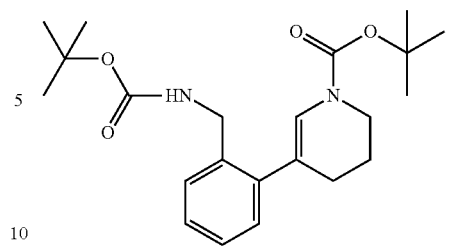
TH03821-134

Into a stirring dry ice cooled solution of tert-butyl 3-oxopiperidine-1-carboxylate (4.8 g, 24 mmol) in THF (100 ml, total following addition of trifylimide) was added dropwise a solution of 2 M LDA (16.5 ml, 33 mmol). After 15 minutes n-phenyl triflimide (10.5 g, 33 mmol) in THF was added. The reaction was stirred with cooling for an additional 15 minutes and then allowed to warm to room temperature and stirred overnight. The reaction was quenched with saturated aqueous NaHCO₃ solution and extracted with ethyl acetate. The combined organic layers were washed with brine and dried over MgSO₄. The solvent was removed under reduced pressure and the crude product was purified by column chromatography to afford 2.8 g of TH03821-120.

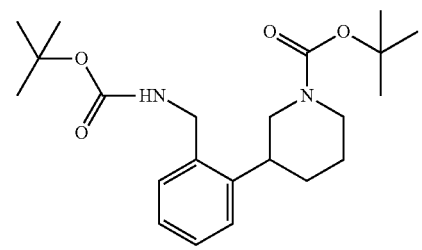
TH03821-148

To a solution of TH03821-134 (540 mg, 1.39 mmol) in methanol (80 ml) was added Raney Ni (270 mg). The reaction was stirred was 16 h. As the reaction was going slowly it was filtered to remove the Raney Ni and Pd/C was added. The reaction was stirred an additional 16 h under an atmosphere of H2 (14 psi) in order to complete the hydrogenation. The reaction was filtered and the filtrate was concentrated under reduced pressure to afford the crude product which was used without purification in the next step.

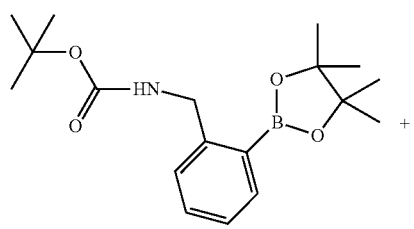

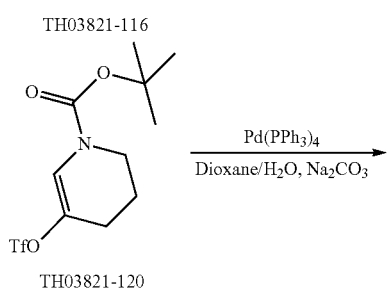
TH03821-120

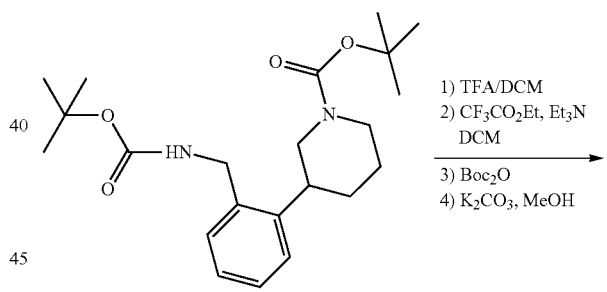
TH03821-148

1) TFA/DCM
2) CF₃CO₂Et, Et₃N
   DCM
3) Boc₂O
4) K₂CO₃, MeOH

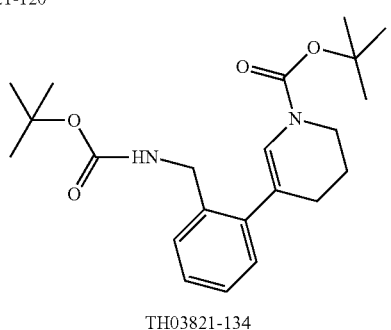
TH03821-134

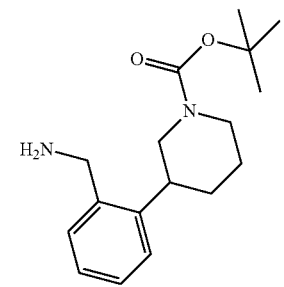
TH04092-008

To a solution of TH03821-116 (166 mg, 0.5 mmol) and TH03821-120 (165 mg, 0.5 mmol) in 4:1 dioxane:water (2.5 ml) was added Na₂CO₃ (212 mg, 2 mmol). Under an atmosphere of N₂ Pd (PPh₃)₄ (58 mg, 0.05 mmol). The reaction was heated 2 hours at 120° C. in a microwave reactor for 0.5 h, cooled, filtered, concentrated under reduced pressure, and purified by column chromatography to afford TH03821-134.

Into a solution of TH03831-148 (540 mg, 1.38 mmol) in CH₂Cl₂ (20 mL) was added TFA (4 mL) dropwise. The reaction was stirred overnight at room temperature at which point the solvent was removed under reduced pressure. The crude product was dissolved in CH₂Cl₂ (20 mL) and Et₃N (1.5 mL, 11 mmol) was added. To this stirring solution, ethyl trifluroacetate (294 mg, 2.07 mmol) was added dropwise. The reaction was stirred overnight at room temperature at which time di-t-butyl dicarbonate (271 mg, 1.2 mmol) was added dropwise and stirring continued for an additional 16 h. Water was added, the layers separated and the aqueous was extracted with additional $CH_2Cl_2$. The combined organic was washed with brine, dried over $MgSO_4$ and then concentrated under reduced pressure. The crude product was dissolved in MeOH (30 mL) and K2CO3 (762 mg, 5.5 mmol) was added. The reaction was heated at reflux overnight, cooled, filtered and concentrated under reduced pressure. The residue was purified by column chromatography to afford TH04092-008 (400 mg, 43% yield).

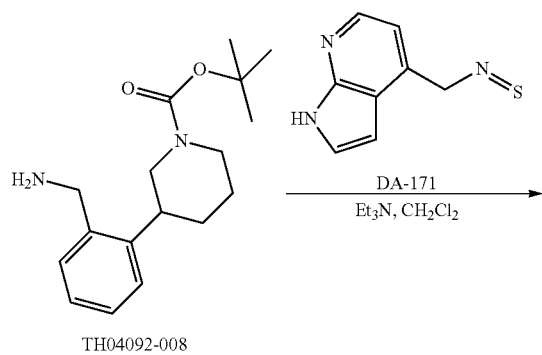

Triethylamine (0.24 mL, 1.7 mmol) was added to a solution of TH04092-008 (170 mg, 0.58 mmol) and DA-171 (110 mg, 0.58 mmol) in $CH_2Cl_2$ (10 ml). The reaction mixture was stirred overnight at room temperature. The solvent was removed under reduced pressure and the crude product was purified by flash chromatography eluting with MeOH: $CH_2Cl_2$ (1:30) to afford 240 mg of the desired product (TH04092-014, 82% yield).

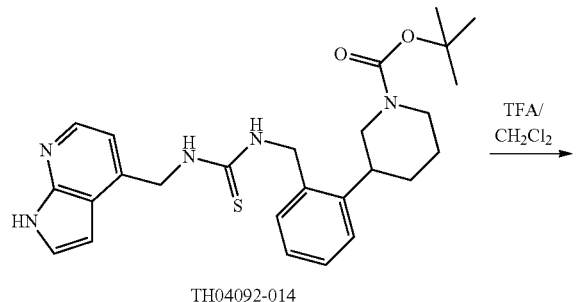

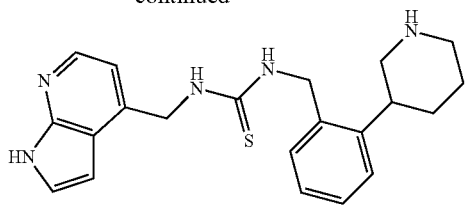

Example 116

TFA (5 mL) was added dropwise to a solution containing TH04092-014 (220 mg, 0.46 mmol) in $CH_2Cl_2$ (20 ml). After stirring for 1.5 h at room temperature, the solvent was removed under reduced pressure and the residue was purified by HPLC to afford 60 mg of Example 116 as a white solid (35% yield). $^1$H NMR (400 MHz, MeOD) δ ppm 1.87 (brm, 2H), 2.00 (brm, 2H), 1.87 (brm, 2H), 3.17 (brm, 2H), 3.40 (brm, 2H), 4.78 (brm, 1H), 4.95 (brm, 1H), 5.25 (brm, 2H), 6.89 (brm, 1H), 7.33 (brm, 5H) 7.60 (brm, 1H) 8.28 (brm, 1H); MS[MH]$^+$=380.0.

Example 117

N-(3-((3-((1H-pyrrolo[2,3-b]pyridin-4-yl)methyl)thioureido)methyl)phenyl)-N-methyl-3-phenylpropiolamide

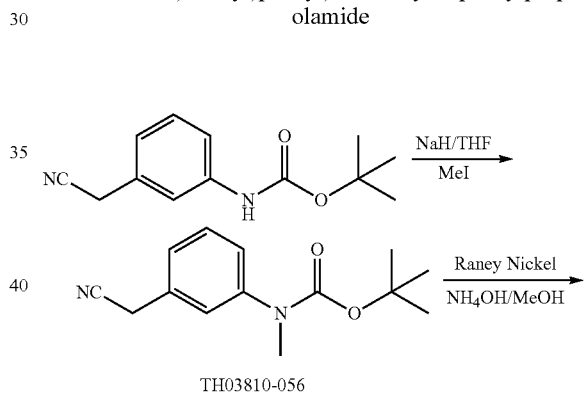

NaH (828 mg, 20.7 mmol) was added to a stirring solution of tert-butyl(3-(cyanomethyl)phenyl)carbamate (3.0 g, 13.8 mmol) in TNF (50 mL). After stirring for 0.5 h, MeI (2.2 g, 15.2 mmol) was added and the reaction was stirred for an additional 3 h. The reaction was quenched with water and an aqueous workup using ethyl acetate as the organic solvent was performed. The combined organic was dried and concentrated to afford TH03810-056 which was used in the subsequent step without purification. A solution of Raney Nickel (0.5 g), methanolic ammonium hydroxide (80 mL) and TH03810-056 (1.5 g, 6.5 mmol) was stirred overnight at room temperature, filtered and then concentrated to afford the product (TH03810-059) as a residue that was used without further purification.

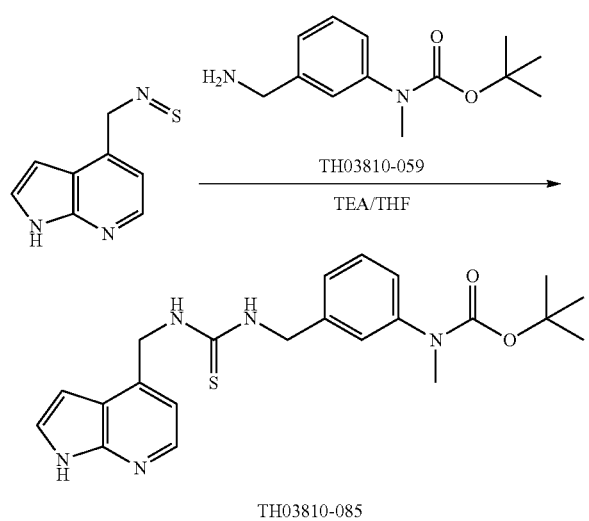

TH03810-085

A solution of 4-(isothiocyanatomethyl)-1H-pyrrolo[2,3-b]pyridine (189 mg, 1 mmol), TH03810-059 (236 mg, 1 mmol) and triethylamine (202 mg, 2 mmol) in THF (5 mL) was stirred overnight at room temperature. The reaction mixture was concentrated and purified by column chromatography to afford 350 mg of the desired product (TH03810-085).

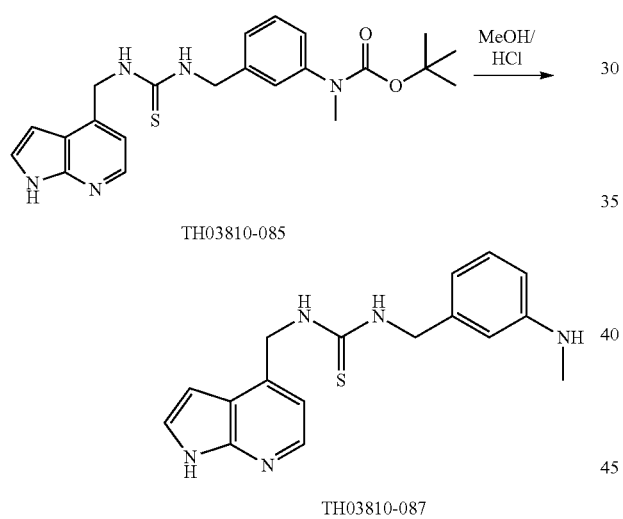

TH03810-087

In a flask containing TH03810-085 (250 mg, 0.83 mmol) was added methanolic HCl (5 ml). The mixture was stirred overnight, concentrated and purified by column chromatography to afford 200 mg of the amine.

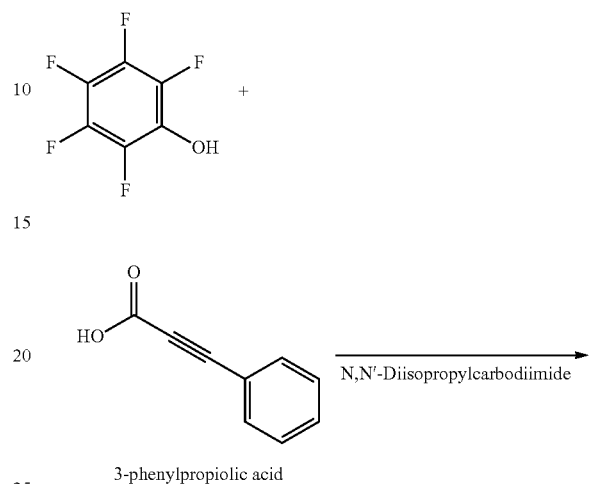

TH03810-088

N,N'-Diisopropylcarbodiimide (262 mg, 2 mmol) was added to a stirring solution of pentaflurophenol (368 mg, 2 mmol) and 3-phenylpropiolic acid (292 mg, 2 mmol) in dichloromethane (5 ml) at room temperature. The reaction was stirred overnight, then concentrated under reduced pressure and purified by column chromatography to yield TH03810-088 (500 mg, 80% yield).

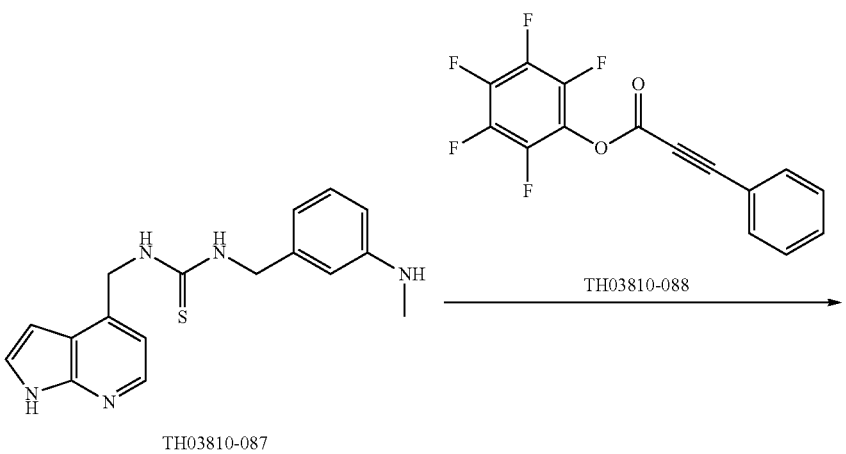

TH03810-087

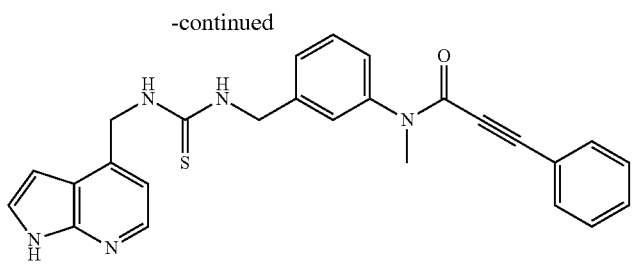

Example 117

A solution of TH03810-087 (65 mg, 0.20 mmol), TH03810-088 (63 mg, 0.2 mmol) and triethylamine (40 mg, 0.40 mmol) in 2 mL of THF was stirred overnight at room temperature. The reaction mixture was concentrated and the residue purified by chromatography to afford 10 mg of Example 117. $^1$H NMR (400 MHz, MeOD) δ ppm 3.33 (s, 3H), 4.89 (brs, 2H), 5.23 (brs, 2H), 6.94 (d, J=9 hz, 1H), 7.1-7.5 (m, 10H), 7.63 (d, J=10 hz, 1H), 8.24 (d, J=16 hz, 1H).

Example 118

N-(3-((3-((1H-pyrrolo[2,3-b]pyridin-4-yl)methyl)ureido)methyl)phenyl)-3-cyclopentylpropiolamide

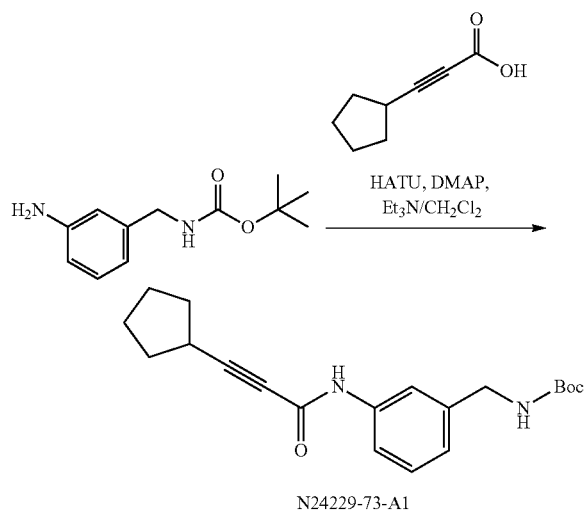

To a solution of tert-butyl 3-aminobenzylcarbamate (1.2 g, 5.40 mmol) in dichloromethane (20 mL) were added 3-cyclopentylpropiolic acid (0.746 g, 5.40 mmol), triethylamine (2.257 mL, 16.20 mmol), HATU (3.08 g, 8.10 mmol) and DMAP (0.066 g, 0.540 mmol), and the mixture was stirred at room temperature for 18 h. The mixture was quenched with 10% NaHCO$_3$ aq. solution and diluted with DCM. The organic layer was collected, dried and concentrated. The residue was purified using column chromatography (silica gel, 20 to 80% EtOAc/hexanes) to give 760 mg of product as a colorless oil. MS: (M+H)$^+$=343.3; $^1$H NMR (400 MHz, DMSO-d$_6$) δ ppm 1.18-1.46 (m, 9H), 1.53-1.78 (m, 6H), 1.93-2.08 (m, 2H), 2.85 (t, J=7.45 Hz, 1H), 4.08 (d, J=6.06 Hz, 2H), 6.94 (d, J=7.33 Hz, 1H), 7.24 (t, J=7.83 Hz, 1H), 7.34-7.60 (m, 2H), 10.52 (s, 1H).

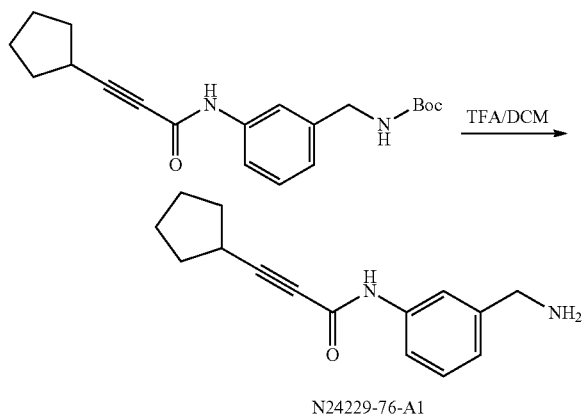

To a solution of tert-butyl 3-(3-cyclopentylpropiolamido)benzylcarbamate (460 mg, 1.343 mmol) in dichloromethane (5 mL) was added TFA (1 ml, 12.98 mmol), and the reaction mixture was stirred room temperature for 3 h. The mixture was concentrated and the residue was treated with 10% NaHCO$_3$ aq. solution and extracted with DCM (3×). The extract was dried (Na$_2$SO$_4$) and concentrated. The residue was dried under vacuum to give 315 mg of product (N24229-76-A1) as an off-white solid. MS: (M+H)$^+$=243.2; $^1$H NMR (400 MHz, DMSO-d$_6$) δ ppm 1.52-1.78 (m, 6H), 1.90-2.19 (m, 4H), 2.79-2.93 (m, 1H), 3.68 (s, 2H), 7.05 (d, J=7.58 Hz, 1H), 7.23 (t, J=7.83 Hz, 1H), 7.42 (d, J=8.34 Hz, 1H), 7.55 (s, 1H), 10.48 (s, 1H).

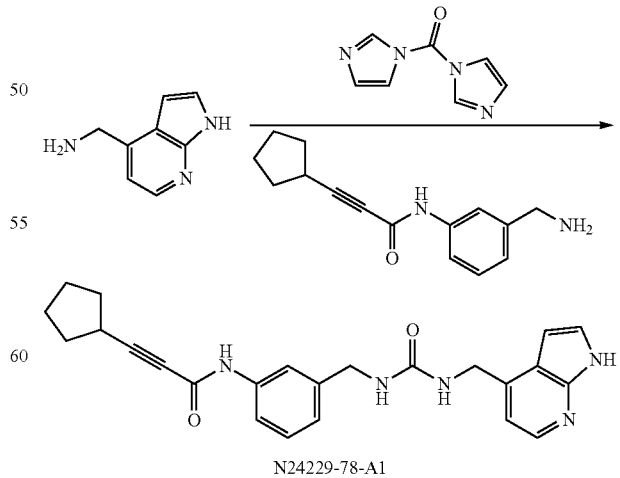

To a solution of (1H-pyrrolo[2,3-b]pyridin-4-yl)methanamine (198 mg, 1.345 mmol) in tetrahydrofuran (6 mL)

were added triethylamine (0.563 mL, 4.04 mmol) and carbonyldiimidazole (327 mg, 2.018 mmol), and the mixture was stirred at room temperature for 18 h. N-(3-(aminomethyl)phenyl)-3-cyclopentylpropiolamide (326 mg, 1.345 mmol) was added and the mixture was stirred at room temperature for 18 h. The mixture was quenched with water (10 mL) and extracted with EtOAc (3×). The extract was dried (Na$_2$SO$_4$) and concentrated. The residue was purified using reverse-phase HPLC. The fractions containing the product were combined and concentrated. The residue was washed with 10% NaHCO$_3$ and dried under vacuum to give 185 mg of product (N24229-78-A1)) as a white solid. MS: (M+H)$^+$=416.3 $^1$H NMR (400 MHz, DMSO-d$_6$) δ ppm 2.75-2.86 (m, 6H), 3.16-3.27 (m, 2H), 3.57 (t, J=6.44 Hz, 2H), 5.41 (s, 2H), 6.56 (dd, J=8.08, 1.77 Hz, 1H), 7.10 (d, J=1.77 Hz, 1H), 7.20-7.29 (m, 1H), 8.56 (s, 1H), 8.77 (s, 1H).

Example 119

1-((1H-pyrrolo[2,3-b]pyridin-4-yl)methyl)-3-(1-(3-cyclohexylpropioloyl)azetidin-3-yl)urea

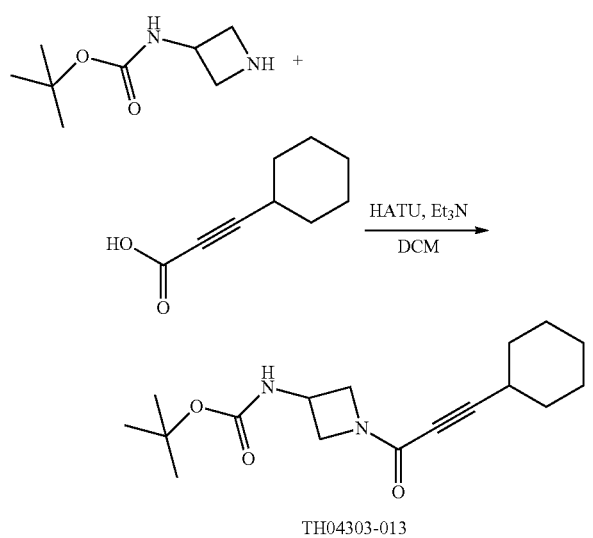

HUTU (1.14 g, 3 mmol) was added into a stirring solution of 3-cyclohexylpropiolic acid (300 mg, 2 mmol), tert-butyl azetidin-3-ylcarbamate (345 mg, 2 mmol) and Et$_3$N (0.83 ml, 6 mmol) in dichloromethane (15 ml). The next day water was added and the reaction was extracted with DCM. The combined organic was washed with saturated NaHCO$_3$, dried over MgSO$_4$ and the ten concentrated under reduced pressure. The residue was purified by flash chromatography to yield TH04303-013 (60 mg, 10% yield).

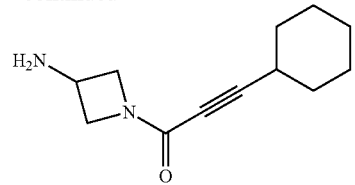

TFA (2 ml) was added dropwise to a stirring solution of TH04303-013 (150 mg, 0.5 mmol) in dichloromethane (8 ml) and the reaction was stirred for an additional 2 h. The solvent was removed under reduced pressure. The residue was dissolved in methanol and treated with A-21 ion exchange resin, filtered and concentrated to afford the crude product which was used without further purification.

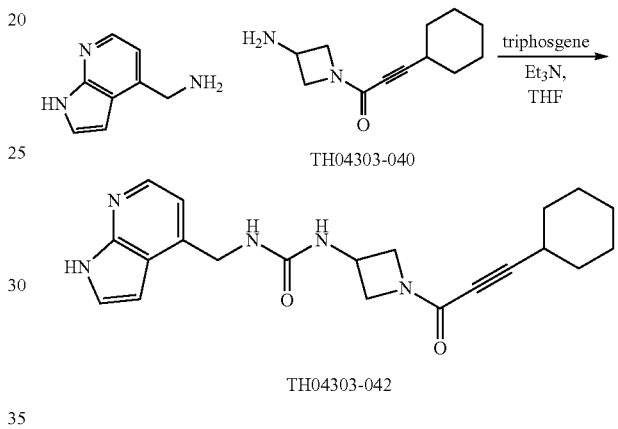

A solution of (1H-pyrrolo[2,3-b]pyridin-4-yl)methanamine-2HCl (110 mg, 0.5 mmol), TH04303-040 (100 mg, 0.5 mmol) and Et$_3$N (0.30 ml, 2 mmol) in THF (30 ml) was stirred at room temperature for 40 minutes. The stirring solution was cooled to 0° C. and triphosgene was added (80 mg, 0.25 mmol). After 2 h the reaction was filtered and the organic concentrated under reduced pressure. The crude product was purified by HPLC (acidic conditions) to yield TH04303-042 (27 mg, 15% yield). MS: (M+H)$^+$=380.2; $^1$H NMR (400 MHz, MeOD) δ ppm 1.4-1.6 (m, 6H), 1.7-1.9 (m, 4H), 2.64 (m, 1H), 3.85 (m, 1H), 6.90 (d, J=8 Hz, 1H), 7.37 (d, J=14 Hz, 1H), 7.62 (d, J=9 Hz, 1H), 8.31 (d, J=15 Hz, 1H).

Example 120

1-((1H-pyrrolo[2,3-b]pyridin-4-yl)methyl)-3-(2-(thiazol-4-yl)benzyl)urea

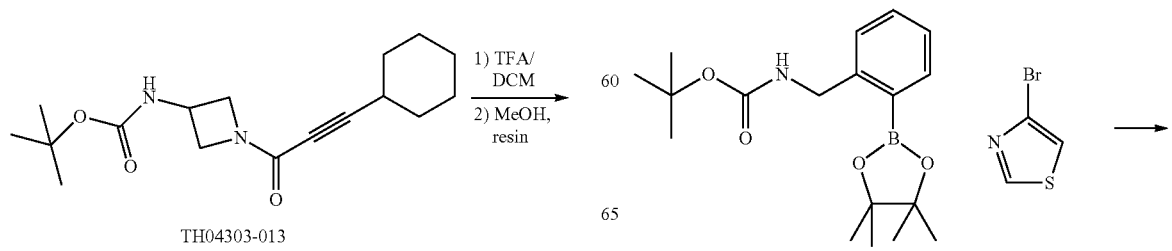

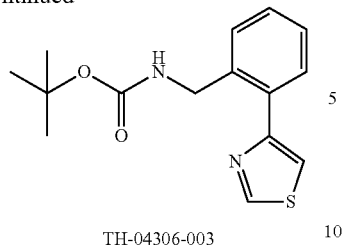

TH-04306-003

To a solution of tert-butyl 2-(4,4,5,5-tetramethyl-1,3,2-dioxaborolan-2-yl)benzylcarbamate (666 mg, 2 mmol) and 4-bromothiazole (326 mg, 2 mmol) in dioxane (4 ml) and water (16 ml) under an nitrogen atmosphere was added K$_2$CO$_3$ (552 mg, 4 mmol) and Pd(PPh$_3$)$_4$ (232 mg, 0.2 mmol). The solution was stirred and heated to 120° C. for 30 minutes using a microwave reactor. The mixture was diluted with water (50 ml) and the aqueous was extracted twice with EtOAc (2×50 ml). The combined organic was dried over MgSO4, concentrated under reduced pressure and the residue was purified by flash chromatography (hexanes:EtOAc—5:1) to afford TH04306-003 (200 mg, 35% yield) as a yellow oil.

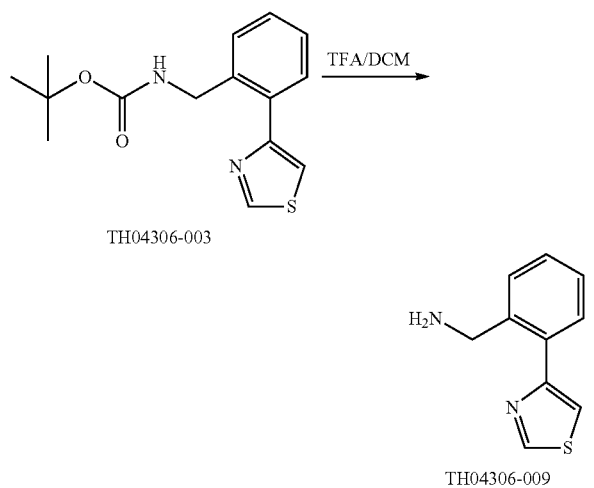

TH04306-003

TH04306-009

Trifluroacetic acid (4 ml) was added dropwise to a stirring room temperature solution of TH04303-003 (200 mg, 0.69 mmol) in dichloromethane (20 ml). Stirring was continued for 30 minutes following the addition at which point the solvent was removed under reduced pressure to afford 130 mg of the crude product (TH04303-009) as a yellow oil.

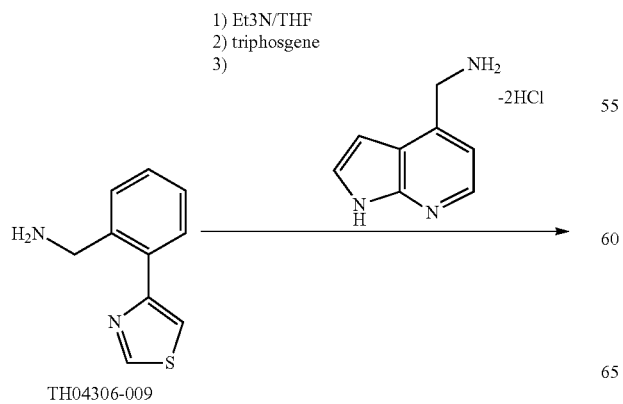

TH04306-009

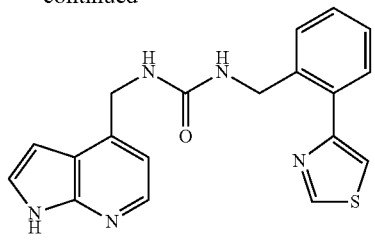

TH04306-050

To a solution of (1H-pyrrolo[2,3-b]pyridin-4-yl)methanamine-2HCl (220 mg, 1.0 mmol) in THF (20 ml) was added Et3N (152 mg, 1.5 mmol). After stirring for 30 minutes the reaction was cooled to 0° C. and triphosgene (98 mg, 0.33 mmol) was added. Following an additional 1 h, Th04306-009 (190 mg, 1 mmol) was added. The cooling bath was removed and the reaction was stirred for an additional 2 h, then concentrated under reduced pressure and the residue was purified by prep HPLC to afford TH04306-050 as a white solid (30 mg, 8.3% yield). MS: (M+H)$^+$=364.1; $^1$H NMR (400 MHz, MeOD) δ ppm 4.43 (s, 2H), 4.81 (s, 2H), 6.92 (d, J=9 Hz, 1H), 7.4 (m, 3H), 7.55 (m, 2H) 7.63 (d, J=9 Hz, 1H), 7.70 (d, J=5 Hz, 1H), 8.30 (d, J=15 Hz, 1H), 9.10 (d, J=4 Hz, 1H).

Protocols for DNMT Inhibition Assays

DNMT Assays Used for Examples 1-114

Human DNMT3b/3L was coexpressed using truncated 3b (catalytic domain) and 3L (DNA binding domain) at GSK. Human full-length DNMT1 enzyme purchased from BPS Biosciences. Poly(dIdC) DNA (Sigma) was used at 0.002 mg/mL. Tritiated SAM (Perkin Elmer) was used at 500 nM. DNA, DNMT enzyme, and inhibitors were mixed with assay buffer (20 mM Tris pH8, 5% glycerol, 1 mM EDTA, 100 μg/mL BSA, 1 mM DTT, 50 mM NaCl) and pre-incubated without SAM for 30 min. H3 SAM was then added to initiate the methylation reaction which continues at 37° C. for 1 h. Reaction mixture was then transferred to a filter plate (Millipore Multiscreen HTS DE), then washed with 50 mM H2PO4 and 95% Ethanol. Scintillation counts were measured on the Perkin Elmer Microbeta scintillation counter.

DNMT Assays Used for Examples 115-120

DNMT enzymes were produced by GlaxoSmithKline. Human DNMT3b/3L was coexpressed using truncated 3b (catalytic domain) and 3L (DNA binding domain). DNMT1 was human, full-length protein. 3H-SAM was purchased from Perkin Elmer. Custon DNA oligonucleotide substrates were purchased from Integrated DNA technologies.

40-mer DNA Oligonucleotide Duplex (for DNMT1)

```
5'-CCTCTTCTAACTGCCAT/iMedC/GATCCTGATAGCAGGTGC
ATGC-3'

5'-GCATGCACCTGCTATCAGGATCGATGGCAGTTAGAAGAGG-3'
```

28-mer DNA Oligonucleotide Duplex (for DNMT3b/3L)

```
5'-GTACAGTATCCGGCACTGACCCACAACAA-3'

5'-/5BiodT/TGTTGTGGGTCAGTGCCGGATACTGTAC-3'
```

DNMT enzyme was preincubated with compound for 1 hr at RT, after which SAM and DNA were added to initiate the methylation reaction. The methylation reaction was quenched after 20 min upon the addition of >100 fold excess non-radioactive SAM. The quenched reaction mixture (80%) was transferred to a DEAE filter binding plate (Millipore Multiscreen HTS DE), washed with 3 volumes of 50 mM phosphate buffer and dried. Scintillation cocktail (MicroScint-20) was added to the plate and radioactivity (3H-DNA) was measured using a Perkin Elmer TopCount scintillation counter.

Final reagent concentrations (prior to quench) consisted of the following:
DNMT1 (20 nM), 100 nM DNA, 1500 nM SAM (0.0195 uCi/uL 3H-SAM) in 20 mM Tris (pH 7.5), 1 mM DTT, 0.5 mM EDTA, 5% glycerol and 2% DMSO.
DNMT3b/3L (10 nM), 200 nM DNA, 200 nM 3H-SAM in 20 mM Tris (pH 8), 1 mM DTT, 1 mM EDTA, 25 mM NaCl, 1 mM CHAPS and 2% DMSO.

The compounds of Examples 1 to 120 were tested for DNMT inhibition activity generally according to one or more of the above indicated assays and in at least one experimental run or as an average of several experimental runs exhibited an $IC_{50}$ (μM) value: between 0.025 (inclusive) and >300 against DNMT 3b/3L.

The compound of Example 52 was tested generally according to the above indicated DNMT inhibition assays and in at least one experimental run or as an average of several experimental runs exhibited an $IC_{50}$ (μM) value of 7.1 against DNMT 3b/3L.

The compounds of Examples 9, 14, 33, 35, 36, 42, and 112 were tested generally according to the above indicated DNMT inhibition assays and in at least one experimental run or as an average of several experimental runs exhibited an $IC_{50}$ (μM) value: ≤20 against DNMT 3b/3L.

The compounds of Examples 10, 11, 15, 17, 20, 39, 50, 64, 74, 111, 116, and 117 were tested generally according to the above indicated DNMT inhibition assays and in at least one experimental run or as an average of several experimental runs exhibited an $IC_{50}$ (μM) value: ≤10 against DNMT 3b/3L.

The compounds of Examples 1, 3, 7, 18, 19, 21, 24, 41, 48, 49, 53, 55, 56, 57, 58, 62, 63, 76, 82, 87, 115, 118, 119, and 120 were tested generally according to the above indicated DNMT inhibition assays and in at least one experimental run or as an average of several experimental runs exhibited an $IC_{50}$ (μM) value: ≤1 against DNMT 3b/3L.

The compounds of Examples 6, 10, 26, 30, 35, 41, 42, 46, 85, 86, 87, 88, 89, 92, 93, 110, and 114 were tested for DNMT inhibition activity generally according to the above indicated assays and in at least one experimental run or as an average of several experimental runs exhibited an $IC_{50}$ (μM) value: between 19.1 and 300 (inclusive) against DNMT 1.

The compound of Example 86 was tested generally according to the above indicated DNMT inhibition assays and in at least one experimental run or as an average of several experimental runs exhibited an $IC_{50}$ (μM) value of 75 against DNMT 1.

The compounds of Examples 41, 85, 89, and 114 were tested generally according to the above indicated DNMT inhibition assays and in at least one experimental run or as an average of several experimental runs exhibited an $IC_{50}$ (μM) value: ≤200 against DNMT 1.

The compounds of Examples 10, 30, 86, 87, 92, 93, and 116 were tested generally according to the above indicated DNMT inhibition assays and in at least one experimental run or as an average of several experimental runs exhibited an $IC_{50}$ (μM) value: ≤100 against DNMT 1.

The invention claimed is:
1. A compound of the following formula:

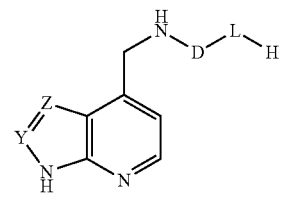

wherein:
Y represents CH or N;
Z represents $CR_1$ or N;
$R_1$ represents hydrogen, halogen, alkyl, cycloalkyl, heterocyclyl, aryl, heteroaryl, alkylaryl, alkylheterocyclyl, alkylheteroaryl, wherein cycloalkyl, heterocyclyl, aryl, heteroaryl, at each occurrence, may be optionally substituted by one or more $R_c$ groups;
D represents C=O, C=S, C=N—C=N, C=N—$NO_2$, or C=N—$SO_2Me$;
L represents

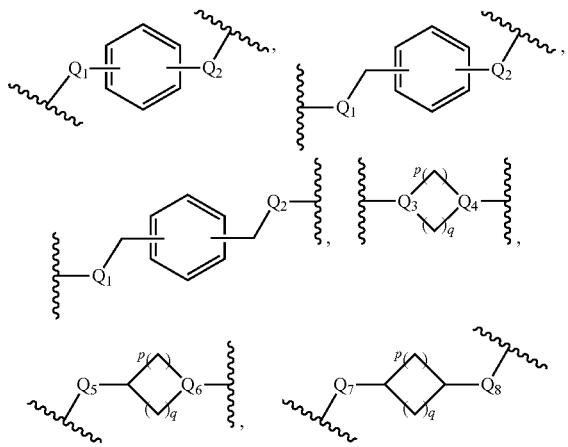

or $-Q_9-(CR_aR_b)_n-Q_{10}-$, wherein the ring systems of L may be optionally substituted by one or more $R_c$ groups;
$Q_1$ represents $CR_2R_3$, $NR_4$, $NR_4CR_2R_3$ or O;
$R_2$, $R_3$ and $R_4$ independently represent hydrogen, alkyl, cycloalkyl, heterocyclyl, aryl, heteroaryl, wherein alkyl, cycloalkyl, heterocyclyl, aryl, heteroaryl, at each occurrence, may be optionally substituted by one or more $R_c$ groups; $R_2$ and $R_3$ together with the carbon atom to which they are attached may form a carbocyclic or heterocyclic ring which may be optionally substituted by one or more $R_c$ groups;
$Q_2$ is absent or represents $CR_2R_3$, $NR_4$, $NR_4CR_2R_3$ or O;
$R_2$, $R_3$ and $R_4$ independently represent hydrogen, alkyl, cycloalkyl, heterocyclyl, aryl, heteroaryl, wherein alkyl, cycloalkyl, heterocyclyl, aryl, heteroaryl, at each occurrence, may be optionally substituted by one or more $R_c$ groups; $R_2$ and $R_3$ together with the carbon atom to which they are attached may form a carbocyclic or heterocyclic ring which may be optionally substituted by one or more $R_c$ groups;
$Q_3$ and $Q_4$ independently represent $CR_5$ or N;
$R_5$ represents hydrogen, alkyl, cycloalkyl, heterocyclyl, aryl, heteroaryl, wherein cycloalkyl, heterocyclyl, aryl, heteroaryl, at each occurrence may be optionally substituted by one or more $R_c$ groups;

p and q independently represent an integer selected from 0 to 4, such that the sum of integers for p and q do not exceed 5;

$Q_5$ represents $CR_6R_7$, $NR_8$, $NR_8CR_6R_7$ or O;

$R_6$, $R_7$ and $R_8$ independently represent hydrogen, alkyl, cycloalkyl, heterocyclyl, aryl, heteroaryl, wherein cycloalkyl, heterocyclyl, aryl, heteroaryl, at each occurrence, may be optionally substituted by one or more $R_c$ groups; $R_6$ and $R_7$ together with the carbon atom to which they are attached may form a carbocyclic or heterocyclic ring which may be optionally substituted by one or more $R_c$ groups;

$Q_6$ represents $CR_9$ or N;

$R_9$ represents hydrogen, alkyl, cycloalkyl, heterocyclyl, aryl, heteroaryl, wherein cycloalkyl, heterocyclyl, aryl, heteroaryl, at each occurrence, may be optionally substituted by one or more $R_c$ groups;

$Q_7$ and $Q_8$ are independently $CR_{10}R_{11}$, $NR_{12}$ or O;

$R_{10}$, $R_{11}$ and $R_{12}$ independently represent hydrogen, alkyl, cycloalkyl, heterocyclyl, aryl, heteroaryl, wherein cycloalkyl, heterocyclyl, aryl, heteroaryl, at each occurrence, may be optionally substituted by one or more $R_c$ groups; $R_{10}$ and $R_{11}$ together with the carbon atom to which they are attached may form a carbocyclic or heterocyclic ring which may be optionally substituted by one or more $R_c$ groups;

$Q_9$ and $Q_{10}$ independently represent $CR_{14}R_{15}$, $NR_{16}$, $CR_{14}R_{15}NR_{16}$ or O;

$R_a$ and $R_b$ independently represent hydrogen, alkyl or alkenyl;

$R_{14}$, $R_{15}$ and $R_{16}$ independently represent hydrogen, alkyl, amino, alkenyl, cycloalkyl, heterocyclyl, aryl, heteroaryl, wherein cycloalkyl, heterocyclyl, aryl, heteroaryl, at each occurrence, may be optionally substituted by one or more $R_c$ groups; $R_{14}$ and $R_{15}$ together with the carbon atom to which they are attached may form a carbocyclic or heterocyclic ring which may be optionally substituted by one or more $R_c$ groups;

n represents an integer selected from 0 to 5;

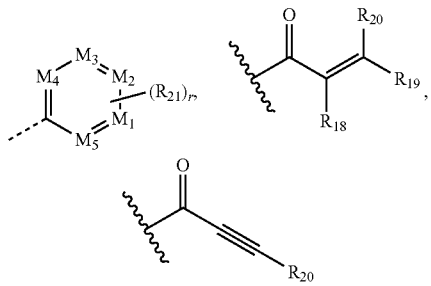

M is absent or represents or —CO—$R_{22}$;

$M_1$, $M_2$, $M_3$, $M_4$ and $M_5$ independently represent CH or N;

$R_{18}$, $R_{19}$ and $R_{20}$ independently represent hydrogen, alkyl, alkoxy, cycloalkyl, heterocyclyl, aryl, heteroaryl, wherein cycloalkyl, heterocyclyl, aryl, heteroaryl, at each occurrence, may be optionally substituted by one or more $R_c$ groups;

$R_{21}$ represents hydrogen, F, Cl, $CF_3$, $NH_2$, $NO_2$, thiazolyl or pyridyl;

r represents an integer selected from 0 to 3;

$R_{22}$ represents alkyl, hydroxyl, alkanol, alkoxy, haloalkyl or aminoalkyl;

$R_c$ represents halogen, $C_{1-6}$ alkyl, $C_{2-6}$ alkenyl, $C_{2-6}$ alkynyl, —$(CH_2)_{0-4}$—$C_{3-8}$ cycloalkyl, —$(CH_2)_{0-4}$—$C_{3-8}$ cycloalkenyl, —$(CH_2)_{0-4}$-phenyl, —$(CH_2)_{0-4}$-(heterocyclyl), —$(CH_2)_{0-4}$-(heteroaryl), —$(CR^xR^y)_{0-4}$—O—$R^z$, —O—$(CR^xR^y)_{1-4}$—$OR^z$, halo$C_{1-6}$ alkyl, halo$C_{1-6}$ alkoxy, $C_{1-6}$ alkanol, =O, =S, nitro, $Si(R^x)_4$, —$(CH_2)_{0-4}$—CN, —$S(O)_{0-2}$—$R^x$, —C(=O)$R^x$, —$(CR^xR^y)_{0-4}$—C(=O)$OR^z$, —$(CR^xR^y)_{0-4}$—O—C(=O)—$R^z$, —$(CR^xR^y)_{0-4}$—C(=O)$NR^xR^y$, —$(CH_2)_{0-4}$—$NR^xC(=O)R^y$, —$(CH_2)_{0-4}$—OC(=O)$NR^xR^y$, —$(CH_2)_{0-4}$—$NR^xC(=O)OR^y$, —$(CH_2)_{0-4}$—$NR^xR^y$, —$NR^x$—$(CH_2)_{0-4}$—$R^z$, —$(CH_2)_{0-4}$—O—C(=O)—$C_{1-4}$alkyl-$NR^xR^y$, —$(CH_2)_{0-4}$—$NR^x$—$(CH_2)_{1-4}$—O—C(=O)—$R^z$, —$(CH_2)_{0-4}$—$NR^x$—$(CH_2)_{0-4}$—$SO_2$—$R^y$, —$(CH_2)_{0-4}$—NH—$SO_2$—$NR^xR^y$, —$(CH_2)_{0-4}$—$SO_2NR^xR^y$ and —P(=O)$(R^x)_2$ groups;

$R^x$, $R^y$ and $R^z$ independently represent hydrogen, $C_{1-6}$ alkyl, $C_{2-6}$ alkenyl, $C_{2-6}$ alkynyl, —$(CH_2)_{0-4}$—$C_{3-8}$ cycloalkyl, —$(CH_2)_{0-4}$—$C_{3-8}$ cycloalkenyl, —$(CH_2)_{0-4}$-(heterocyclyl), —$(CH_2)_{0-4}$-(heteroaryl), $C_{1-6}$ alkanol optionally substituted with one or more halo, —C(=O)$OC_{1-6}$ alkyl, hydroxy, $C_{1-6}$ alkoxy, halo$C_{1-6}$ alkyl, —$(CH_2)_{1-4}$—O—$C_{1-6}$alkyl, —C(=O)—$(CH_2)_{1-4}$—$C_{1-6}$ alkoxy, —C(=O)—$C_{1-6}$alkyl, —$(CH_2)_{0-4}$—CN, $C_{1-6}$ alkyl-$N(H)_{2-s}$$(C_{1-6}$alkyl$)_s$, —$N(H)_{2-s}$$(C_{1-6}$alkyl$)_s$, —C(=O)—$N(H)_{2-s}$$(C_{1-6}$alkyl$)_s$, —$(CH_2)_{0-4}$—NH—$SO_2$—$N(H)_{2-s}$$(C_{1-6}$alkyl$)_s$, —$(CH_2)_{0-4}$—$N(C_{1-4}$alkyl)-$SO_2$—$N(H)_{2-s}$$(C_{1-6}$alkyl$)_s$ and —$(CH_2)_{0-4}$—O—C(=O)—$C_{1-4}$alkyl-$N(H)_{2-s}$$(C_{1-6}$alkyl$)_s$, and when attached to nitrogen or carbon or phosphorus or silicon atom $R^x$ and $R^y$ may join to form a 3-7 membered ring optionally containing a one or two heteroatoms selected from O, N, S and oxidised forms of N or S; and s represents an integer selected from 0 to 2;

provided that when $Q_2$ is absent, M is absent;

or a pharmaceutically acceptable salt thereof.

2. A compound as defined in claim 1, wherein Y represents CH.

3. A compound as defined in claim 1, wherein Z represents $CR_1$.

4. A compound as defined in claim 1, wherein $R_1$ represents hydrogen, halogen or alkylheterocyclyl.

5. A compound as defined in claim 1, wherein L represents

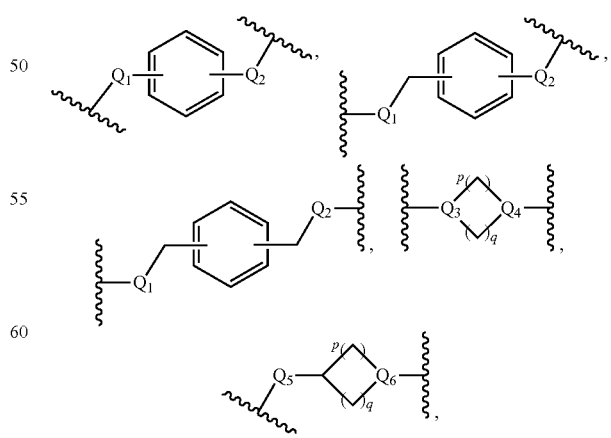

or -$Q_9$-$(CH_2)_n$-$Q_{10}$-, wherein the ring systems of L may be optionally substituted by one or more $R_c$ groups.

6. A compound as defined in claim 1, wherein L represents

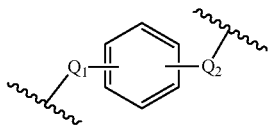

and $Q_1$ and $Q_2$ both represent $NR_4$, wherein the phenyl ring of L may be optionally substituted by one or two $R_c$ groups selected from hydroxy, $NO_2$, $CF_3$, alkoxy or halogen.

7. A compound as defined in claim 1, wherein L represents and

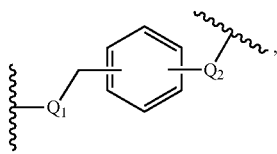

$Q_1$ and $Q_2$ both represent $NR_4$ or $Q_1$ represents $NR_4CR_2R_3$ and $Q_2$ represents $NR_4$ or $Q_1$ represents $CR_2R_3$ and $Q_2$ represents $NR_4$ wherein said phenyl ring of L may be optionally substituted by one or two $R_c$ groups selected from hydroxy, $NO_2$, $CF_3$, alkoxy or halogen.

8. A compound as defined in claim 1, wherein L represents

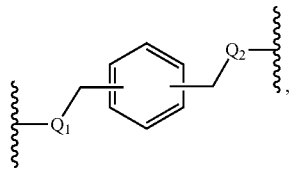

and $Q_1$ and $Q_2$ both represent $NR_4$ wherein said phenyl ring of L may be optionally substituted by one or two $R_c$ groups selected from hydroxy, $NO_2$, $CF_3$, alkoxy or halogen.

9. A compound as defined in claim 1, wherein L represents $-Q_9-(CR_aR_b)_n-Q_{10}-$ and:

$Q_9$ and $Q_{10}$ both represent $NR_{16}$ and n represents 2; or $Q_9$ and $Q_{10}$ both represent $NR_{16}$ and n represents 3; or $Q_9$ represents $NR_{16}$, n represents 0 and $Q_{10}$ represents $C_{14}R_{15}$; or $Q_9$ represents $C_{14}R_{15}$, n represents 2 and $Q_{10}$ represents $NR_{16}$; or $Q_9$ represents $NR_{16}$, n represents 4 and $Q_{10}$ represents $C_{14}R_{15}$; or $Q_9$ represents $NR_{16}$, n represents 1 and $Q_{10}$ represents $C_{14}R_{15}NR_{16}$.

10. A compound as defined in claim 1, wherein L represents

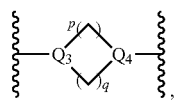

and p and q both represent 2 and $Q_3$ and $Q_4$ both represent N.

11. A compound as defined in claim 1, wherein L represents

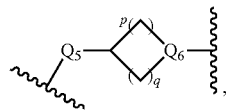

and:

$Q_5$ represents $NR_8$ or $CR_6R_7$, p and q both represent 1 and $Q_6$ represents N; or $Q_5$ represents $NR_8$, p and q both represent 2 and $Q_6$ represents N; or $Q_5$ represents $NR_8$, p represents 1, q represents 2 and $Q_6$ represents N; or $Q_5$ represents $NR_8CR_6R_7$, p represents 0 and q represents 4 and $Q_6$ represents N; or $Q_5$ represents $NR_8CR_6R_7$, p and q both represent 2 and $Q_6$ represents N; or $Q_5$ represents $NR_8CR_6R_7$, p represents 1 and q represents 3 and $Q_6$ represents N; or $Q_5$ represents $NR_8CR_6R_7$, p represents 1, q represents 2 and $Q_6$ represents N.

12. A compound as defined in claim 1, wherein M represents

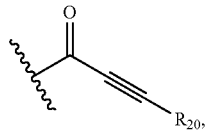

and $R_{20}$ represents hydrogen, alkyl, cycloalkyl, alkoxy, aryl, wherein said phenyl ring may be optionally substituted by one or two $R_c$ groups selected from halogen, alkyl, alkoxy or $NO_2$ groups.

13. A compound as defined in claim 1, wherein M represents

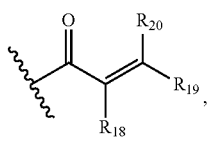

and $R_{18}$, $R_{19}$ and $R_{20}$ each represent hydrogen.

14. A compound as defined in claim 1, wherein M represents $-CO-R_{22}$, and $R_{22}$ represents alkyl, hydroxyl, alkanol, alkoxy, haloalkyl or aminoalkyl.

15. A compound as defined in claim 1, wherein M represents

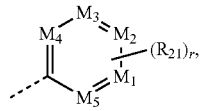

and $M_1$, $M_2$, $M_3$, $M_4$ and $M_5$ each represent CH, r represents 1 or 2 and $R_{21}$ represents hydrogen, F, Cl, $CF_3$, $NH_2$, $NO_2$, thiazolyl or pyridyl.

16. A compound as defined in claim 1, wherein M represents

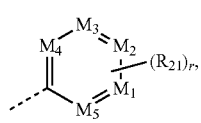

and $M_1$, $M_2$, $M_3$ each represent CH and $M_4$ and $M_5$ both represent N, r represents 1 and $R_{21}$ represents Cl.

17. A pharmaceutical composition comprising a compound of claim 1.

18. A method of in inhibiting DNA methyltransferase activity by administering an effective amount of the compound according to claim 1.

19. A process for preparing a compound according to claim 1, which comprises:
(a) preparing a compound of claim 1 wherein $Q_2$ represents $NR_4$ or $Q_4$ represents N or $Q_6$ represents N or $Q_8$ represents $NR_{12}$ or $Q_{10}$ represents $NR_{16}$ and M represents

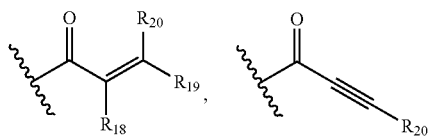

or —CO—$R_{22}$ by reacting a compound of the formula:

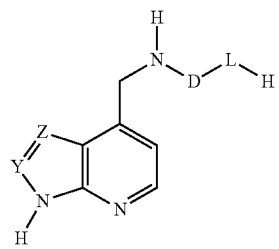

wherein Y, Z, D and L are as defined in claim 1, with a compound of formula HO-M wherein M is as defined in claim 1;

(b) preparing a compound of claim 1 wherein D represents C=S, L represents -$Q_9$-$(CR_aR_b)_n$-$Q_{10}$-, $Q_9$ represents NH and M represents

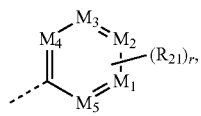

which comprises reacting a compound of the formula

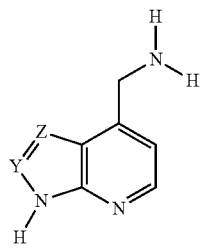

wherein Y and Z are as defined in claim 1, with a compound of formula S=C=N—$(CR_aR_b)_n$-$Q_{10}$-M, wherein $R_a$, $R_b$, n, $Q_{10}$ and M are as defined in claim 1;

(c) reacting a compound of the formula

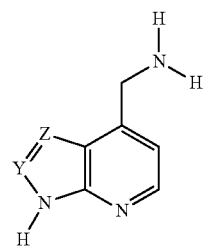

wherein Y and Z are as defined in claim 1, with a compound of formula $L_1$-D-$L_2$ and a compound of formula H-L-M wherein D, L and M are as defined in claim 1 and $L_1$ and $L_2$ represent a suitable leaving group, such as chlorine;

(d) preparing a compound of claim 1 wherein $Q_2$ represents $NR_4$ or $Q_4$ represents N or $Q_6$ represents N or $Q_8$ represents $NR_{12}$ or $Q_{10}$ represents $NR_{16}$ and M represents

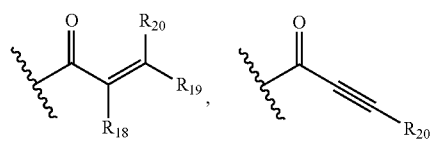

or —CO—$R_{22}$ by reacting a compound of the formula:

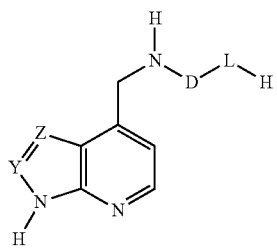

wherein Y, Z, D and L are as defined in claim 1, with a compound of formula $L_3$-M, wherein M is as defined in claim 1 and $L_3$ represents a suitable leaving group, such as chlorine;

(e) preparing a compound of claim 1 wherein D represents C=S, $Q_2$ represents $NR_4$, $Q_4$ represents N, $Q_6$ represents N, $Q_9$ represents $NR_{12}$ or $Q_{10}$ represents $NR_{16}$, which comprises reacting a compound of the formula

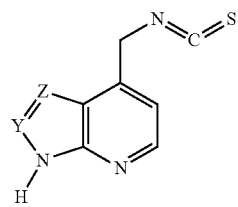

wherein Y and Z are as defined in claim 1, with a compound of formula H-L-M, wherein L and M are as defined in claim 1;

(f) preparing a compound of claim 1 wherein $Q_2$ represents $NR_4$ or $Q_4$ represents N or $Q_6$ represents N or $Q_8$ represents $NR_{12}$ or $Q_{10}$ represents $NR_{16}$ and M represents

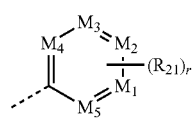

by reacting a compound of the formula:

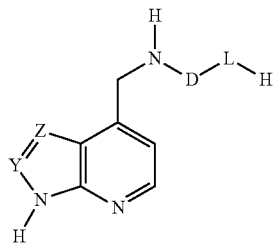

wherein Y, Z, D and L are as defined in claim 1, with a compound of formula (V)

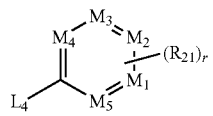
(V)

wherein $M_1$, $M_2$, $M_3$, $M_4$, $M_5$, $R_{21}$ and r are as defined in claim 1 and $L_4$ represents a suitable leaving group, such as chlorine;

(g) preparing a compound of claim 1 wherein D represents C=O, which comprises reacting a compound of the formula

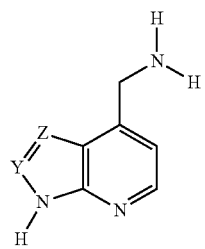

wherein Y and Z are as defined in claim 1, with a compound of formula (VI)

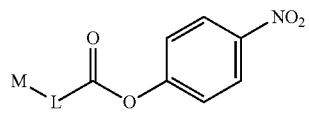
(VI)

wherein M and L are as defined in claim 1.

* * * * *